(12) United States Patent
Leo et al.

(10) Patent No.: US 11,584,922 B2
(45) Date of Patent: Feb. 21, 2023

(54) PROTEASE AND BINDING POLYPEPTIDE FOR O-GLYCOPROTEINS

(71) Applicant: Genovis AB, Lund (SE)

(72) Inventors: Fredrik Leo, Lund (SE); Rolf Lood, Lund (SE); Stephan Bjork, Lund (SE); Malin Mejare, Lund (SE); Fredrik Olsson, Lund (SE)

(73) Assignee: Genovis AB, Lund (SE)

( * ) Notice: Subject to any disclaimer, the term of this patent is extended or adjusted under 35 U.S.C. 154(b) by 0 days.

(21) Appl. No.: 16/616,827

(22) PCT Filed: May 25, 2018

(86) PCT No.: PCT/EP2018/063832
§ 371 (c)(1),
(2) Date: Nov. 25, 2019

(87) PCT Pub. No.: WO2018/215656
PCT Pub. Date: Nov. 29, 2018

(65) Prior Publication Data
US 2020/0172889 A1    Jun. 4, 2020

(30) Foreign Application Priority Data

| May 26, 2017 | (GB) | ..................................... | 1708471 |
| May 26, 2017 | (GB) | ..................................... | 1708476 |
| Apr. 24, 2018 | (GB) | ..................................... | 1806655 |

(51) Int. Cl.
| C12N 9/24 | (2006.01) |
| C12N 9/52 | (2006.01) |
| G01N 33/84 | (2006.01) |
| G01N 33/68 | (2006.01) |

(52) U.S. Cl.
CPC ............ *C12N 9/2402* (2013.01); *C12N 9/52* (2013.01); *G01N 33/68* (2013.01); *G01N 33/84* (2013.01); *C12Y 304/24057* (2013.01); *G01N 2333/924* (2013.01); *G01N 2333/952* (2013.01)

(58) Field of Classification Search
CPC ........ C12N 9/6424; C12N 9/50; C12P 21/005
See application file for complete search history.

(56) References Cited

U.S. PATENT DOCUMENTS

| 2002/0193573 A1 | 12/2002 | Nock et al. | |
| 2005/0112751 A1 | 5/2005 | Fang et al. | |
| 2014/0308730 A1* | 10/2014 | Nikiforov | ............ G01N 33/582 |
| | | | 435/188 |

FOREIGN PATENT DOCUMENTS

| WO | WO 2008071418 | 6/2008 |
| WO | 2009129086 | 10/2009 |
| WO | WO 2010007214 | 1/2010 |
| WO | WO 2013037824 | 3/2013 |
| WO | WO 2015040125 | 3/2015 |
| WO | WO 2016003795 | 1/2016 |
| WO | WO 2017052463 | 3/2017 |
| WO | 2017134274 | 8/2017 |

OTHER PUBLICATIONS

Nakjang et al. (2012) A Novel Extracellular Metallopeptidase Domain Shared by Animal Host-Associated Mutualistic and Pathogenic Microbes, PLos One, vol. 7, e30287, pp. 1-18.*
NCBI (2021, updated) BT_4244 [Bacteroides thetaiotaomicron], https://www.ncbi.nlm.nih.gov/protein/NP_813155.1?report=genpept, pp. 1-2.*
Tarp et al (2007) Identification of a novel cancer-specific immunodominant glycopeptide epitope in the MUC1 tandem repeat, Glycobiol., vol. 17, No. 2, pp. 197-209.*
Huang et al. (2015) Biochemical characterisation of the neuraminidase pool of the human gut symbiont Akkermansia muciniphila, Carbohyd. Res., vol. 415, pp. 60-65.*
Abdullah et al. (1991) "Cloning, Nucleotide Sequence, and Expression of the Pasteurella haemolytica Al Glycoprotease Gene" J. Bacteriol., 173(18):5597-5603.
Abdullah et al. (1992) "A Neutral Glycoprotease of Pasteurella haemolytica Al Specifically Cleaves O-Sialoglycoproteins" Infect. Immun., 60:56-62.
Caputo et al. (2015) "Whole-genome assembly of *Akkermansia muciniphila* sequenced directly from human stool." Biol. Direct., 10(5):1-11.
Database EMBL [Online], May 6, 2008, "Akkermansia muciniphila ATCC BAA-835 hypothetical protein", retrieved from EBI accession No. ACD04945 Database accession No. ACD04945.
Debray et al. (2006) "Glycoprotein Analysis: General Methods" Encyclopedia of Analytical Chemistry, John Wiley & Sons, Ltd, pp. 6-17.
Huang et al. (2015) "Biochemical characterisation of the neuraminidase pool of the human gut symbiont *Akkermansia muciniphila*" Carbohydrate Research, 415:60-65.
Juge et al. (2016) "Sialidases from gut bacteria: a mini-review" Biochem Soc Transactions, 44:166-175.
Lee et al. (2015) "rbCLCA1 is a putative metalloprotease family member: localization and catalytic domain identification" Amino Acids, Springer Verlag, AU, 48(3):707-720.
Lucas et al. (2013) "Akkermansia muciniphila ATCC BAA-835, complete genome" Genbank accession No. CP001071.1, NCBI website.
Noach et al. (2017) "Recognition of protein-linked glycans as a determinant of peptidase activity" PNAS, p. E679-E688 and supporting appendices.
Rawlings et al. (1995) "Evolutionary Families of Metallopeptidases", Methods in Enzymology, Academic Press, US, 248:183-228.
Van Passel et al. (2011) "The Genome of *Akkermansia muciniphila*, a Dedicated Intestinal Mucin Degrader, and Its Use in Exploring Intestinal Metagenomes" Plos One, 6(3):1-8.

(Continued)

*Primary Examiner* — Anand U Desai
(74) *Attorney, Agent, or Firm* — Brian E. Davy; Bozicevic, Field & Francis LLP

(57) ABSTRACT

The present invention relates to a novel endoprotease, mutants thereof having binding but lacking or having reduced hydrolyzing activity, and use in methods of studying and isolating O-linked glycoproteins.

21 Claims, 34 Drawing Sheets

Specification includes a Sequence Listing.

(56) References Cited

OTHER PUBLICATIONS

Vazeux et al. (1996) "Identification of Glutamate Residues Essential for Catalytic Activity and Zinc Coordination in Aminopeptidase A" Journal of Biological Chemistry, 271(15):9069-9074.
Database UniProt [Online], Jul. 1, 2008, "SubName: Full=Exo-alpha-sialidase {ECO:0000313|EMBL:ACD04462.1}; EC=3.2.1.18 {ECO:0000313|EMBL:ACD04462.1};", retrieved from EBI accession No. UniProt:B2UPI5, Database accession No. B2UPI5.
Database UniProt [Online], Jul. 1, 2008, "SubName: Full= Uncharacterized protein {ECO:0000313| EMBL: ACD05368.1},", retrieved from EBI accession No. UniProt:B2ULI1, Database accession No. B2ULI1.
Database UniProt [Online], Oct. 29, 2014, "RecName: Full=Serine protease {ECO:0000256|RuleBase: RU004296}; EC=3.4.21.-{ECO:0000256|RuleBase:RU004296};", retrieved from EBI accession No. UniProt: A0A081R2Z4, Database accession No. A0A081R2Z4.
Magnelli et al. (2011) "Identification and characterization of protein glycosylation using specific endo- and exoglycosidases" Journal of Visualized Experiments, 58:1-5.

Altschul et al. (1990) "Basic local alignment search tool" J Mol Biol 215:403-10.
Altschul (1993) "A Protein Alignment Scoring System Sensitive at All Evolutionary Distances" J Mol Evol 36:290-300.
"Database UniProt [Online] Jul. 1, 2008, "SubName: Full= Uncharacterized protein {EC0:0000313 EMBL: ACD04945.1 };", XP55755394, retrieved from EBI accession No. UniProt:B2UR60".
Datta et al. (2013) "Enzyme immobilization: an overview on techniques and support materials" 3 Biotech, 3(1):1-9.
Devereux et al. (1984) "A comprehensive set of sequence analysis programs for the VAX" Nucleic Acids Research 12, 387-395.
Examination Report dated Dec. 8, 2020, EP18728576.2, 5 pp.
Henikoff (1992) "Amino acid substitution matrices from protein blocks" Proc. Nat. Acad Sci. USA 89:10915-10919.
Karlin and Altschul (1993) "Applications and statistics for multiple high-scoring segments in molecular sequences" Proc. Nat. Acad Sci. USA 90:5873-5787.
Sambrook et al. (1989) Molecular Cloning—a laboratory manual; Cold Spring Harbor Press. 30 pp.

* cited by examiner

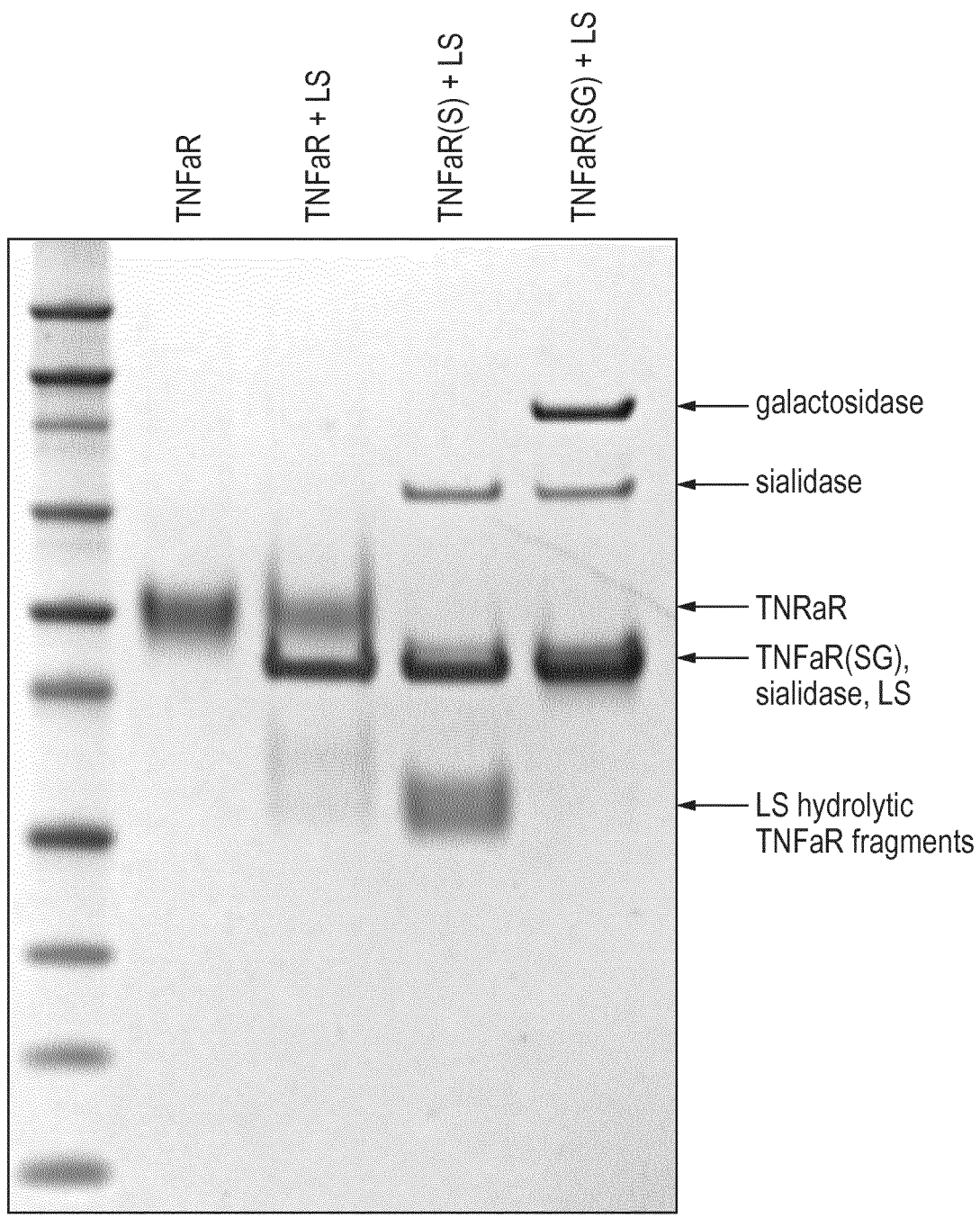

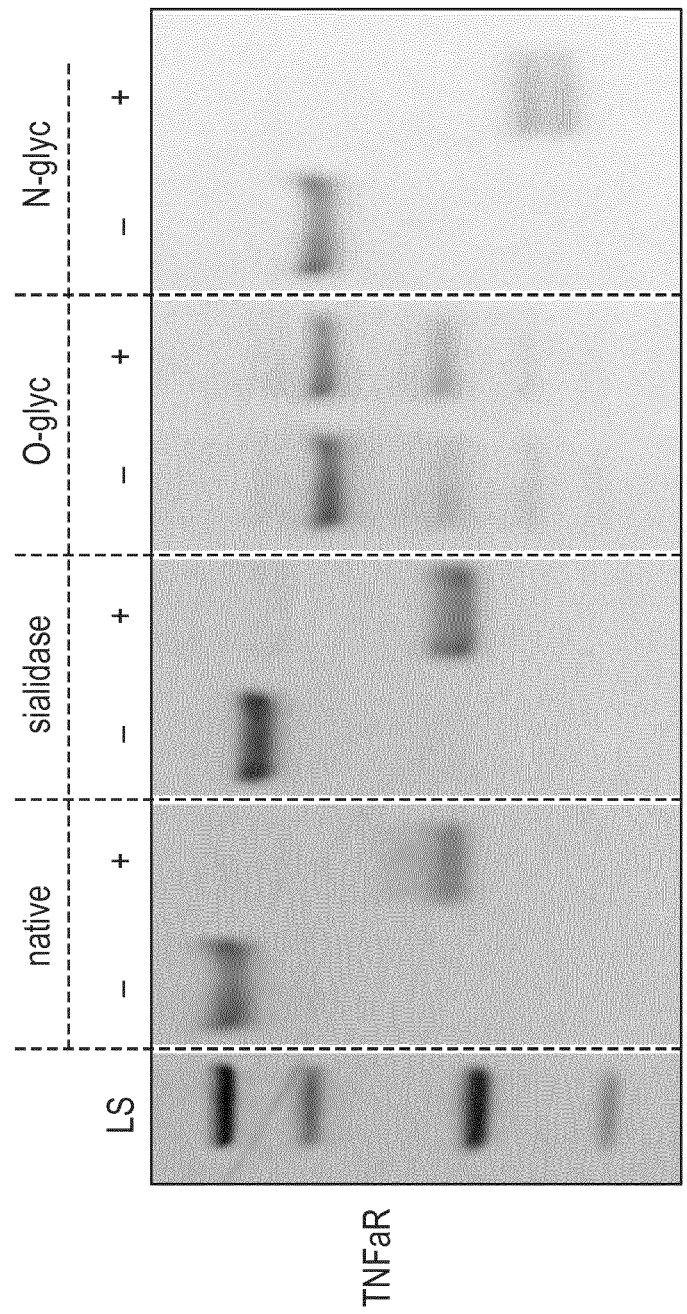

Fig. 5B

```
    10          20          30          40          50          60          70          80          90
LPAQVAFTPY  APEPGSTCRL  REYYDQTAQM  CCSKCSPGQH  AKVFCTKTSD  TVCDSCEDST  YTQLWNWVPE  CLSCGSRCSS  DQVETQACTR 100         110         120         130         140         150         160         170         180
EQNRICTCRP  GWYCALSKQE  GCRLCAPLRK  CRPGFGVARP  GTETSDVVCK  PCAPGTFSNT  TSSTDICRPH  QICNVVAIPG  NASMDAVCTS 190         200         210         220         230         240         250         260         270
TSPTRSMAPG  AVHLPQPVST  RSQHTQPTPE  PSTAPSTSFL  LPMGPSPPAE  GSTGDEPKSC  DKTHTCPPCP  APELLGGPSV  FLFPPKPKDT 280         290         300         310         320         330         340         350         360
LMISRTPEVT  CVVVDVSHED  PEVKFNWYVD  GVEVHNAKTK  PREEQYNSTY  RVVSVLTVLH  QDWLNGKEYK  CKVSNKALPA  PIEKTISKAK 370         380         390         400         410         420         430         440         450
GQPREPQVYT  LPPSREEMTK  NQVSLTCLVK  GFYPSDIAVE  WESNGQPENN  YKTTPPVLDS  DGSFFLYSKL  TVDKSRWQQG  NVFSCSVMHE 460         470
ALHNHYTQKS  LSLSPGK
```

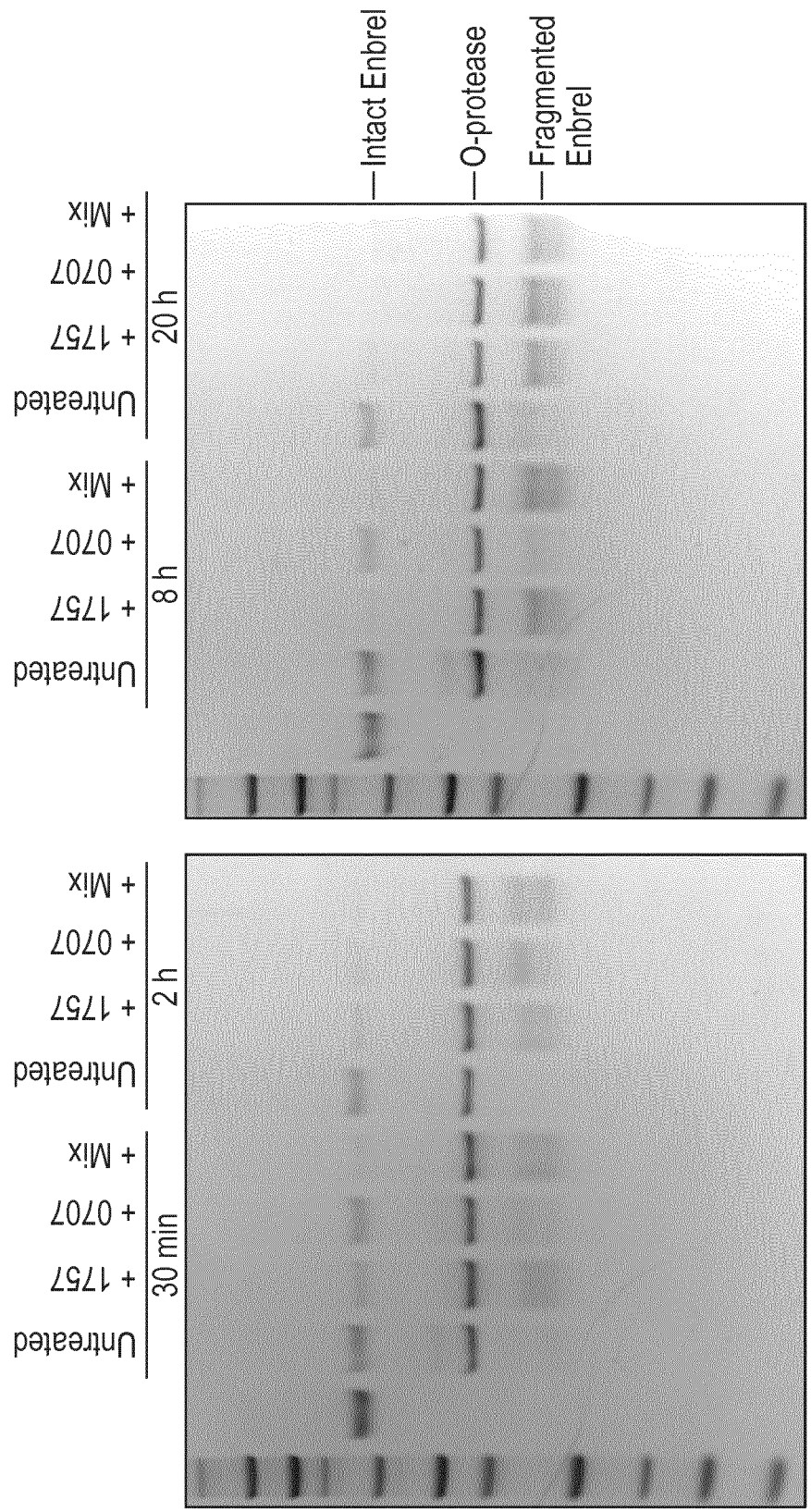

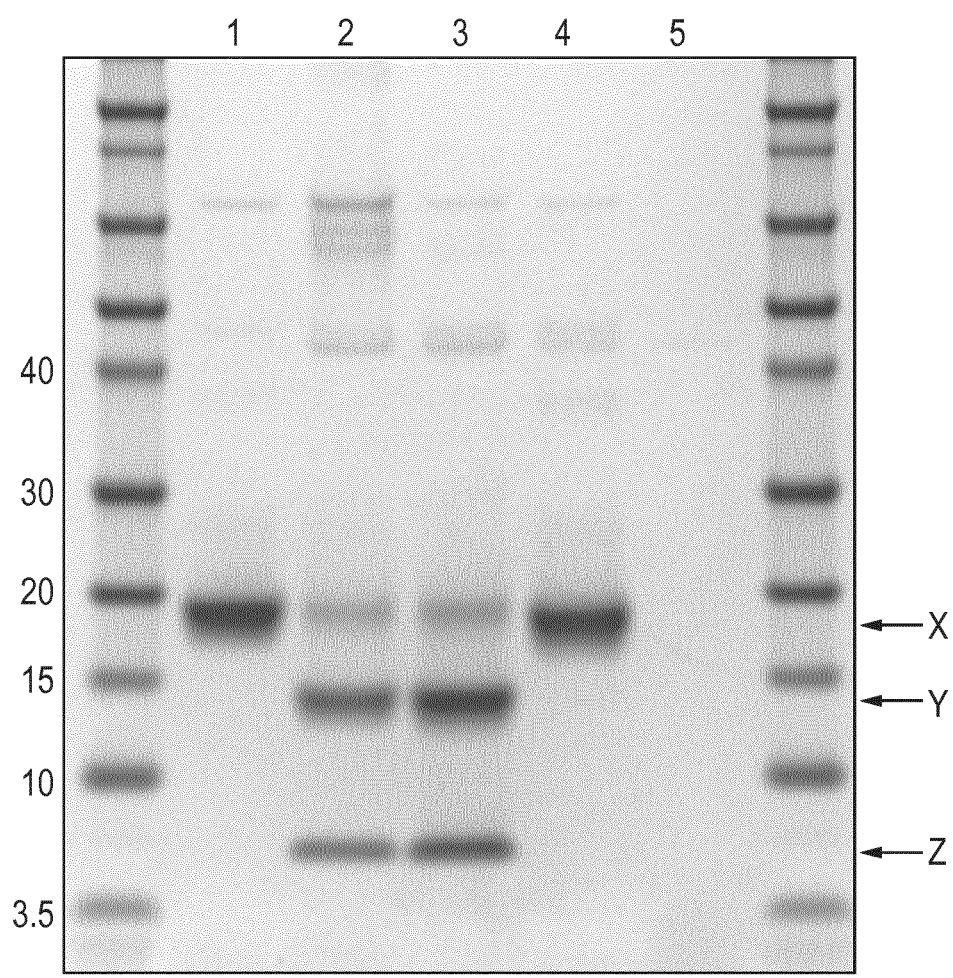

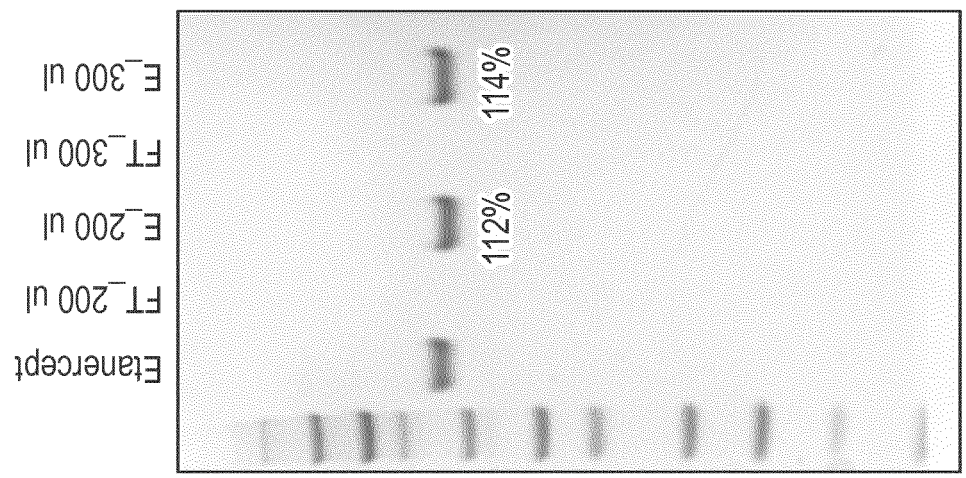
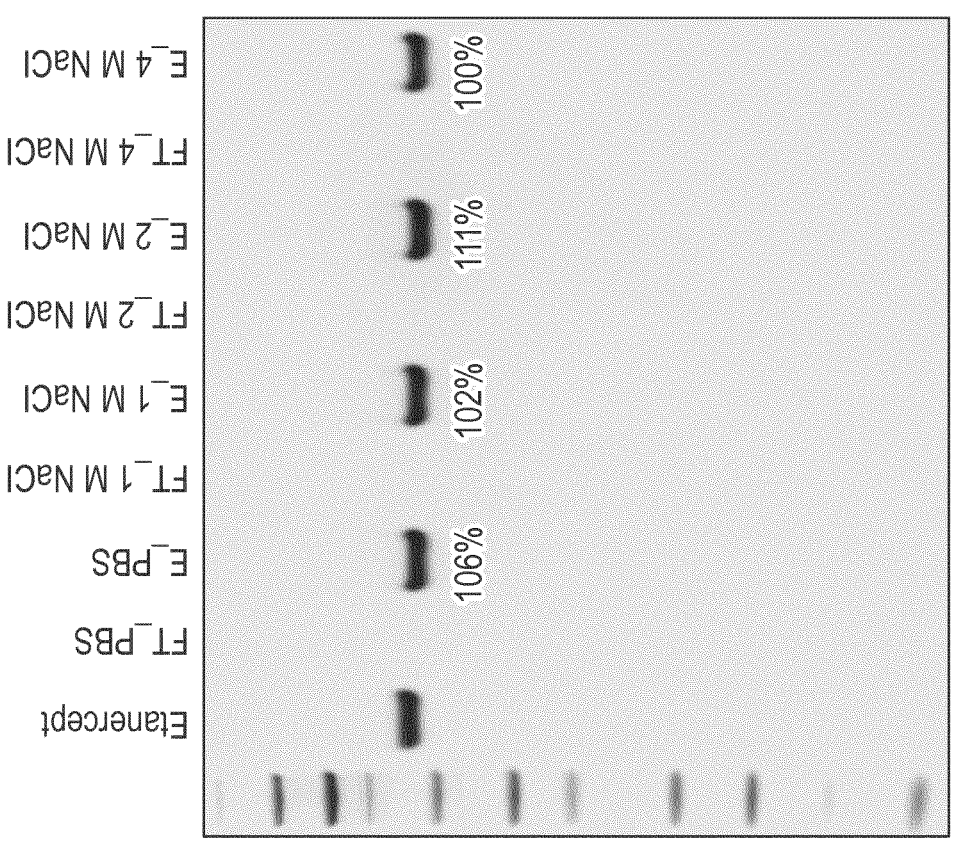

Fig. 16B.1

| 10 | 20 | 30 | 40 | 50 | 60 | 70 | 80 | 90 | 100 | 110 | 120 | 130 |
|---|---|---|---|---|---|---|---|---|---|---|---|---|
| LPAQVAFTPY | APEPGSTCRL | REYYDQTAQM | CCSKCSPGQH | AKVFCTKTSD | TVCDSCEDST | YTQLNWVPE | CLSCGSRCSS | DQVETQACTR | EQNRICTCRP | GWYCALSKQE | GCRLCAPLRK | CRPGFGVARP |

| 140 | 150 | 160 | 170 | 180 | 190 | 200 | 210 | 220 | 230 | 240 | 250 | 260 |
|---|---|---|---|---|---|---|---|---|---|---|---|---|
| GTETSDVVCK | PCAPGTFSNT | TSSTDICRPH | QICNVVAIPG | NASMDAVCTS | TSPTRSMAPG | AVHLPQPVST | RSQHTQPTPE | PSTAPSTSFL | LPMGPSPPAE | GSTGDEPKSC | DKTHTCPCP | APELLGGPSV |

| 270 | 280 | 290 | 300 | 310 | 320 | 330 | 340 | 350 | 360 | 370 | 380 | 390 |
|---|---|---|---|---|---|---|---|---|---|---|---|---|
| FLFPPKPKDT | LMISRTPEVT | CVVVDVSHED | PEVKFNWYVD | GVEVHNAKTK | PREEQYNSTY | RVVSVLTVLH | QDWLNGKEYK | CKVSNKALPA | PIEKTISKAK | GQPREPQVYT | LPPSREEMTK | NQVSLTCLVK |

| 400 | 410 | 420 | 430 | 440 | 450 | 460 | 470 |
|---|---|---|---|---|---|---|---|
| GFYPSDIAVE | WESNGQPENN | YKTTPPVLDS | DGSFFLYSKL | TVDKSRWQQG | NVFSCSVMHE | ALHNHYTQKS | LSLSPGK |

Fig. 16B.2

| | | | | | | | | | | | | |
|---|---|---|---|---|---|---|---|---|---|---|---|---|
| 10 | 20 | 30 | 40 | 50 | 60 | 70 | 80 | 90 | 100 | 110 | 120 | 130 |
| LPAQVAFTPY | APEPGSTCRL | REYDQTAQM | CCSKCSPGQH | AKVFCTKTSD | TVCDSCEDST | YTQLMWVPE | CLSCGSRCSS | DQVETQACTR | EQNRICTCRP | GWVCALSKQE | GCRLCAPLRK | CRPGFGVARP |

| | | | | | | | | | | | | |
|---|---|---|---|---|---|---|---|---|---|---|---|---|
| 140 | 150 | 160 | 170 | 180 | 190 | 200 | 210 | 220 | 230 | 240 | 250 | 260 |
| GTETSDVVCK | PCAPGTFSNT | TSSTDICRPH | QICNVVAIPG | NASMDAVCTS | TSPPRSMAPG | AVHLPQPVST | RSQHTQPTPE | PSTAPSTSFL | LPMGPSPPAE | GSTGDEPKSC | DKTHTCPPCP | APELLGGPSV |

| | | | | | | | | | | | | |
|---|---|---|---|---|---|---|---|---|---|---|---|---|
| 270 | 280 | 290 | 300 | 310 | 320 | 330 | 340 | 350 | 360 | 370 | 380 | 390 |
| FLFPPKPKDT | LMISRTPEVT | CVVVDVSHED | PEVKFNWYVD | GVEVHNAKTK | PREEQYNSTY | RVVSVLTVLH | QDWLNGKEYK | CKVSNKALPA | PIEKTISKAK | GQPREPQVYT | LPPSREEMTK | NQVSLTCLVK |

| | | | | | | | | |
|---|---|---|---|---|---|---|---|---|
| 400 | 410 | 420 | 430 | 440 | 450 | 460 | 470 | |
| GFYPSDIAVE | WESNGQPENN | YKTTPPVLDS | DGSFFLYSKL | TVDKSRWQQG | NVFSCSVMHE | ALHNHYTQKS | LSLSPGK | |

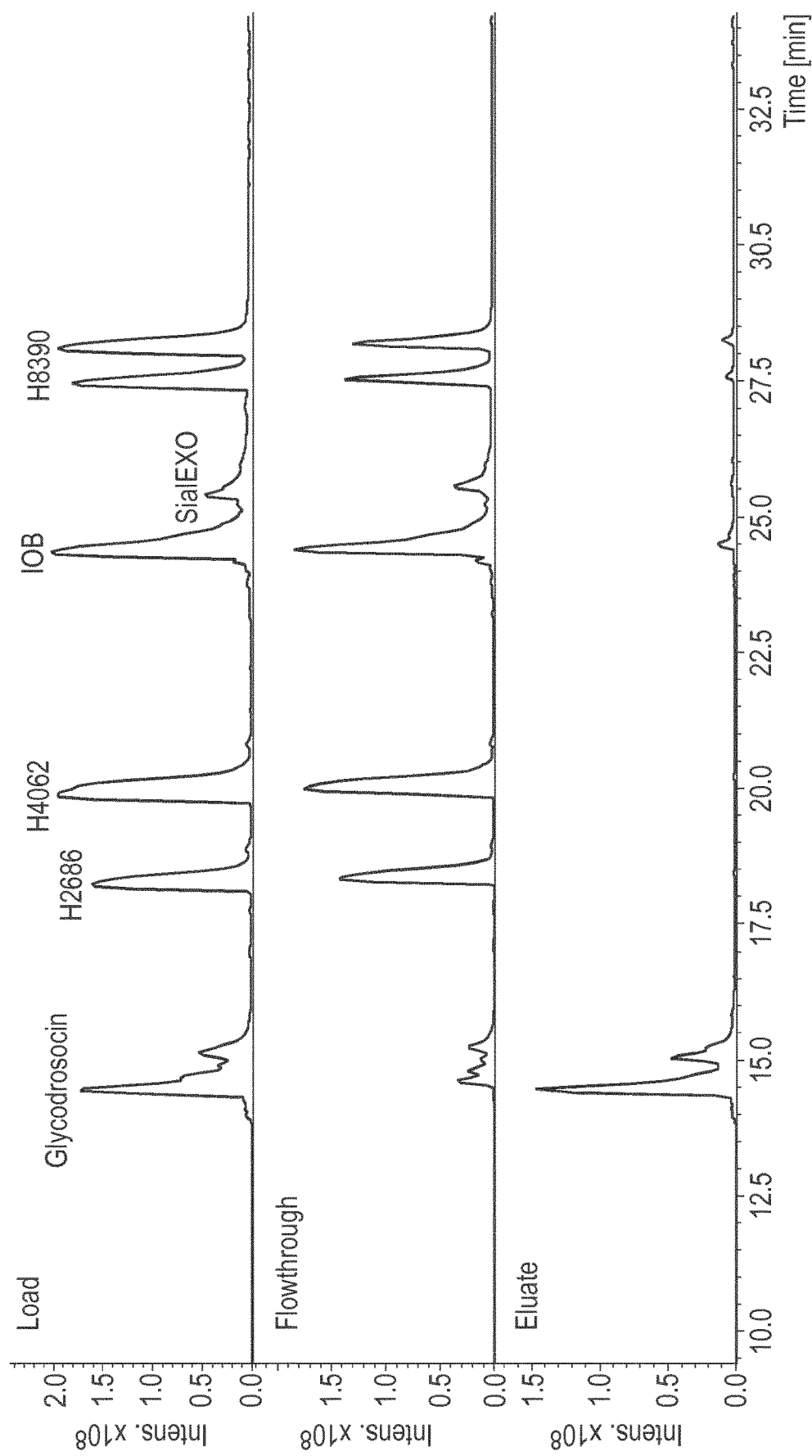

Fig. 19B

Reported O-glycosylation sites

```
Trypsin
        10         20         30         40         50         60         70         80
ASPTS PKVFP LSLCS TQPDG NVVIA CLVQG FFPQE PLSVT WSESG QGVTA RNFPP SQDAS GDLYT TSSQL TLPAT QCLAG
        90        100        110        120        130        140        150        160
KSVTC HVKHY TNPSQ DVTVP CPVPS TPPTP SPSTP PTPSP SCCHP RLSLH RPALE DLLLG SEANL TCTLT GLRDA SGVTF
       170        180        190        200        210        220        230        240
TWTPS SGKSA VQGPP ERDLC GCYSV SSVLP GCAEP WNHGK TFTCT AAYPE SKTPL TATLS KSGNT FRPEV HLLPP PSEEL
       250        260        270        280        290        300        310        320
ALNEL VTLTC LARGF SPKDV LVRWL QGSQE LPREK YLTWA SRQEP SQGTT TFAVT SILRV AAEDW KKGDT FSCMV GHEAL
       330        340        350        360        370        380        390        400
PLAFT QKTID RLAGK PTHVN VSVVM AEVDG TCY
```

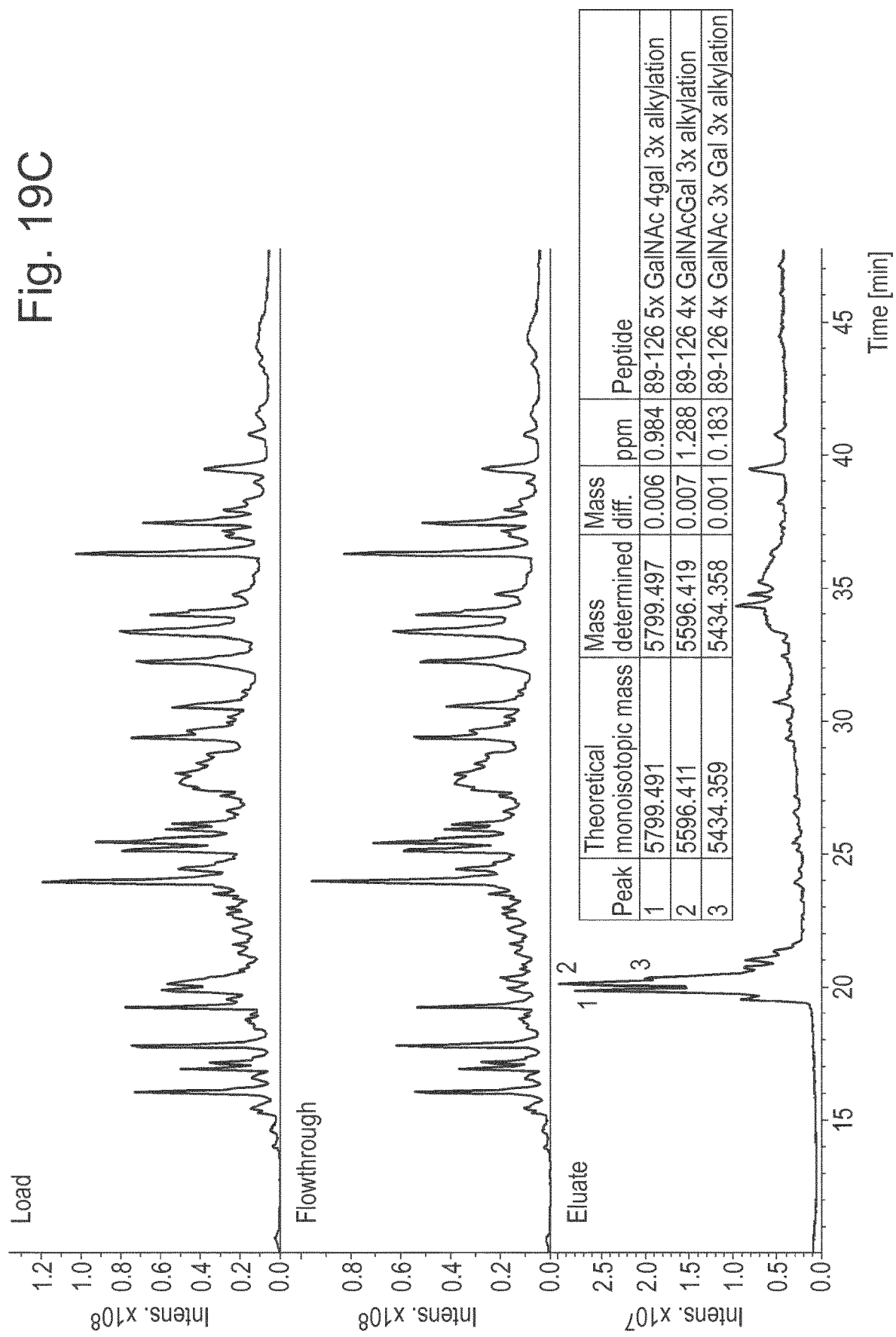

PROTEASE AND BINDING POLYPEPTIDE FOR O-GLYCOPROTEINS

FIELD OF THE INVENTION

The present invention relates to a novel endoprotease, mutants thereof having binding but lacking or having reduced hydrolyzing activity, and use in methods of studying and isolating O-linked glycoproteins.

INCORPORATION BY REFERENCE OF SEQUENCE LISTING PROVIDED AS A TEXT FILE

A Sequence Listing is provided herewith in a text file, "DYNG-003 SEQ LIST (rev January 2022)_ST25", created on Jan. 26, 2022 and having a size of 195,343 bytes. The contents of the text file are incorporated herein by reference in its entirety.

BACKGROUND OF THE INVENTION

Recently, the impact of glycosylation on biological functions has gathered increased attention, in particular in regards to O-linked glycans. However, while the interest for these important protein modifications have been renewed, the tools to efficiently study the glycans, and the glycoproteins, have been lacking.

Several exo- and endoglycosidases which are highly useful for both O-linked glycan removal from native proteins and for glycan sequencing have been developed. Both of these approaches can be used individually to reduce the heterogeneity of glycoproteins, thus facilitating the analysis of the protein and its fragmented peptides in mass spectrometry. A more efficient analysis of the biological effect of the glycans by downstream analysis of the functions affected by the hydrolysis can also be carried out. However, such tools are not efficient, for example, for facilitating the identification of O-linked glycoproteins, determination of the site of glycosylation and purification of O-linked glycopeptides.

The first O-glycoprotein-specific endoprotease, binding to O-glycans and mainly hydrolyzing R—N-bonds close to the glycan, was reported in 1991/1992 (Abdullah et al., J Bacteriol 173, 5597-5603 (1991); Abdullah et al., Infect Immun 60, 56-62 (1992). However, this enzyme is of limited usefulness for medicine and biotechnology because it is specific only for O-glycans comprising sialic acids (most but far from all O-linked glycans) and has specific amino acid demands, resulting in low levels of hydrolysis in general. There is a need for better tools for studying O-linked glycoproteins.

SUMMARY OF THE INVENTION

The present inventors have identified, purified and characterised a novel polypeptide from *Akkermansia muciniphila*, referred to herein as LS. This polypeptide acts as an endoprotease, specifically cleaving/hydrolysing amino acid bonds N terminal to and in proximity of an O-linked glycan, without showing any specificity or limitation to a particular amino acid sequence.

The inventors have also modified the sequence of LS and have identified mutants that are able to bind to O-linked glycans but lack or have a reduced ability to hydrolyze the glycoproteins. These mutants can be used for selective removal, enrichment or purification of free O-glycans, O-glycopeptides and/or O-glycoproteins.

Accordingly, in a first aspect of the invention, there is provided a polypeptide having endoprotease activity specific for O-glycosylated proteins which comprises:
(a) an amino acid sequence of SEQ ID NO: 1;
(b) an amino acid sequence which is at least 85% identical to the amino acid sequence of SEQ ID NO: 1 or
(c) an amino acid sequence which is a fragment of the sequence of SEQ ID NO: 1 or a fragment of an amino acid sequence which is 85% identical to the amino acid sequence of SEQ ID NO: 1.

The invention also provides a method of hydrolysing an O-glycoprotein, wherein the method comprises contacting a sample comprising the protein with a polypeptide of the invention and optionally further comprising the detection or analysis of the hydrolysis products.

Additionally there is provided a method for assessing the glycosylation status of a protein, comprising contacting a sample comprising the protein with a polypeptide of the invention and detecting and/or analysing the products produced, optionally wherein the presence or absence of cleavage products is used to determine the presence or absence of an O-glycoprotein in the sample, and/or wherein said analysis is conducted to identify the type of a O-glycan chain and/or its position of attachment to an O-glycoprotein.

In a second aspect of the invention, there is provided a polypeptide which is capable of binding to an O-glycan, O-glycopeptide and/or O-glycoprotein and which lacks or has reduced endoprotease activity specific for O-glycosylated proteins comprising:
(a) an amino acid sequence of SEQ ID NO: 5;
(b) an amino acid sequence which is at least 85% identical to the amino acid sequence of SEQ ID NO: 5 or SEQ ID NO: 20; or
(c) an amino acid sequence which is a fragment of the sequence of SEQ ID NO: 5 or SEQ ID NO: 20, or a fragment of an amino acid sequence which is 85% identical to the amino acid sequence of SEQ ID NO: 5 or SEQ ID NO: 20.

The invention also provides a method of binding to an O-glycan, O-glycopeptide and/or O-glycoprotein, wherein the method comprises contacting a sample comprising the O-glycan, O-glycopeptide and/or O-glycoprotein with a polypeptide of the invention, and optionally determining whether or not an O-glycan, O-glycopeptide or O-glycoprotein has been bound and/or separating the O-glycan and any linked glycoprotein, the O-glycopeptide or the O-glycoprotein from the resulting mixture.

Additionally there is provided a method for assessing the glycosylation status of a protein, comprising contacting a sample comprising the protein with a polypeptide of the invention and determining whether or not the protein is bound by the said polypeptide.

There is also provided a method for detecting O-glycopeptides and/or O-glycoproteins in a sample, wherein the method comprises:
(a) contacting said sample with a polypeptide of the invention to thereby allow formation of a complex between the polypeptide of the invention and the O-linked glycopeptide and/or O-glycoprotein (an O-linked glycopeptide/protein-polypeptide complex);
(b) optionally separating said polypeptide from the contacted sample; and
(c) determining whether the separated polypeptide is bound to an O-linked glycopeptide or glycoprotein, thereby determining the presence or absence of O-linked glycopeptides or glycoproteins in the sample.

(a)+ vector. After transformation into BL21(DE3) Star, four individual clones were expressed and purified on His GravityFlow columns to homogeneity. Based on total quantity of protein in the purified samples, as well as purity based on SDS-PAGE, all four investigated clones expressed equally well.

Figure 2:
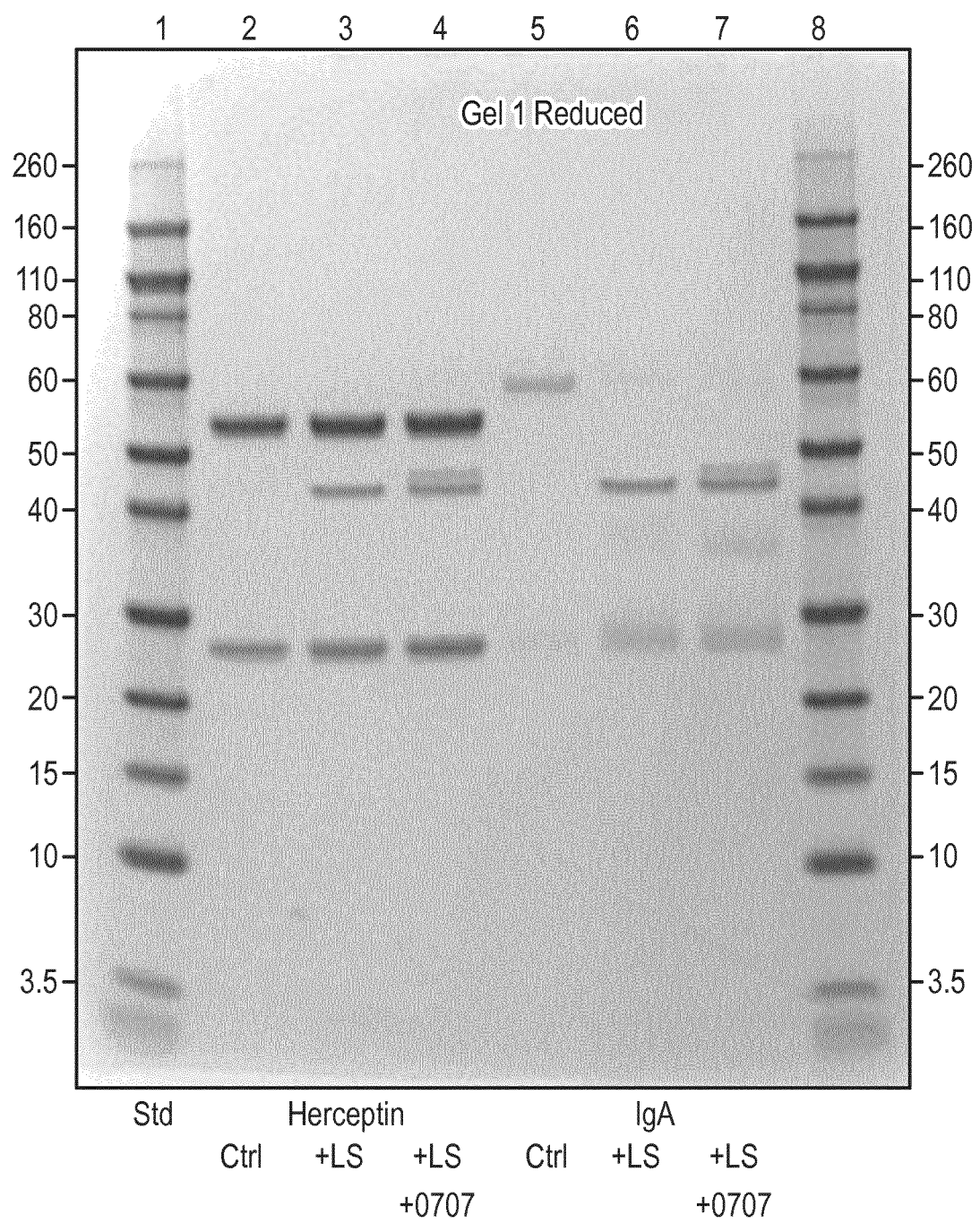

FIG. 2: LS specifically acts upon proteins containing O-glycans—figure shows the products analysed by SDS-PAGE. Incubation of LS with IgG or IgA resulted in a specific degradation of IgA, but no visible activity against IgG (Herceptin/trastuzumab). All incubations took place o/n at 37° C. in PBS. Addition of sialidase (Am0707) was not necessary for the activity of LS during these conditions.

FIG. 3: Optimal enzymatic conditions. LS is active in a broad pH range (A), tolerates NaCl well (B), but is highly sensitive against EDTA (C, D), and is partly inhibited by Zn2+ (D). All experiments (except pH assay) were conducted in PBS o/n, at 37° C. For pH optimum determination, the enzyme was incubated in 20 mM Tris-HCl (pH 6.8-8.8) or 50 mM acetic acid (pH 5.6).

FIG. 4: Activity of LS is regulated by glycan composition. (A) Sequential removal of specific glycans before hydrolysis with LS for 30 minutes resulted in very low activity in a sialylated protein, high activity in an asialylated protein, and no activity in a sample with removed galactoses. (S) sialidase, (SG) sialidase and galactosidase, (LS) LS. (B) Prolonged incubation (o/n) of fully glycosylated (Enbrel) or sialidase treated (Enbrel(S)) glycoproteins resulted in full hydrolysis in both samples Enbrel may also be referred to herein as etanercept. (C) The TNFα binding part of etanercept (TNFαR) was pretreated with sialidase ("sialidase"), O-glycosidase/sialidase ("O-glyc"), or with PNGaseF ("N-glyc"), to remove sialic acids, O-glycans, and N-glycans, respectively. LS was added to the samples, and incubation was allowed to continue o/n before analysis. LS had activity in all samples except those treated with O-glycosidase.

FIG. 5: Search results showing that LS hydrolyses the glycoprotein N-terminal of O-glycans. Etanercept hydrolyzed to fragments with LS, and subsequently deglycosylated with O-glycosidase treatment were subjected to mass spec analysis (liquid chromatography mass spectrometry (LC/MS) and tandem mass spectrometry (MS/MS)). Identified peptides (white and hatched boxes) were fitted to the sequence of Etanercept based on m/z values and MS/MS data, with y' and b' ions marked as small grey boxes. All white and hatched boxes (e.g. peptides) start directly at a T or an S, where O-glycans have been attached. The preceding amino acid varies (P, S, H, T, G), and seems likely to not influence the hydrolysis. (A) Analysis using a biased approach, specifically searching for peptides generated with an S/T-peptidase (SEQ ID NO: 51). (B) Analysis using an unbiased approach (SEQ ID NO: 51).

FIG. 6: Inactivated LS specifically binds to O-linked glycoproteins. The metalloprotease active site was mutated to remove the catalytic capacity while not affecting substrate affinity or interaction. Specifically this was done by exchanging an E to an A, thus creating clone "$LS_{mut}$" (also referred to as $LS_{E206A}$). (A) While LS was able to hydrolyze Enbrel in the presence of sialidase, the inactivated Lsmut could not hydrolyze Enbrel under the conditions tested. Loss of activity was verified on SDS-PAGE. (B) Despite having lost hydrolytic activity, $LS_{mut}$ was still able to bind to O-glycoprotein. Specific binding was verified on spin columns with immobilized $LS_{E206A}$, demonstrating a specific affinity for O-linked glycoproteins. By immobilizing LSmut on sepharose we were able to affinity purify IgA. Herceptin (Trastuzumab), lacking O-glycans, as well as O-glycosidase treated IgA, did not bind to the column, but could be detected in the flowthrough (FT). Neur=Neuraminidase/Sialidase 0707.

FIG. 7: α2-3 bonded sialic acids limit the efficiency of LS. Concurrent incubation of LS with a set of diverse sialidases for 30 min-20 h, using Enbrel as a glycoprotein substrate, revealed the higher efficiency in the presence of the α2-3 specific sialidase 1757, or with the Mix (0707+1757), while the broad spectrum sialidase 0707 was not necessary for seemingly full activity of LS, thus suggesting that α2-6 (and α2-8) bonds are not a concern for LS activity.

Figure 8:
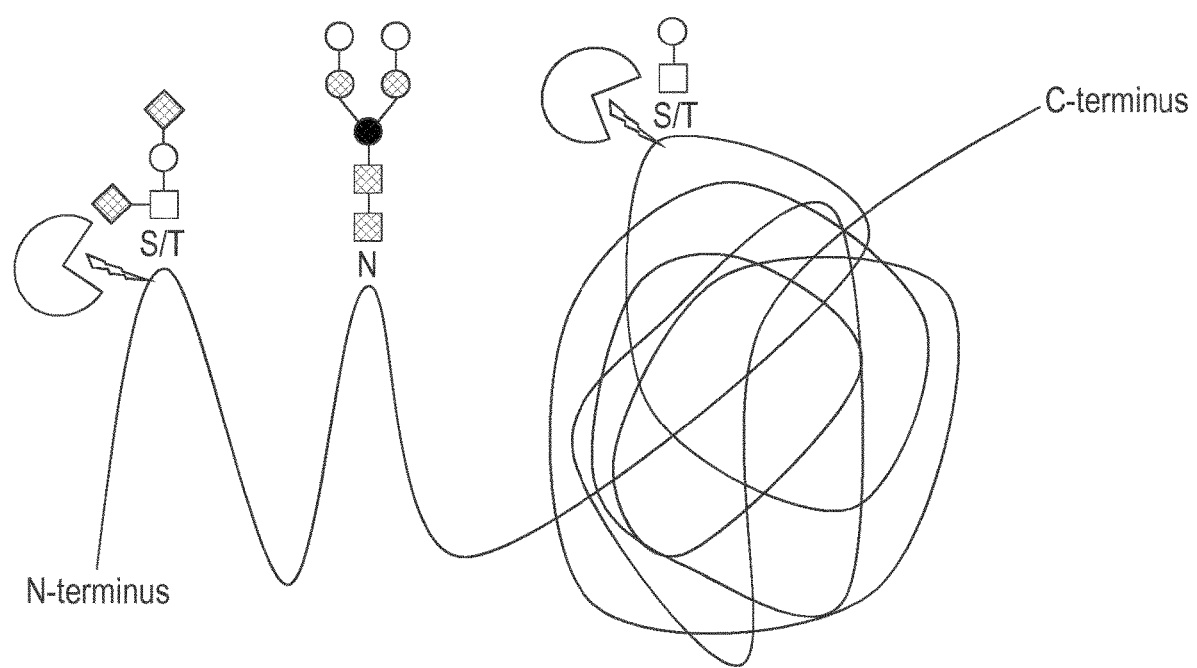

FIG. 8: Schematic presentation of LS activity. LS preferentially binds terminal galactoses attached to O-linked GalNAc, resulting in an N-terminal hydrolysis of the serine or threonine upon which the glycan is attached. Presence of sialic acids will reduce the efficiency of LS, but not inhibit it. No activity can be seen upon N-linked glycans.

Figure 9B:
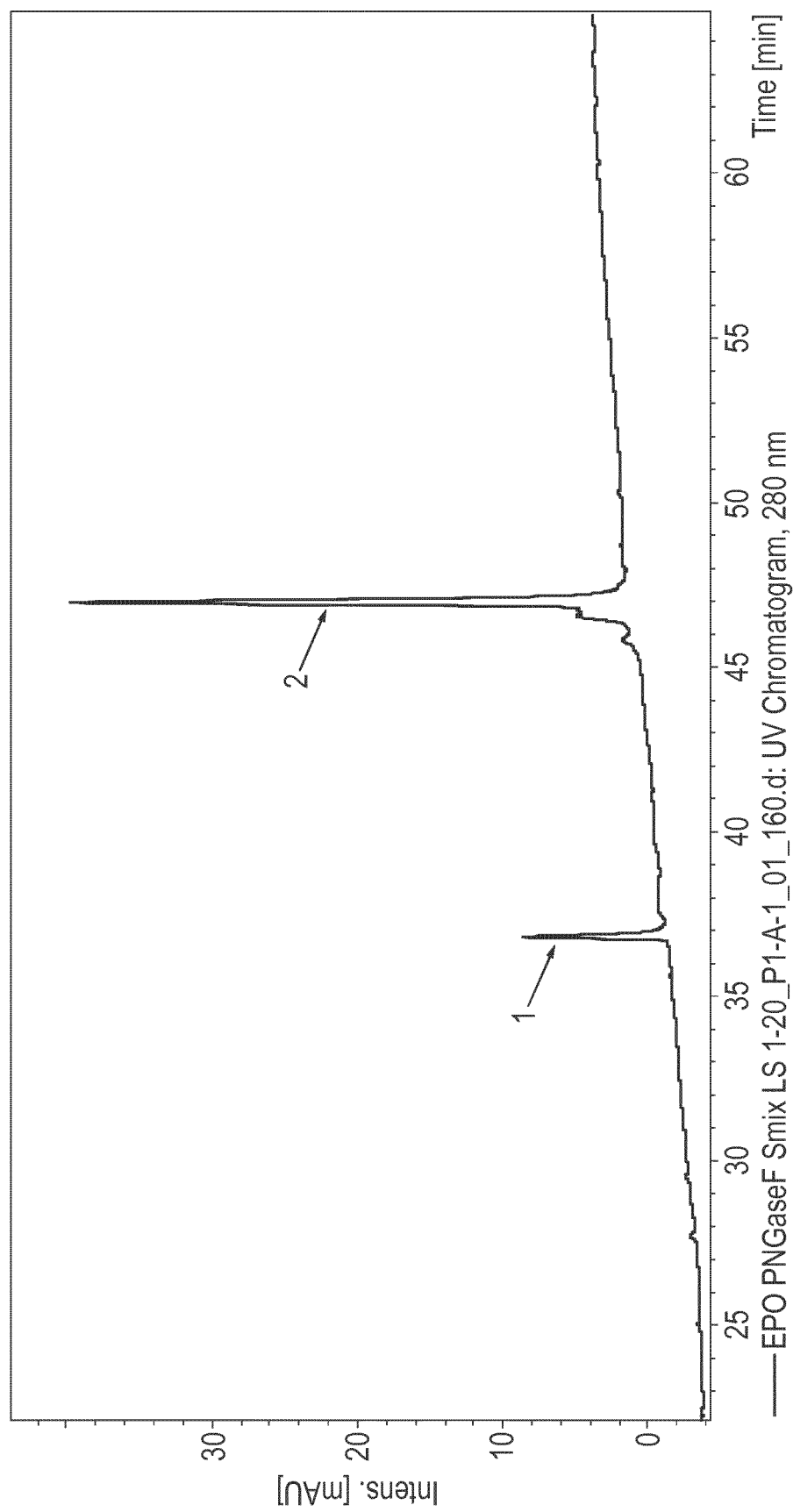
Figure 9C:
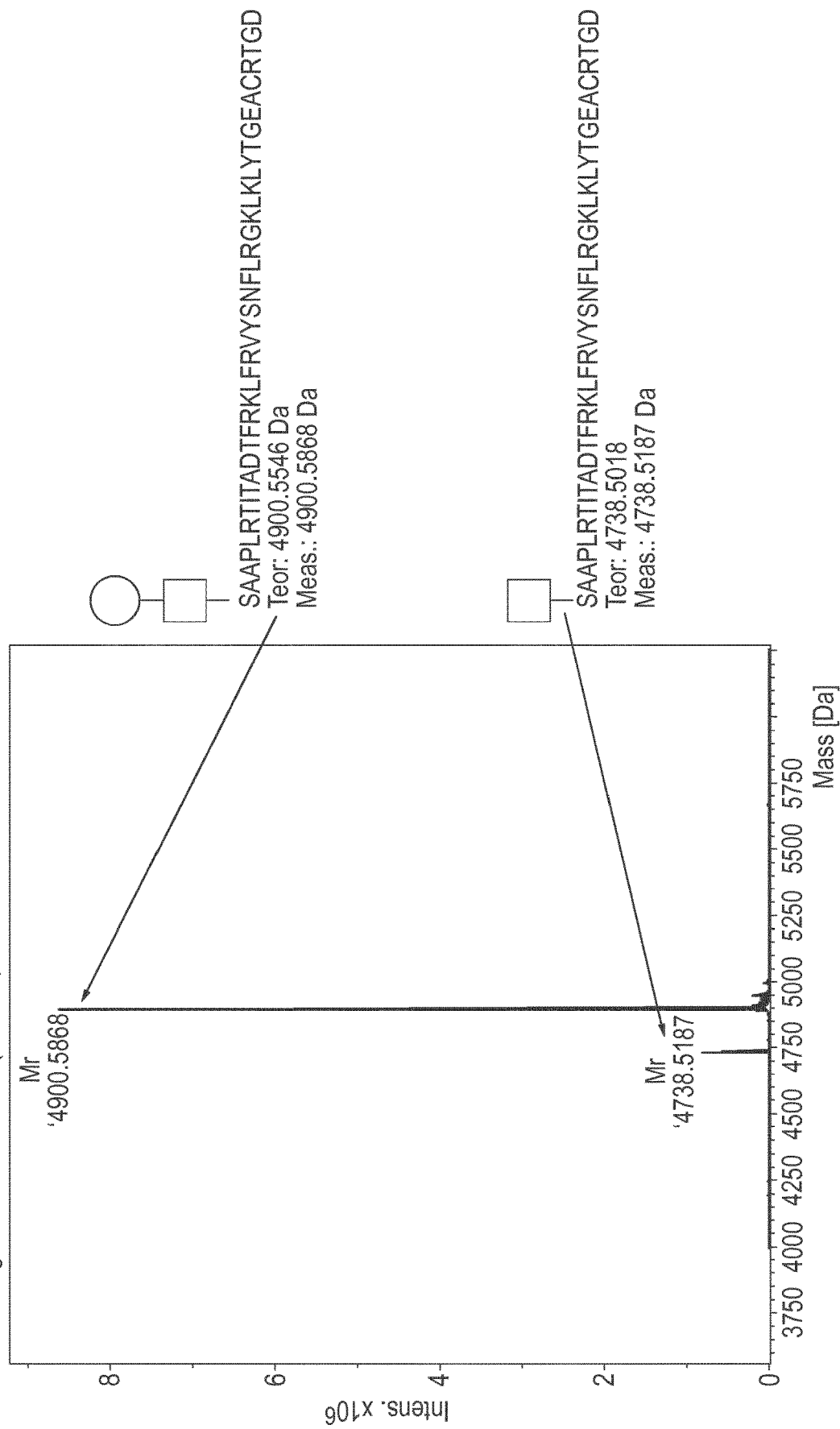
Figure 9D:
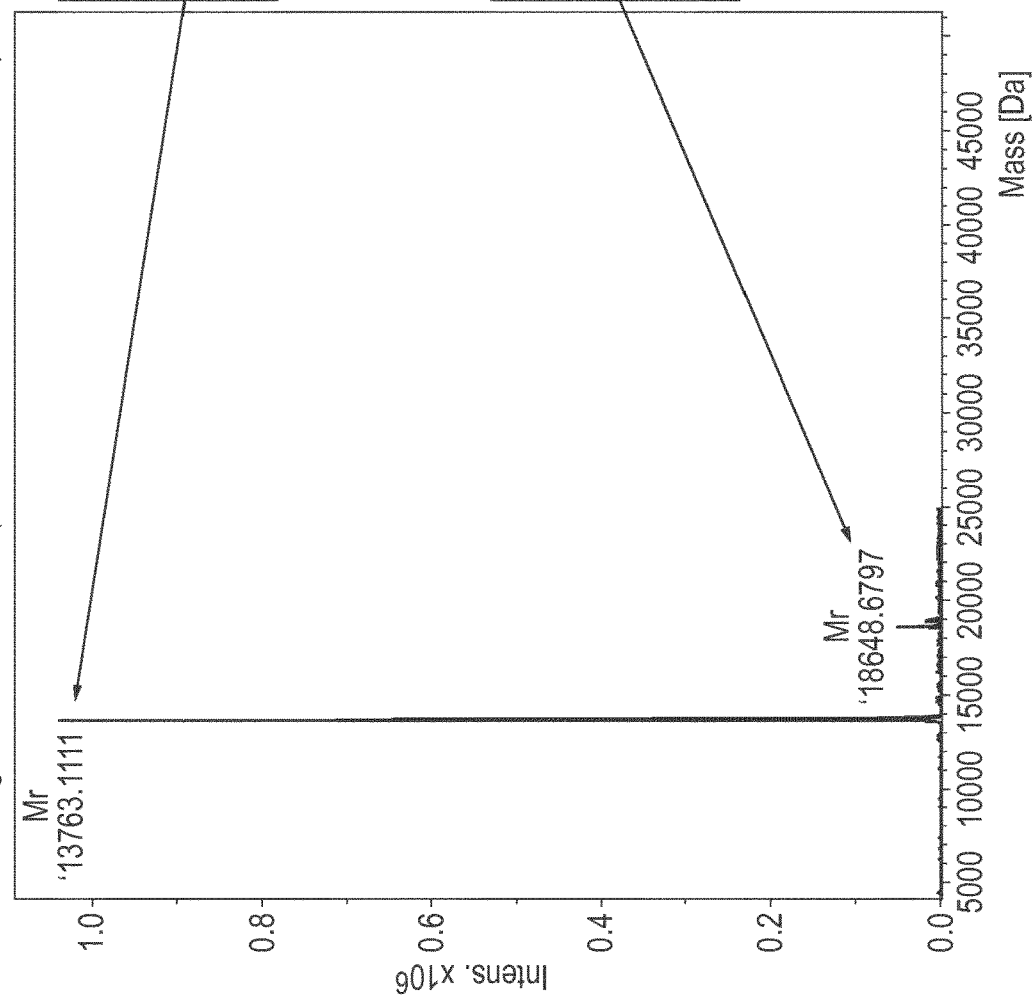

FIG. 9: Results of an experiment in which erythropoietin is cleaved with different combinations of LS, PNGaseF to remove N-glycans, Sialidases to remove sialic acid, and with an O-glycosidase to remove O-glycans. Reaction products were analysed by SDS-PAGE, RPLC and ESI mass spectrometry (A) Results of SDS-PAGE analysis: Lane 1=EPO treated with PNGaseF and sialidase; Lane 2=EPO treated with PNGaseF and sialidase+LS; Lane 3=EPO treated with PNGaseF+LS; Lane 4=EPO treated with PNGaseF, sialidase, O-glycosidase before LS; Lane 5=enzyme control. Band X=uncleaved EPO; Band Y=N terminal fragment of EPO digested by LS; Band Z=C terminal fragment of EPO digested by LS. Lanes 2 and 3 show that LS cleaves EPO where the sialic acids have been removed as well as where they are intact. Lanes 2-3 show that LS also cleaves EPO where N-glycans have been removed with PNGaseF. Lane 4 shows that LS does not cleave EPO where the O-glycans have been removed. (B) UV chromatogram shows results of RPLC separation for EPO treated with PNGaseF and sialidase+LS. Two major peaks were identified as shown. Peak 1 is the C terminal fragment of EPO digested by LS; Peak 2 is the N terminal fragment of EPO digested by LS; (C,D) show results of mass spectrometry analysis. Fig C shows masses of the C terminal fragment of EPO (from top to bottom SEQ ID NOs: 52 and 53) with O-glycan still attached to the (now N terminal) serine (Square=GlcNAc, Circle=Galactose). Differences in mass are due to differences in degradation of the O-glycan (loss of a terminal Galactose) in some parts of the sample, likely caused by the ionisation energy in the MS instrument; Fig D shows the N terminal fragment of EPO lacking glycan (SEQ ID NO: 54), plus undigested EPO with glycan still attached (SEQ ID NO: 55).

Figure 10B:
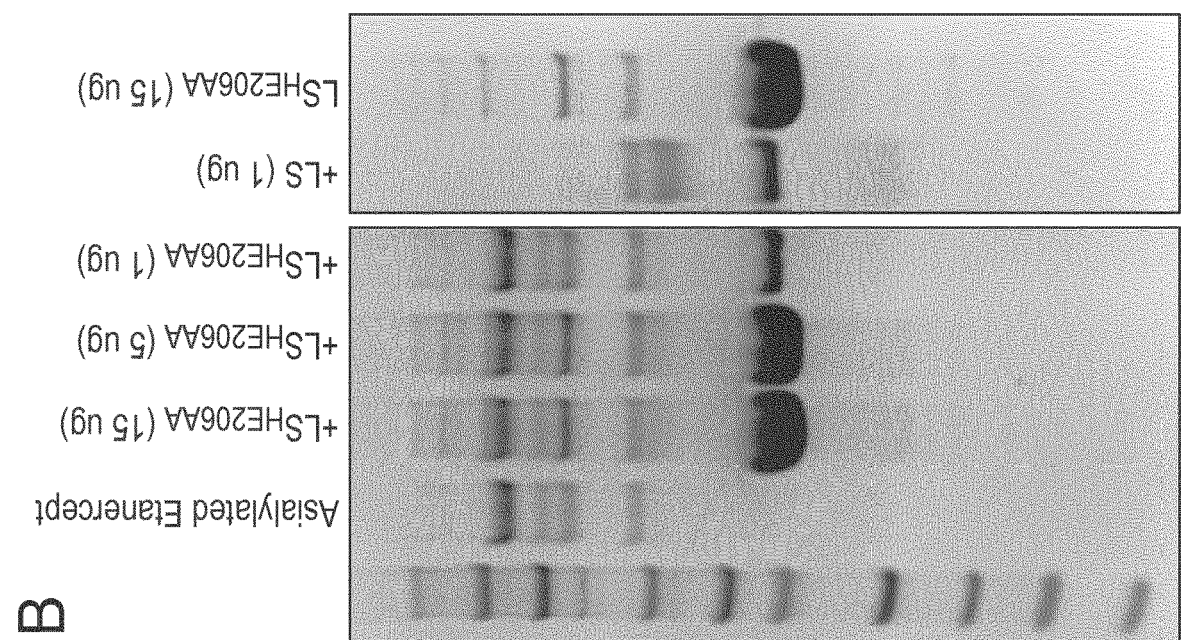

FIG. 10: Results of experiments which show that $LS_{E206A}$ retains some activity whereas $LS_{H205A/E206A}$ (may also be referred to as $LS_{HE206AA}$) is completely inactive. The activity of the LS mutants $LS_{E206A}$ (A) and $LS_{H205A/E206A}$ (B) was evaluated against asialylated O-glycosylated substrates including the TNFα binding part of etanercept (TNFaR2; may also be referred to herein as TNFaR) and etanercept itself (Etanercept), as compared to the wild type LS enzyme. Different concentrations of the LS mutants were added to 1 μg substrate (1:1-15:1, enzyme:substrate), incubating in PBS at 37° C. overnight before analysis on SDS-PAGE.

A) Lane 1: Asialylated substrate only; Lane 2: LS only, lane 3: 0.5 μg $LS_{E206A}$, lane 4: 5 μg $LS_{E206A}$, lane 5: TNFaR2+LS (1:1 ratio), lane 6: TNFaR2+$LS_{E206A}$ (1:1 ratio).

Figure 11A:
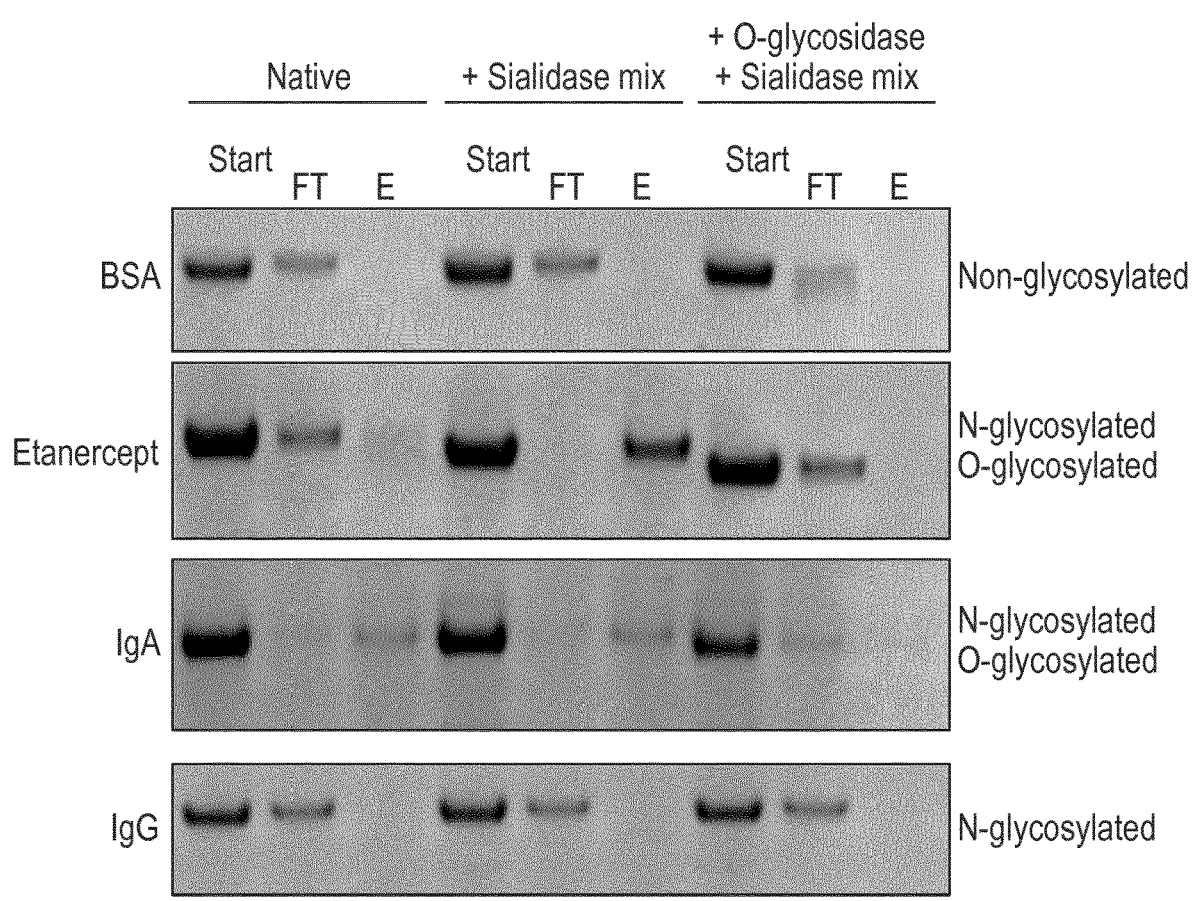
Figure 11B:
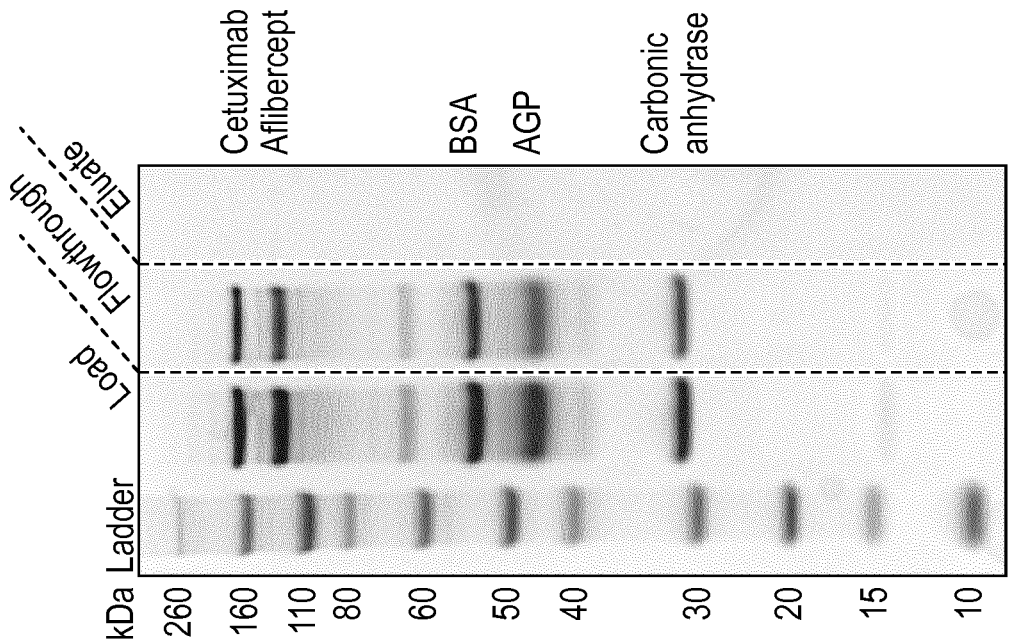
Figure 11C:
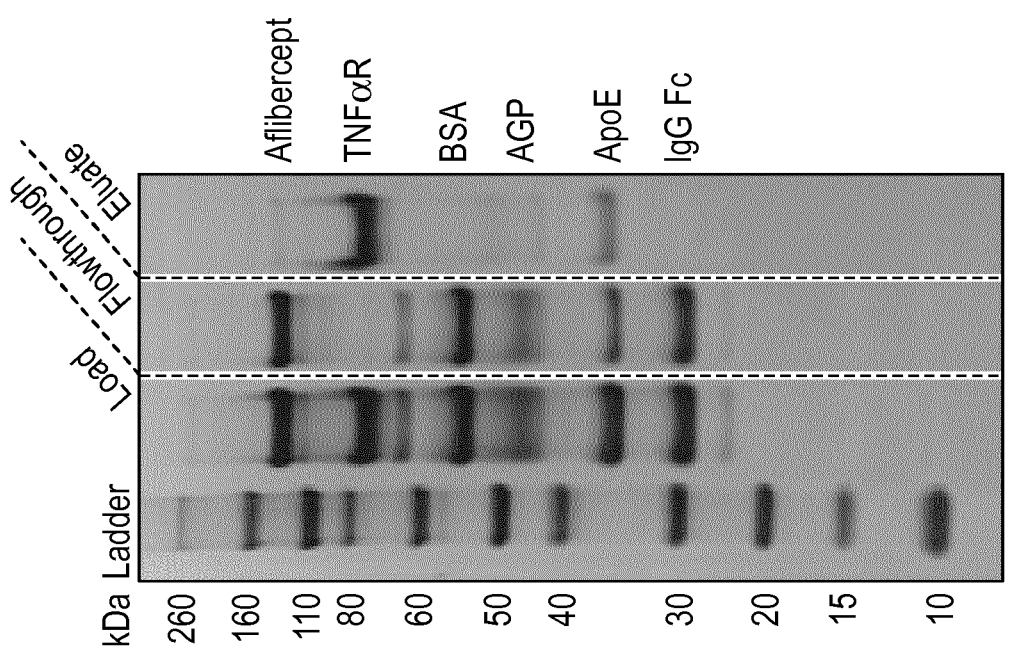

B) Lane 1: Asialylated substrate only; Lane 2: $LS_{H205A/E206A}$+Etanercept (15:1 ratio), lane 3:

LS$_{H205A/E206A}$+Etanercept (5:1 ratio), lane 4: LS$_{H205A/E206A}$+Etanercept (1:1 ratio), lane 5: LS+Etanercept (1:1 ratio), lane 6: LS$_{H205A/E206A}$ FIG. 11: Results of experiments which show that LS$_{H205A/E206A}$ immobilised on resin specifically binds to O-glycan containing proteins. Figures show SDS-PAGE analyses for starting/loading material, flowthrough (FT) and Eluate (E) in each case (A) Samples included BSA (bovine serum albumin), Etanercept, IgA, and IgG, native or pretreated with Sialidase mixtures+/−O-glycosidase as shown. (B) Sample included a mix of O-glycosylated proteins (TNFαR and ApoE), N-glycosylated proteins (aflibercept, AGP (alpha-1-acid glycoprotein), IgG Fc (Fc domain of IgG) and non-glycosylated proteins (BSA), pre-treated with Sialidase mixture. (C) Sample included a mix of N-glycosylated proteins (cetuximab, aflibercept, AGP) and non-glycosylated proteins (BSA, carbonic anhydrase), pre-treated with Sialidase mixture.

FIG. 12: Results of experiment showing that immobilised LS$_{H205A/E206A}$ has a concentration dependent capacity for binding of O-glycoproteins. Asialylated Etanercept (50-250 µg; in 100 µl PBS) was added to 50 µl PBS-equilibrated LS$_{H205A/E206A}$ resin with different immobilization conditions of LS$_{H205A/E206A}$ (5-15 mg/mL). Proteins were allowed to bind to the resin for 2 hours at room temperature with end-over-end rotation. The resin was washed three times with PBS (350 µl) and then eluted with the addition of 8 M Urea (50 µl, 5 min incubation; 2 repeats). To study the effect of urea and guanidine hydrochloride (GHCl) in the binding, it was included in the binding buffer together with 50 µg asialylated Etanercept, but otherwise handled identically. (A) All samples were separated on SDS-PAGE, and band intensities determined through densitometry using GelDoc EZ and the software ImageLab. Stated percentages indicate the band intensity as compared to the control. (B) Protein binding capacity, as determined by the band intensity, was plotted versus the amount of immobilized LS$_{H205A/E206A}$.

Figure 13:
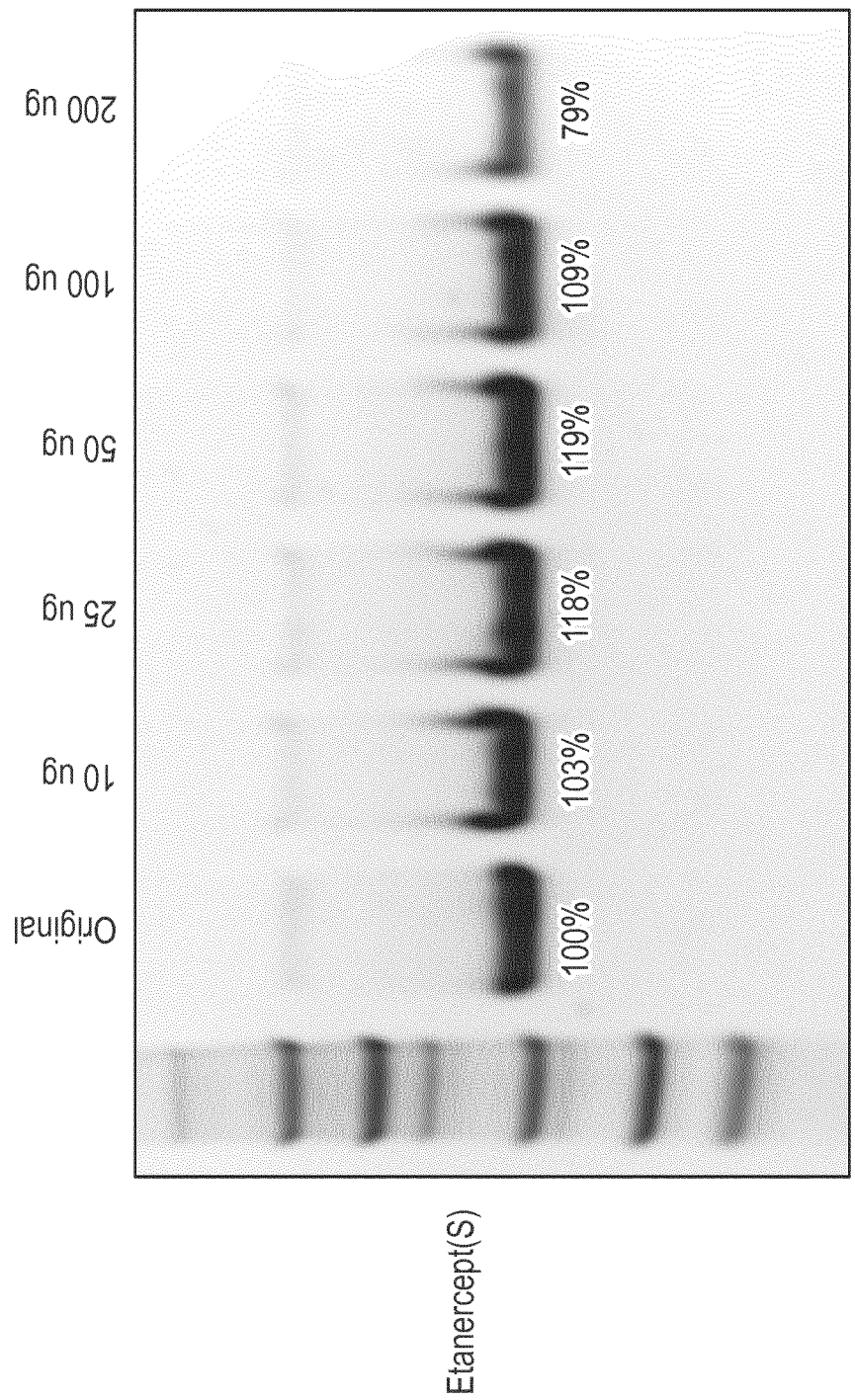

FIG. 13: Results of experiment showing that LS$_{H205A/E206A}$ can affinity purify around 3 mg of etanercept/mL of resin. Asialylated etanercept (10-200 µg; 100 µl in PBS) was added to 50 µl PBS-equilibrated LS$_{H205A/E206A}$ resin. Proteins were allowed to bind to the resin for 2 hours at room temperature with end-over-end rotation. The resin was washed three times with PBS (350 µl) and then eluted with the addition of 8 M Urea (50 µl, 5 min incubation; 2 repeats). All samples were separated on SDS-PAGE, and band intensities determined through densitometry using GelDoc EZ and the software ImageLab. Stated percentages indicate the band intensity as compared to the control.

Figure 14C:
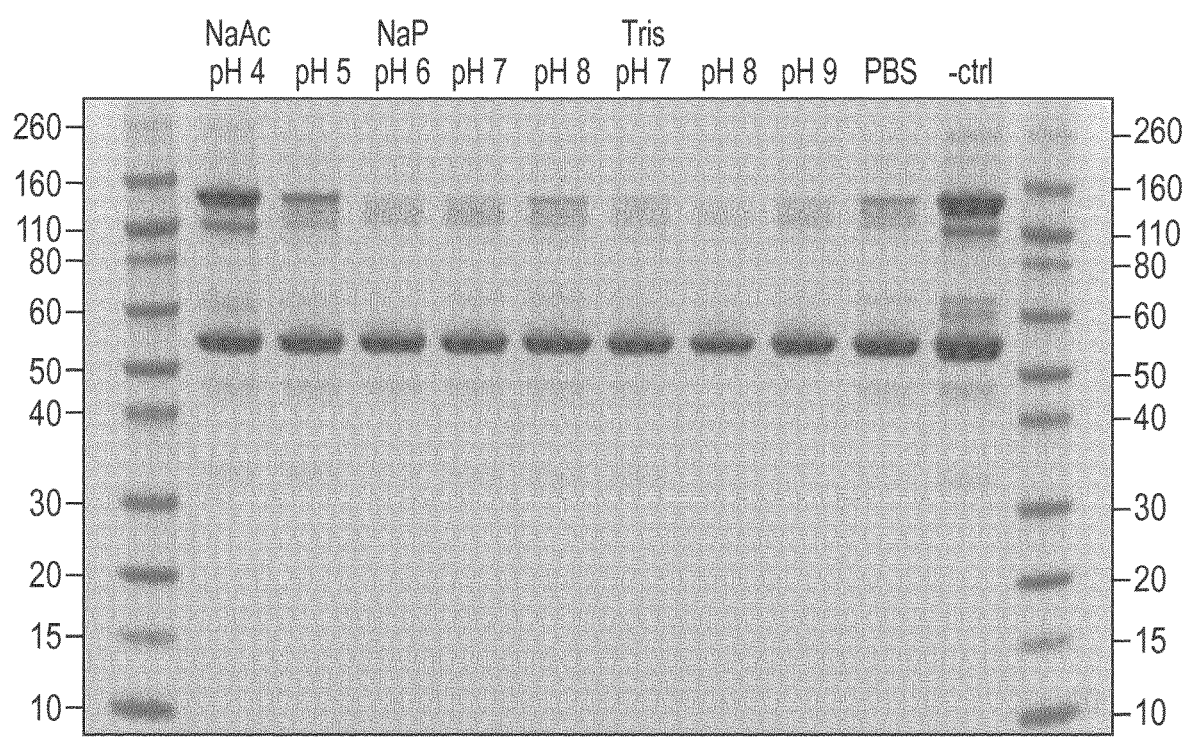
Figure 14D:
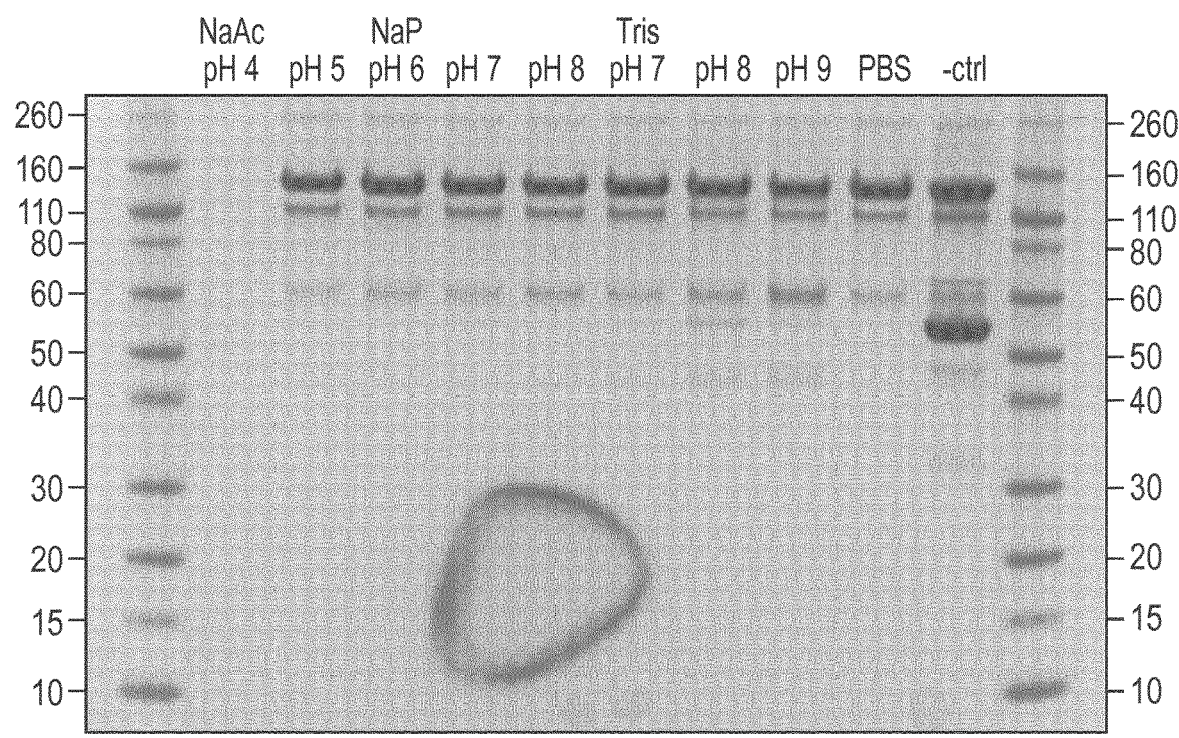

FIG. 14: Results of experiment showing that LS$_{H205A/E206A}$-substrate interaction is insensitive to high ionic strengths and differences in buffer volume/type, and works over a broad pH range. (A) Asialylated etanercept, 50 µg; 100 µl in PBS with added NaCl at concentrations as shown (B) Asialylated etanercept, 50 µg; 100-300 µl in PBS as shown; (C) Flow through from samples of asialylated etanercept (50 µg) and BSA (50 µg) in different buffers at different pHs as shown; (D) Eluates from the samples of C.

FIG. 15: Results of experiment showing that denaturation or addition of detergents elutes O-glycoproteins bound to LS$_{H205A/E206A}$. Asialylated Etanercept (50 µg; 100 µl in PBS) was added to 50 µl PBS-equilibrated LS$_{H205A/E206A}$ resin. Proteins were allowed to bind to the resin for 2 hours at room temperature with end-over-end rotation. The resin was washed three times with PBS (350 µl) and then eluted with the addition of (A) 1-8 M Urea or (B) 1.25-10% SDS (50 µl, 5 min incubation; 2 repeats). All samples were separated on SDS-PAGE for analysis.

Figure 16A:
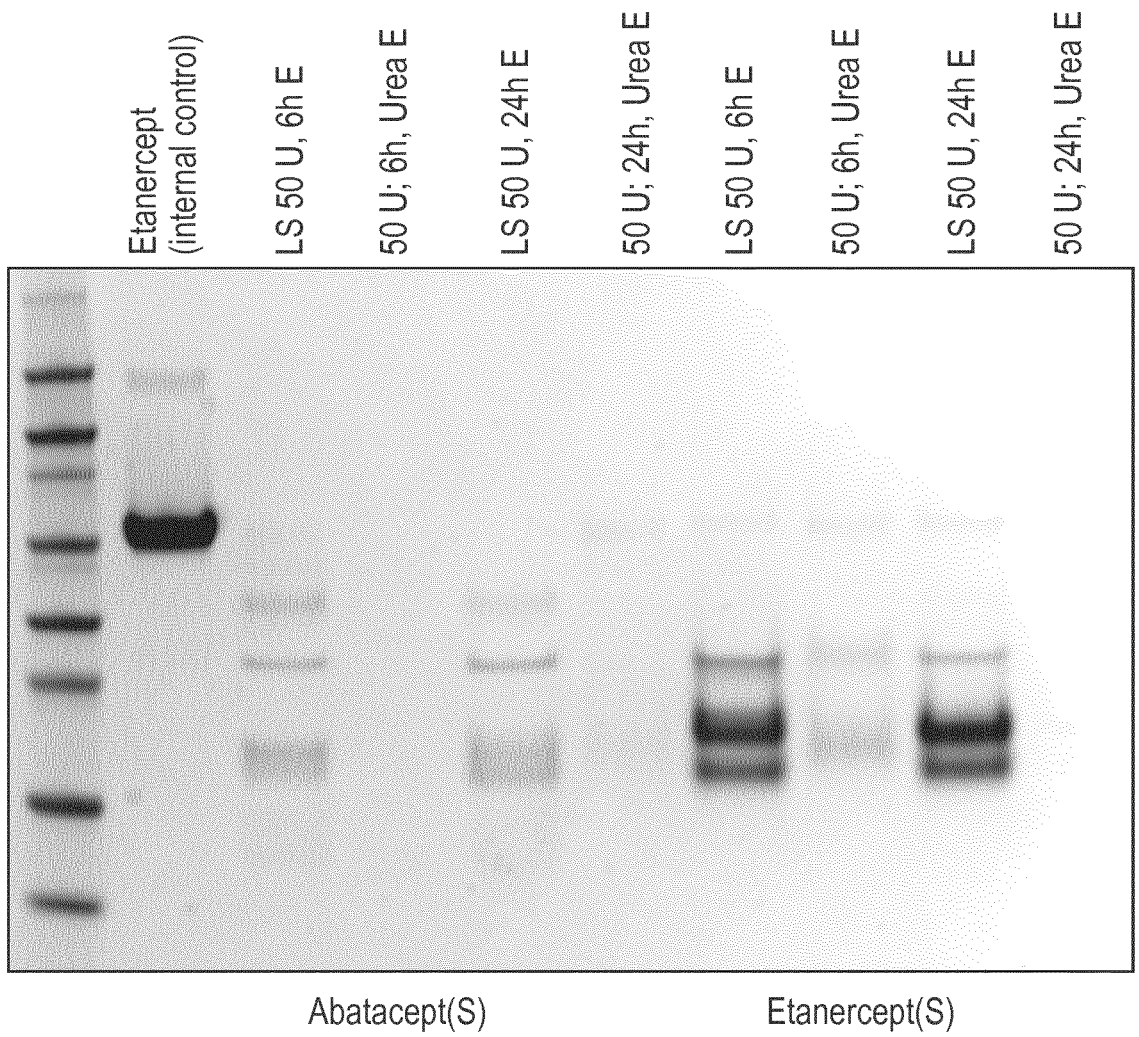

FIG. 16A: Results of experiment showing enzymatic elution of LS$_{H205A/E206A}$-bound O-glycoproteins using LS. Asialylated Abatacept (10 µg, 100 µl in PBS) and Etanercept (50 µg; 100 µl in PBS) were added to 50 µl PBS-equilibrated LS$_{H205A/E206A}$ resin. Proteins were allowed to bind to the resin for 2 hours at room temperature with end-over-end rotation. The resin was washed three times with binding buffers (350 µl) before addition of 50 Units LS in a total volume of 100 µl PBS. The samples were incubated for an additional 6-24 hours at 37° C. with shaking (450 rpm). LS released O-glycoproteins/glycopeptides were collected through centrifugation (1000 g, 1 min) before the column was finally eluted with the addition of 8 M Urea (50 µl, 5 min incubation; 2 repeats). All samples were separated on SDS-PAGE for analysis.

FIG. 16B: Results of mass spec analysis (liquid chromatography mass spectrometry (LC/MS) and tandem mass spectrometry (MS/MS)) of Etanercept eluted with LS. Identified peptides (FIG. 16B.1; SEQ ID NO: 51) were consistent with those generated in a LS digestion of etanercept (FIG. 16B.2: SEQ ID NO: 51). Identified peptides (white boxes) were fitted to the sequence of Etanercept based on m/z values and MS/MS data, with y' and b' ions marked as small grey boxes. All white boxes (e.g. peptides) start directly at a T or an S, where O-glycans are attached.

FIG. 17: Results demonstrating the affinity purification and enrichment of O-glycosylated serum proteins. (A) Asialylated serum (20 µl; 100 µl in PBS) was added to 50 µl PBS equilibrated LS$_{H205A/E206A}$ resin. Proteins were allowed to bind to the resin for 2 hours at room temperature with end-over-end rotation. The resin was washed three times with binding buffer (350 µl) and then eluted with the addition of 8 M Urea. (B) To investigate the impact of glycans for the interaction, samples were pre-treated with a sialidase mixture+/− O-glycosidase. The downstream purification was performed as described above. (C) Serum (40 µl) was mixed with PBS (up to 100 µl) and sialidase mixture (50-500 Units) and added to a PBS equilibrated column, incubating for 2 hours at room temperature with end-over-end rotation, after which the samples were washed and eluted as described above. All samples were separated on SDS-PAGE for analysis.

FIG. 18: Results showing enrichment of O-glycoproteins from human serum. Human serum diluted 2.5× in PBS to 100 µl was applied on 50 µl PBS equilibrated LS$_{H205A/E206A}$ resin in a spin column 50-500 Units Sialidase mixture, was added and co-incubated on the resin at RT for 2 h. Flow through was collected, and the resin was washed 5-10 times with PBS. The bound proteins were eluted in 8 M urea followed by denaturation and reduction with the addition of 5 mM DTT and a 60-minute incubation at 37° C. The reduced cysteines were alkylated with 15 mM iodoacetamide at RT in dark for 30 minutes. Samples were buffer exchanged to 50 mM Tris pH 8.0 on a Spin Desalting Column. Trypsin (2.5 µg) was added to the solution and digestion was overnight at 37° C. Peptides were separated and analysed using RP-LC MS/MS on a C18 column in a 0.1% FA in MQ: 0.1% FA in 95% ACN gradient at 45° C. and a flow of 0.2 ml/min. Detection was on an ESI-Q-TOF. Data were converted to mgf format files and searched against the Swiss Prot database (A) Identified peptides coming from proteins annotated as O-glycosylated proteins or non-O-glycosylated. Only proteins with >6 matching peptides and a MASCOT score >200 were included. (B) Different washing steps resulted in changes in identified peptides, as well as changed ratio of O-glycosylated to non-O-glycosylated proteins (C). Sia=Sialidase treated; Sia Pre=Sialidase Pre-treated.

FIG. 19: Results of experiments that show that the immobilized double-mutant also binds to shorter O-glycopeptides. A shows representative results for LC/MS analysis of binding to a prepared mix of an O-glycosylated peptide (glycodrosocin (GD)) and several non-glycosylated peptides (H2686, H4062 H8390 and insulin oxidized beta chain (IOB). B shows a schematic diagram of IgA illustrating that tryptic digest will product a single O-glycosylated peptide (SEQ ID NO: 58). C shows representative results for LC/MS analysis of binding to the tryptic digest of IgA.

FIG. 20: Results of experiments that show that the immobilized double-mutant compares favorably to other commercially available O-glycoprotein binding matrixes. A shows representative SDS-PAGE gels comparing the presence of etanercept or asialylated etanercept (etanercept(S)) in flow through (FT) or Eluate (E) following incubation with different immobilized lectins or LS double mutant as shown. B shows densitometry analysis of the gels, relative to positive control of 1.5 µg directly-loaded substrate.

BRIEF DESCRIPTION OF THE SEQUENCES

SEQ ID NO: 1 is the amino acid sequence of a polypeptide having O-glycoprotein-specific endoprotease activity.

SEQ ID NO: 2 is an amino acid sequence of an exemplary polypeptide of the invention having O-glycoprotein-specific endoprotease activity. Relative to SEQ ID NO: 1 it includes an additional N terminal Methionine and a C-terminal linker+His$_6$ (SEQ ID NO: 62) tag. The polypeptide consisting of this sequence may be referred to herein as LS.

SEQ ID NO: 3 is a nucleotide sequence encoding a polypeptide having the sequence of SEQ ID NO: 2.

SEQ ID NO: 4 is the wild-type amino acid sequence of a polypeptide isolated from *Akkermansia muciniphila* having O-glycoprotein-specific endoprotease activity. Relative to SEQ ID NO: 1 it includes a signal motif at the N terminus.

SEQ ID NO: 5 is the amino acid sequence of a polypeptide that is capable of binding to O-glycans but lacks or has reduced O-glycoprotein-specific endoprotease activity.

SEQ ID NO: 6 is an amino acid sequence of an exemplary polypeptide of the invention that is capable of binding to O-glycans but lacks or has reduced O-glycoprotein-specific endoprotease activity. Relative to SEQ ID NO: 5 it includes an additional N terminal Methionine and a C-terminal linker+His$_6$ (SEQ ID NO: 62) tag. The polypeptide consisting of this sequence may be referred to herein as LS$_{E206A}$.

SEQ ID NO: 7 is a nucleotide sequence encoding a polypeptide having the sequence of SEQ ID NO: 6.

SEQ ID NO: 8 is the metalloprotease domain motif of an exemplary polypeptide of the invention that has O-glycoprotein-specific endoprotease activity.

SEQ ID NO: 9 is the wild-type amino acid sequence of a sialidase, Am1757, isolated from *Akkermansia muciniphila*. It includes a signal motif at the N terminus.

SEQ ID NO: 10 is the wild-type amino acid sequence of a sialidase, Am1757, lacking a signal motif at the N terminus relative to SEQ ID NO: 9.

SEQ ID NO: 11 is an amino acid sequence of an exemplary sialidase, Am1757. Relative to SEQ ID NO: 10 it includes an additional N terminal Methionine and a C-terminal linker+His$_6$ (SEQ ID NO: 62) tag.

SEQ ID NO: 12 is wild-type amino acid sequence of a sialidase, Am0707, isolated from *Akkermansia muciniphila*. It includes a signal motif at the N terminus.

SEQ ID NO: 13 is the wild-type amino acid sequence of a sialidase, Am0707, lacking a signal motif at the N terminus relative to SEQ ID NO: 12.

SEQ ID NO: 14 is an amino acid sequence of an exemplary sialidase, Am0707. Relative to SEQ ID NO: 13 it includes an additional N terminal Methionine and a C-terminal linker+His$_6$ (SEQ ID NO: 62) tag.

SEQ ID NO: 15 is the amino acid sequence of an O-glycosidase isolated from *S. oralis*.

SEQ ID NOs: 16 and 17 are primer sequences.

SEQ ID NO: 18 shows the amino acid sequence of EPO.

SEQ ID NO: 20 is the amino acid sequence of a polypeptide that is capable of binding to O-glycans but lacks or has reduced O-glycoprotein-specific endoprotease activity.

SEQ ID NO: 21 is an amino acid sequence of an exemplary polypeptide of the invention that is capable of binding to O-glycans but lacks or has reduced O-glycoprotein-specific endoprotease activity. Relative to SEQ ID NO: 20 it includes an additional N terminal Methionine and a C-terminal linker+His$_6$ (SEQ ID NO: 62) tag. The polypeptide consisting of this sequence may be referred to herein as LS$_{H206AA}$ or LS$_{H205A/E206A}$.

SEQ ID NO: 22 is a nucleotide sequence encoding a polypeptide having the sequence of SEQ ID NO: 21.

SEQ ID NOs: 23, 24 and 25 are sequences of disrupted metalloprotease domain motifs, each from a polypeptide of the invention that is capable of binding to O-glycans but lacks or has reduced O-glycoprotein-specific endoprotease activity.

SEQ ID NOs: 26, 27 and 28 are the amino acid sequences of polypeptides each having O-glycoprotein-specific endoprotease activity.

SEQ ID NO: 29, 30 and 31 are the amino acid sequences of exemplary polypeptides having O-glycoprotein-specific endoprotease activity. Relative to SEQ ID NOs: 26, 27 and 28, respectively, SEQ ID NOs: 29, 30 and 31 each include an additional N terminal Methionine and a C-terminal linker+His$_6$ (SEQ ID NO: 62) tag.

SEQ ID NOs: 32, 33 and 34 are wild-type amino acid sequences of polypeptides having O-glycoprotein-specific endoprotease activity, which were isolated from *Pseudomonas aeruginosa* PAO1, *Bacteroides thetaiotaomicron* VPI-5482, and *Clostridium perfringens*, respectively. Relative to SEQ ID NOs: 26, 27 and 28, respectively, each includes a signal motif at the N terminus.

SEQ ID NOs: 35, 36 and 37 are the amino acid sequences of polypeptides that are each capable of binding to O-glycans but lack or have reduced O-glycoprotein-specific endoprotease activity.

SEQ ID NO: 38, 39, and 40 are the amino acid sequences of exemplary polypeptides of the invention that are each capable of binding to O-glycans but lack or have reduced O-glycoprotein-specific endoprotease activity. Relative to SEQ ID NOs: 35, 36 and 37, respectively, SEQ ID NOs: 38, 39 and 40 each include an additional N terminal Methionine and a C-terminal linker+His$_6$ (SEQ ID NO: 62) tag.

SEQ ID NOs: 41-43 are the amino aid sequences of representative metalloprotease motifs of O-glycoprotein-specific endoproteases.

SEQ ID NOs: 44-46 are the amino acid sequences of representative disrupted metalloprotease motifs of polypeptides that are capable of binding to O-glycans but lack or have reduced O-glycoprotein-specific endoprotease activity.

SEQ ID NO: 47 is the amino acid sequence of the glycodrosocin peptide. There is a O-glycosylation site on the T residue.

SEQ ID NOs: 48 to 50 are the amino acid sequences of peptides which are not O-glycosylated.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting. All publications, patents and patent applications cited herein, whether supra or infra, are hereby incorporated by reference in their entirety.

As used in this specification and the appended claims, the singular forms "a", "an", and "the" include plural referents unless the content clearly dictates otherwise. Thus, for example, reference to "a polypeptide" includes "polypeptides", and the like.

General Polypeptide Features

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. The terms "protein", "peptide" and "polypeptide" may be used interchangeably. As used herein, the term "amino acid" refers to either natural and/or unnatural or synthetic amino acids, including both D or L optical isomers, and amino acid analogs and peptidomimetics.

A polypeptide may be produced by suitable method, including recombinant or synthetic methods. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide. Production of polypeptides by expression in bacterial host cells is described below and is exemplified in the Examples. The invention provides nucleic acid molecules and vectors which encode a polypeptide of the invention. The invention also provides a host cell comprising such a nucleic acid or vector. Exemplary polynucleotide molecules encoding polypeptides disclosed herein are provided as SEQ ID NOs: 3 and 7. Each of these sequences includes at the 5' end a codon for the N terminal methionine (ATG) and, prior to the stop codon (TAA) at the 3' end, codons for a Gly-Ser-Gly linker and a 6× His tag, which may optionally be excluded. The optional inclusion of an additional methionine and a tag are discussed in more detail below.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention encodes a polypeptide of the invention and may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo (e.g. in prokaryotic or eukaryotic expression systems). These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example E. coli. Such cells may be cultured using routine methods to produce a polypeptide of the invention.

A polypeptide may be derivatised or modified to assist with their production, isolation or purification. For example, where a polypeptide of the invention is produced by recombinant expression in a bacterial host cell, the sequence of the polypeptide may include an additional methionine (M) residue at the N terminus to improve expression. As another example, the polypeptide of the invention may be derivatised or modified by addition of a ligand which is capable of binding directly and specifically to a separation means. Alternatively, the polypeptide may be derivatised or modified by addition of one member of a binding pair and the separation means comprises a reagent that is derivatised or modified by addition of the other member of a binding pair. Any suitable binding pair can be used. In a preferred embodiment where the polypeptide for use in the invention is derivatised or modified by addition of one member of a binding pair, the polypeptide is preferably histidine-tagged or biotin-tagged. Typically the amino acid coding sequence of the histidine or biotin tag is included at the gene level and the polypeptide is expressed recombinantly in E. coli. The histidine or biotin tag is typically present at either end of the polypeptide, preferably at the C-terminus. It may be joined directly to the polypeptide or joined indirectly by any suitable linker sequence, such as 3, 4 or 5 glycine residues, or a mixture of glycine and serine residues. The histidine tag typically consists of six histidine residues, although it can be longer than this, typically up to 7, 8, 9, 10 or 20 amino acids or shorter, for example 5, 4, 3, 2 or 1 amino acids.

A polypeptide may be provided in a substantially isolated or purified form. That is, isolated from the majority of the other components present in a cellular extract from a cell in which the polypeptide was expressed. By substantially purified, it will be understood that the polypeptide is purified to at least 50%, 60%, 70%, 80% or preferably at least 90% homogeneity. Purity level may be assessed by any suitable means, but typically involves SDS-PAGE analysis of a sample, followed by Coomassie Blue detection. A polypeptide may be mixed with carriers, diluents or preservatives which will not interfere with the intended purpose of the polypeptide and still be regarded as substantially isolated or purified. Where a polypeptide is provided in a composition with an additional active component, such as another polypeptide, each said polypeptide will individually be purified to a high level of homogeneity prior to mixing in an appropriate ratio for the intended purpose of each. For example, two polypeptides may be each be purified to at least 90% homogeneity prior to combining in a 1:1 ratio.

A polypeptide (or mixture thereof) may be provided in lyophilised form, suitable for reconstitution in aqueous solution prior to use. The lyophilised composition has improved stability enabling longer storage of the polypeptide. A method of preparing a polypeptide (or mixture thereof) in lyophilised form, comprising freeze-drying said polypeptide (or mixture) in a suitable buffer, such as Tris-buffered saline (TBS), is provided herein. A polypeptide is typically substantially purified prior to freeze-drying. The resulting polypeptide (or mixture) in lyophilised form is also provided. A method of preparing a solution of a polypeptide (or mixture), comprising providing the polypeptide (or mixture) in lyophilised form and reconstituting with a suitable carrier or diluent, such as water, is also provided.

A polypeptide may be immobilised using methods known in the art, for example as described in Datta S et al., Enzyme immobilization: an overview on techniques and support materials, 3 *Biotech*, 3(1):1-9 (2013). For example, the polypeptide may be immobilised by adsorption, covalent binding, affinity immobilization or entrapment. Materials that can be used as supports include but are not limited to for example, natural supports such as agarose, collagen, gelatin, cellulose, pectin, sepharose, inorganic materials such as ceramics, silica, glass, activated carbon or charcoal, or synthetic polymers. For example, the polypeptide may be immobilised on sepharose or agarose, optionally provided as a resin.

Polypeptides Having Endoprotease Activity
Functional Features of a Polypeptide Having Endoprotease Activity In one embodiment, the present invention relates to a polypeptide having endoprotease activity specific for O-glycosylated proteins. In other words, the polypeptide has O-glycoprotein-specific endoprotease activity. The polypeptide cleaves any O-linked glycoprotein, preferably any human O-linked glycoprotein. Examples of O-linked glycoproteins include any protein that comprises or consists all or part of an immunoglobulin, including full length antibodies, Fc fragments and Fc fusion proteins, particularly those of the IgA, IgD and IgG3 isotypes. Another example of an O-linked glycoprotein is Etanercept, which is a fusion protein of the ligand binding domain of human TNFα receptor 2 linked to the Fc portion of IgG1, with numerous O-glycosylation sites. Other examples of O-linked glycoproteins include erythropoietin (EPO), TNFα Receptors, fetuin, and plasminogen.

The hydrolysis (i.e. cleavage) of the substrate glycoprotein typically occurs with high specificity at a peptide bond N-terminal to and in close proximity to an O-glycosylated serine or threonine, and is O-glycan dependent. A polypeptide of the invention is preferably capable of cleaving such a peptide bond in close proximity to every O-glycosylated site in the substrate glycoprotein. The reaction preferably does not show any amino acid specificity or limitation, and in particular does not require any specific amino acid(s) to be present N-terminal to the O-glycosylated serine or threonine. When assessed using standard mass spectrometry parameters, the cleavage site is generally observed to be at the peptide bond immediately N terminal to each O-glycosylated residue.

Endoprotease activity and specificity of a given polypeptide may be determined by means of a suitable assay. For example, a standard O-glycoprotein substrate, such as an IgA molecule or erythropoietin (EPO), may be incubated with a test polypeptide. The starting materials and the reaction products may then be analysed by SDS-PAGE and/or mass spectrometry to determine the presence of cleavage products (if any) and if required also to further characterise those products. A glycoprotein substrate which is not O-glycosylated, such as an IgG1 molecule, may be used as a negative control. The results may be compared to those obtained in the same assay when the substrate is contacted with an exemplary polypeptide of the invention, such as a polypeptide consisting of the amino acid sequence of SEQ ID NO: 2. One unit of the polypeptide of SEQ ID NO: 2 is defined as the amount required to digest >90% of 1 µg of Erythropoietin (EPO) in combination with one unit of a sialidase mixture in 20 mM Tris buffer pH 6.8, overnight at 37° C. as monitored by SDS-PAGE (preferred sialidase mixtures are described further below). A test polypeptide preferably achieves a similar level of activity when present in the same amount. Exemplary assays are also described in the Examples.

Structural Features of a Polypeptide Having Endoprotease Activity

This section sets out the structural features of a polypeptide in accordance with this embodiment, which apply in addition to the functional features outlined in the preceding section.

The polypeptide is typically at least 150, 200, 250, 275, 280, 290, 300, 310, 320, 330, 340, 350 or 360 amino acids in length. The polypeptide is typically no larger than 400, 395, 390, 385, 380, 375, 370 or 365 amino acids in length. It will be appreciated that any of the above listed lower limits may be combined with any of the above listed upper limits to provide a range for the length the polypeptide. For example, the polypeptide may be 150 to 400 amino acids in length, or 280 to 380 amino acids in length. The polypeptide is preferably 340 to 380 amino acids in length, most preferably 360 to 375 amino acids in length.

The primary structure (amino acid sequence) of the polypeptide is based on the primary structure of the polypeptide encoded by the Amuc1119 gene of *Akkermansia muciniphila*. The full sequence of this polypeptide is shown in SEQ ID NO: 4, which includes a signal motif at positions 1-24. The sequence with the signal motif removed is shown in SEQ ID NO: 1.

The polypeptide of the invention may comprise, consist essentially, or consist of the sequence of SEQ ID NO: 1.

Alternatively, the polypeptide of the invention may comprise, consist essentially, or consist of a variant of the amino acid sequence of SEQ ID NO: 1 which is at least 50% identical to the amino acid sequence of SEQ ID NO: 1. The variant sequence may be at least 60%, at least 70%, at least 80%, at least, 85%, at least 90%, at least 95%, at least 98% or at least 99% identical to the sequence of SEQ ID NO:1. The identity level is preferably at least 85% or higher. Identity relative to the sequence of SEQ ID NO: 1 can be measured over a region of at least 100, at least 200, at least 300 or at least 350 or more contiguous amino acids of the sequence shown in SEQ ID NO: 1, or more preferably over the full length of SEQ ID NO: 1. A variant is typically of a length which is no more than 50 amino acids longer or shorter than the reference sequence, and is preferably of approximately (or exactly) the same length as the reference sequence.

Amino acid identity may be calculated using any suitable algorithm. For example the PILEUP and BLAST algorithms can be used to calculate identity or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al (1984) Nucleic Acids Research 12, 387-395).

The sequence of a polypeptide of the invention may comprise a variant of the amino acid sequence of SEQ ID NO: 1 in which modifications, such as amino acid additions, deletions or substitutions are made relative to the sequence of SEQ ID NO: 1. Unless otherwise specified, the modifications are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2. A sequence of a polypeptide of the invention may comprise a variant of the amino acid sequence of SEQ ID NO: 1 in which up to 10, 20, 30, 40, 50 or 60 conservative substitutions are made.

TABLE A1

| Chemical properties of amino acids | | | |
|---|---|---|---|
| Ala (A) | aliphatic, hydrophobic, neutral | Met (M) | hydrophobic, neutral |
| Cys (C) | polar, hydrophobic, neutral | Asn (N) | polar, hydrophilic, neutral |
| Asp (D) | polar, hydrophilic, charged (−) | Pro (P) | hydrophobic, neutral |
| Glu (E) | polar, hydrophilic, charged (−) | Gln (Q) | polar, hydrophilic, neutral |
| Phe (F) | aromatic, hydrophobic, neutral | Arg (R) | polar, hydrophilic, charged (+) |
| Gly (G) | aliphatic, neutral | Ser (S) | polar, hydrophilic, neutral |
| His (H) | aromatic, polar, hydrophilic, charged (+) | Thr (T) | polar, hydrophilic, neutral |
| Ile (I) | aliphatic, hydrophobic, neutral | Val (V) | aliphatic, hydrophobic, neutral |
| Lys (K) | polar, hydrophilic, charged(+) | Trp (W) | aromatic, hydrophobic, neutral |
| Leu (L) | aliphatic, hydrophobic, neutral | Tyr (Y) | aromatic, polar, hydrophobic |

TABLE A2

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |

TABLE A2-continued

Hydropathy scale

| Side Chain | Hydropathy |
|---|---|
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The amino acid sequence of a polypeptide of the invention may comprises a variant of the amino acid sequence of SEQ ID NO: 1 as described above. However, certain residues in the amino acid sequence of SEQ ID NO: 1 are preferably retained within the said variant sequence. For example, the said variant sequence typically retains certain residues which are known to be required for endoprotease activity. Thus, the glutamate at position 182 of SEQ ID NO: 1 (corresponds to position 206 of SEQ ID NO: 4) is preferably retained in the amino acid sequence of a polypeptide of the invention. This residue is thought to be required for electron transfer in the active site. Thus, a polypeptide of the invention typically comprises a variant of the amino acid sequence of SEQ ID NO: 1 which has a glutamate (E) at the position in said variant sequence which corresponds to position 182 of SEQ ID NO: 1. Similarly, the histidine at position 181 of SEQ ID NO: 1 (corresponds to position 205 of SEQ ID NO: 4) is preferably retained in the amino acid sequence of a polypeptide of the invention. This residue is thought to be required for binding to a zinc ion co-factor.

The said glutamate and said histidine residue are both typically comprised within a metalloprotease domain having the motif HEbbH (SEQ ID NO: 59), where b is an amino acid with no charge, such as amino acid A, C, F, G, I, L, M, N, P, Q, S, T, V or W. A preferred example of such a domain has the sequence HELGH (SEQ ID NO: 41), which corresponds to positions 181 to 185 of SEQ ID NO: 1 (positions 205 to 209 in SEQ ID NO: 4). Thus, a polypeptide of the invention typically comprises a variant of the amino acid sequence of SEQ ID NO: 1 which comprises the motif HEbbH (SEQ ID NO: 59) (such as HEIGH (SEQ ID NO: 42) or HELGH (SEQ ID NO: 41), preferably HELGH (SEQ ID NO:41)), at positions corresponding to positions 181 to 185 of SEQ ID NO: 1. A polypeptide of the invention typically comprises an O-glycan specific binding domain located C-terminal to the metalloprotease domain.

The motif HEbbH (SEQ ID NO: 59) may be compromised within a larger metalloprotease domain having the motif abxHEbbHbc (SEQ ID NO: 60), where a is amino acid V, T or G, b is an amino acid with no charge, such as amino acid A, C, F, G, I, L, M, N, P, Q, S, T, V or W, x is any amino acid, and c is a hydrophobic amino acid such as A, C, F, I, L, M, P, V, W or Y. A preferred example of such a domain has the sequence GMAHELGHGL (SEQ ID NO: 8), which corresponds to positions 178 to 187 of SEQ ID NO: 1 (positions 202 to 211 in SEQ ID NO: 4). Other examples include GVAHELGHNF (SEQ ID NO: 43). Thus, a polypeptide of the invention preferably comprises a variant of the amino acid sequence of SEQ ID NO: 1 which comprises the motif abxHEbbHbc (SEQ ID NO: 60), (such as GMAHELGHGL (SEQ ID NO: 8) or GVAHELGHNF (SEQ ID NO:43), preferably GMAHELGHGL (SEQ ID NO: 8)), at positions corresponding to positions 178 to 187 of SEQ ID NO: 1. A polypeptide of the invention typically comprises an O-glycan specific binding domain located C-terminal to the metalloprotease domain.

Alternatively, a polypeptide of the invention may comprise, consist essentially, or consist of a shorter fragment of SEQ ID NO: 1 or of a variant thereof as described above. The fragments may be described as a truncated form of SEQ ID NO: 1 which retains O-glycoprotein specific-endoprotease activity. Such fragments are shorter than SEQ ID NO: 1 and are typically at least 100, 150 or 200 amino acids in length. The fragments typically comprise a metalloprotease domain at positions corresponding to positions 178 to 187 of SEQ ID NO: 1, including a glutamic acid residue (E) at a position which corresponds to position 182 of SEQ ID NO: 1 and a histidine residue (H) at a position which corresponds to position 181 of SEQ ID NO: 1, and an O-glycan specific binding domain located C-terminal to the metalloprotease domain.

Any polypeptide of the invention which comprises SEQ ID NO:1 or a variant thereof, or a fragment of either thereof, may optionally include an additional methionine at the N terminus and/or a histidine or other tag at the C terminus. Such additional sequences may aid with expression and/or purification. A histidine tag preferably consists of six histidine residues. The histidine tag is preferably linked to the C terminus by a linker, which is typically a short sequence of amino acids, such as 3-5 amino acids. The linker typically consists predominantly of glycine and serine residues, and may preferably include the sequence GSG. For example GSG and GSGLE (SEQ ID NO: 61) are suitable linkers.

In summary therefore, a polypeptide of the invention is a polypeptide having O-glycoprotein-specific endoprotease activity which comprises:
  (a) an amino acid sequence of SEQ ID NO: 1;
  (b) an amino acid sequence which is at least 85% identical to the amino acid sequence of SEQ ID NO: 1 or
  (c) an amino acid sequence which is a fragment of the sequence of SEQ ID NO: 1 or a fragment of an amino acid which is 85% identical to the amino acid sequence of SEQ ID NO: 1;
  optionally wherein said polypeptide includes an additional methionine at the N terminus and/or a histidine tag at the C terminus, which tag may be joined to the C terminus by a linker.

The sequence of an exemplary polypeptide of the invention is provided as SEQ ID NO: 2. The polypeptide may comprise or consist of the amino acid sequence of SEQ ID NO: 2. An exemplary polynucleotide sequence encoding this polypeptide is shown in SEQ ID NO: 3.

Alternative polypeptides which have O-glycoprotein-specific endoprotease activity have been identified in *Pseudomonas aeruginosa* PAO1, *Bacteroides thetaiotaomicron* VPI-5482, and *Clostridium perfringens* (see three peptidases described in Noach et al; PNAS 2017, pE679-688 and supporting appendices, specifically Materials and Methods for Cloning, Protein Expression and Purification). The full length sequences of these polypeptides are provided as SEQ ID NOs: 32, 33 and 34. Each of these sequences includes a metalloprotease domain having the motif HEbbH (SEQ ID NO: 59) as described above. The *Clostridium perfringens* sequence also has the longer metalloprotease domain having the motif abxHEbbHbc (SEQ ID NO: 60) as described above. Each of these sequences can be optionally modified to remove any signal sequence or pro-enzyme sequences that may be present and/or to include an additional methionine at the N terminus and/or a histidine or other tag at the C terminus. Such additional sequences may aid with expression (e.g. in *E. coli*) and/or purification. Corresponding sequences with signal and other immature sequences removed are provided as SEQ ID NOs: 26, 27 and 28. Versions of these sequences optimised for expression in *E. coli* and subsequent purification (by inclusion of an additional methionine at the N terminus and a histidine tag at the C terminus) are provided as SEQ ID NOs: 29, 30 and 31. In methods described herein for use of a polypeptide of the invention having O-glycoprotein-specific endoprotease activity, the polypeptide of the invention may optionally be replaced with one of these polypeptides. Preferred polypeptides for use in such methods therefore comprise, consist essentially, or consist of any one of SEQ ID NOs: 26 to 31.

Methods Using the Endoprotease Activity of the Polypeptide

The present invention also provides a method of hydrolysing an O-glycoprotein, wherein the method comprises contacting a sample of said protein with a polypeptide of the invention having O-glycoprotein-specific endoprotease activity and optionally further comprising detection of the hydrolysis products.

The present invention may also include a method for assessing the glycosylation status of a protein, comprising contacting a sample of said with a polypeptide of the invention having O-glycoprotein-specific endoprotease activity and analysing the products produced. The presence of cleavage products indicates that the protein in said sample is O-glycosylated, and thus the method may also be used for the detection of O-glycoproteins. The cleavage products may optionally be further analysed to identify the glycan chain and its position of attachment to the protein.

In such methods, a sample is contacted with a polypeptide of the invention under conditions suitable for polypeptide to interact with any proteins in the sample and for hydrolysis/cleavage reactions (endoprotease activity) to occur. Suitable conditions include incubation with a polypeptide of the invention for at least 20 minutes, 30 minutes, 40 minutes, 50 minutes, 60 minutes, 70 minutes, 80 minutes, 90 minutes or 120 minutes, 3 hours, 5 hours, 10 hours, or overnight. Incubation preferably takes place at room temperature, more preferably at approximately 20° C., 25° C., 30° C., 35° C., 40° C. or 45° C., and most preferably at approximately 37° C. The methods described above may be carried out under any suitable pH. Suitable pH values include, for example, a pH of around 3.0, 3.5, 4, 4.5, 5, 5.5, 6, 6.5, 7, 7.5, 8, 8.5, 9 or 9.5. Preferred pH for the activity of a polypeptide of the invention is in the range 5.6 to 6.8. The method may be conducted in any suitable buffer, such as tris buffered saline (TBS) or phosphate buffered saline (PBS). The approximate ratio of the polypeptide of the invention to the protein content of the sample (enzyme:substrate) may be 1:1, 2:1, 4:1, 6:1, 10:1, 15:1, 20:1, 1:2, 1:4, or 1:6, 1:10, 1:15, 1:20, 1:40, 1:100, 1:200 or 1:400. A preferred ratio is 1:20. Higher proportions of enzyme to substrate may be beneficial if a shorter reaction time is required, or if the O-glycoprotein is heavily sialyated. Alternatively an earlier or simultaneous sialidase incubation step may be used to reduce sialic acid content, as is discussed in more detail below. The substrate is typically present at a concentration of 0.1 mg/ml to 10 mg/ml, preferably around 0.1 to 2 mg/ml.

The detection or analysis of the products produced may be assessed by any suitable analytical method, such as but not limited to mass spectrometry, HPLC, affinity chromatography, gel electrophoresis, SDS-PAGE, ELISA, lectin blotting, spectrometry, capillary electrophoresis and other standard laboratory techniques for the analysis of proteins.

The sample in any of the above methods may be a sample taken from a patient, preferably a human patient. The results obtained may be used for a diagnostic purpose, for example to detect the presence of cancers which involve O-linked glycosylation. Such a use may involve comparison of the results obtained from the patient sample to those obtained using a sample obtained from a healthy control.

In any method of the invention, the polypeptide can be used in combination with another enzyme such as a protease or glycosidase. The additional protease or glycosidase will typically further digest the substrate proteins, which may enhance the activity of the polypeptide of the invention and/or permit easier or more detailed analysis of the products.

For example, the present inventors have determined that a polypeptide of the invention demonstrates improved endoprotease activity if the O-glycans of a substrate protein are first modified to remove sialic acid. Thus, in a preferred method of the invention, the sample is contacted with an agent to remove sialic acid. Said agent may preferably be a sialidase enzyme or a mixture of such enzymes, which may be present in a suitable buffer such as TBS or PBS. The buffer preferably comprises a low concentration of NaCl, typically up to 300 mM, 250 mM, 200 mM, or 150 mM. The NaCl concentration is preferably around 150 mM, such as between 125 mM and 175 mM. Sialidases (or neuraminidases) catalyse the cleavage of terminal sialic acids from complex carbohydrates on glycoproteins and show a high degree of specificity. These enzymes target three distinct sialic acid bonds which are commonly found within O-glycoproteins, namely α2-3, α2-6 and α2-8 bonds. Sialidases that are suitable for use in the methods described include broad spectrum sialidases that target all of the α2-3, α2-6, or α2-8 bonds, as well as narrow spectrum sialidases that typically target only one type of bond. The α2-3 bond is the most common in human glycoproteins, so if a narrow spectrum sialidase is used it is preferable that it targets this bond. Suitable sialidases may include viral or mammalian sialidases but are preferably sialidases isolated from bacteria, including but are not limited to strains of *Clostridium perfringens*, *Arthrobacter ureafaciens*, *Streptococcus pneumoniae*, *Vibrio cholera* and *Akkermansia muciniphila*.

A preferred narrow spectrum sialidase is Am1757 isolated from *Akkermansia muciniphila*. Am1757 has specific activity against α2-3 bonds. The wild-type sequence of Am1757 is provided as SEQ ID NO: 9, which includes a signal sequence. The wild-type sequence of Am1757 lacking the signal sequence is provided as SEQ ID NO: 10. These sequences can be optionally modified to include an additional methionine at the N terminus and/or a histidine or other tag at the C terminus. Such additional sequences may aid with expression (e.g. in *E. coli*) and/or purification. A histidine tag preferably consists of six histidine residues. The histidine tag is preferably linked to the C terminus by a linker, which is typically a short sequence of amino acids, such as 3-5 amino acids. The linker typically consists predominantly of glycine and serine residues, and may preferably include the sequence GSG. For example GSG and GSGLE (SEQ ID NO: 61) are suitable linkers. An exemplary Am1757 sequence having an additional methionine at the N terminus and a GSGLE (SEQ ID NO: 61) linker and His$_6$ (SEQ ID NO: 62) tag at the C terminus is provided as SEQ ID NO: 11. Any reference to Am1757 in the present disclosure may mean any of SEQ ID NOs: 9, 10 or 11, but preferably refers to a polypeptide which comprises or consists of the amino acid sequence of SEQ ID NO: 10. Most preferred is a polypeptide which consists of the amino acid sequence of SEQ ID NO: 11.

A preferred broad spectrum sialidase is Am0707 isolated from *Akkermansia muciniphila*. Am0707 has activity against α2-3, α2-6 and α2-8 bonds. The wild-type sequence of Am0707 is provided as SEQ ID NO: 12, which includes a signal sequence. The wild-type sequence of Am0707 lacking the signal sequence is provided as SEQ ID NO: 13. These sequences can be optionally modified to include an additional methionine at the N terminus and/or a histidine or other tag at the C terminus. Such additional sequences may aid with expression and/or purification. A histidine tag preferably consists of six histidine residues. The histidine tag is preferably linked to the C terminus by a linker, which is typically a short sequence of amino acids, such as 3-5 amino acids. The linker typically consists predominantly of glycine and serine residues, and may preferably include the sequence GSG. For example GSG and GSGLE (SEQ ID NO: 61) are suitable linkers. An exemplary Am0707 sequence having an additional methionine at the N terminus and a GSGLE (SEQ ID NO: 61) linker and $His_6$ (SEQ ID NO: 62) tag at the C terminus is provided as SEQ ID NO: 14. Any reference to Am0707 in the present disclosure may mean any of SEQ ID NOs: 12, 13 or 14, but preferably refers to a polypeptide which comprises or consists of the amino acid sequence of SEQ ID NO: 13. Most preferred is a polypeptide which consists of the amino acid sequence of SEQ ID NO: 14.

A preferred sialidase mixture capable of hydrolyzing all sialic acid bonds comprises Am1757 and Am0707 isolated from *Akkermansia muciniphila*. The mixture of Am1757 and Am0707 is typically in a 1:1 ratio. A particularly preferred mixture may comprise a polypeptide consisting of the amino acid sequence of SEQ ID NO: 11 and a polypeptide consisting of the amino acid sequence of SEQ ID NO: 14.

Methods of the invention may preferably comprise incubating a sample with Am1757 or with a mixture of Am1757 and Am0707 prior to or simultaneously with the polypeptide of invention, under conditions suitable for activity of the sialidases. The invention also provides a composition (in lyophilised or solution form) comprising a polypeptide of the invention and Am1757 or a mixture of Am1757 and Am0707. Such a composition may preferably be lyophilised in tris buffered saline, which may be at around pH7.6. In such a composition, Am1757 and Am0707 will preferably be present in a 1:1 ratio to each other, with the total sialidase content (Am1757+Am0707) also being present at a 1:1 ratio relative to the polypeptide of the invention. For example, if a composition includes 2000 units of the polypeptide of the invention, it will also include 2000 units of sialidase, in which said 2000 units of sialidase comprise 1000 units Am1757 and 1000 units Am0707. A unit of sialidase mixture is typically the amount required to hydrolyse sialic acids from ≥90% of 1 µg glycoprotein (fetuin) when incubated in 20 mM Tris pH 6.8 at 37° C. for 2 h at 37° C. as monitored by SDS-PAGE. A unit of the polypeptide of the invention is typically the amount required to digest >90% of 1 µg of Erythropoietin (EPO) when incubated in 20 mM Tris buffer pH 6.8, overnight with one unit of sialidase mixture at 37° C. as monitored by SDS-PAGE.

The invention also provides a kit comprising a polypeptide of the invention in a separate container from Am1757 or a mixture of Am1757 and Am0707, with instructions for the combined use of the different enzymes.

As another example, in any of the methods described herein, the sample may be incubated with an N-glycosidase prior to, at the same time as, or after contacting the sample with the polypeptide of the invention, to remove N-glycans from target proteins. An exemplary N-glycosidase is PNGaseF. Other N-glycosidases that may be used when the sample includes immunoglobulins are EndoS (see SEQ ID NO: 1 of WO2008071418) or EndoS2 (may be referred to as EndoS49—see SEQ ID NO: 1 of WO2013037824). Each of these enzymes removes the N-linked glycoprotein from Asn-297 of IgG1. In a particular embodiment, the sample may be contacted with an N-glycosidase and a sialidase (or mixture thereof) in addition to the polypeptide of the invention. In such a method, the sialidase (or mixture) may be applied first, prior to simultaneous addition of the N-glycosidase and the polypeptide of the invention. Such a method is particularly suitable for the subsequent assessment of O-glycosylation sites, typically achieved by separation of the products e.g. using RPLC and subsequent analysis of the different fractions e.g. using mass spectrometry.

As another example, in any of the methods described herein, the sample may be incubated with a protease prior to, at the same time as, or after contacting the sample with the polypeptide of the invention, to further digest the target protein. Suitable general proteases include trypsin, chymotrypsin, Lys-C, Asp-N, Glu-C, Arg-C or similar endoproteases, or Arg-gingipain (RgpB) of *Porphyromonas gingivalis*.

If the sample includes immunoglobulins, immunoglobulin proteases may be used such as SpeB (see sequence in WO2015040125), Immunoglobulin G-degrading enzyme of *S. pyogenes* (IdeS—see sequence in WO2015040125), Immunoglobulin G-degrading enzyme of *S. equi* subspecies *zooepidemicus* (IdeZ), Lys-gingipain (Kgp) of *Porphyromonas gingivalis*, and Immunoglobulin G-degrading Enzyme of *S. agalactiae* ($IgdE_{agalactiae}$—see SEQ ID NO: 3 of PCT/EP2017/052463). Use of any combination of these proteases in a method of the present invention may assist with determination of O-glycosylation sites on monoclonal antibodies and subunits thereof, for example using mass spectrometry (middle down approach).

As another example, in any of the methods described herein, the sample may be incubated with an O-glycosidase after contacting the sample with a polypeptide of the invention. For instance, to simplify the analysis of the products produced, the products are subjected to digestion by an O-glycosidase for removal of the O-glycans prior to further analysis by any suitable method. Suitable O-glycosidases may be obtained from a strain of *Enterococcus faecalis*, *Streptococcus oralis*, or *Bifidobacterium bifidum*, preferably *Enterococcus faecalis* or *Streptococcus oralis*, most preferably *Streptococcus oralis*. The sequence of an exemplary O-glycosidase from *Streptococcus oralis* is provided as SEQ ID NO: 15.

Polypeptides which Bind to O-Linked Glycoproteins but Lack or have a Reduced Endoprotease Activity
Functional Features of a Polypeptide Lacking Endoprotease Activity In one embodiment, the present invention relates to a polypeptide lacking or having a reduced endoprotease activity, whilst retaining the ability to bind O-glycans. In other words, the polypeptide may be described as an O-glycan-specific binding agent which does not significantly hydrolyse a glycoprotein to which said glycan is attached.

O-glycoprotein endoprotease activity may be determined using any suitable method, but may typically employ the same assay as described above for polypeptides of the invention which posses such activity. A lack of activity in a test polypeptide will be indicated by the absence of cleavage products following incubation with an O-glycoprotein substrate. Cleavage of the same substrate by a polypeptide comprising the amino acid sequence of SEQ ID NO: 1 may be used as a positive control. A reduction in activity in the test polypeptide may be determined by comparison to the same control. The polypeptide of the invention typically has O-glycoprotein endoprotease activity which is reduced relative to the activity of a polypeptide comprising the amino acid sequence of SEQ ID NO: 1. The polypeptide of the invention typically has O-glycoprotein endoprotease activity which is less than 95%, 90%, 85%, 80%, 75%, 70%, 65%, 60%, 55%, 50%, 45%, 40%, 35%, 30%, 25%, 20%, 15%, 10% or 5% compared to the activity of a polypeptide comprising the amino acid sequence of SEQ ID NO: 1.

The ability of a polypeptide to bind to O-glycan or O-glycoprotein may also be assessed by any suitable method. One such method involves immobilising a test polypeptide, e.g. on sepharose in a spin column, followed by incubation with a sample containing O-glycoproteins and/or O-glycans. If the test polypeptide has O-glycan and/or O-glycoprotein binding ability, the O-glycoproteins and/or O-glycans will be detectable bound to the column or in a subsequent eluent. Preferably, the polypeptide is able to bind all O-glycoproteins which are hydrolysable by a polypeptide comprising the amino acid sequence of SEQ ID NO: 1.

Exemplary assays of this type are described in the examples.

Structural Features of a Polypeptide Lacking Endoprotease Activity

This section sets out the structural features of a polypeptide in accordance with this embodiment, which apply in addition to the functional features outlined in the preceding section. A polypeptide in accordance with this embodiment of the invention may possess the same structural features as described above in connection with a polypeptide having endoprotease activity, with the exception that the amino acid sequence is modified by one or more amino acid additions, deletions or substitutions such that said activity is reduced or eliminated. Typically, a polypeptide in accordance with this embodiment of the invention will not include an intact metalloprotease motif of HEbbH (SEQ ID NO: 59) or abxHEbbHbc (SEQ ID NO: 60). Said motif may be disrupted by addition, deletion or substitution, but is preferably disrupted by at least one amino acid substitution. Preferably, the substitution involves replacement of the glutamic acid (E) residue in the said motif with an alternative amino acid and/or the replacement of the histidine (H) residue in the position corresponding to the $1^{st}$ position of the shorter motif (the $4^{th}$ position of the longer motif) and/or replacement of the histidine (H) residue in the position corresponding to the $5^{th}$ position of the shorter motif (the $8^{th}$ position of the longer motif). Preferably, either or both or all three said substitutions is non-conservative. The substitution of the E residue should reduce or eliminate electron transfer. The substitution of either of the H residues should reduce or eliminate Zinc ion co-factor binding. The E residue is therefore preferably substituted with a non-polar or uncharged amino acid, such as A, C, F, G, I, L, M, N, P, Q, S, T, V or W, but is most preferably substituted with Alanine (A) or Glycine (G). The H residues may each individually be substituted with any non-H amino acid, but non-polar amino acids such as A and G are again preferred.

Thus, a polypeptide of the invention may comprise, consist essentially, or consist of the amino acid sequence of SEQ ID NO: 1 in which the metalloprotease motif of HEbbH (SEQ ID NO: 59) or abxHEbbHbc (SEQ ID NO: 60) is disrupted, preferably by the replacement of the glutamic acid residue in the position corresponding to position 182 of SEQ ID NO: 1 and/or the replacement of the histidine residue corresponding to position 181 of SEQ ID NO: 1 with an alternative amino acid and/or the replacement of the histidine residue corresponding to position 185 of SEQ ID NO: 1 with an alternative amino acid. In other words, the polypeptide may be described as not comprising the metalloprotease motif HEbbH (SEQ ID NO: 59) and preferably comprising a disrupted version of said motif, such that:
　(a) H in the first position is replaced with an alternative amino acid, preferably A or G; and/or
　(b) E in the second position is replaced with an uncharged amino acid, optionally A, C, F, G, I, L, M, N, P, Q, S, T, V or W, preferably A or G; and/or
　(c) H in the fifth position is replaced with an alternative amino acid, preferably A or G
wherein b in the said motif is an uncharged amino acid, optionally A, C, F, G, I, L, M, N, P, Q, S, T, V or W.

The said polypeptide may therefore be described as comprising the motif xbbbx (SEQ ID NO: 63), wherein:
　(a) x is preferably any amino acid except H, and is preferably A or G; and/or
　(b) b is an uncharged amino acid, optionally A, C, F, G, I, L, M, N, P, Q, S, T, V or W, preferably A or G;
optionally wherein said motif is present in said polypeptide at positions corresponding to positions 181 to 185 of SEQ ID NO: 1.

The said polypeptide may therefore comprise a disrupted metalloprotease motif, for example with any one of the following sequences: HALGH (SEQ ID NO: 44), AELGH (SEQ ID NO: 45) or most preferably AALGH (SEQ ID NO: 46). Sequences comprising this type of specific change to SEQ ID NO: 1 are shown in SEQ ID NO: 5 and SEQ ID NO: 20. In other words therefore, a polypeptide of this embodiment of the invention may comprise, consist essentially, or consist of the amino acid sequence of SEQ ID NO: 5 or SEQ ID NO: 20.

The said polypeptide may alternatively be described as comprising the motif abxxbbbxbc (SEQ ID NO: 64), wherein:
　(a) a is amino acid V, T or G;
　(b) b is an uncharged amino acid, optionally A, C, F, G, I, L, M, N, P, Q, S, T, V or W, preferably A or G;
　(c) x is any amino acid except that the amino acid in the $4^{th}$ and/or $8^{th}$ position of the motif is preferably not H, and is preferably A or G; and
　(d) c is a hydrophobic amino acid, optionally A, C, F, I, L, M, P, V, W or Y;
optionally wherein said motif is present in said polypeptide at positions corresponding to positions 178 to 187 of SEQ ID NO: 1.

The said polypeptide may therefore comprise a disrupted metalloprotease motif, for example with any one of the following sequences: GMAHALGHGL (SEQ ID NO: 23), GMAAELGHGL (SEQ ID NO: 24) or most preferably GMAAALGHGL (SEQ ID NO: 25). Sequences comprising this type of specific change to SEQ ID NO: 1 are shown in SEQ ID NO: 5 and SEQ ID NO: 20. In other words therefore, a polypeptide of this embodiment of the invention may comprise, consist essentially, or consist of the amino acid sequence of SEQ ID NO: 5 or SEQ ID NO: 20.

Alternatively, the polypeptide of the invention may comprise, consist essentially, or consist of a variant of the amino acid sequence of SEQ ID NO: 5 or SEQ ID NO: 20 which is at least 50% identical to the amino acid sequence of SEQ ID NO: 5, provided that a glutamic acid residue is not introduced in the position corresponding to position 182 of SEQ ID NO: 1 and/or a histidine residue is not introduced in the position corresponding to position 181 of SEQ ID NO: 1 and/or a histidine residue is not introduced in the position corresponding to position 185 of SEQ ID NO: 1.

The variant sequence may be at least 60%, at least 70%, at least 80%, at least, 85%, at least 90%, at least 95%, at least 98% or at least 99% identical to the sequence of SEQ ID NO: 5. The identity level is preferably at least 85% or higher. Identity relative to the sequence of SEQ ID NO: 5 or SEQ ID NO: 20 can be measured over a region of at least 100, at least 200, at least 300 or at least 350 or more contiguous amino acids of the sequence shown in SEQ ID NO: 5 or SEQ ID NO: 20, or more preferably over the full length of SEQ ID NO: 5 or SEQ ID NO: 20. A sequence of a polypeptide of the invention may comprise a variant of the amino acid sequence of SEQ ID NO: 5 or SEQ ID NO: 20 in which up to 10, 20, 30, 40, 50 or 60 conservative substitutions are made. Determinations of sequence identity and an explanation of conservative and non-conservative substitutions are providing in the section relating to polypeptides having endoprotease activity and apply equally here.

Alternatively, a polypeptide of the invention may comprise, consist essentially, or consist of a shorter fragment of SEQ ID NO: 5 or SEQ ID NO: 20, or of a variant thereof as described above. The fragments may be described as a truncated form of SEQ ID NO: 5 or SEQ ID NO: 20 which retains O-glycoprotein binding activity. Such fragments are shorter than SEQ ID NO: 1 and are typically at least 100, 150 or 200 amino acids in length.

Any polypeptide of the invention which comprises SEQ ID NO: 5 or SEQ ID NO: 20, or a variant thereof, or a fragment of either thereof, may optionally include an additional methionine at the N terminus and/or a histidine or other tag at the C terminus. Such additional sequences may aid with expression and/or purification. A histidine tag preferably consists of six histidine residues. The histidine tag is preferably linked to the C terminus by a linker, which is typically a short sequence of amino acids, such as 3-5 amino acids. The linker typically consists predominantly of glycine and serine residues, and may preferably include the sequence GSG. For example GSG and GSGLE (SEQ ID NO: 61) are suitable linkers.

In summary therefore, a polypeptide of the invention is a polypeptide having O-glycoprotein binding activity but lacking or having reduced O-glycoprotein-specific endoprotease activity which comprises:
  (a) an amino acid sequence of SEQ ID NO: 5 or SEQ ID NO: 20;
  (b) an amino acid sequence which is at least 85% identical to the amino acid sequence of SEQ ID NO: 5 or SEQ ID NO: 20;
  (c) an amino acid sequence which is a fragment of the sequence of SEQ ID NO: 5 or SEQ ID NO: 20, or a fragment of an amino acid which is 85% identical to the amino acid sequence of SEQ ID NO: 5 or SEQ ID NO: 20;
  optionally wherein said polypeptide includes an additional methionine at the N terminus and/or a histidine tag at the C terminus, which tag may be joined to the C terminus by a linker.

The sequence of an exemplary polypeptide of the invention is provided as SEQ ID NO: 6. The polypeptide may comprise or consist of the amino acid sequence of SEQ ID NO: 6. An exemplary polynucleotide sequence encoding this polypeptide is shown in SEQ ID NO: 7. The sequence of another exemplary polypeptide of the invention is provided as SEQ ID NO: 21. The polypeptide may comprise or consist of the amino acid sequence of SEQ ID NO: 21. An exemplary polynucleotide sequence encoding this polypeptide is shown in SEQ ID NO: 22.

The said polypeptide is preferably provided in immobilised form, such as on agarose or sepharose, optionally provided as a resin.

Additional polypeptides of the invention having O-glycoprotein binding activity but lacking or having reduced O-glycoprotein-specific endoprotease activity may be produced by disrupting the metalloprotease domain motif HEbbH (SEQ ID NO: 59) or abxHEbbHbc (SEQ ID NO: 60) in any other polypeptide having O-glycoprotein-specific endoprotease activity which comprises such a motif. In methods described herein for use of a polypeptide of the invention lacking or having reduced endoprotease activity, references to the polypeptide of the invention include such polypeptides. Disruption of the said motif is preferably achieved as described above such that:
  (a) H in the first position is replaced with an alternative amino acid, preferably A or G; and/or
  (b) E in the second position is replaced with an uncharged amino acid, optionally A, C, F, G, I, L, M, N, P, Q, S, T, V or W, preferably A or G; and/or
  (c) H in the fifth position is replaced with an alternative amino acid, preferably A or G
wherein b in the said motif is an uncharged amino acid, optionally A, C, F, G, I, L, M, N, P, Q, S, T, V or W.

The said polypeptide may therefore be described as comprising the motif xbbbx (SEQ ID NO: 63), wherein:
  (a) x is preferably any amino acid except H, and is preferably A or G; and/or
  (b) b is an uncharged amino acid, optionally A, C, F, G, I, L, M, N, P, Q, S, T, V or W, preferably A or G;

Other polypeptides having O-glycoprotein-specific endoprotease activity and which may be disrupted in this way are described above as having been identified in *Pseudomonas aeruginosa* PAO1, *Bacteroides thetaiotaomicron* VPI-5482, and *Clostridium perfringens* (see three peptidases described in Noach et al; PNAS 2017, pE679-688 and supporting appendices, specifically Materials and Methods for Cloning, Protein Expression and Purification). The full length sequences of these polypeptides are provided as SEQ ID NOs: 32, 33 and 34. Corresponding mature sequences (e.g. with signal and other sequences removed) are provided as SEQ ID NOs: 26, 27 and 28. Versions of these sequences optimised for expression in *E. coli* and subsequent purification (by inclusion of an additional methionine at the N terminus and a histidine tag at the C terminus) are provided as SEQ ID NO: 29, 30 and 31. Each of SEQ ID NOs: 26 to 34 therefore includes a metalloprotease domain having the motif HEbbH (SEQ ID NO: 59) which may be disrupted to produce a motif xbbbx (SEQ ID NO: 63) as described above, to product an additional polypeptide of the invention. Versions of SEQ ID NOs: 26, 27 and 28 in which the HEbbH (SEQ ID NO: 59) motif has been so disrupted are provided as SEQ ID NOs: 35, 36 and 37. Versions of these sequences optimised for expression in *E. coli* and subsequent purification (by inclusion of an additional methionine at the N terminus and a histidine tag at the C terminus) are provided as SEQ ID NO: 38, 39, and 40. Polypeptides of the invention which lack or have reduced O-glycoprotein-specific endoprotease activity may comprises, consist essentially, or consist of any one of SEQ ID NOs: 35, 36, 37, 38, 39 or 40.

Methods Using LS Mutant Lacking or Having Reduced Endoprotease Activity

The present invention also provides a method of binding to an O-glycan, wherein the method comprises contacting a sample comprising the O-glycan with a polypeptide of the invention capable of binding to an O-glycan and which lacks or has reduced endoprotease activity specific for O-glycosylated proteins. The method optionally further includes determining whether or not an O-glycan has been bound and/or separating the O-glycan and any linked glycoprotein from the resulting mixture.

The present invention may also include a method for assessing the glycosylation status of a protein, comprising contacting a sample of said with a polypeptide of the invention capable of binding to an O-glycan and which lacks or has reduced endoprotease activity specific for O-glycosylated proteins, and determining whether or not the protein is bound by the said polypeptide.

The present invention may also include a method for detecting O-linked glycoproteins in a sample, wherein the method comprises contacting said sample with a polypeptide of the invention capable of binding to an O-glycan and which lacks or has reduced endoprotease activity specific for O-glycosylated proteins, to thereby allow formation of an O-linked glycoprotein-polypeptide complex. The method may optionally include separating said polypeptide from the contacted sample and determining whether the separated polypeptide is bound to the O-linked glycoproteins, thereby determining the presence or absence of O-linked glycoproteins in the sample can thereby be determined. The method may also be used for isolating an O-glycan or O-linked glycoprotein from a sample containing O-glycans or O-linked glycoproteins.

In such methods, a sample is contacted with a polypeptide of the invention under conditions suitable for the polypeptide to interact with any O-glycan or proteins in the sample and for binding to occur. Suitable conditions include incubation with a polypeptide of the invention for at least 20 minutes, 30 minutes, 40 minutes, 50 minutes, 60 minutes, 70 minutes, 80 minutes, 90 minutes or 120 minutes, 3 hours, 5 hours, 10 hours, or overnight, typically with mixing e.g. end-over-end mixing. Incubation preferably takes place at room temperature, more preferably at approximately 20° C., 25° C., 30° C., 35° C., 40° C. or 45° C., and most preferably at approximately 37° C. The methods described above may be carried out under any suitable pH. Suitable pH values include, for example, a pH of around 3.0, 3.5, 4, 4.5, 5, 5.5, 6, 6.5, 7, 7.5, 8, 8.5, 9 or 9.5. Preferred pH for the activity of a polypeptide of the invention is in the range 5.6 to 6.8. The method may be conducted in any suitable buffer, such as tris buffered saline (TBS) or phosphate buffered saline (PBS). The approximate ratio of the polypeptide of the invention to the protein content of the sample may be 1:1, 2:1, 4:1, 6:1, 10:1, 15:1, 20:1, 1:2, 1:4, or 1:6, 1:10, 1:15, 1:20, 1:40, 1:100, 1:200 or 1:400 (wt:wt). A preferred ratio is 1:1 (wt:wt). Higher proportions of polypeptide to substrate may be beneficial if a shorter reaction time is required, or if the O-glycoprotein is heavily sialylated. Alternatively an earlier or simultaneous sialidase incubation step may be used to reduce sialic acid content, as is discussed in more detail below. The substrate is typically present at a concentration of around 0.01 mg/ml to 10 mg/ml, preferably around 0.1 mg/ml to 10 mg/ml, around 0.01 mg/ml to 2 mg/ml, or around 0.1 mg/ml to 2 mg/ml.

The detection or analysis of the sample to determine whether an O-glycan or O-linked glycoprotein has been bound may be assessed by any suitable analytical method, such as but not limited to mass spectrometry, HPLC, affinity chromatography, gel electrophoresis, SDS-PAGE, ELISA, lectin blotting, spectrometry, capillary electrophoresis and other standard laboratory techniques for the analysis of proteins. For example, the molecular weight of the polypeptide may be analysed. The polypeptide of the invention bound to an O-glycan or O-linked glycoprotein will have a higher molecular weight than a polypeptide not bound to an O-glycan or O-linked glycoprotein.

Separation of the bound O-glycan or O-linked glycoprotein and the polypeptide of the invention may be carried out by any suitable separation means. For example, the separation means may comprise a population of magnetic nanoparticles. These may be separated from a sample using magnetic field separation, preferably high-gradient magnetic field separation. Examples of reagents or separating means are populations of magnetic particles capable of binding to the polypeptide of the invention. For example, where the polypeptide is derivatised with a histidine tag, the magnetic particles contain on their surface chelating groups which carry a nickel, copper or zinc ion. Alternatively, where the polypeptide is derivatised with a biotin tag, the magnetic particles contain on their surface streptavidin.

The separation means may also comprise a solid support to which the polypeptide of the invention is immobilised. Examples of solid supports include those described in previous sections, and may include agarose or sepharose resins, cross-linked agarose beads, or similar. The support may be used as the matrix in an affinity chromatography column. Alternatively the solid support may comprise a suitable silica-based material or polystyrene, or a plastic container such as a microtiter plate or equivalent, to which the polypeptide of the invention can be directly adsorbed.

Alternative separation means include reagents comprising antibodies specific to the polypeptide of the invention, which may be generated by methods standard in the art. Antibodies in this sense include a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')2 or Fv fragment. If more than one antibody is present, the antibodies preferably have different non-overlapping determinants such that they may bind to the polypeptide of the invention simultaneously. The antibody may be bound to a solid support or may be labeled or conjugated to another chemical group or molecule to assist with their separation or isolation. For example, typical chemical groups include fluorescent labels such as Fluorescein (FITC) or Phycoerythrin (PE), or tags such as biotin.

Other suitable means of separation include elution of the protein from the (typically immobilised) polypeptide by contacting the polypeptide from the contacted sample with a suitable elution buffer. The choice of elution buffer may depend on the acid-sensitivity of the protein. Preferred elution buffers may comprise high molar concentrations of urea (typically at least 5, 6, 7 or most preferably at least 8M) or high concentrations of a detergent (typically at least around 1%, 5% or 10%). Suitable detergents include Nonidet P40, Triton X-100, Tween 20, CHAPS, sodium deoxycholate, and RapiGest SF surfactant, but Sodium dodecyl sulphate (SDS) is preferred. High molar urea is preferred over detergent since downstream procedures are more likely to be sensitive to the presence of detergent.

Another preferred elution buffer comprises a suitable concentration of a polypeptide of the invention which has O-glycoprotein endoprotease activity, e.g a polypeptide of SEQ ID NO: 1. Cleavage at the O-glycan by this polypeptide will release bound O-glycoproteins, thus obviating the need for Urea or detergent-based elution.

Preferred methods of elution of O-glycoproteins from immobilised polypeptides of the invention are demonstrated in the Examples.

The sample in any of the above methods may be a sample taken from a patient, preferably a human patient. The results obtained may be used for a diagnostic purpose, for example to detect the presence of cancers which involve O-linked glycosylation. Such a use may involve comparison of the results obtained from the patient sample to those obtained using a sample obtained from a healthy control.

In any method of the invention, the polypeptide can be used in combination with another enzyme such as a protease or glycosidase. The additional protease or glycosidase will typically further digest the substrate proteins or glycans, which may permit easier or more detailed analysis of the products.

For example, the polypeptide of the invention may be used in combination with an agent to remove sialic acid. Said agent may preferably be a sialidase enzyme or a mixture of such enzymes as described in the section above. The invention also provides a composition (in lyophilised or solution form) comprising a polypeptide of the invention and Am1757 or a mixture of Am1757 and Am0707. The invention also provides a kit comprising a polypeptide of the invention in a separate container from Am1757 or a mixture of Am1757 and Am0707, with instructions for the combined use of the different enzymes.

As another example, in any of the methods described herein, the sample may be incubated with an N-glycosidase prior to, at the same time as, or after contacting the sample with the polypeptide of the invention, to remove N-glycans from target proteins. An exemplary N-glycosidase is PNGaseF. Other N-glycosidases that may be used when the sample includes immunoglobulins are EndoS (see SEQ ID NO: 1 of WO2008071418) or EndoS2 (may be referred to as EndoS49—see SEQ ID NO: 1 of WO2013037824). Each of these enzymes removes the N-linked glycoprotein from Asn-297 of IgG1. The sample may be contacted with an N-glycosidase and a sialidase (or mixture thereof) in addition to the polypeptide of the invention. In such a method, the sialidase (or mixture) may be applied first, prior to simultaneous addition of the N-glycosidase and the polypeptide of the invention.

As another example, in any of the methods described herein, the sample may be incubated with a protease prior to, at the same time as, or after contacting the sample with the polypeptide of the invention, to further digest the target protein. Suitable general proteases include trypsin, chymotrypsin, Lys-C, Asp-N, Glu-C, Arg-C or similar endoproteases, or Arg-gingipain (RgpB) of *Porphyromonas gingivalis*.

If the sample includes immunoglobulins, immunoglobulin proteases may be used such as SpeB (see sequence in WO2015040125), Immunoglobulin G-degrading enzyme of *S. pyogenes* (IdeS—see sequence in WO2015040125), Immunoglobulin G-degrading enzyme of *S. equi* subspecies *zooepidemicus* (IdeZ), Lys-gingipain (Kgp) of *Porphyromonas gingivalis*, and Immunoglobulin G-degrading Enzyme of *S. agalactiae* (IgdE$_{agalactiae}$—see SEQ ID NO: 3 of PCT/EP2017/052463). Use of any combination of these proteases in a method of the present invention may assist with analysis of the substrate protein or glycan, for example using mass spectrometry.

As another example, in any of the methods described herein, the isolated O-linked glycoprotein may be incubated with an O-glycosidase to remove the O-glycans prior to further analysis by any suitable method. Suitable O-glycosidases may be obtained from a strain of *Enterococcus faecalis, Streptococcus oralis*, or *Bifidobacterium bifidum*, preferably *Enterococcus faecalis* or *Streptococcus oralis*, most preferably *Streptococcus oralis*. The sequence of an exemplary O-glycosidase from *Streptococcus oralis* is provided as SEQ ID NO: 15.

The following Examples illustrate the invention:

Example 1

Materials and Methods
Mutagenesis of LS

Site-directed mutagenesis using Q5 (NEB) was performed according to manufacturer's instructions (annealing temperature 68° C., 3 min elongation) using primers E206A_fwd 5'-ATGGCGCACGC GCTGGGCCACG-3' (SEQ ID NO: 16) and 5'-GCCACCGTAC CATTTCGTC-3' (rev) (SEQ ID NO: 17); thus changing a glutamic acid to an alanine in an Amuc1119 gene from *Akkermansia muciniphila* to create the mutant, Amuc1119$_{E206A}$ (LS$_{E206A}$). The construct was transformed into DH5α *E. coli*, isolated and verified using sequencing (GATC Biotech).

Recombinant Expression of LS and LS$_{E206A}$

The gene Amuc1119 from *Akkermansia muciniphila* ATCC BAA-835, and a mutant, Amuc1119$_{E206A}$ (Amuc1119—LS; Amuc1119$_{E206A}$—LS$_{E206A}$), were codon optimized for expression in *E. coli* (DNA 2.0) and cloned into an expression vector with a C-terminal 6×His-tag as part of the fusion protein.

The codon-optimized genes were transformed into BL21 (DE3) Star cells. *E. coli* was routinely cultured in LB at 37° C., 180 rpm. In the presence of the plasmid, 50 µg/mL kanamycin was added. After overnight incubation, cultures were diluted 1:20 in fresh LB(kana), and grown until OD$_{620}$~0.7-0.8, after which recombinant protein expression was induced by addition of 1 mM IPTG, and the expression continued for 6 hours before the cells were collected and frozen. Frozen cells were thawed and resolved in His binding buffer (20 mM NaP pH 7.4, 500 mM NaCl, 20 mM imidazole), and sonicated for release of intracellular proteins. Cell debris was removed by centrifugation. Sterile filtered supernatant was affinity purified on a nickel column, and re-buffered to 20 mM Tris-HCl pH 8.0 on a PD-25 column Concentration of the proteins was determined using the Nanodrop, and purity estimated through SDS-PAGE.

Activity Assessment Using Protein Substrate

TNFαR was mixed together with LS at a 2:1 ratio and incubated for 15-60 minutes at 37° C. after which the proteins were separated on a 4-20% Novex gradient SDS-PAGE. The impact of NaCl (0-1 M), divalent cations, EDTA, and pH on LS activity was investigated, and differences in generated hydrolytic fragments measured through densitometric analysis using Gel Doc EZ (BioRad).

Time and Dose Dependency for Activity

TNFαR (0.5 µg) was incubated with varying doses of LS for 15 or 60 minutes at 37° C. in PBS after which the proteins were separated on a 4-20% Novex gradient SDS-PAGE. The intensity of the generated fragments (densitometry) was used for determining optimal dose and time for efficient incubation conditions.

Substrate Specificity

LS was incubated with a variety of N- and O-linked substrates overnight at 37° C. at a ratio of 2:1 (substrate:

enzyme). LS was incubated with EPO (0.3 mg/ml) at a ratio of 50:1 (substrate:enzyme). The proteins were separated and analyzed on 4-20% Novex gradient SDS-PAGE gels.

Immobilization of $LS_{E206A}$ $LS_{E206A}$ was resuspended into a coupling buffer (0.2 M $NaHCO_3$, 0.5 M NaCl pH 8.3), and concentrated to 20 mg/ml. NHS-activated sepharose 4 Fast Flow (GE Healthcare) was prepared for coupling according to manufacturer's instructions (e.g. HCl wash and equilibration in coupling buffer). $LS_{E206A}$ was immobilized by overnight incubation with the sepharose at 4° C., slowly rocking for constant mixing. The sepharose was blocked by addition of 0.1 M Tris pH 8.5, washed with 3 repetitions of 0.1 M Tris pH 8.5/0.1 M NaAc, 0.5 M NaCl pH 5.0, and stored in EtOH until usage.

Binding Affinity of $LS_{E206A}$

Spin columns with 50 µl immobilized $LS_{E206A}$ (e.g. ca 50 µg protein) equilibrated in PBS were incubated with 10 µg glycoprotein pretreated with either a sialidase mix (Am0707:Am1757), or with a combination of sialidases and a *Streptococcus oralis* Endo-α-N-acetyl-galactosaminidase (e.g. an O-glycosidase). The samples were allowed to incubate for 2 h at 37° C. after which the columns were washed with PBS (10 volumes; 100 g, 30 s) and eluted with 0.1 M glycine pH 3.0. Fractions were analyzed on SDS-PAGE.

Mass Spectrometry Analysis

Etanercept (Enbrel®) is clinically approved Fc-fusion protein that binds to TNFα. etanercept contains several O-glycans. In order to test enzymatic cleavage specificities the endoprotease was incubated together with etanercept overnight at 37° C. To simplify mass spectrometric analysis, a second round of enzymatic treatment was done to remove the remaining O-glycans using sialidase and O-glycosidase (overnight, in PBS, 1:40 ratio of all single enzymes). The generated peptides were analyzed by MS/MS after separating the peptides by C18 reversed phase liquid chromatography.

Results

LS is a Putative Metalloprotease

Figure 1:
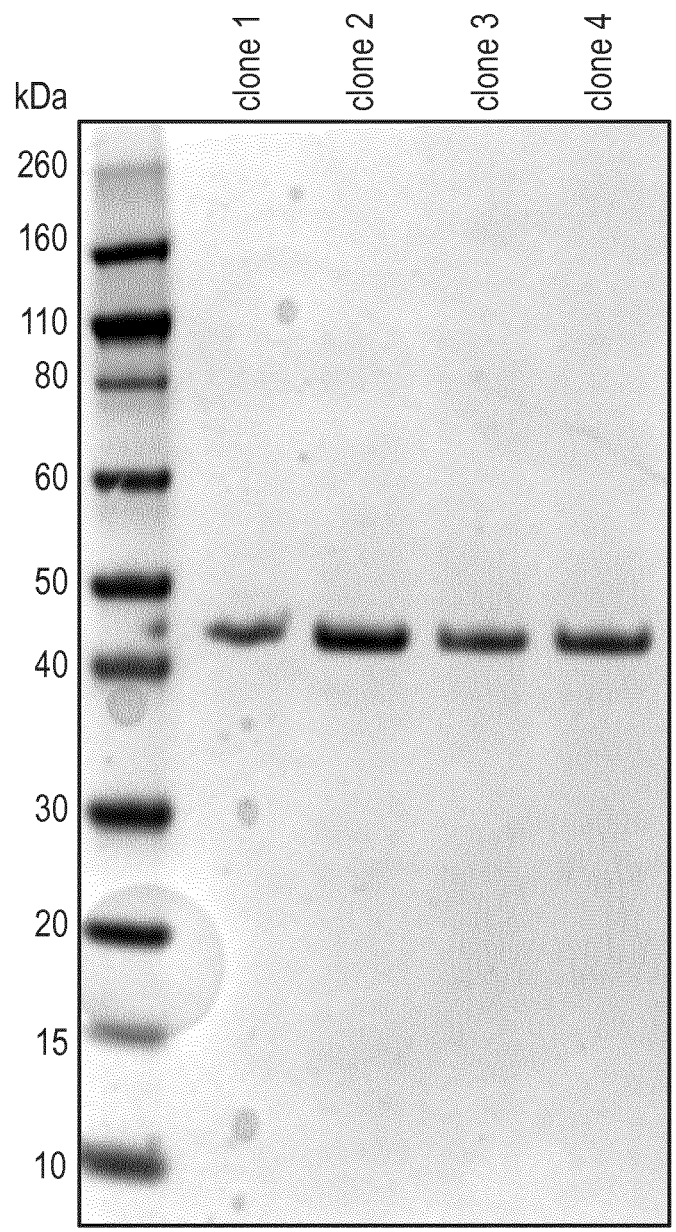
FIG. 1: LS expression and purification. LS was expressed as a fusion protein with a C-terminal His-tag in the pET21

Based on sequence and domains similarity, LS shares homology with several metalloproteases, containing the putative active site sequence GMAHELGHGL (SEQ ID NO: 8), sharing similarity to the general metalloprotease sequence abxHEbbHbc (SEQ ID NO: 60; a=V/T, b=no charge, c=hydrophobic). The histidines are generally involved in substrate binding and $Zn^{2+}$ affinity, while the glutamic acid together with the histidines mediate the electron transfer, and thus the hydrolytic effect. To be able to further characterize the enzyme, we constructed an $LS_{E206A}$ mutant, capable of binding the substrates, but lacking or having reduced hydrolytic capabilities by altering the E to an A. Further modifications (e.g. altering H to A) may be necessary for full inactivity. Both constructs expressed well, and were readily purified using affinity chromatography based on their His-tags (FIG. 1).

LS Specifically Hydrolyses Glycoproteins with O-Glycans

In order to investigate the substrate specificity of LS, the protease was incubated with a diversity of proteins. As shown in FIG. 2, LS was incubated with IgA and Herceptin (trastuzumab). LS was only able to act upon proteins having O-linked glycans, such as IgA. While the presence of terminal sialic acids seemingly partly inhibits the activity of LS, the absence of sialic acids is not a prerequisite for hydrolysis (FIG. 4).

LS can Act Upon O-Linked Glycoproteins Under Diverse Conditions

Figure 3A:
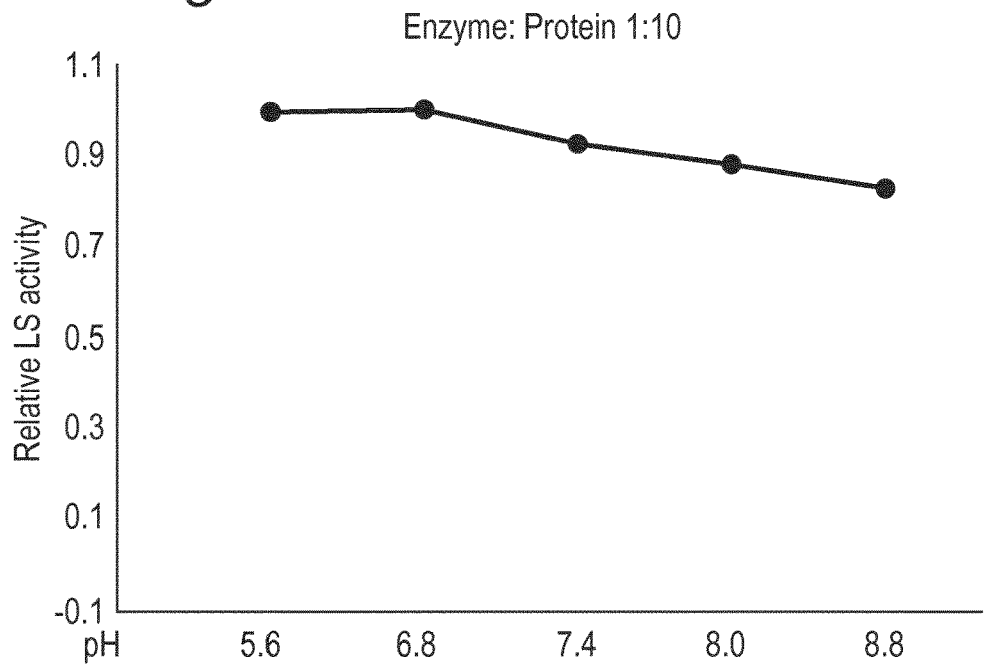
Figure 3B:
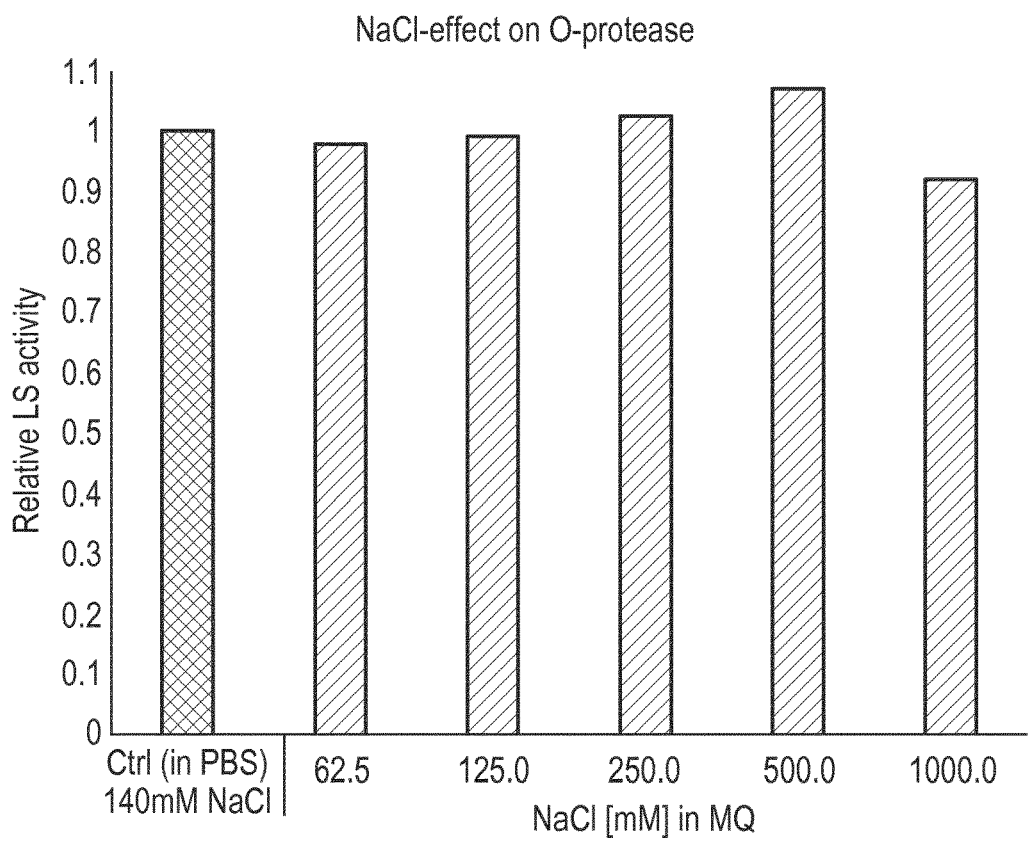
Figure 3C:
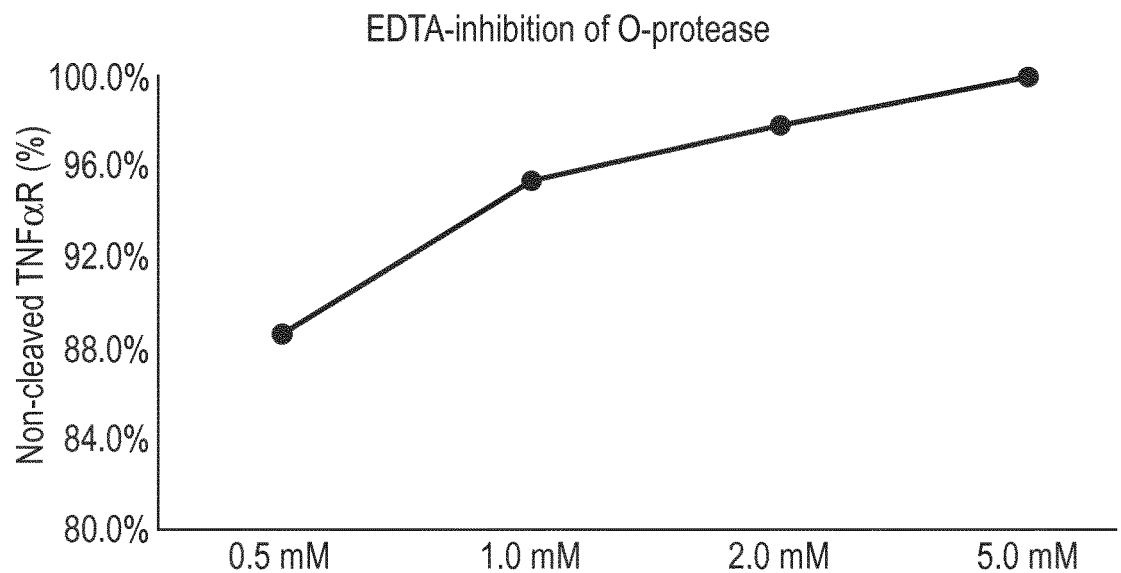
Figure 3D:
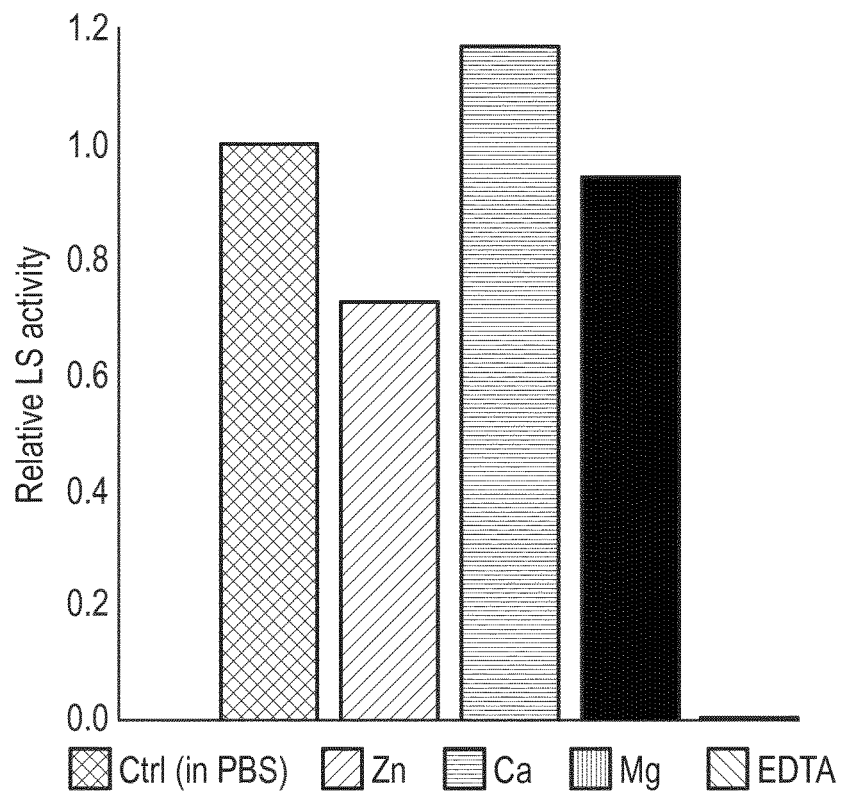

Densitometric analyses of SDS-PAGE gels were carried out to evaluate the enzymatic properties of LS. LS is active under most conditions, with a preference for a slightly acidic pH and a low NaCl concentration (FIG. 3A-B). While both $Mg^{2+}$ and $Ca^{2+}$ ions positively affected the hydrolytic activity of LS, the presence of $Zn^{2+}$ significantly lowered the activity, and EDTA completely abolished it (FIG. 3C-D).

O-Linked Galactosidase Residues are Critical for Activity of LS

Figure 4B:
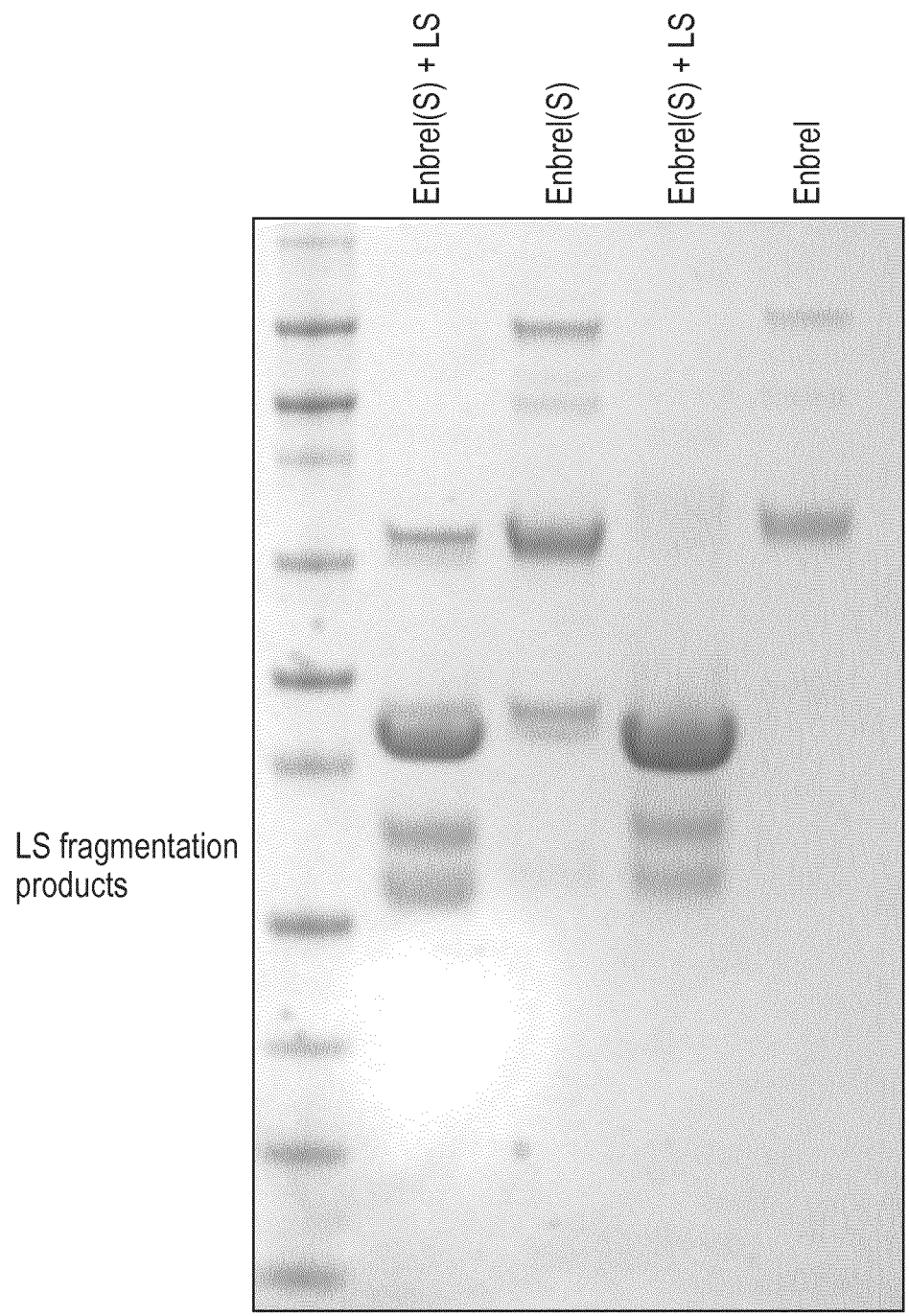

While having an increased activity in the absence of terminal sialic acids, the importance of the other carbohydrates in the O-glycans for the activity of LS was not fully understood. While the activity of LS is significantly increased in the absence of terminal sialic acids, the removal of galactoses completely inhibits the activity of LS (FIG. 4A). Further, the lower activity of LS on sialylated proteins is not due to an inability to hydrolyze the bond in the presence of sialic acids, as demonstrated by the full hydrolysis after overnight incubation (FIG. 4B). The activity of LS fully relies on O-glycans, since removal of N-glycans did not affect the hydrolysis by LS (FIG. 4C).

O-Linked Glycans Direct the Cleavage Site of LS

Having demonstrated that the O-glycan is critical for activity, we next sought to investigate the specific cleavage site of LS. Using mass spectrometry, we were able to demonstrate that LS hydrolyzes the amino bond between the O-glycosylated Ser/Thr and its N-terminal amino acid, regardless of its type (e.g. proline does not seem to inhibit the hydrolysis) (FIG. 5).

Figure 5A:
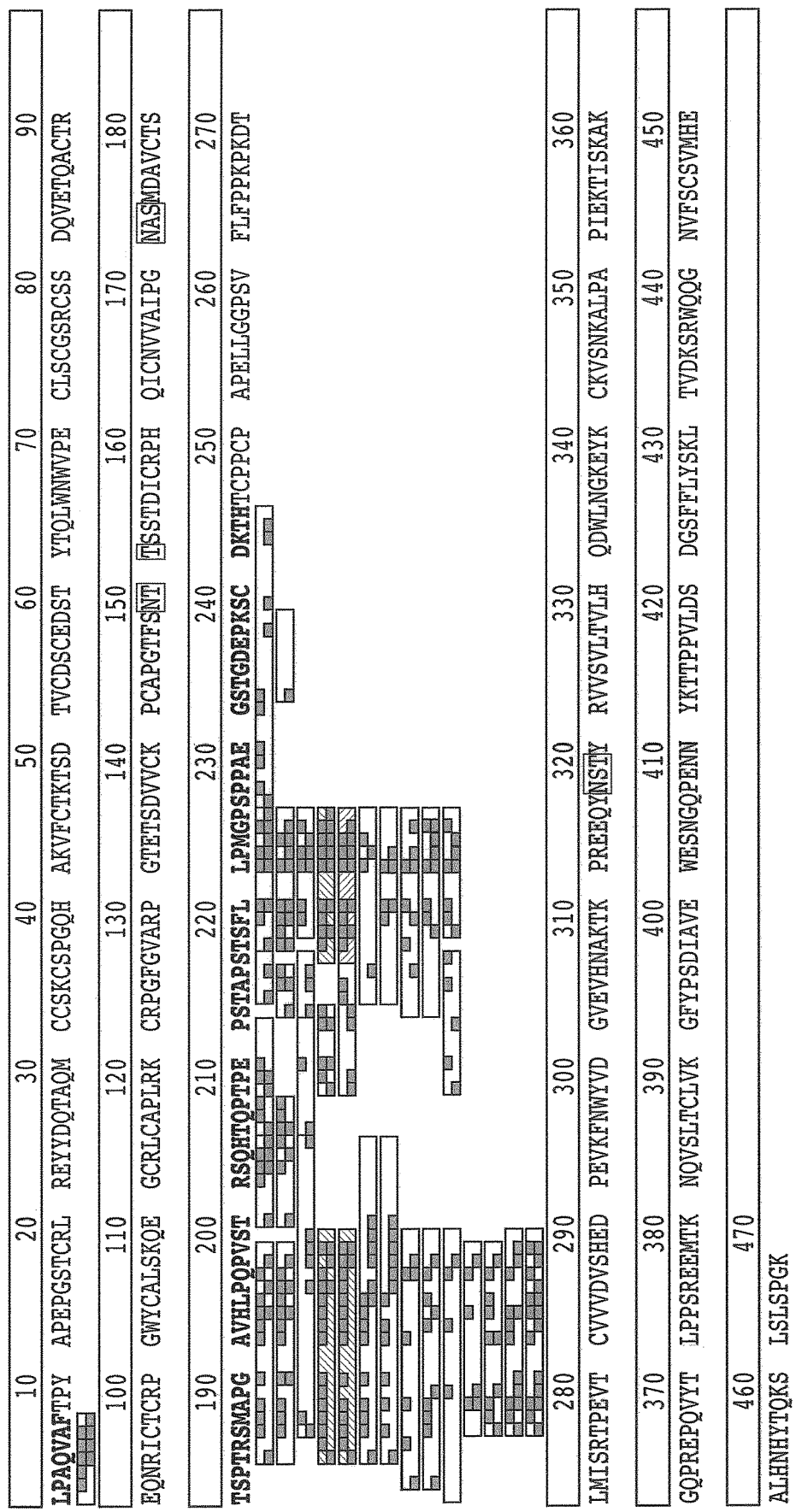

Using etanercept as a model protein due to its high abundance of O-linked glycans, the glycoprotein was treated with LS, after which it was subsequently treated with O-glycosidases to facilitate the mass spec analysis. m/z values generated from the mass spec analysis, in combination with MS/MS data, were fitted to etanercept. All identified peptides had an N-terminal serine or threonine, consistent with LS cleaving just N-terminal of the O-glycans (FIG. 5). The analysis identified peptides both in a directed search (defining S/T hydrolysis in the parameters; FIG. 5A), and in an unbiased approach (FIG. 5B).

A Hydrolytic Inactive Variant of LS Specifically Bind to O-Glycan Containing Proteins With the ability of LS to bind to O-glycans and specifically hydrolyze the amino acid bond next to the glycan (e.g. next to Ser/Thr), we hypothesized that an $E_{206}A$ mutant of LS would lack hydrolytic activity, but retain binding ability. Such a tool would be valuable among others for a) identifying O-linked glycoproteins, b) affinity-purify O-linked glycopeptides for removal or for study, and c) affinity-purify O-glycans.

Figure 6A:
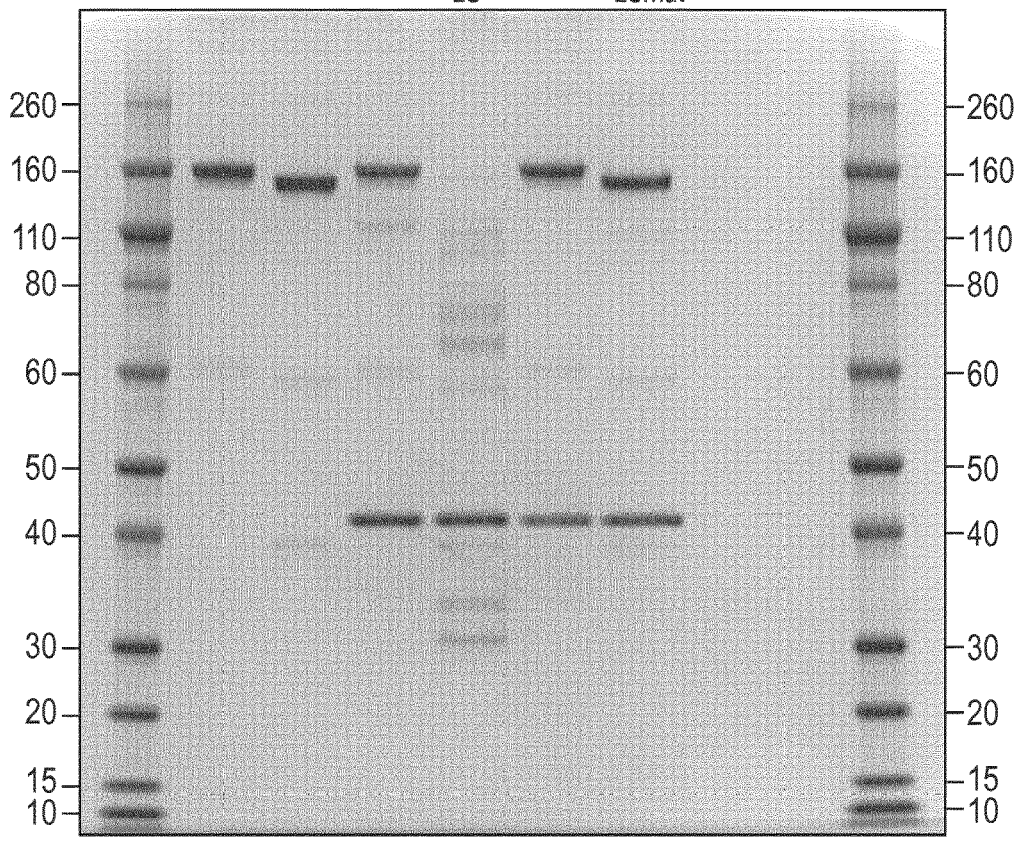

FIG. 6A shows that the mutant LS did not have any detectable hydrolytic activity. While LS was able to hydrolyze etanercept in the presence of sialidase, the LSmut could not hydrolyze etanercept, confirming that the genetic alteration indeed inactivated O-glycoprotease under the conditions tested.

Figure 6B:
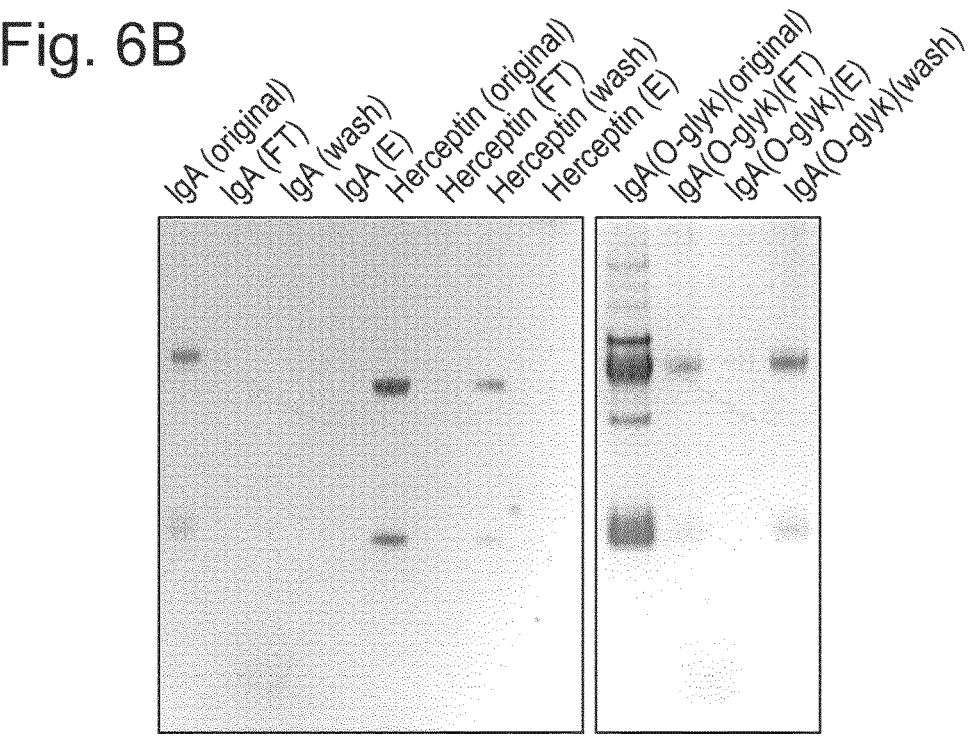

$LS_{E206A}$ was immobilised onto sepharose and added onto spin columns for easier handling. Importantly, the binding of $LS_{E206A}$ to different substrates perfectly correlated with the hydrolytic activity of LS (FIG. 6B). $LS_{E206A}$ (labelled as $LS_{mut}$) demonstrated a specific affinity for O-linked glycoproteins. By immobilizing $LS_{mut}$ on sepharose we were able to affinity purify IgA. However, we were not able to elute the protein, likely due to a strong affinity. Herceptin (trastuzumab), lacking O-glycans, as well as O-glycosidase treated IgA, did not bind to the column, but could be detected in the flowthrough (FT).

2-3 Sialic Bonds are Important to Remove for Full LS Activity

We recently determined that endoprotease activity relied on specific sialic acid bonds, necessitating the removal of both 2-3 and 2-6 linked sialic acids for full effect. To determine the individual role of specific sialic acid bonds for the activity of LS, we incubated Enbrel with different sialidases in combination with LS for 30 min-20 h. Removal of 2-3 bonds seemed sufficient for hydrolysis by LS (FIG. 7).

LS Cleaves Erythropoietin (EPO)

EPO was treated with PNGaseF, a sialidase (Smix, comprises Am0707 and Am1757) and/or an O-glycosidase and incubated with LS.

The resulting products were then analysed by SDS-PAGE and Coomassie blue staining, as well as RPLC and mass spectrometry. Results of SDS-PAGE are shown in FIG. 9A, which shows that LS cleaves EPO both when sialic acids have been removed and when they are intact. Furthermore, LS also digests EPO where the N-glycans have been removed with PNGaseF, confirming that LS activity is not affected by N-glycan removal. However, LS did not cleave EPO when the O-glycans were removed with O-glycosidase, showing that O-glycan is needed for LS to cleave a protein. Equivalent results were observed at ratios of 10:1, 5:1 and 2:1 (substrate:enzyme) (data not shown).

The sample mixtures following incubation with PNGaseF, Smix and LS were separated by Reverse Phase Liquid Chromatography and analyzed by ESI mass spectrometry for identification of reaction products after enzymatic treatment.

FIG. 9B shows an UV chromatogram from the RPLC. As expected, given that EPO has only one suggested O-glycan position (see predicted position in SEQ ID NO: 14 below), the chromatogram shows 2 peaks which correspond to the 2 fragments resulting from cleavage by LS.

These fragments were further analysed by MS (see FIGS. 9C and D) and identified as follows:
SAAPLRTITADTFRKLFRVYSNFLRGKLKLYT-GEACRTGD (SEQ ID NO: 53; Mass=4900.5868 Da—corresponds to the sequence C terminal to the cleavage point and thus includes the O-glycan still linked to the N terminal serine); and
APPRLICDSRVLERYLLEAKEAEDITTG-CAEHCSLDENITVPDTKVDFYAWKRMEV GQQAVEVWQGLALLSEAVLRGQALLVNSSQPWE-PLQLHVDKAVSGLRSLTTLLR ALGAQKEAISPPDAA (SEQ ID NO: 54; Mass=13714.1199 Da, corresponds to the sequence N terminal to the cleavage point).

Therefore the combined use of PNGaseF, sialidase mix and LS permitted the isolation and precise identification of the O-glycan-bearing serine in EPO. Methods of this type are applicable to any O-glycoprotein and permit the rapid identification of O-glycan attachment positions.

Example 2

Introduction

The LSE206A mutant described in Example 1 incorporates a site-directed mutation of the active site of LS (abxHEbbHbc (SEQ ID NO: 60) to abxHAbbHbc (SEQ ID NO: 65)), removing the electron transfer capacity of the enzymatic cleft. As is explained further below, upon further stress testing it was found that although this change reduced O-glycoprotease activity relative to the wild-type sequence it did not completely eliminate it. Accordingly the inventors have developed and characterized another mutant incorporating an additional substitution in the enzymatic cleft. Specifically, a His residue important in the orientation of the co-factor zinc ion was replaced with an Ala. The resulting double-mutant is referred to as H205A/E206A (abxHEbbHbc (SEQ ID NO: 60) to abxAAbbHbc (SEQ ID NO: 66)).

2.1 Production of the Double-Mutant

Site-directed mutagenesis using standard protocols (e.g. as in Example 1) was used to change both a histidine and a glutamic acid to alanine relative to the Amuc1119 gene of *Akkermansia muciniphila*, to create the double mutant, Amuc1119H205A/E206A (LS$_{H205A/E206A}$) The construct was transformed into *E. coli*, isolated and verified using sequencing as in Example 1. Expression in *E. coli* was conducted as described in Example 1. The sequence of the expressed protein is provided as SEQ ID NO: 21.

2.2 Characterization of the Double-Mutant 2.2.1 Double Mutant Fully Inactivates the Activity of LS As shown in Example 1, the single mutant LSE206A was seen to be inactive given its inability to hydrolyze an O-glycoprotein in 2 hours. However, in a stress test it was found that O-glycoprotease activity was not completely abolished, but was rather only reduced in that some activity was observed at higher ratios of enzyme: O-glycoprotein and longer incubation times.

Figure 10A:
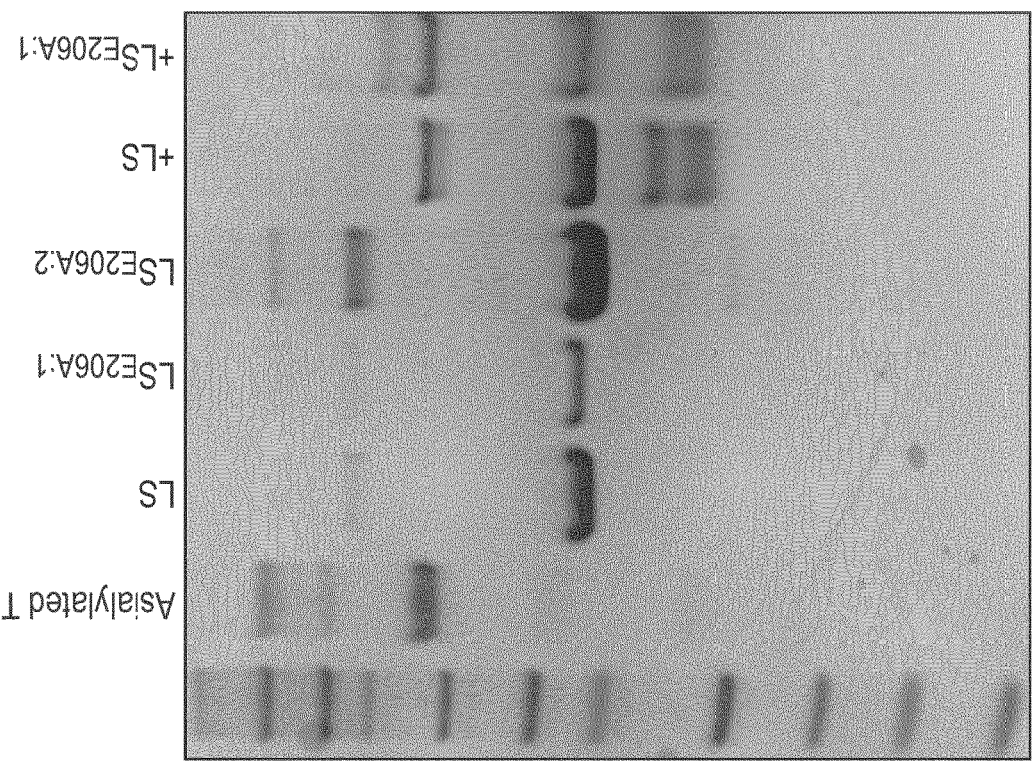

Incubation for 24 hours at a 1:1 (wt:wt) ratio for LSE206A:asialylated O-glycoprotein resulted in a significant hydrolysis of the substrate, though not to the same extent as wild type LS (FIG. 10A). By contrast, the double-mutant LSH205A/E206A did not produce any evidence of hydrolysis even at 15:1 (wt:wt) ratios for the enzyme: O-glycoprotein after overnight incubation (FIG. 10B), suggesting that the enzyme was completely inactive with the addition of the second mutation.

2.2.2 Double Mutant Specifically Binds O-Glycoproteins

To assess binding to different proteins, immobilized LSH205A/E206A (50 μl resin) (prepared using the same protocol as Example 1) was equilibrated in PBS, after which 50 μg of different samples of proteins were added in a concentration of 0.5 mg/mL and incubated with end-over-end rotation for 2 hours at room temperature. The flow-through was collected through centrifugation (200 g, 1 min) and the resin washed 3× with 200 μl PBS. Bound proteins were eluted by two sequential 5 minutes incubations with 50 μl 8 M Urea followed by centrifugation (1000 g, 1 min). All samples were loaded in equal volumes. Starting/loading material, flowthrough, and eluate were assessed by SDS-PAGE.

In the first experiment (see FIG. 11A), glycosylated or non-glycosylated proteins were pretreated with either a sialidase mix (Am0707:Am1757), or with a combination of the sialidase mix and a *Streptococcus oralis* Endo-α-N-acetyl-galactosaminidase (e.g. an O-glycosidase) before being incubated with the resin, washed, and eluted. Pretreatment of the samples (Sialidase mixture+/−O-glycosidase) was done in accordance with the manufacturer's instructions. Only proteins with O-glycans bound to the resin, with an increased affinity in the absence of sialic acids. The presence of O-glycans was imperative for any binding to take place, as shown by the lack of interaction after treatment with O-glycosidase.

In the second experiment (see FIG. 11B), a mix of N-glycosylated, O-glycosylated and non-glycosylated proteins was incubated with LS double mutant resin. Only O-glycosylated proteins (TNFαR and ApoE) were bound to the matrix and eluted with 8 M urea. N-glycosylated (aflibercept, AGP (alpha-1-acid glycoprotein), Fc domain of IgG (IgG Fc) and non-glycosylated (BSA) did not bind to the LS double mutant resin and were found in the flow through. Thus the double mutant resin specifically binds to only O-glycosylated proteins when a sample contains a mixture of N-, O- and non-glycosylated proteins.

In the third experiment (see FIG. 11C), a mix of N-glycosylated and non-glycosylated proteins was incubated with LS double mutant resin. There was no non-specific binding even in the absence of possible competition from O-glycoproteins (none are present). No proteins were found in the eluate. Thus the double mutant resin does not bind to proteins lacking O-glycans.

Figure 12A:
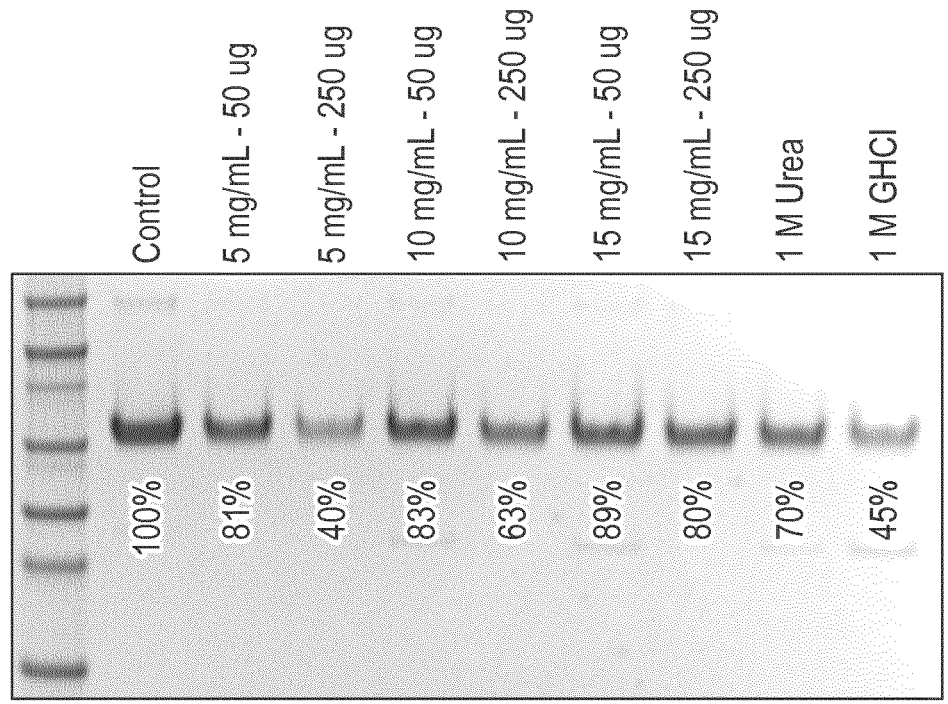
Figure 12B:
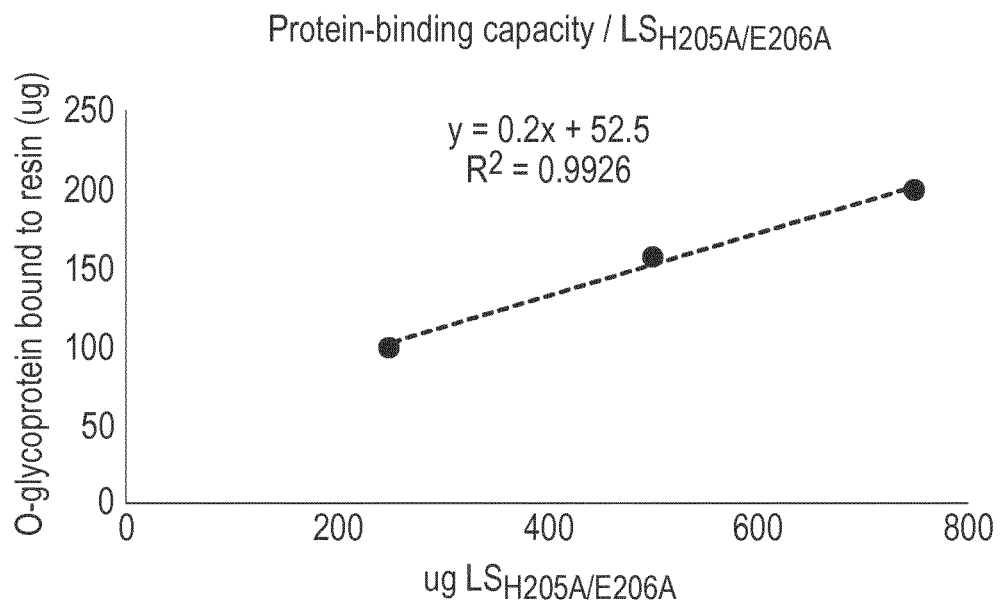

2.2.3 Double Mutant can be Immobilized on Resin at Different Concentrations to Enhance Capacity To investigate the ability to improve the capacity of the immobilized double-mutant resin to bind more O-glycosylated proteins, different concentrations of double mutant (5-15 mg/mL) were used during immobilisation on resin. A representative gel is shown in FIG. 12A. The % shown is the level of binding relative to positive control and was determined by densitometry analysis of the gel. The results are shown in the graph in FIG. 12B. A dose-dependent increase in capacity with higher O-glycoprotein binding capacity was seen when using a higher concentration of double mutant during immobilization. Further experiments continued using 15 mg/mL of immobilized double mutant. Further, a high degree of O-glycoprotein binding was maintained even in the presence of 1 M Urea and 1 M GHCl, even though the latter significantly reduced binding efficiency.

2.2.4 the Affinity Purification Ability of the Double Mutant is ~0.3 mg Glycoprotein/mL Resin In order to specifically investigate the ability of the double-mutant resin to affinity purify O-glycoproteins, as well as the impact of sample concentration on this ability, different quantities and concentrations of asialylated etanercept were added to the resin. An individual column (containing 50 µl of double mutant resin) had a capacity of binding around 150 µg O-glycoprotein, i.e. 3 mg O-glycoprotein/mL resin). FIG. 13 shows a representative gel.

2.2.5 the Binding of O-Glycoproteins to Double-Mutant is not Significantly Affected by Ionic Strength or Buffer Volume/Type, and Works Over a Broad pH Range Sample proteins were allowed to bind to double-mutant resin for 2 hours at room temperature with end-over-end rotation under a range of different conditions to test the effect of ionic strength, buffer volume/type and pH on the binding ability of the resin. In each case, the resin was then washed three times with its respective binding buffer (350 µl) and then eluted with the addition of 8 M Urea (50 µl, 5 min incubation; 2 repeats). All samples were then analysed by SDS-PAGE.

In a first experiment (see FIG. 14A), to investigate the stability of the interaction in buffers with varying ionic strength, the sample consisted of asialylated etanercept, which was incubated with double-mutant-resin in 0-4 M NaCl, as well as performing all washing steps with the respective concentration of NaCl. Addition of NaCl did not significantly affect the binding of asialylated etanercept.

In a second experiment (see FIG. 14B), the sample consisted of asialylated etanercept in a range of different volumes of PBS. Wash steps used PBS. Varying the substrate volume between 100-300 µl did not affect the efficiency significantly.

In a third experiment (see FIGS. 14C and D), the sample consisted of asialylated etanercept and BSA in different buffers (100 mM sodium acetate, 50 mM sodium phosphate and 50 mM Tris) at different pHs (pH 4-9). Wash steps used matching buffers. pH 6-8 was found to work best whereas pH 4 did not work at all and pH 9 slightly less efficiently than pH 8. BSA, which does not contain any O-glycans, did not bind to the resin under any of the binding conditions.

2.2.6 Urea and SDS can Elute Affinity-Bound O-Glycoproteins

Figure 15A:
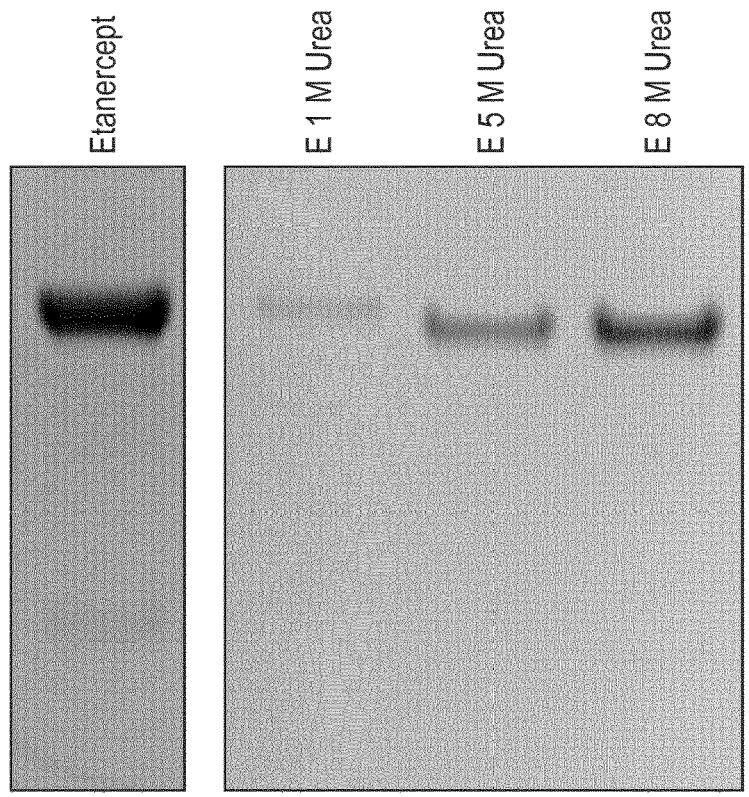
Figure 15B:
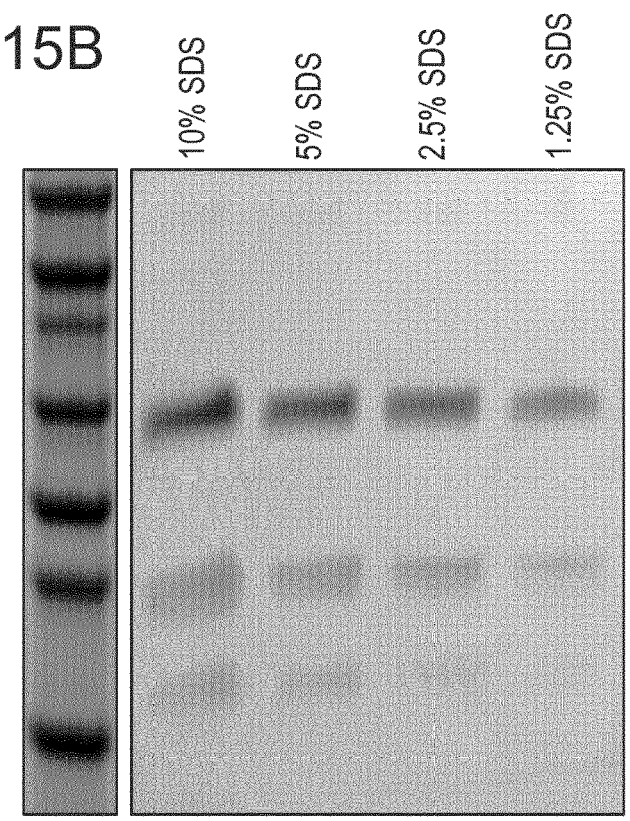

Based on the high affinity between the double mutant and its O-glycoprotein substrate, the inventors investigated different means to elute the bound protein from the resin, not based on ionic strength. Urea had a dose dependent elution, with close to 100% elution with the usage of 8 M Urea (FIG. 15A). High concentrations of SDS (eg 5-10%) also eluted most of the bound protein (FIG. 15B). However, since many downstream applications are sensitive to the presence of detergents, use of high levels Urea is likely to be of more practical utility for non-enzymatic release of bound proteins/peptides.

2.2.7 Wildtype LS can be Used to Elute Double-Mutant-Bound O-Glycoproteins

The inventors speculated that the addition of LS to double-mutant-bound proteins may result in a release thereof, and thus not necessitate the addition of urea for elution. Both abatacept and etanercept could be hydrolyzed and eluted from the double-mutant-resin by LS in 6 h but had a slightly more complete elution after 24 h (FIG. 16A). Addition of urea afterwards showed that very little O-glycoprotein remained attached to the affinity matrix, demonstrating that the LS elution strategy was highly efficient.

Etanercept eluted with LS was also subjected to mass spec analysis (LC/MS and MS/MS). Identified peptides (FIG. 16B.1) were consistent with those generated in a LS digestion of etanercept (FIG. 16B.2). Additional MS data from this experiment is shown in the following table:

| Row | OK | Cmpd. | m/z meas. | Mr calc. | z | Δ m/z [ppm] | RMS90 [ppm] |
|---|---|---|---|---|---|---|---|
| 1 | TRUE | 1901 | 392.18578 | 782.3545447 | 2 | 3.139355727 | 39.5628229 |
| 2 | TRUE | 1240 | 460.24964 | 459.2441464 | 1 | -3.873732048 | 6.970140396 |
| 3 | TRUE | 2395 | 593.93513 | 1778.79071 | 3 | -4.012614897 | 37.85883109 |
| 4 | TRUE | 1019 | 598.28693 | 2986.418959 | 5 | -6.916951725 | 23.18052633 |
| 5 | TRUE | 1388 | 642.65448 | 1924.956428 | 3 | -7.685331295 | 12.36799202 |
| 6 | TRUE | 2169 | 672.31437 | 1342.621401 | 2 | -5.364932116 | 7.267732308 |
| 7 | TRUE | 2169 | 672.31437 | 1342.621401 | 2 | -5.364932116 | 7.267732308 |
| 8 | TRUE | 1666 | 695.85597 | 1389.70747 | 2 | -7.245075789 | 13.08730439 |
| 9 | TRUE | 1887 | 745.4213 | 744.4170254 | 1 | -4.027105599 | 40.39538537 |
| 10 | TRUE | 2308 | 846.8813 | 1691.758682 | 2 | -6.278826744 | 10.77131727 |
| 11 | TRUE | 1636 | 878.42107 | 1754.839667 | 2 | -6.875687278 | 9.154478723 |
| 12 | TRUE | 2298 | 895.05953 | 2682.161633 | 3 | -1.814552481 | 8.770132859 |
| 13 | TRUE | 2048 | 898.39499 | 1794.785625 | 2 | -5.675814522 | 10.69492018 |
| 14 | TRUE | 2319 | 924.06736 | 2769.193661 | 3 | -4.837599076 | 9.79089835 |
| 15 | TRUE | 2299 | 1072.96596 | 2143.922906 | 2 | -2.58127791 | 10.42173435 |

-continued

| | | | | | | | |
|---|---|---|---|---|---|---|---|
| 16 | TRUE | 1315 | 1189.55981 | 2377.120652 | 2 | -6.550738429 | 9.551870744 |
| 17 | TRUE | 1325 | 1189.55981 | 2377.120652 | 2 | -6.550738429 | 9.851027886 |
| 18 | TRUE | 2377 | 1219.18407 | 3654.552682 | 3 | -6.097374291 | 9.225746116 |

| Row | Int. | Scores | Range |
|---|---|---|---|
| 1 | 100030 | 20.3 (D.metascore:20.3,D.btScore:4.0,D.fragCov:50.0,D.intCov:8.2) | 457-459 |
| 2 | 29654 | 23.0 (D.metascore:23.0,D.btScore:0.0,D.fragCov:12.5,D.intCov:42.3) | 182-185 |
| 3 | 30476 | 31.2 (D.metascore:31.2,D.btScore:127.0,D.fragCov:40.0,D.intCov:24.3) | 216-225 |
| 4 | 219206 | 26.5 (D.metascore:26.5,D.btScore:265.0,D.fragCov:33.3,D.intCov:21.1) | 184-204 |
| 5 | 655550 | 23.9 (D.metascore:23.9,D.btScore:136.0,D.fragCov:46.7,D.intCov:12.3) | 184-198 |
| 6 | 374698 | 36.2 (D.metascore:36.2,D.btScore:61.0,D.fragCov:33.3,D.intCov:39.2) | 217-225 |
| 7 | 374698 | 36.2 (D.metascore:36.2,D.btScore:61.0,D.fragCov:33.3,D.intCov:39.2) | 217-225 |
| 8 | 39488 | 26.9 (D.metascore:26.9,D.btScore:12.0,D.fragCov:35.7,D.intCov:20.3) | 186-199 |
| 9 | 18900 | 66.8 (D.metascore:66.8,D.btScore:191.0,D.fragCov:92.9,D.intCov:48.1) | 1-7 |
| 10 | 108010 | 22.4 (D.metascore:22.4,D.btScore:13.0,D.fragCov:22.2,D.intCov:22.5) | 217-225 |
| 11 | 275854 | 29.6 (D.metascore:29.6,D.btScore:260.0,D.fragCov:39.3,D.intCov:22.3) | 186-199 |
| 12 | 30586 | 24.2 (D.metascore:24.2,D.btScore:509.0,D.fragCov:28.1,D.intCov:20.8) | 216-231 |
| 13 | 48978 | 35.0 (D.metascore:35.0,D.btScore:125.0,D.fragCov:35.0,D.intCov:35.0) | 216-225 |
| 14 | 38966 | 23.7 (D.metascore:23.7,D.btScore:253.0,D.fragCov:23.5,D.intCov:23.8) | 216-232 |
| 15 | 29176 | 20.1 (D.metascore:20.1,D.btScore:29.0,D.fragCov:25.0,D.intCov:16.2) | 216-225 |
| 16 | 2495538 | 23.1 (D.metascore:23.1,D.btScore:535.0,D.fragCov:59.4,D.intCov:9.0) | 184-199 |
| 17 | 182236 | 22.9 (D.metascore:22.9,D.btScore:4096.0,D.fragCov:43.8,D.intCov:12.0) | 184-199 |
| 18 | 360318 | 21.1 (D.metascore:21.1,D.btScore:33.0,D.fragCov:22.2,D.intCov:20.0) | 208-225 |

| Row # | Cmpds. | P | Sequence | Modifications | Protein |
|---|---|---|---|---|---|
| 1 | 1 | 0 | Y.TQK.S (SEQ ID NO: 67) | Acetyl: 1; Hex(1)HexNAc(1): 1 | Etanercept |
| 2 | 1 | 1 | T.SPTR.S (SEQ ID NO: 68) | | Etanercept |
| 3 | 5 | 2 | P.STSFLLPMGP.S (SEQ ID NO: 69) | Hex(1)HexNAc(1): 1, 2 | Etanercept |
| 4 | 13 | 4 | P.TRSMAPGAVHLPQPVSTRSQH.T (SEQ ID NO: 70) | Hex(1)HexNAc(1): 16, 17 | Etanercept |
| 5 | 6 | 1 | P.TRSMAPGAVHLPQPV.S (SEQ ID NO: 71) | Hex(1)HexNAc(1): 3 | Etanercept |
| 6 | 4 | 1 | S.TSFLLPMGP.S (SEQ ID NO: 72) | Oxidation: 7; Hex(1)HexNAc(1): 2 | Etanercept |
| 7 | 4 | 1 | S.TSFLLPMGP.S (SEQ ID NO: 72) | Oxidation: 7; Hex(1)HexNAc(1): 1 | Etanercept |
| 8 | 2 | 1 | R.SMAPGAVHLPQPVS.T (SEQ ID NO: 73) | | Etanercept |
| 9 | 5 | 0 | -.LPAQVAF.T (SEQ ID NO: 74) | | Etanercept |
| 10 | 2 | 1 | S.TSFLLPMGP.S (SEQ ID NO: 72) | Hex(1)HexNAc(1): 1, 2 | Etanercept |
| 11 | 5 | 1 | R.SMAPGAVHLPQPVS.T (SEQ ID NO: 73) | Hex(1)HexNAc(1): 14 | Etanercept |
| 12 | 2 | 3 | P.STSELLPMGPSPPAEG.S (SEQ ID NO: 75) | Hex(1)HexNAc(1): 1, 2, 3 | Etanercept |
| 13 | 10 | 2 | P.STSFLLPMGP.S (SEQ ID NO: 69) | Oxidation: 8; Hex(1)HexNAc(1): 1, 2 | Etanercept |
| 14 | 3 | 4 | P.STSELLPMGPSPPAEGS.T (SEQ ID NO: 76) | Hex(1)HexNAc(1): 1, 2, 3 | Etanercept |
| 15 | 5 | 2 | P.STSFLLPMGP.S (SEQ ID NO: 69) | Hex(1)HexNAc(1): 1, 2, 3 | Etanercept |
| 16 | 19 | 2 | P.TRSMAPGAVHLPQPVS.T (SEQ ID NO: 77) | Hex(1)HexNAc(1): 3, 16 | Etanercept |
| 17 | 19 | 2 | P.TRSMAPGAVHLPQPVS.T (SEQ ID NO: 77) | Hex(1)HexNAc(1): 1, 3 | Etanercept |
| 18 | 8 | 5 | P.TPEPSTAPSTSFLLPMGP.S (SEQ ID NO: 78) | Hex(1)HexNAc(1): 5, 6, 9, 10, 11 | Etanercept |

2.2.8 Double Mutant can be Used to Affinity-Purify O-Glycoproteins from Complex Samples As a proof of concept that the system can function as a general affinity matrix for O-glycosylated proteins, not only in simplified systems but in complex media, the inventors investigated the ability of the double-mutant to purify O-glycoproteins from human serum. Human serum mainly consists of non-glycosylated (BSA) and N-glycosylated (IgG) proteins, with only a small fraction of the total serum proteome being O-glycosylated.

Figure 17C:
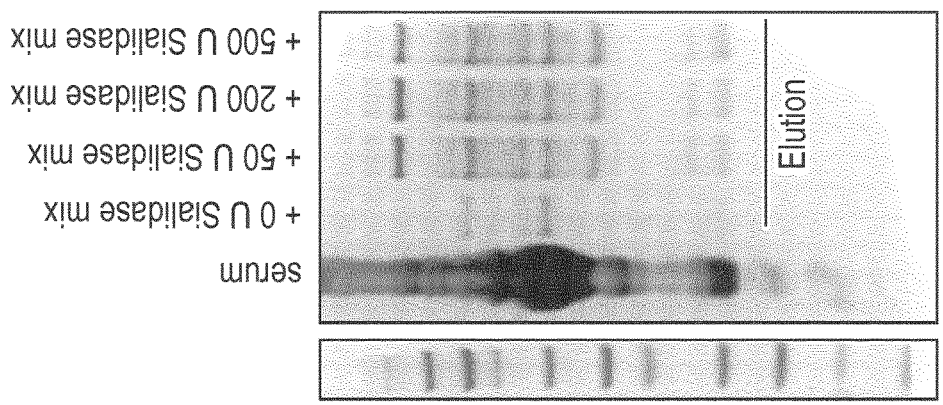
Figure 17B:
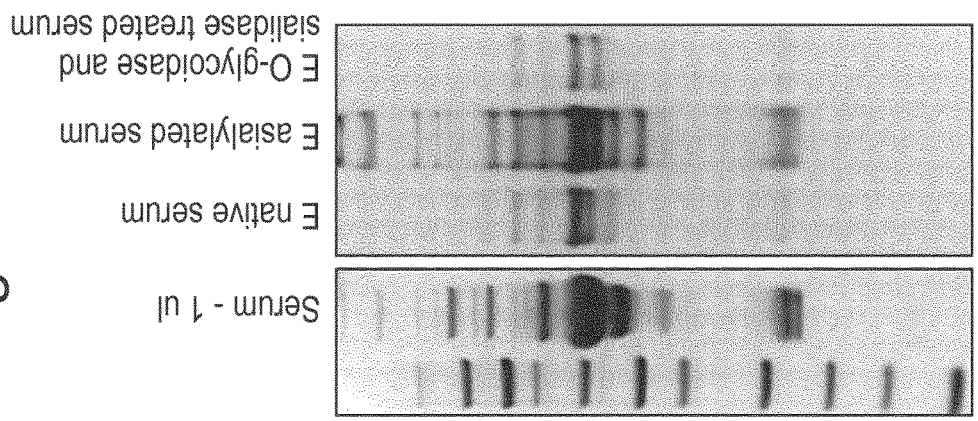
Figure 17A:
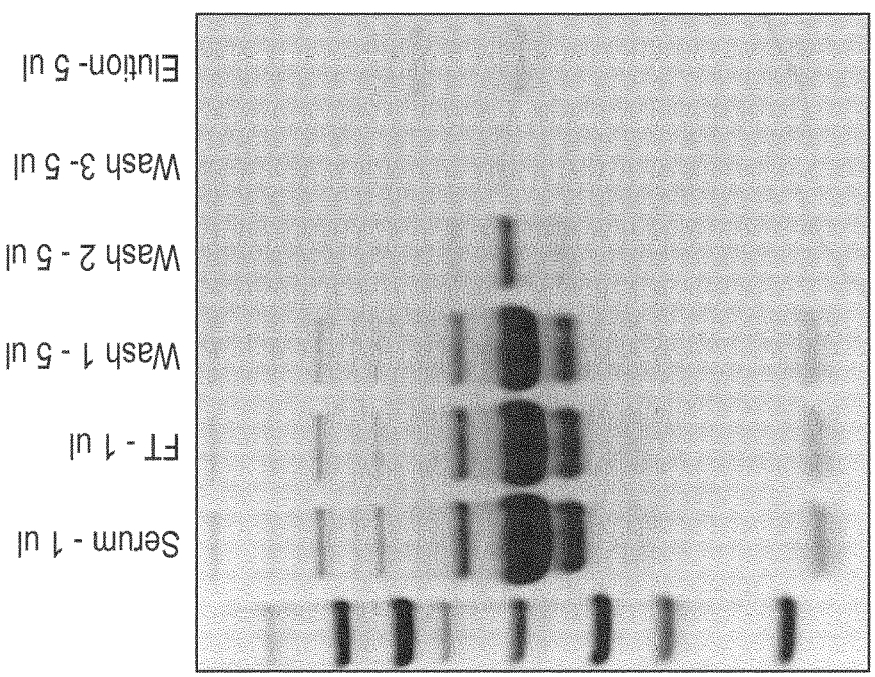

Applying 20 μl sialidase treated serum (ca 1.2 mg protein) to a 50 μl immobilized double-mutant resin column allowed the removal of almost all of the non-glycosylated and N-glycosylated proteins, while eluting a few selected proteins (FIG. 17A). By adding higher quantities of serum (e.g. 2.5 mg protein) with or without pre-treatment of sialidases and O-glycosidases it was demonstrated that the interaction is dependent on O-glycans and removal of terminal sialic acids (FIG. 17B). Further, it was concluded that pre-treatment with sialidases significantly increased the amount of bound O-glycoproteins as compared to non-sialidase-treated samples. Addition of 50 U sialidase mix (Am0707:Am1757) was sufficient to improve the amount of affinity purified O-glycoproteins (FIG. 17C).

Figure 18A:
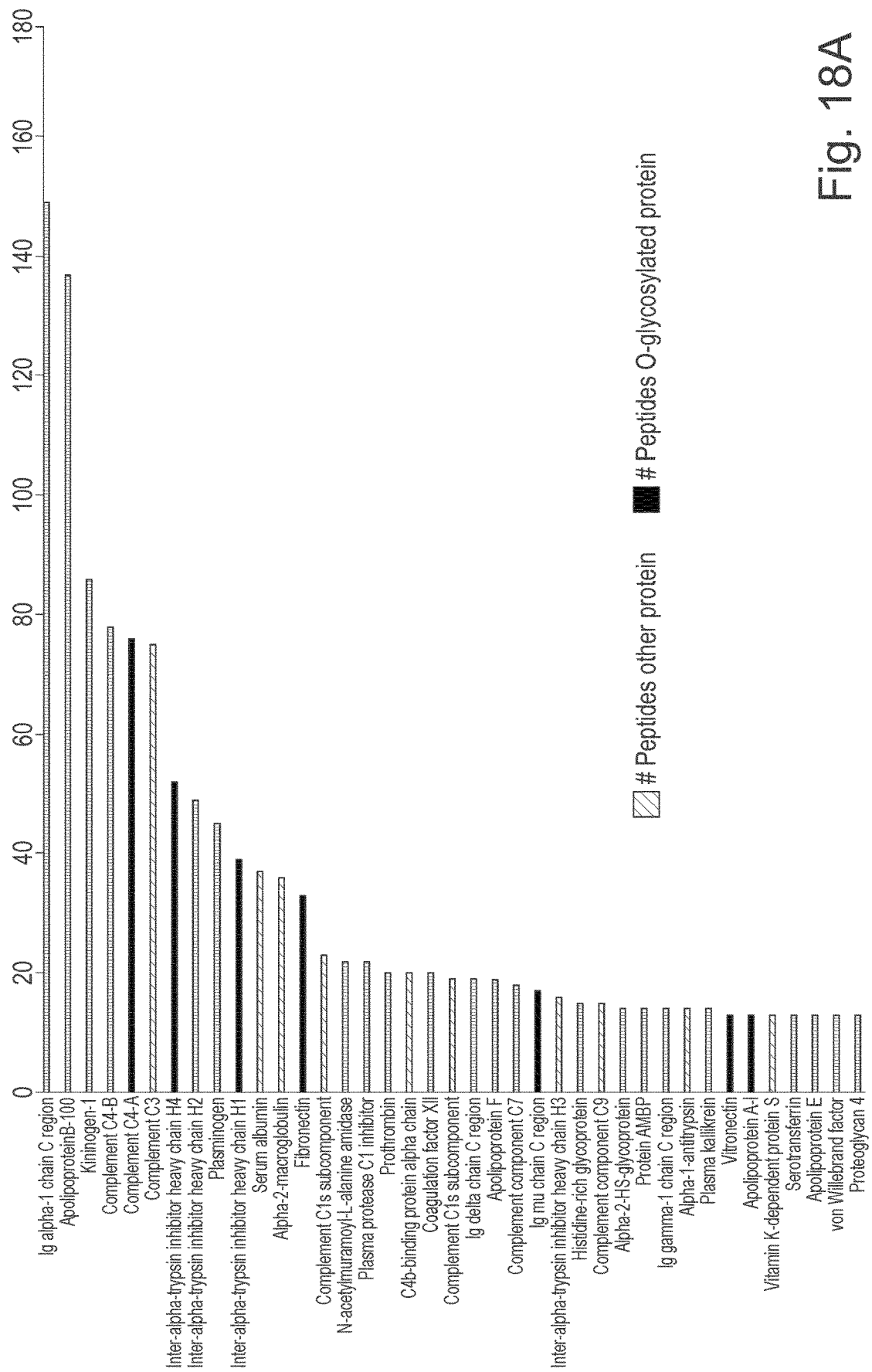
Figure 18B:
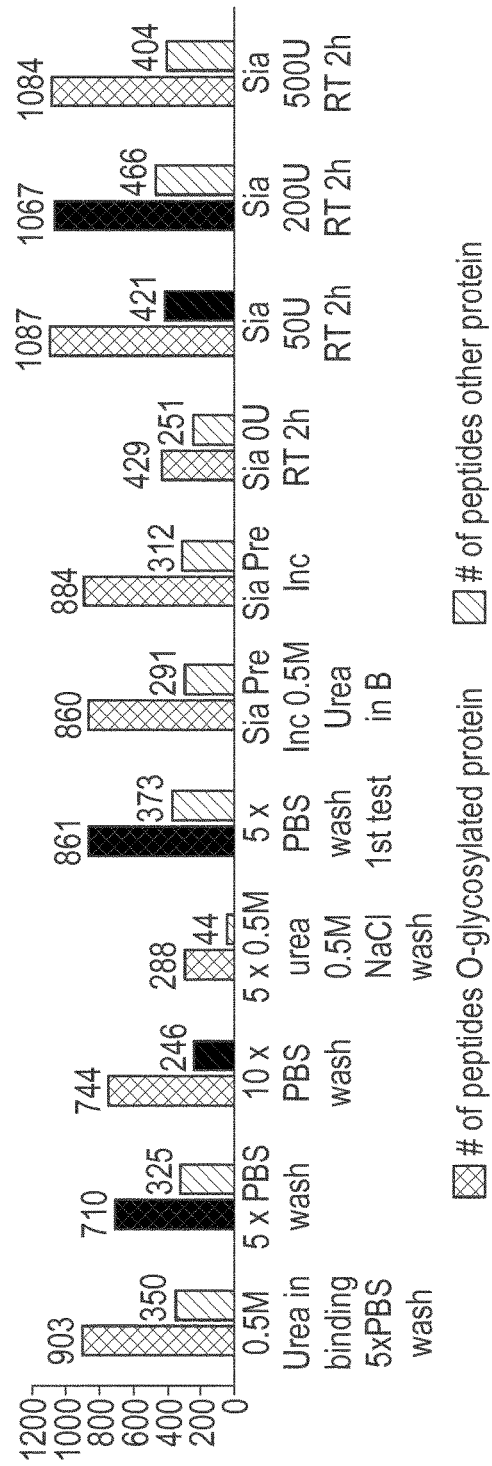
Figure 18C:
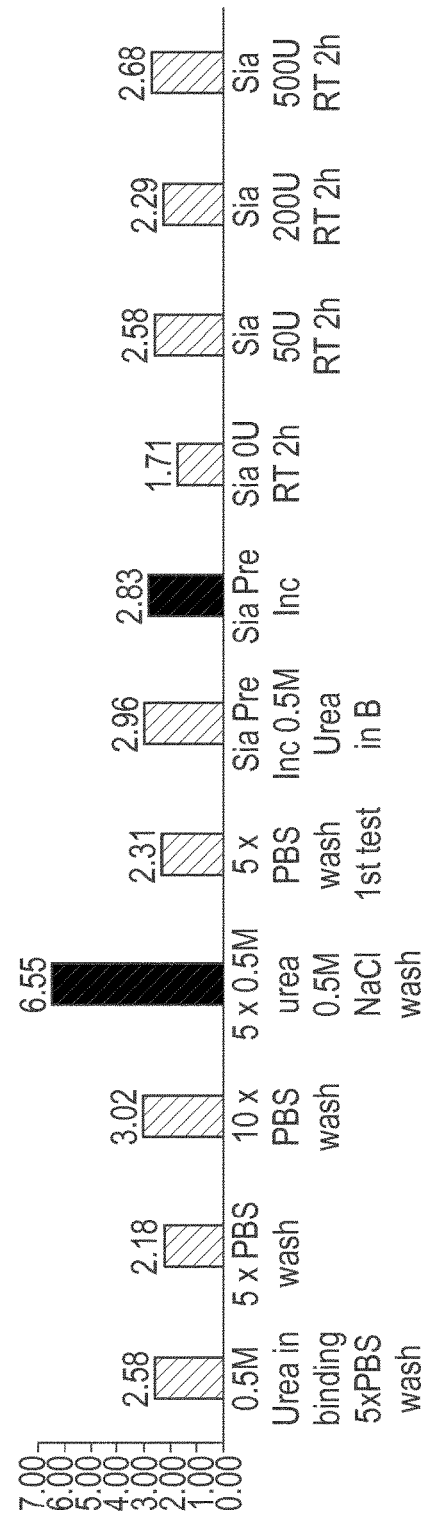

By analysis in mass spectrometry the vast majority of the affinity purified serum proteins can be annotated as O-glycosylated proteins (see FIG. 18A, and the names in bold-italics in the following table). The number of identified O-glycoprotein peptides in relation to non-O-glycoprotein peptides could be affected by different stringencies in the washing steps, both in terms of total number of identified peptides (FIG. 18B) as well as on the ratio O-glycoprotein peptides vs non-O-glycoprotein peptides (FIG. 18C). Thus it is clear that the affinity resin is highly efficient in its ability to specifically and selectively affinity purify and enrich O-glycoproteins. Additional MS data from this experiment is shown in the following table.

| Row | OK | Protein | MW [kDa] |
|---|---|---|---|
| 1 | TRUE | *Ig alpha-1 chain C region* OS = Homo sapiens GN = IGHA1 PE = 1 SV = 2 | 37.6 |
| 2 | TRUE | *Apolipoprotein B-100* OS = Homo sapiens GN = APOB PE = 1 SV = 2 | 515.3 |
| 3 | TRUE | *Kininogen-1* OS = Homo sapiens GN = KNG1 PE = 1 SV = 2 | 71.9 |
| 4 | TRUE | *Complement C4-B* OS = Homo sapiens GN = C4B PE = 1 SV = 2 | 192.6 |
| 5 | TRUE | *Complement C4-A* OS = Homo sapiens GN = C4A PE = 1 SV = 2 | 192.7 |
| 6 | TRUE | Complement C3 OS = Homo sapiens GN = C3 PE = 1 SV = 2 | 187 |
| 7 | TRUE | *Inter-alpha-trypsin inhibitor heavy chain H4* OS = Homo sapiens GN = ITIH4 PE = 1 SV = 4 | 103.3 |
| 8 | TRUE | *Inter-alpha-trypsin inhibitor heavy chain H2* OS = Homo sapiens GN = ITIH2 PE = 1 SV = 2 | 106.4 |
| 9 | TRUE | *Plasminogen* OS = Homo sapiens GN = PLG PE = 1 SV = 2 | 90.5 |
| 10 | TRUE | *Inter-alpha-trypsin inhibitor heavy chain H1* OS = Homo sapiens GN = ITIH1 PE = 1 SV = 3 | 101.3 |
| 11 | TRUE | Serum albumin OS = Homo sapiens GN = ALB PE = 1 SV = 2 | 69.3 |
| 12 | TRUE | Alpha-2-macroglobulin OS = Homo sapiens GN = A2M PE = 1 SV = 3 | 163.2 |
| 13 | TRUE | *Fibronectin* OS = Homo sapiens GN = FN1 PE = 1 SV = 4 | 262.5 |
| 14 | TRUE | Complement C1s subcomponent OS = Homo sapiens GN = C1S PE = 1 SV = 1 | 76.6 |
| 15 | TRUE | *N-acetylmuramoyl-L-alanine amidase* OS = Homo sapiens GN = PGLYRP2 PE = 1 SV = 1 | 62.2 |
| 16 | TRUE | *Plasma protease C1 inhibitor* OS = Homo sapiens GN = SERPING1 PE = 1 SV = 2 | 55.1 |
| 17 | TRUE | *Prothrombin* OS = Homo sapiens GN = F2 PE = 1 SV = 2 | 70 |
| 18 | TRUE | C4b-binding protein alpha chain OS = Homo sapiens GN = C4BPA PE = 1 SV = 2 | 67 |
| 19 | TRUE | *Coagulation factor XII* OS = Homo sapiens GN = F12 PE = 1 SV = 3 | 67.7 |
| 20 | TRUE | Complement C1r subcomponent OS = Homo sapiens GN = C1R PE = 1 SV = 2 | 80.1 |
| 21 | TRUE | *Ig delta chain C region* OS = Homo sapiens GN = IGHD PE = 1 SV = 2 | 42.2 |
| 22 | TRUE | *Apolipoprotein* OS = Homo sapiens GN = APOF PE = 1 SV = 2 | 35.4 |
| 23 | TRUE | *Complement component C7* OS = Homo sapiens GN = C7 PE = 1 SV = 2 | 93.5 |
| 24 | TRUE | Ig mu chain C region OS = Homo sapiens GN = IGHM PE = 1 SV = 3 | 49.3 |
| 25 | TRUE | Inter-alpha-trypsin inhibitor heavy chain H3 OS = Homo sapiens GN = ITIH3 PE = 1 SV = 2 | 99.8 |
| 26 | TRUE | *Histidine-rich glycoprotein* OS = Homo sapiens GN = HRG PE = 1 SV = 1 | 59.5 |
| 27 | TRUE | Complement component C9 OS = Homo sapiens GN = C9 PE = 1 SV = 2 | 63.1 |
| 28 | TRUE | *Alpha-2-HS-glycoprotein* OS = Homo sapiens GN = AHSG PE = 1 SV = 1 | 39.3 |
| 29 | TRUE | *Protein AMBP* OS = Homo sapiens GN = AMBP PE = 1 SV = 1 | 39 |
| 30 | TRUE | *Ig gamma-1 chain C region* OS = Homo sapiens GN = IGHG1 PE = 1 SV = 1 | 36.1 |
| 31 | TRUE | Alpha-1-antitrypsin OS = Homo sapiens GN = SERPINA1 PE = 1 SV = 3 | 46.7 |
| 32 | TRUE | *Plasma kallikrein* OS = Homo sapiens GN = KLKB1 PE = 1 SV = 1 | 71.3 |
| 33 | TRUE | *Vitronectin* OS = Homo sapiens GN = VTN PE = 1 SV = 1 | 54.3 |
| 34 | TRUE | *Apolipoprotein A-I* OS = Homo sapiens GN = APOA1 PE = 1 SV = 1 | 30.8 |
| 35 | TRUE | Vitamin K-dependent protein S OS = Homo sapiens GN = PROS1 PE = 1 SV = 1 | 75.1 |
| 36 | TRUE | *Serotransferrin* OS = Homo sapiens GN = TF PE = 1 SV = 3 | 77 |
| 37 | TRUE | *Apolipoprein E* OS = Homo sapiens GN = APOE PE = 1 SV = 1 | 36.1 |
| 38 | TRUE | *von Willebrand factor* OS = Homo sapiens GN = VWF PE = 1 SV = 4 | 309.1 |
| 39 | TRUE | *Proteoglycan 4* OS = Homo sapiens GN = PRG4 PE = 1 SV = 2 | 151 |

| Row | pI | #Peptides | SC [%] | Scores | RMS90 [ppm] |
|---|---|---|---|---|---|
| 1 | 6.1 | 149 | 75.1 | 1239.4 (M. expect: 0.0, M. score: 1239.4, M. siglimit: 38.0) | 5.46 |
| 2 | 6.6 | 137 | 41.2 | 7043.5 (M. expect: 0.0, M. score: 7043.5, M. siglimit: 38.0) | 6.02 |
| 3 | 6.3 | 86 | 45.7 | 1638.5 (M. expect: 0.0, M. score: 1638.5, M. siglimit: 38.0) | 5.49 |
| 4 | 6.9 | 78 | 63.3 | 4951.3 (M. expect: 0.0, M. score: 4951.3, M. siglimit: 38.0) | 6.46 |
| 5 | 6.7 | 76 | 61.3 | 4468.7 (M. expect: 0.0, M. score: 4468.7, M. siglimit: 38.0) | 6.12 |
| 6 | 6 | 75 | 64.1 | 4596.8 (M. expect: 0.0, M. score: 4596.8, M. siglimit: 38.0) | 6.13 |
| 7 | 6.5 | 52 | 56.9 | 2389.7 (M. expect: 0.0, M. score: 2389.7, M. siglimit: 38.0) | 6.29 |
| 8 | 6.4 | 49 | 50.4 | 2175.2 (M. expect: 0.0, M. score: 2175.2, M. siglimit: 38.0) | 7.02 |
| 9 | 7 | 45 | 67.3 | 2752.5 (M. expect: 0.0, M. score: 2752.5, M. siglimit: 38.0) | 5.54 |
| 10 | 6.3 | 39 | 43.8 | 1838.3 (M. expect: 0.0, M. score: 1838.3, M. siglimit: 38.0) | 5.16 |
| 11 | 5.9 | 37 | 63.7 | 2350.1 (M. expect: 0.0, M. score: 2350.1, M. siglimit: 38.0) | 5.59 |
| 12 | 6 | 36 | 38.1 | 1970.3 (M. expect: 0.0, M. score: 1970.3, M. siglimit: 38.0) | 5.67 |
| 13 | 5.5 | 33 | 25.3 | 1632.8 (M. expect: 0.0, M. score: 1632.8, M. siglimit: 38.0) | 5.58 |
| 14 | 4.8 | 23 | 46.1 | 1454.6 (M. expect: 0.0, M. score: 1454.6, M. siglimit: 38.0) | 6.01 |
| 15 | 7.3 | 22 | 56.4 | 1288.8 (M. expect: 0.0, M. score: 1288.8, M. siglimit: 38.0) | 5.72 |
| 16 | 6.1 | 22 | 46.2 | 1166.8 (M. expect: 0.0, M. score: 1166.8, M. siglimit: 38.0) | 6.15 |
| 17 | 5.6 | 20 | 43.4 | 1158.1 (M. expect: 0.0, M. score: 1158.1, M. siglimit: 38.0) | 6.13 |
| 18 | 7.2 | 20 | 51.4 | 1111.9 (M. expect: 0.0, M. score: 1111.9, M. siglimit: 38.0) | 5.13 |
| 19 | 8 | 20 | 39.7 | 691.9 (M. expect: 0.0, M. score: 691.9, M. siglimit: 38.0) | 5.03 |
| 20 | 5.8 | 19 | 39.6 | 1097.7 (M. expect: 0.0, M. score: 1097.7, M. siglimit: 38.0) | 6.07 |
| 21 | 8.1 | 19 | 46.9 | 687.5 (M. expect: 0.0, M. score: 687.5, M. siglimit: 38.0) | 4.87 |
| 22 | 5.4 | 19 | 43.3 | 344.0 (M. expect: 0.0, M. score: 344.0, M. siglimit: 38.0) | 7.71 |
| 23 | 6.1 | 18 | 38.3 | 1100.7 (M. expect: 0.0, M. score: 1100.7, M. siglimit: 38.0) | 5.73 |

| | | | | | |
|---|---|---|---|---|---|
| 24 | 6.3 | 17 | 50.9 | 1159.0 (M. expect: 0.0, M. score: 1159.0, M. siglimit: 38.0) | 5.25 |
| 25 | 5.5 | 16 | 28.3 | 747.2 (M. expect: 0.0, M. score: 747.2, M. siglimit: 38.0) | 5.8 |
| 26 | 7.1 | 15 | 35.4 | 964.5 (M. expect: 0.0, M. score: 964.5, M. siglimit: 38.0) | 5.33 |
| 27 | 5.4 | 15 | 34.3 | 876.5 (M. expect: 0.0, M. score: 876.5, M. siglimit:38.0) | 5.86 |
| 28 | 5.4 | 14 | 46 | 941.9 (M. expect: 0.0, M. score: 941.9, M. siglimit: 38.0) | 5.78 |
| 29 | 5.9 | 14 | 55.4 | 886.3 (M. expect: 0.0, M. score: 886.3, M. siglimit: 38.0) | 6.06 |
| 30 | 8.5 | 14 | 60.3 | 825.9 (M. expect: 0.0, M. score: 825.9, M. siglimit: 38.0) | 6.04 |
| 31 | 5.4 | 14 | 39 | 740.9 (M. expect: 0.0, M. score: 740.9, M. siglimit: 38.0) | 6.02 |
| 32 | 8.6 | 14 | 26 | 647.7 (M. expect: 0.0, M. score: 647.7, M. siglimit: 38.0) | 5.62 |
| 33 | 5.6 | 13 | 37 | 752.2 (M. expect: 0.0, M. score: 752.2, M. siglimit: 38.0) | 5.1 |
| 34 | 5.6 | 13 | 46.8 | 723.0 (M. expect: 0.0, M. score: 723.0, M. siglimit: 38.0) | 5.57 |
| 35 | 5.5 | 13 | 27.7 | 676.0 (M. expect: 0.0, M. score: 676.0, M. siglimit: 38.0) | 6.18 |
| 36 | 6.8 | 13 | 22.9 | 544.9 (M. expect: 0.0, M. score: 544.9, M. siglimit: 38.0) | 6.02 |
| 37 | 5.6 | 13 | 45.1 | 535.3 (M. expect: 0.0, M. score: 535.3, M. siglimit: 38.0) | 5.73 |
| 38 | 5.3 | 13 | 6.3 | 505.5 (M. expect: 0.0, M. score: 505.5, M. siglimit: 38.0) | 5.52 |
| 39 | 9.5 | 13 | 5.6 | 214.2 (M. expect: 0.0, M. score: 214.2, M. siglimit: 38.0) | 4.7 |

2.2.9 Immobilized Double-Mutant Also Binds to Shorter O-Glycopeptides

A series of experiments was performed to demonstrate the specificity of the LS double mutant also for O-glycopeptides. In the first experiment, a mix of an O-glycosylated peptide (glycodrosocin (GD)=GKPRPYSPRPTSHPRPIRV (SEQ ID NO: 47) with a core 1 O-glycan on the threonine) and several non-glycosylated peptides (H2686, H4062 H8390 and insulin oxidized beta chain (IOB)) was incubated with LS double mutant resin. (H2686=YIYGSFK (SEQ ID NO: 48), H4062=KKLVFFA (SEQ ID NO: 49), H8390=FLPLILGKLVKGLL (SEQ ID NO: 50)).

The peptide mix was allowed to bind to 50 µl immobilized double-mutant resin for 2 hours at room temperature with end-over-end rotation. The resin was washed five times with binding buffer (300 µl) and then eluted with the addition of 8 M Urea. The peptides in load, flow through and eluate were analyzed with LC/MS. Separation was performed on a RP-LC C18 column (Advance BioPeptide Map 2.1×100 2.7 µm from Agilent) and detected with ESI-Q-TOF Bruker Impact II. The results are shown in FIG. 19A. Glycodrosocin, the only peptide in the mix containing an O-GalNAc-Gal, was predominantly found in the eluted fraction and the non-glycosylated peptides in the flow-through fraction In the second experiment, it was investigated whether the LS double-mutant could enrich O-glycosylated peptides from a tryptic protein digest (e.g a different type of peptide mix). IgA was chosen as the target for digest. Based on the trypsin sites and reported O-glycosylation sites in IgA, a trypsin digest should result in only a single O-glycosylated peptide corresponding to positions 89-126 of IgA (see schematic diagram in FIG. 19B). To create the tryptic digest, IgA was mixed with urea to 6M and DTT to 5 mM followed by incubation at 37° C. for 1 h. IAM was added to 15 mM followed by incubation at room temperature for 30 min in the dark. The sample was then buffer exchanged to 50 mM Tris, pH 8.0 on Zeba spin 7000 K column. Trypsin was then added at 1:20 followed by incubation at 37° C. overnight. Trypsin inhibitor 1 mg/mg was added followed by incubation at room temperature for 20 min. Sialidase mix and NaCl were added to the resulting tryptic digest. The mix was allowed to bind to the resin for 2 h at room temperature with end-over-end rotation. The resin was washed ten times with PBS buffer (300 µl) and then eluted with the addition of 8 M Urea (50 µl, 2 min, 2 repeats).

Peptides of the load, flowthrough and eluate were separated and analysed using RP-LC MSMS on a C18 column (Advance BioPeptide Plus 2.1×150 mm 2.7 µm from Agilent Technologies) in a 0.1% FA in MQ: 0.1% FA in 95% ACN gradient at 45° C. and a flow of 0.2 ml/min. Detection was on an ESI-Q-TOF Bruker Impact II instrument. The results are shown in FIG. 19C. O-glycosylated peptide 89-126 were significantly enriched in the eluate and the specific O-glycopeptide 89-126 was identified with intact mass.

2.2.10 Immobilized Double-Mutant Compares Favorably to Other O-Glycoprotein Binding Matrixes The inventors evaluated the ability of the double-mutant to affinity purify O-glycoprotein as compared to other commercially available O-glycoprotein binding matrices, specifically the lectins Peanut agglutinin (PNA), and Vicia villosa lectin (VVA). Etanercept and asialylated etanercept were used as model substrates.

Figure 20A:
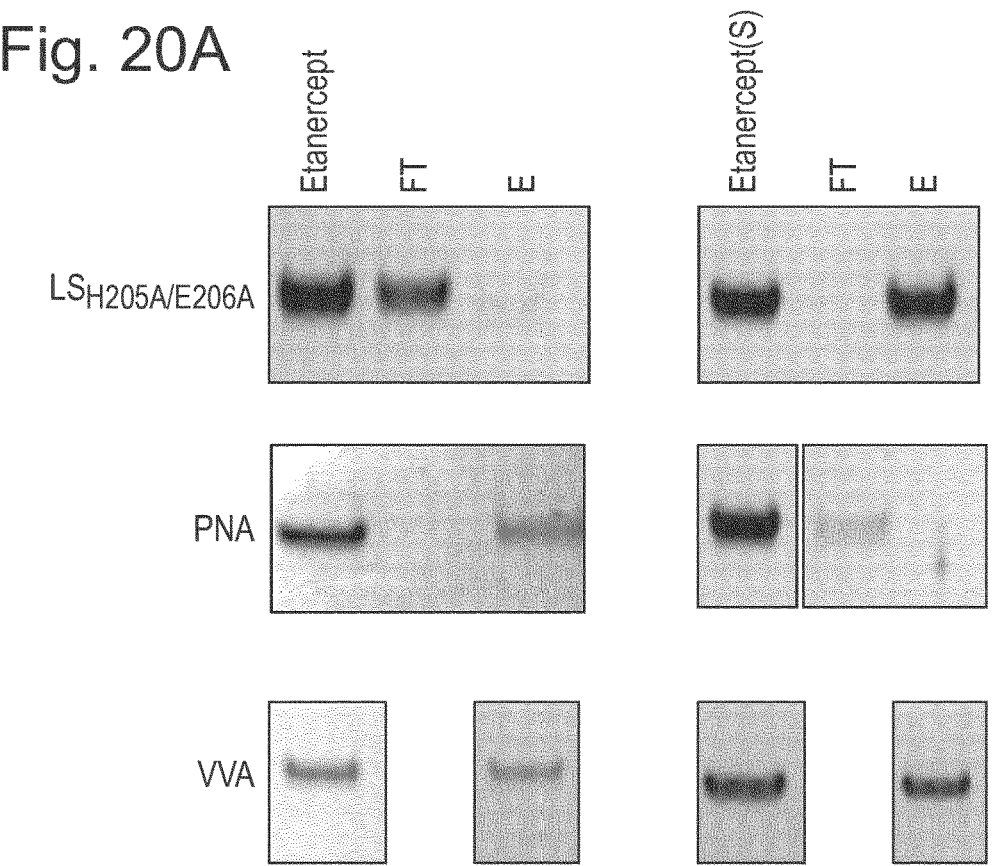
Figure 20B:
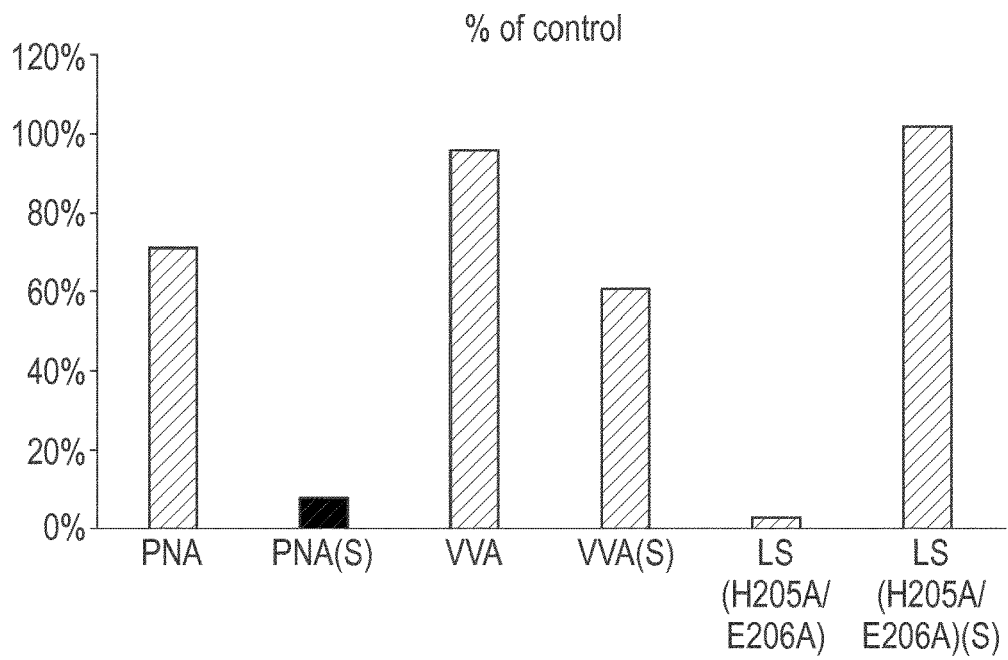

50 µg substrate was added in PBS (PNA and LS double mutant) or lectin binding buffer (VVA) to 50 µl volume of different immobilized lectin or LS double-mutant resins pre-equilibrated in the respective buffers (total 100 µl). (Lectin binding buffer is 20 mM Tris-HCl pH 7.4, 150 mM NaCl, 1 mM each of MgCl2, CaCl2, ZnCl2, and MnCl2). The substrate was allowed to interact with the resins with end-over-end-mixture for 2 h at room temperature. Non-bound proteins were washed away (100 g, 1 min; 3×) with PBS or lectin binding buffer, respectively. The resins were dried by centrifugation (1000 g, 1 min). Bound proteins were eluted with the addition of 8 M urea (for PNA and LS double mutant resins) or VVA elution buffer according to manufacturer (for VVA resin) (50 µl, 5 min treatment before centrifugation 1000 g 1 min; 2×) and both flow through (FT) and eluate (E) were analyzed on SDS-PAGE. 1.5 µg substrate was added to each gel (e.g. 3 µl) as a positive control and a densitometric analysis was performed to evaluate the efficiency of the resins, relative to the 1.5 µg loaded substrate which has assumed 100% efficiency. Representative gels for etanercept and asialylated etanercept (Etanercept S) are shown in FIG. 20A. The results of the densitometric analysis are shown in FIG. 20B. LSH205A/E206A double mutant performs at least as well as the best performing commercial lectin for efficiency of purification of asialylated substrate.

Sequences

SEQ ID NO: 1
EVTVPDALKDRIALKKTARQLNIVYFLGSDTEPVPDYERRLSELLLYLQQFYGKEMQRHGYGARSFGLDIKSP

GRVNIIEYKAKNPAAHYPYENGGGWKAAQELDEFFKAHPDRKKSQHTLIIMPTWNDEKNGPDNPGGVPFYGMG

```
                                                                -continued

Sequences

RNCFALDYPAFDIKHLGQKTREGRLLTKWYGGMAHELGHGLNLPHNHQTASDGKKYGTALMGSGNYTFGTSPT

FLTPASCALLDACEVFSVTPSQQFYEGKPEVEVGDVAISFKGDQILVSGNYKSPQTVKALNVYIQDPPYAVNQ

DYDAVSFSRRLGKKSGKFSMKIDKKELEGLNNNEFRISLMFILANGLHMQKHFTFHWDALQDYRDGSKS

SEQ ID NO: 2
MEVTVPDALKDRIALKKTARQLNIVYFLGSDTEPVPDYERRLSELLLYLQQFYGKEMQRHGYGARSFGLDIKS

PGRVNIIEYKAKNPAAHYPYENGGGWKAAQELDEFFKAHPDRKKSQHTLIIMPTWNDEKNGPDNPGGVPFYGM

GRNCFALDYPAFDIKHLGQKTREGRLLTKWYGGMAHELGHGLNLPHNHQTASDGKKYGTALMGSGNYTFGTSP

TFLTPASCALLDACEVFSVTPSQQFYEGKPEVEVGDVAISFKGDQILVSGNYKSPQTVKALNVYIQDPPYAVN

QDYDAVSFSRRLGKKSGKFSMKIDKKELEGLNNNEFRISLMFILANGLHMQKHFTFHWDALQDYRDGSKSGSG

HHHHHH

SEQ ID NO: 3
ATGGAAGTCACTGTGCCGGACGCCCTGAAAGATCGCATCGCGCTGAAGAAAACCGCTCGTCAGCTGAATATCG

TCTACTTCCTGGGTTCTGATACCGAACCGGTTCCGGACTACGAGCGCCGTCTGAGCGAGCTGCTGTTGTATCT

GCAGCAATTCTATGGTAAAGAAATGCAGCGCCATGGCTATGGCGCACGCAGCTTTGGTCTGGACATTAAGTCA

CCGGGTCGTGTGAACATTATCGAGTACAAAGCGAAGAACCCGGCAGCGCATTACCCGTATGAGAATGGTGGCG

GCTGGAAAGCTGCACAAGAACTGGACGAATTTTTCAAGGCCCATCCAGACCGCAAGAAAAGCCAGCACACCCT

GATCATCATGCCTACCTGGAATGATGAGAAAAATGGTCCTGACAATCCGGGTGGCGTTCCGTTCTATGGTATG

GGTCGTAATTGTTTTGCGTTGGACTACCCGGCGTTTGATATCAAGCACCTGGGTCAGAAAACGCGTGAGGGTC

GTCTGCTGACGAAATGGTACGGTGGCATGGCGCACGAACTGGGCCACGGCCTGAATCTGCCGCACAATCACCA

GACCGCGAGCGATGGCAAGAAATATGGCACCGCCCTGATGGGTAGCGGCAACTACACGTTCGGTACCAGCCCG

ACGTTCCTGACCCCGGCGAGCTGTGCGCTGCTGGATGCCTGCGAAGTGTTCAGCGTTACCCCGAGCCAACAGT

TTTATGAGGGTAAGCCAGAAGTCGAGGTTGGTGATGTTGCAATTTCCTTCAAGGGTGATCAAATCTTGGTCAG

CGGTAACTACAAGAGCCCGCAAACCGTGAAAGCTCTGAACGTTTACATTCAGGATCCGCCGTACGCCGTGAAC

CAAGACTACGATGCAGTGAGCTTTAGCCGTCGTCTGGGCAAAAAGTCCGGTAAGTTTAGCATGAAGATTGACA

AAAAAGAACTGGAAGGCCTGAATAACAACGAATTCCGTATTTCCTTGATGTTCATTCTGGCAAACGGCTTACA

CATGCAGAAGCACTTTACGTTTCACTGGGATGCGCTGCAAGACTACCGTGACGGTAGCAAATCTGGTTCGGGT

CATCATCACCACCATCACTGA

SEQ ID NO: 4
MLKRLLSAFFSLFFLGAASGTSFAEVTVPDALKDRIALKKTARQLNIVYFLGSDTEPVPDYERRLSELLLYLQ

QFYGKEMQRHGYGARSFGLDIKSPGRVNIIEYKAKNPAAHYPYENGGGWKAAQELDEFFKAHPDRKKSQHTLI

IMPTWNDEKNGPDNPGGVPFYGMGRNCFALDYPAFDIKHLGQKTREGRLLTKWYGGMAHELGHGLNLPHNHQT

ASDGKKYGTALMGSGNYTFGTSPTFLTPASCALLDACEVFSVTPSQQFYEGKPEVEVGDVAISFKGDQILVSG

NYKSPQTVKALNVYIQDPPYAVNQDYDAVSFSRRLGKKSGKFSMKIDKKELEGLNNNEFRISLMFILANGLHM

QKHFTFHWDALQDYRDGSKS
(signal sequence underlined)

SEQ ID NO: 5
EVTVPDALKDRIALKKTARQLNIVYFLGSDTEPVPDYERRLSELLLYLQQFYGKEMQRHGYGARSFGLDIKSP

GRVNIIEYKAKNPAAHYPYENGGGWKAAQELDEFFKAHPDRKKSQHTLIIMPTWNDEKNGPDNPGGVPFYGMG

RNCFALDYPAFDIKHLGQKTREGRLLTKWYGGMAHALGHGLNLPHNHQTASDGKKYGTALMGSGNYTFGTSPT

FLTPASCALLDACEVFSVTPSQQFYEGKPEVEVGDVAISFKGDQILVSGNYKSPQTVKALNVYIQDPPYAVNQ

DYDAVSFSRRLGKKSGKFSMKIDKKELEGLNNNEFRISLMFILANGLHMQKHFTFHWDALQDYRDGSKS
```

| | |
|---|---|
| | SEQ ID NO: 6 |

MEVTVPDALKDRIALKKTARQLNIVYFLGSDTEPVPDYERRLSELLLYLQQFYGKEMQRHGYGARSFGLDIKS

PGRVNIIEYKAKNPAAHYPYENGGGWKAAQELDEFFKAHPDRKKSQHTLIIMPTWNDEKNGPDNPGGVPFYGM

GRNCFALDYPAFDIKHLGQKTREGRLLTKWYGGMAHALGHGLNLPHNHQTASDGKKYGTALMGSGNYTFGTSP

TFLTPASCALLDACEVFSVTPSQQFYEGKPEVEVGDVAISFKGDQILVSGNYKSPQTVKALNVYIQDPPYAVN

QDYDAVSFSRRLGKKSGKFSMKIDKKELEGLNNNEFRISLMFILANGLHMQKHFTFHWDALQDYRDGSKSGSG

HHHHHH

| | |
|---|---|
| | SEQ ID NO: 7 |

ATGGAAGTCACTGTGCCGGACGCCCTGAAAGATCGCATCGCGCTGAAGAAAACCGCTCGTCAGCTGAATATCG

TCTACTTCCTGGGTTCTGATACCGAACCGGTTCCGGACTACGAGCGCCGTCTGAGCGAGCTGCTGTTGTATCT

GCAGCAATTCTATGGTAAAGAAATGCAGCGCCATGGCTATGGCGCACGCAGCTTTGGTCTGGACATTAAGTCA

CCGGGTCGTGTGAACATTATCGAGTACAAAGCGAAGAACCCGGCAGCGCATTACCCGTATGAGAATGGTGGCG

GCTGGAAAGCTGCACAAGAACTGGACGAATTTTTCAAGGCCCATCCAGACCGCAAGAAAAGCCAGCACACCCT

GATCATCATGCCTACCTGGAATGATGAGAAAAATGGTCCTGACAATCCGGGTGGCGTTCCGTTCTATGGTATG

GGTCGTAATTGTTTTGCGTTGGACTACCCGGCGTTTGATATCAAGCACCTGGGTCAGAAAACGCGTGAGGGTC

GTCTGCTGACGAAATGGTACGGTGGCATGGCGCACGCGCTGGGCCACGGCCTGAATCTGCCGCACAATCACCA

GACCGCGAGCGATGGCAAGAAATATGGCACCGCCCTGATGGGTAGCGGCAACTACACGTTCGGTACCAGCCCG

ACGTTCCTGACCCCGGCGAGCTGTGCGCTGCTGGATGCCTGCGAAGTGTTCAGCGTTACCCCGAGCCAACAGT

TTTATGAGGGTAAGCCAGAAGTCGAGGTTGGTGATGTTGCAATTTCCTTCAAGGGTGATCAAATCTTGGTCAG

CGGTAACTACAAGAGCCCGCAAACCGTGAAAGCTCTGAACGTTTACATTCAGGATCCGCCGTACGCCGTGAAC

CAAGACTACGATGCAGTGAGCTTTAGCCGTCGTCTGGGCAAAAAGTCCGGTAAGTTTAGCATGAAGATTGACA

AAAAAGAACTGGAAGGCCTGAATAACAACGAATTCCGTATTTCCTTGATGTTCATTCTGGCAAACGGCTTACA

CATGCAGAAGCACTTTACGTTTCACTGGGATGCGCTGCAAGACTACCGTGACGGTAGCAAATCTGGTTCGGGT

CATCATCACCACCATCACTGA

| | |
|---|---|
| | SEQ ID NO: 8 |

GMAHELGHGL
(metalloprotease motif)

| | |
|---|---|
| | SEQ ID NO: 9 |

<u>MKNLLFALLTGSFCCCYA</u>QQKAAPVPEPEVVATPPADAGRGLIRVDSREIRHYSGTRKEPDYLVSRDNGKTWE

MKAAPAGYPPNYGGIPKESPAIVRNPLTREFIRVQPIGGFVFLSRGGLDGKWLAVTNDGKLEEDWKDPEKRKN

LKKLGGIMRTPVFVNKGRRVIVPFHNMGGGTKFHISDDGGLTWHVSRNGVTSPRHEARPPHQGVRWFNNAVEA

TVLEMKDGTLWALARTSQDQAWQAFSKDYGETWSKPEPSRFFGTLTMNTLGRLDDGTIVSLWTNTMALPENAT

AGNGTWEDVFTNRDSHHIAMSGDEGKTWYGFREIILDEHRNHPGYATLDGPEDRGKHQSEMVQLDKNRILISL

GQHKNHRRLVIVDRRWVGAKTRATQTGKDLDSQWTIHTYIPQKKGHCSYNRKPSAELVQDPSGGTKKVLQIKR

LDDPELVNEKSNVDYRNGGATWNFPNGTTGLVKFRFRVVDGEQADDSGLQVSLTDRLFNACDSTTKDYALFTF

PIRLKPAPHLLLGMKKVPFTPGAWHEISLLWQGGQAVVSLDGKKAGTLKMANKSPNGASYIHFISTGSQPDAG

ILLDTVNARVK
(signal sequence underlined)

| | |
|---|---|
| | SEQ ID NO: 10 |

QQKAAPVPEPEVVATPPADAGRGLIRVDSREIRHYSGTRKEPDYLVSRDNGKTWEMKAAPAGYPPNYGGIPKE

SPAIVRNPLTREFIRVQPIGGFVFLSRGGLDGKWLAVTNDGKLEEDWKDPEKRKNLKKLGGIMRTPVFVNKGR

RVIVPFHNMGGGTKFHISDDGGLTWHVSRNGVTSPRHEARPPHQGVRWFNNAVEATVLEMKDGTLWALARTSQ

| Sequences |
|---|
| DQAWQAFSKDYGETWSKPEPSRFFGTLTMNTLGRLDDGTIVSLWTNTMALPENATAGNGTWEDVFTNRDSHHI<br>AMSGDEGKTWYGFREIILDEHRNHPGYATLDGPEDRGKHQSEMVQLDKNRILISLGQHKNHRRLVIVDRRWVG<br>AKTRATQTGKDLDSQWTIHTYIPQKKGHCSYNRKPSAELVQDPSGGTKKVLQIKRLDDPELVNEKSNVDYRNG<br>GATWNFPNGTTGLVKFRFRVVDGEQADDSGLQVSLTDRLFNACDSTTKDYALFTFPIRLKPAPHLLLGMKKVP<br>FTPGAWHEISLLWQGGQAVVSLDGKKAGTLKMANKSPNGASYIHFISTGSQPDAGILLDTVNARVK |
| SEQ ID NO: 11<br>MQQKAAPVPEPEVVATPPADAGRGLIRVDSREIRHYSGTRKEPDYLVSRDNGKTWEMKAAPAGYPPNYGGIPK<br>ESPAIVRNPLTREFIRVQPIGGFVFLSRGGLDGKWLAVTNDGKLEEDWKDPEKRKNLKKLGGIMRTPVFVNKG<br>RRVIVPFHNMGGGTKFHISDDGGLTWHVSRNGVTSPRHEARPPHQGVRWFNNAVEATVLEMKDGTLWALARTS<br>QDQAWQAFSKDYGETWSKPEPSRFFGTLTMNTLGRLDDGTIVSLWTNTMALPENATAGNGTWEDVFTNRDSHH<br>IAMSGDEGKTWYGFREIILDEHRNHPGYATLDGPEDRGKHQSEMVQLDKNRILISLGQHKNHRRLVIVDRRWV<br>GAKTRATQTGKDLDSQWTIHTYIPQKKGHCSYNRKPSAELVQDPSGGTKKVLQIKRLDDPELVNEKSNVDYRN<br>GGATWNFPNGTTGLVKFRFRVVDGEQADDSGLQVSLTDRLFNACDSTTKDYALFTFPIRLKPAPHLLLGMKKV<br>PFTPGAWHEISLLWQGGQAVVSLDGKKAGTLKMANKSPNGASYIHFISTGSQPDAGILLDTVNARVKGSGLEH<br>HHHHH |
| SEQ ID NO: 12<br><u>MTWLLCGRGKWNKVKRMMNSVFKCLMSAVCAVALPAFG</u>QEEKTGFPTDRAVTVFSAGEGNPYASIRIPALLSI<br>GKGQLLAFAEGRYKNTDQGENDIIMSVSKNGGKTWSRPRAIAKAHGATFNNPCPVYDAKTRTVTVVFQRYPAG<br>VKERQPNIPDGWDDEKCIRNFMIQSRNGGSSWTKPQEITKTTKRPSGVDIMASGPNAGTQLKSGAHKGRLVIP<br>MNEGPFGKWVISCIYSDDGGKSWKLGQPTANMKGMVNETSIAETDNGGVVMVARHWGAGNCRRIAWSQDGGET<br>WGQVEDAPELFCDSTQNSLMTYSLSDQPAYGGKSRILFSGPSAGRRIKGQVAMSYDNGKTWPVKKLLGEGGFA<br>YSSLAMVEPGIVGVLYEENQEHIKKLKFVPITMEWLTDGEDTGLAPGKKAPVLK<br>(signal sequence underlined) |
| SEQ ID NO: 13<br>QEEKTGFPTDRAVTVFSAGEGNPYASIRIPALLSIGKGQLLAFAEGRYKNTDQGENDIIMSVSKNGGKTWSRP<br>RAIAKAHGATFNNPCPVYDAKTRTVTVVFQRYPAGVKERQPNIPDGWDDEKCIRNFMIQSRNGGSSWTKPQEI<br>TKTTKRPSGVDIMASGPNAGTQLKSGAHKGRLVIPMNEGPFGKWVISCIYSDDGGKSWKLGQPTANMKGMVNE<br>TSIAETDNGGVVMVARHWGAGNCRRIAWSQDGGETWGQVEDAPELFCDSTQNSLMTYSLSDQPAYGGKSRILF<br>SGPSAGRRIKGQVAMSYDNGKTWPVKKLLGEGGFAYSSLAMVEPGIVGVLYEENQEHIKKLKFVPITMEWLTD<br>GEDTGLAPGKKAPVLK |
| SEQ ID NO: 14<br>MQEEKTGFPTDRAVTVFSAGEGNPYASIRIPALLSIGKGQLLAFAEGRYKNTDQGENDIIMSVSKNGGKTWSR<br>PRAIAKAHGATFNNPCPVYDAKTRTVTVVFQRYPAGVKERQPNIPDGWDDEKCIRNFMIQSRNGGSSWTKPQE<br>ITKTTKRPSGVDIMASGPNAGTQLKSGAHKGRLVIPMNEGPFGKWVISCIYSDDGGKSWKLGQPTANMKGMVN<br>ETSIAETDNGGVVMVARHWGAGNCRRIAWSQDGGETWGQVEDAPELFCDSTQNSLMTYSLSDQPAYGGKSRIL<br>FSGPSAGRRIKGQVAMSYDNGKTWPVKKLLGEGGFAYSSLAMVEPGIVGVLYEENQEHIKKLKFVPITMEWLT<br>DGEDTGLAPGKKAPVLKGSGLEHHHHHH |
| O-glycosidase from *S. oralis*<br>SEQ ID NO: 15<br>MDKRFFEKRCKFSIRKFTLGVASVMIGATFFAASPVLADQARVGSTDNLPSELADLDKKASDEGHDFDKEAAA<br>QNPGSAETTEGPQTEEELLAQEKEKSEKPSNLPKELEDKLEKAEDNGREVDKDQLAQDTGKLVPEDVAKTTNG<br>ELNYGATVKIKTPSGEGSGIVVAKDLVLTVSHNFIKDSQEGNIRKVVDNDQGDGDIYSISYPGLPDVKFSKKD |

-continued

| Sequences |
|---|
| IIHWDREGYLKGFKNDLALVRLRTVLENTPVEVTKKPVVKKIGDKLHVFGYPEGKLNPIVNTTVDFAEPYGEG |
| VQGIGYQGGKPGASGGGIFDTEGKLVGVHQNGVVGKRSGGILFSPAQLKWIQDHMQGISSVKPADLEEKEKPA |
| EEKPKEDKPAAAKPETPKAVTPEWQTVANKEQQGTVTIREEKGVRYNQLSSTAQNDNDGKPALFEKQGLTVDA |
| NGNATVDLTFKDDSEKGKSRFGVFLKFKDTKNNVFVGYDQGGWFWEYKTPGNSTWYKGNRVAAPEPGSVNRLS |
| ITLKSDGQLNASNNDVNLFDTVTLPGAVNENLKNEKKILLKAGTYSNDRTVVSVKTDNQEGVKADDTPAQKET |
| GPAVDDSKVTYDTIQSKVLKAVIDQAFPRVKEYTLNGHTLPGQVQQFNQVFINNHRITPEVTYKKINETTAEY |
| LMKLRDDAHLINAEMTVRLQVVDNQLHFDVTKIVNHNQVTPGQKIDDERKLLSTISFLGNALVSVSSDQAGAK |
| FDGATMSNNTHVSGDDHIDVTNPMKDLAKGYMYGFVSTDKLAAGVWSNSQNSYGGGSNDWTRLTAYKETVGNA |
| NYVGIHSSEWQWEKAYKGIVFPEYTKELPSAKVVITEDANADNKVDWQDGAIAYRSIMNNPQGWEKVKDITAY |
| RIAMNFGSQAQNPFLMTLDGIKKINLHTDGLGQGVLLKGYGSEGHDSGHLNYADIGKRIGGVEDFKTLIEKAK |
| KYGAHLGIHVNASETYPESKYFNENILRKNPDGSYSYGWNWLDQGINIDAAYDLAHGRLARWEDLKKKLGEGL |
| DFIYVDVWGNGQSGDNGAWATHVLAKEINKQGWRFAIEWGHGGEYDSTFQHWAADLTYGGYTNKGINSAITRF |
| IRNHQKDSWVGDYRSYGGAANYPLLGGYSMKDFEGWQGRSDYNGYVTNLFAHDVMTKYFQHFTVSKWENGTPV |
| TMTDNGSTYKWTPEMKVELVDAAGNKVVVTRKSNDVNSPQYRERTVTLNGRVIQDGSAYLTPWNWDANGKKLP |
| TEKEKMYYFNTQAGATTWTLPSDWANSKVYLYKLTDQGKTEEQELTVTDGKITLDLLANQPYVLYRSKQTNPE |
| MSWSEGMHIYDQGFNSGTLKHWTISGDASKAEIVKSQGANEMLRIQGNKSKVSLTQKLTGLKPNTKYAVYVGV |
| DNRSNAKASITVNTGEKEVTTYTNKSLALNYIKAYAHNNRRENATVDDTSYFQNMYAFFTTGSDVSNVTLTLS |
| REAGDEATYFDEIRTFENNSSMYGDKHDTGQGTFKQDFENVAQGIFPFVVGGVEGVEDNRTHLSEKHDPYTQR |
| GWNGKKVDDVIEGNWSLKTNGLVSRRNLVYQTIPQNFRFEAGKTYRVTFEYEAGSDNTYAFVVGKGEFQSGRR |
| GTQASNLEMHELPNTWTDSKKAKKVTFLVTGAETGDTWVGIYSTGNASNTRGDAGGNANFRGYNDFMMDNLQI |
| EEITLTGKMLTENALKNYLPTVAMTNYTKESMDALKEAVFNLSQADDDISVEEARAEIAKIEALKNALVQKKT |
| ALVAEDFESLDAPAQPGEGLENAFDGNVSSLWHTSWNGGDVGKPATMVLKEPTEITGLRYVPRASDSNGNLRD |
| VKLVVTDESGKEHTFNVTDWPNNNKPKDIDFGKTIKAKKIVLTGTKTYGDGGDKYQSAAELIFTRPQVAETPL |
| DLSGYEAALAKAQKLTDKDNQEEVASVQASMKYATDNHLLTERMVAYFADYLNQLKDSATKPDAPTSSKGEEQ |
| PPVLDVPEFKGGVNATEAAVHEVPEFKGGVNAVQALVHELPEYKGGANAVLAAANEVPEYKGGANAVEALVNE |
| KPAYTGVLATAGDQAAPTVEKPEYPLTPSPVADTKTPGAKDEEKLPATGEHSSEVALFLASVSIALSAAVLAT |
| KRKEEGSGLEHHHHHH |

E206A_forward primer
SEQ ID NO: 16
ATGGCGCACGC GCTGGGCCACG

E206A_reverse primer
SEQ ID NO: 17
GCCACCGTAC CATTTCGTC

EPO
SEQ ID NO: 18
APPRLICDSRVLERYLLEAKEAEDITTGCAEHCSLDENITVPDTKVDFYAWKRMEVGQQAVEVWQGLALLSEA

VLRGQALLVNSSQPWEPLQLHVDKAVSGLRSLTTLLRALGAQKEAISPPDAA<u>S</u>AAPLRTITADTFRKLFRVYS

NFLRGKLKLYTGEACRTGDR
(Notes: predicted O-glycan bearing Serine is underlined; C terminal
Arginine is commonly truncated during expression)

SEQ ID NO: 20
EVTVPDALKDRIALKKTARQLNIVYFLGSDTEPVPDYERRLSELLLYLQQFYGKEMQRHGYGARSFGLDIKSP

GRVNIIEYKAKNPAAHYPYENGGGWKAAQELDEFFKAHPDRKKSQHTLIIMPTWNDEKNGPDNPGGVPFYGMG

```
Sequences
RNCFALDYPAFDIKHLGQKTREGRLLTKWYGGMAAALGHGLNLPHNHQTASDGKKYGTALMGSGNYTFGTSPT

FLTPASCALLDACEVFSVTPSQQFYEGKPEVEVGDVAISFKGDQILVSGNYKSPQTVKALNVYIQDPPYAVNQ

DYDAVSFSRRLGKKSGKFSMKIDKKELEGLNNNEFRISLMFILANGLHMQKHFTFHWDALQDYRDGSKS

SEQ ID NO: 21
MEVTVPDALKDRIALKKTARQLNIVYFLGSDTEPVPDYERRLSELLLYLQQFYGKEMQRHGYGARSFGLDIKS

PGRVNIIEYKAKNPAAHYPYENGGGWKAAQELDEFFKAHPDRKKSQHTLIIMPTWNDEKNGPDNPGGVPFYGM

GRNCFALDYPAFDIKHLGQTREGRLLTKWYGGMAAALGHGLNLPHNHQTASDGKKYGTALMGSGNYTFGTSP

TFLTPASCALLDACEVFSVTPSQQFYEGKPEVEVGDVAISFKGDQILVSGNYKSPQTVKALNVYIQDPPYAVN

QDYDAVSFSRRLGKKSGKFSMKIDKKELEGLNNNEFRISLMFILANGLHMQKHFTFHWDALQDYRDGSKSGSG

HHHHHH
                                                                SEQ ID NO: 22
ATGGAAGTCACTGTGCCGGACGCCCTGAAAGATCGCATCGCGCTGAAGAAAACCGCTCGTCAGCTGAATATCG

TCTACTTCCTGGGTTCTGATACCGAACCGGTTCCGGACTACGAGCGCCGTCTGAGCGAGCTGCTGTTGTATCT

GCAGCAATTCTATGGTAAAGAAATGCAGCGCCATGGCTATGGCGCACGCAGCTTTGGTCTGGACATTAAGTCA

CCGGGTCGTGTGAACATTATCGAGTACAAAGCGAAGAACCCGGCAGCGCATTACCCGTATGAGAATGGTGGCG

GCTGGAAAGCTGCACAAGAACTGGACGAATTTTTCAAGGCCCATCCAGACCGCAAGAAAAGCCAGCACACCCT

GATCATCATGCCTACCTGGAATGATGAGAAAAATGGTCCTGACAATCCGGGTGGCGTTCCGTTCTATGGTATG

GGTCGTAATTGTTTTGCGTTGGACTACCCGGCGTTTGATATCAAGCACCTGGGTCAGAAAACGCGTGAGGGTC

GTCTGCTGACGAAATGGTACGGTGGCATGGCGGCCGCGCTGGGCCACGGCCTGAATCTGCCGCACAATCACCA

GACCGCGAGCGATGGCAAGAAATATGGCACCGCCCTGATGGGTAGCGGCAACTACACGTTCGGTACCAGCCCG

ACGTTCCTGACCCCGGCGAGCTGTGCGCTGCTGGATGCCTGCGAAGTGTTCAGCGTTACCCCGAGCCAACAGT

TTTATGAGGGTAAGCCAGAAGTCGAGGTTGGTGATGTTGCAATTTCCTTCAAGGGTGATCAAATCTTGGTCAG

CGGTAACTACAAGAGCCCGCAAACCGTGAAAGCTCTGAACGTTTACATTCAGGATCCGCCGTACGCCGTGAAC

CAAGACTACGATGCAGTGAGCTTTAGCCGTCGTCTGGGCAAAAAGTCCGGTAAGTTTAGCATGAAGATTGACA

AAAAAGAACTGGAAGGCCTGAATAACAACGAATTCCGTATTTCCTTGATGTTCATTCTGGCAAACGGCTTACA

CATGCAGAAGCACTTTACGTTTCACTGGGATGCGCTGCAAGACTACCGTGACGGTAGCAAATCTGGTTCGGGT

CATCATCACCACCATCACTGA

SEQ ID NO: 23
GMAHALGHGL
(disrupted metalloprotease motif)
                                                                SEQ ID NO: 24
GMAAELGHGL
(disrupted metalloprotease motif)
                                                                SEQ ID NO: 25
GMAAALGHGL
(disrupted metalloprotease motif)

Pseudomonas aeruginosa PAO1 (native sequence with removed signal sequence)
                                                                SEQ ID 26
ATQEEILDAALVSGDSSQLTDSHLVALRLQQQVERIRQTRTQLLDGLYQNLSQAYDPGAASMWVLPANPDNTL

PFLIGDKGRVLASLSLEAGGRGLAYGTNVLTQLSGTNAAHAPLLKRAVQWLVNGDPGAATAKDFKVSVVGVDK

TAALNGLKSAGLQPADAACNALTDASCASTSKLLVLGNGASAASLSATVRARLQAGLPILFVHTNGWNQSSTG

QQILAGLGLQEGPYGGNYWDKDRVPSSRTRTRSVELGGAYGQDPALVQQIVDGSWRTDYDWSKCTSYVGRTTC

DDVPGLSDFSKRVDVLKGALDAYNQKAQNLFALPGTTSLRLWLLWADAVRQNIRYPMDKAADTARFQETFVAD

AIVGYVREAGAAQKELGSYAGQRQQSMPVSGSEETLTLTLPSAQGFTAIGRMAAPGKRLSIRIEDAGQASLAV

GLNTQRIGSTRLWNTRQYDRPRFLKSPDIKLQANQSVALVSPYGGLLQLVYSGATPGQTVTVKVTGAASQPFL
```

Sequences

DIQPGEDSSQATADFIQALDADKADWLEIRSGSVEVHAKVEKVRGSIDKDYGGDVQRFIRELNEVFIDDAYTL

AGFAIPNQAKTPAIQQECAARGWDCDSETLHKLPGTQHINVDQYAQCGGGCSGNPYDQTWGLNPRGW<u>GESHEL</u>

<u>GHNL</u>QVNRLKVYGGRSGEISNQIFPLHKDWRVLREFGQNLDDTRVNYRNAYNLIVAGRAEADPLAGVYKRLWE

DPGTYALNGERMAFYTQWVHYWADLKNDPLQGWDIWTLLYLHQRQVDKSDWDANKAALGYGTYAQRPGNSGDA

SSTDGNDNLLLGLSWLTQRDQRPTFALWGIRTSAAAQAQVAAYGFAEQPAFFYANNRTNEYSTVKLLDMSQGS

PAWPFP
Metalloprotease motif underlined.

*Bacteroides thetaiotaomicron* VPI-5482 (native sequence with removed signal sequence)
SEQ ID 27

DKWEKEFRIRSYEPYSNIAEWADKLMTKKYSDLDNPTGISVKAGDDIIVLVGDTYGQNISMQCIWETGTEYKQ

TASSGDVYMLNPGVNKLTMKGEGQLFVMYNTELTSNTAKPIKIHIPLGSGTVNGFFDLKEHKTDEKYAELLKK

STHKYFCIRGEKIMFYFHRNKLLEYVPNNILSAIHLWDNIVGWQQELMGIDDVRPSQVNNHLFAISPEGSYMW

ASDYQIGFVYTYLGNILLEDNVMAAEDNAW<u>GPAHEIGHVH</u>QAAINWASSTESSNNLFSNFITYKLGKYKSRGN

GLGSVATARYANGQAWYNMGDATHQNEDTETHMRMNWQLWIYYHRCEYKTDFWQTLFKLMREVNMTEGEDPGK

KQLEFAKMASKAANQNLTDFFEMWGFFEPVNTTIEQYGTYKYYVSDAMIREAKEYMAQFPAPKHAFQYIEDRK

KSEFPSNDYRYSAVGDVGYYTQFKENQKITKAITAELAGRKVSIQNGDEAVAFELRENDENGKLLYFSTFTTF

EIPSSMetalloprotease motif underlined.ILMVNAKLYAVQADGKRILL

*Clostridium perfringens* (native sequence with removed signal sequence)
SEQ ID NO: 28

VLELEMRGDSISEAKKRKVWNFQDWQITGLSARAGDKITVYVDVAEGDPTPTLLYKQSLTQHGGATSFQLKPG

KNEITIPEINYESNGIPKDVIQGGDLFFTNYKSDSQKRAPKVRIEGASKYPVFILGKSDENEVMKELEAYVEK

IKAEPKTTPNIFAVSSNKSLEFVQATYALDWYKKNNKTPKYTAEQWDQYIADAMGFWGFDNSKDVNSDFNFRI

MPMVKNLSGGAFMNAGNGVIGIRPGNQDAILAANKGW<u>GVAHELGHNF</u>DTGGRTIVEVTNNMMPLFFESKYKTK

TRITDQNIWENNTYPKVGLDDYSNNELYNKADSTHLAQLAPLWQLYLYDNTFYGKFERQFRERDFGNKNREDI

YKSWVVAASDAMELDLTEFFARHGIRVDDKVKEDLAKYPKPDKKIYYLNDLAMNYKGDGFTENAKVSVSTSGS

NGNIKLSFSVDDENKDNILGYEIRRDGKYVGFTSNDSFVDTKSNLDEDGVYVVTPYDRKLNTLNPIEVN
Metalloprotease motif underlined.

*Pseudomonas aeruginosa* PA01 (N-term Met, C-term linker/tag)
SED ID NO: 29

MATQEEILDAALVSGDSSQLTDSHLVALRLQQQVERIRQTRTQLLDGLYQNLSQAYDPGAASMWVLPANPDNT

LPFLIGDKGRVLASLSLEAGGRGLAYGTNVLTQLSGTNAAHAPLLKRAVQWLVNGDPGAATAKDFKVSVVGVD

KTAALNGLKSAGLQPADAACNALTDASCASTSKLLVLGNGASAASLSATVRARLQAGLPILFVHTNGWNQSST

GQQILAGLGLQEGPYGGNYWDKDRVPSSRTRTRSVELGGAYGQDPALVQQIVDGSWRTDYDWSKCTSYVGRTT

CDDVPGLSDFSKRVDVLKGALDAYNQKAQNLFALPGTTSLRLWLLWADAVRQNIRYPMDKAADTARFQETFVA

DAIVGYVREAGAAQKELGSYAGQRQQSMPVSGSEETLTLTLPSAQGFTAIGRMAAPGKRLSIRIEDAGQASLA

VGLNTQRIGSTRLWNTRQYDRPRFLKSPDIKLQANQSVALVSPYGGLLQLVYSGATPGQTVTVKVTGAASQPF

LDIQPGEDSSQAIADFIQALDADKADWLEIRSGSVEVHAKVEKVRGSIDKDYGGDVQRFIRELNEVFIDDAYT

LAGFAIPNQAKTPAIQQECAARGWDCDSETLHKLPGTQHINVDQYAQCGGGCSGNPYDQTWGLNPRGW<u>GESHE</u>

<u>LGHNL</u>QVNRLKVYGGRSGEISNQIFPLHKDWRVLREFGQNLDDTRVNYRNAYNLIVAGRAEADPLAGVYKRLW

EDPGTYALNGERMAFYTQWVHYWADLKNDPLQGWDIWTLLYLHQRQVDKSDWDANKAALGYGTYAQRPGNSGD

-continued

| Sequences |
|---|
| ASSTDGNDNLLLGLSWLTQRDQRPTFALWGIRTSAAAQAQVAAYGFAEQPAFFYANNRTNEYSTVKLLDMSQG<br><br>SPAWPFPGSGHHHHHH<br>Metalloprotease motif underlined. |
| *Bacteroides thetaiotaomicron* VPI-5482 (N-term Met, C-term linker/tag)<br>SEQ ID NO: 30<br>MDKWEKEFRIRSYEPYSNIAEWADKLMTKKYSDLDNPTGISVKAGDDIIVLVGDTYGQNISMQCIWETGTEYK<br><br>QTASSGDVYMLNPGVNKLTMKGEGQLFVMYNTELTSNTAKPIKIHIPLGSGTVNGFFDLKEHKTDEKYAELLK<br><br>KSTHKYFCIRGEKIMFYFHRNKLLEYVPNNILSAIHLWDNIVGWQQELMGIDDVRPSQVNNHLFAISPEGSYM<br><br>WASDYQIGFVYTYLGNILLEDNVMAAEDNAWGPAHEIGHVHQAAINWASSTESSNNLFSNFIIYKLGKYKSRG<br><br>NGLGSVATARYANGQAWYNMGDATHQNEDTETHMRMNWQLWIYYHRCEYKTDFWQTLFKLMREVNMTEGEDPG<br><br>KKQLEFAKMASKAANQNLTDFFEMWGFFEPVNTTIEQYGTYKYYVSDAMIREAKEYMAQFPAPKHAFQYIEDR<br><br>KKSEFPSNDYRYSAVGDVGYYTQFKENQKITKAITAELAGRKVSIQNGDEAVAFELRENDENGKLLYFSTFTT<br><br>FEIPSSILMVNAKLYAVQADGKRILLGSGHHHHHH<br>Metalloprotease motif underlined. |
| *Clostridium perfringens* (N-term Met, C-term linker/tag)<br>SEQ ID NO: 31<br>MVLELEMRGDSISEAKKRKVWNFQDWQITGLSARAGDKITVYVDVAEGDPTPTLLYKQSLTQHGGATSFQLKP<br><br>GKNEITIPEINYESNGIPKDVIQGGDLFFTNYKSDSQKRAPKVRIEGASKYPVFILGKSDENEVMKELEAYVE<br><br>KIKAEPKTTPNIFAVSSNKSLEFVQATYALDWYKKNNKTPKYTAEQWDQYIADAMGFWGFDNSKDVNSDFNFR<br><br>IMPMVKNLSGGAFMNAGNGVIGIRPGNQDAILAANKGWGVAHELGHNFDTGGRTIVEVTNNMMPLFFESKYKT<br><br>KTRITDQNIWENNTYPKVGLDDYSNNELYNKADSTHLAQLAPLWQLYLYDNTFYGKFERQFRERDFGNKNRED<br><br>IYKSWVVAASDAMELDLTEFFARHGIRVDDKVKEDLAKYPKPDKKIYYLNDLAMNYKGDGFTENAKVSVSTSG<br><br>SNGNIKLSFSVDDENKDNILGYEIRRDGKYVGFTSNDSFVDTKSNLDEDGVYVVTPYDRKLNTLNPIEVNGSG<br><br>HHHHHH<br>Metalloprotease motif underlined. |
| *Pseudomonas aeruginosa* PAO1 (full native sequence including signal sequence)<br>SEQ ID NO: 32<br>MSLSTTAFPSLQGENMSRSPIPRHRALLAGFCLAGALSAQAATQEEILDAALVSGDSSQLTDSHLVALRLQQQ<br><br>VERIRQTRTQLLDGLYQNLSQAYDPGAASMWVLPANPDNTLPFLIGDKGRVLASLSLEAGGRGLAYGTNVLTQ<br><br>LSGTNAAHAPLLKRAVQWLVNGDPGAATAKDFKVSVVGVDKTAALNGLKSAGLQPADAACNALTDASCASTSK<br><br>LLVLGNGASAASLSATVRARLQAGLPILFVHTNGWNQSSTGQQILAGLGLQEGPYGGNYWDKDRVPSSRTRTR<br><br>SVELGGAYGQDPALVQQIVDGSWRTDYDWSKCTSYVGRTTCDDVPGLSDFSKRVDVLKGALDAYNQKAQNLFA<br><br>LPGTTSLRLWLLWADAVRQNIRYPMDKAADTARFQETFVADAIVGYVREAGAAQKELGSYAGQRQQSMPVSGS<br><br>EETLTLTLPSAQGFTAIGRMAAPGKRLSIRIEDAGQASLAVGLNTQRIGSTRLWNTRQYDRPRFLKSPDIKLQ<br><br>ANQSVALVSPYGGLLQLVYSGATPGQTVTVKVTGAASQPFLDIQPGEDSSQAIADFIQALDADKADWLEIRSG<br><br>SVEVHAKVEKVRGSIDKDYGGDVQRFIRELNEVFIDDAYTLAGFAIPNQAKTPAIQQECAARGWDCDSETLHK<br><br>LPGTQHINVDQYAQCGGGCSGNPYDQTWGLNPRGWGESHELGHNLQVNRLKVYGGRSGEISNQIFPLHKDWRV<br><br>LREFGQNLDDTRVNYRNAYNLIVAGRAEADPLAGVYKRLWEDPGTYALNGERMAFYTQWVHYWADLKNDPLQG |

Sequences

WDIWTLLYLHQRQVDKSDWDANKAALGYGTYAQRPGNSGDASSTDGNDNLLLGLSWLTQRDQRPTFALWGIRT

SAAAQAQVAAYGFAEQPAFFYANNRTNEYSTVKLLDMSQGSPAWPFP
Uniprot accession: Q9I5W4.1
Metalloprotease motif underlined.
Signal sequence bold, underlined.

*Bacteroides thetaiotaomicron* VPI-5482 (full native sequence including signal and other sequences)

SEQ ID NO: 33

MTIKRFITNLLALFTLFTVSLACKDTEKSIINSSFSISEEYLIQNLDKSSTSVQIPINTSMELAQWSVSYEAN

WLQCSKQKTAAEGTFLRITVNENTGETKRTANIKVTSTTATYTITVNQYAKGEVIVEGDIKVTPTGGKASEHQ

EGQDIENTYDGKFSTDGAAPFHTPWGQSAKFPVTLEYYFKGDTEIDYLIYYTRSGNGNFGKVKVYTTTNPDRS

DYTLQGEYDFKEQNAPSKVSFSEGIKATGIKFEVLSGLGDFVSCDEMEFYKTNTDKTLDKQLLTVFTDITCTE

IKNNVTNEQIQALPDYFVRIAEAVRDNTYDKWEKEFRIRSYEPYSNIAEWADKLMTKKYSDLDNPTGISVKAG

DDIIVLVGDTYGQNISMQCIWETGTEYKQTASSGDVYMLNPGVNKLTMKGEGQLFVMYNTELTSNTAKPIKIH

IPLGSGTVNGFFDLKEHKTDEKYAELLKKSTHKYFCIRGEKIMFYFHRNKLLEYVPNNILSAIHLWDNIVGWQ

QELMGIDDVRPSQVNNHLFAISPEGSYMWASDYQIGFVYTYLGNILLEDNVMAAEDNAW<u>GPAHEIGHVH</u>QAAI

NWASSTESSNNLFSNFIIYKLGKYKSRGNGLGSVATARYANGQAWYNMGDATHQNEDTETHMRMNWQLWIYYH

RCEYKTDFWQTLFKLMREVNMTEGEDPGKKQLEFAKMASKAANQNLTDFFEMWGFFEPVNTTIEQYGTYKYYV

SDAMIREAKEYMAQFPAPKHAFQYIEDRKKSEFPSNDYRYSAVGDVGYYTQFKENQKITKAITAELAGRKVSI

QNGDEAVAFELRENDENGKLLYFSTFTTFEIPSSILMVNAKLYAVQADGKRILL
Uniprot accession: Q89ZX7.1
Metalloprotease motif underlined.
Signal sequence bold, underlined.
Other sequences removed in mature protein bold, italic.

*Clostridium perfringens* (full native sequence including signal and other sequences)

SEQ ID NO: 34

MNKRKIAAIILATMITNLSATTIDVLAQELNTKNNSKVEVSHDDESHQARVSKFDLYNSDKLDAYNQEFQVSR

*SNIKSINNNGGKYNSSTIDKAIDGNLETHWETGKPNDANFTNEVVVTFNEITNIDRIVYSARRDSARGKGFAK*

*EFEIYASLKDEGDDFNLVSSGEYTESTRDLVEIKFNPTDFKRLKFKFKKADQNWASAAEFMFYKEDKLNEKFN*

*GLFTDSSMNKVSEEFNTLEKLNAFENELKDHPIYDLYKEGLNNARAILTETSENPTKATLGQITYNLNDDYNN*

*QYRMPYKNIKAIKNNGRHYAAQNIEKAIDNDVNTYWETGTLNSSSFNNEVEFNDLVTLDRIVYGSRQSDLK*

*GFAEEVYIYASRTSKGDTYKLVATGAHEATKGLVEAKFEPTEFKRVKFKFKKSKQNSATLNELMFYKPDEVYS*

*SIPKLFTDGTMSELSEEFNSLEKINAFKEKAKNHPLYNDFNETIELAESLISNPRKED*VLELEMRGDSISEAK

KRKVWNFQDWQITGLSARAGDKITVYVDVAEGDPTPTLLYKQSLTQHGGATSFQLKPGKNEITIPEINYESNG

IPKDVIQGGDLFFTNYKSDSQKRAPKVRIEGASKYPVFILGKSDENEVMKELEAYVEKIKAEPKTTPNIFAVS

SNKSLEFVQATYALDWYKKNNKTPKYTAEQWDQYIADAMGFWGFDNSKDVNSDFNFRIMPMVKNLSGGAFMNA

GNGVIGIRPGNQDAILAANKGWGVAHELGHNFDTGGRTIVEVTNNMMPLFFESKYKTKTRITDQNIWENNTYP

KVGLDDYSNNELYNKADSTHLAQLAPLWQLYLYDNTFYGKFERQFRERDFGNKNREDIYKSWVVAASDAMELD

LTEFFARHGIRVDDKVKEDLAKYPKPDKKIYYLNDLAMNYKGDGFTENAKVSVSTSGSNGNIKLSFSVDDENK

DNILGYEIRRDGKYVGFTSNDSFVDTKSNLDEDGVYVVTPYDRKLNTLNPIEVN*ALQPTLSVNPVITLALGEE*

*FNEEEYIVAKDIKGNSLSESVKVKSSNVTSKVGEYEVLYSLEDSKGNEYTKTSKVNVVSRKEYMSDLTPKQS*

*SNGWGTVRKDKSISGGVIGLTRDGDFVDYNKGLGLHSNAEYVYDLEGKDYDYYFESYVGVDKAMSSRPASSVIF*

*KVLVDGEEKFNSGVMRSTTPQKYVKVDVKNAKELKLIVNDAGDGDSSDHASFGDAKLATLSSKPIIKGENLAY*

*SMDEKVDLMKGITATDIEDGNITSKVQIKSSDFVEGKSGIFTVVYSVTDSDGLTSECSRTIAVTDKETQLSDL*

-continued

Sequences

*NWKSATIGSGSVRKDRAVSGNQIRLLNEDNSVETFAKGIGTHSYSEIVYNSEGYDIFDTWVGIDRHVADKKVS*

*SVKFKVYVDGELKAETDVMRIDTPKKRLVVDVRNSKEIKLVVDVADNGNNWDHADWADAKFRNLAEYDASELN*

*KAIEEAKKLDLNNYTEESSEALKNAISKGEEALLSKDKETINSALEELNKEMNSLVKVDLNAVINIPDKYLLK*

*SIQNQLNKTGDITLGDMYSLTTLTLSGVEDLTGLENAKNLETLNMDYNEVKDLRPLSKLKKLNTLNAQEQFIA*

*AGELKPSNGKVIGDSKVYNREGKNVAKTIRVVDKNGNTILEQDAKDEFTINTKDLSSGLYGVHVLFFEDEGFSG*

*VMFYLFNV*
Uniprot accession: A0A0H2YN38.1
Metalloprotease motif underlined.
Signal sequence bold, underlined.
Other sequences removed in mature protein bold, italic.

*Pseudomonas aeruginosa* PAO1 (double mutant with removed signal sequence)
SEQ ID NO: 35

ATQEEILDAALVSGDSSQLTDSHLVALRLQQQVERIRQTRTQLLDGLYQNLSQAYDPGAASMWVLPANPDNTL
PFLIGDKGRVLASLSLEAGGRGLAYGTNVLTQLSGTNAAHAPLLKRAVQWLVNGDPGAATAKDFKVSVVGVDK
TAALNGLKSAGLQPADAACNALTDASCASTSKLLVLGNGASAASLSATVRARLQAGLPILFVHTNGWNQSSTG
QQILAGLGLQEGPYGGNYWDKDRVPSSRTRTRSVELGGAYGQDPALVQQIVDGSWRTDYDWSKCTSYVGRTTC
DDVPGLSDFSKRVDVLKGALDAYNQKAQNLFALPGTTSLRLWLLWADAVRQNIRYPMDKAADTARFQETFVAD
AIVGYVREAGAAQKELGSYAGQRQQSMPVSGSEETLTLTLPSAQGFTAIGRMAAPGKRLSIRIEDAGQASLAV
GLNTQRIGSTRLWNTRQYDRPRFLKSPDIKLQANQSVALVSPYGGLLQLVYSGATPGQTVTVKVTGAASQPFL
DIQPGEDSSQATADFIQALDADKADWLEIRSGSVEVHAKVEKVRGSIDKDYGGDVQRFIRELNEVFIDDAYTL

AGFAIPNQAKTPAIQQECAARGWDCDSETLHKLPGTQHINVDQYAQCGGGCSGNPYDQTWGLNPRGWGESAAL

GHNLQVNRLKVYGGRSGEISNQIFPLHKDWRVLREFGQNLDDTRVNYRNAYNLIVAGRAEADPLAGVYKRLWE

DPGTYALNGERMAFYTQWVHYWADLKNDPLQGWDIWTLLYLHQRQVDKSDWDANKAALGYGTYAQRPGNSGDA
SSTDGNDNLLLGLSWLTQRDQRPTFALWGIRTSAAAQAQVAAYGFAEQPAFFYANNRTNEYSTVKLLDMSQGS
PAWPFP
Disrupted metalloprotease motif underlined

*Bacteroides thetaiotaomicron* VPI-5482 (double mutant with removed signal and other immature sequences)

SEQ ID NO: 36

DKWEKEFRIRSYEPYSNIAEWADKLMTKKYSDLDNPTGISVKAGDDIIVLVGDTYGQNISMQCIWETGTEYKQ
TASSGDVYMLNPGVNKLTMKGEGQLFVMYNTELTSNTAKPIKIHIPLGSGTVNGFFDLKEHKTDEKYAELLKK
STHKYFCIRGEKIMFYFHRNKLLEYVPNNILSAIHLWDNIVGWQQELMGIDDVRPSQVNNHLFAISPEGSYMW

ASDYQIGFVYTYLGNILLEDNVMAAEDNAWGPAAAIGHVHQAAINWASSTESSNNLFSNFITYKLGKYKSRGN

GLGSVATARYANGQAWYNMGDATHQNEDTETHMRMNWQLWIYYHRCEYKTDFWQTLFKLMREVNMTEGEDPGK
KQLEFAKMASKAANQNLTDFFEMWGFFEPVNTTIEQYGTYKYYVSDAMIREAKEYMAQFPAPKHAFQYIEDRK
KSEFPSNDYRYSAVGDVGYYTQFKENQKITKAITAELAGRKVSIQNGDEAVAFELRENDENGKLLYFSTFTTF
EIPSSILMVNAKLYAVQADGKRILL
Disrupted metalloprotease motif underlined

*Clostridium perfringens* (double mutant with removed signal and other immature sequences)

SEQ ID NO: 37
VLELEMRGDSISEAKKRKVWNFQDWQITGLSARAGDKITVYVDVAEGDPTPTLLYKQSLTQHGGATSFQLKPG

KNEITIPEINYESNGIPKDVIQGGDLFFTNYKSDSQKRAPKVRIEGASKYPVFILGKSDENEVMKELEAYVEK

IKAEPKTTPNIFAVSSNKSLEFVQATYALDWYKKNNKTPKYTAEQWDQYIADAMGFWGFDNSKDVNSDFNFRI

MPMVKNLSGGAFMNAGNGVIGIRPGNQDAILAANKGWGVAAALGHNFDTGGRTIVEVTNNMMPLFFESKYKTK

| Sequences |
|---|

TRITDQNIWENNTYPKVGLDDYSNNELYNKADSTHLAQLAPLWQLYLYDNTFYGKFERQFRERDFGNKNREDI

YKSWVVAASDAMELDLTEFFARHGIRVDDKVKEDLAKYPKPDKKIYYLNDLAMNYKGDGFTENAKVSVSTSGS

NGNIKLSFSVDDENKDNILGYEIRRDGKYVGFTSNDSFVDTKSNLDEDGVYVVTPYDRKLNTLNPIEVN
Disrupted metalloprotease motif underlined

*Pseudomonas aeruginosa* PAO1 (double mutant with removed signal sequence, with N-term Met, C-term linker/tag)
SEQ ID NO: 38

MATQEEILDAALVSGDSSQLTDSHLVALRLQQQVERIRQTRTQLLDGLYQNLSQAYDPGAASMWVLPANPDNT

LPFLIGDKGRVLASLSLEAGGRGLAYGTNVLTQLSGTNAAHAPLLKRAVQWLVNGDPGAATAKDFKVSVVGVD

KTAALNGLKSAGLQPADAACNALTDASCASTSKLLVLGNGASAASLSATVRARLQAGLPILFVHTNGWNQSST

GQQILAGLGLQEGPYGGNYWDKDRVPSSRTRTRSVELGGAYGQDPALVQQIVDGSWRTDYDWSKCTSYVGRTT

CDDVPGLSDFSKRVDVLKGALDAYNQKAQNLFALPGTTSLRLWLLWADAVRQNIRYPMDKAADTARFQETFVA

DAIVGYVREAGAAQKELGSYAGQRQQSMPVSGSEETLTLTLPSAQGFTAIGRMAAPGKRLSIRIEDAGQASLA

VGLNTQRIGSTRLWNTRQYDRPRFLKSPDIKLQANQSVALVSPYGGLLQLVYSGATPGQTVTVKVTGAASQPF

LDIQPGEDSSQATADFIQALDADKADWLEIRSGSVEVHAKVEKVRGSIDKDYGGDVQRFIRELNEVFIDDAYT

LAGFAIPNQAKTPAIQQECAARGWDCDSETLHKLPGTQHINVDQYAQCGGGCSGNPYDQTWGLNPRGWGESAA

LGHNLQVNRLKVYGGRSGEISNQIFPLHKDWRVLREFGQNLDDTRVNYRNAYNLIVAGRAEADPLAGVYKRLW

EDPGTYALNGERMAFYTQWVHYWADLKNDPLQGWDIWTLLYLHQRQVDKSDWDANKAALGYGTYAQRPGNSGD

ASSTDGNDNLLLGLSWLTQRDQRPTFALWGIRTSAAAQAQVAAYGFAEQPAFFYANNRTNEYSTVKLLDMSQG

SPAWPFPGSGHHHHHH
Disrupted metalloprotease motif underlined

*Bacteroides thetaiotaomicron* VPI-5482 (double mutant with removed signal and other sequences from immature protein, with N-term Met, C-term linker/tag)
SEQ ID NO: 39

MDKWEKEFRIRSYEPYSNIAEWADKLMTKKYSDLDNPTGISVKAGDDIIVLVGDTYGQNISMQCIWETGTEYK

QTASSGDVYMLNPGVNKLTMKGEGQLFVMYNTELTSNTAKPIKIHIPLGSGTVNGFFDLKEHKTDEKYAELLK

KSTHKYFCIRGEKIMFYFHRNKLLEYVPNNILSAIHLWDNIVGWQQELMGIDDVRPSQVNNHLFAISPEGSYM

WASDYQIGFVYTYLGNILLEDNVMAAEDNAWGPAAAIGHVHQAAINWASSTESSNNLFSNFITYKLGKYKSRG

NGLGSVATARYANGQAWYNMGDATHQNEDTETHMRMNWQLWIYYHRCEYKTDFWQTLFKLMREVNMTEGEDPG

KKQLEFAKMASKAANQNLTDFFEMWGFFEPVNTTIEQYGTYKYYVSDAMIREAKEYMAQFPAPKHAFQYIEDR

KKSEFPSNDYRYSAVGDVGYYTQFKENQKITKAITAELAGRKVSIQNGDEAVAFELRENDENGKLLYFSTFTT

FEIPSSILMVNAKLYAVQADGKRILLGSGHHHHHH
Disrupted metalloprotease motif underlined

*Clostridium perfringens* (double mutant with removed signal and other sequences from immature protein, with N-term Met, C-term linker/tag)
SEQ ID NO: 40
MVLELEMRGDSISEAKKRKVWNFQDWQITGLSARAGDKITVYVDVAEGDPTPTLLYKQSLTQHGGATSFQLKP

GKNEITIPEINYESNGIPKDVIQGGDLFFTNYKSDSQKRAPKVRIEGASKYPVFILGKSDENEVMKELEAYVE

KIKAEPKTTPNIFAVSSNKSLEFVQATYALDWYKKNNKTPKYTAEQWDQYIADAMGFWGFDNSKDVNSDFNFR

IMPMVKNLSGGAFMNAGNGVIGIRPGNQDAILAANKGWGVAAALGHNFDTGGRTIVEVTNNMMPLFFESKYKT

KTRITDQNIWENNTYPKVGLDDYSNNELYNKADSTHLAQLAPLWQLYLYDNTFYGKFERQFRERDFGNKNRED

IYKSWVVAASDAMELDLTEFFARHGIRVDDKVKEDLAKYPKPDKKIYYLNDLAMNYKGDGFTENAKVSVSTSG

SNGNIKLSFSVDDENKDNILGYEIRRDGKYVGFTSNDSFVDTKSNLDEDGVYVVTPYDRKLNTLNPIEVNGSG

HHHHHH
Disrupted metalloprotease motif underlined

| Sequences | |
|---|---|
| HELGH (metalloprotease motif) | SEQ ID NO: 41 |
| HEIGH (metalloprotease motif) | SEQ ID NO: 42 |
| GVAHELGHNF (metalloprotease motif) | SEQ ID NO: 43 |
| HALGH (disrupted metalloprotease motif) | SEQ ID NO: 44 |
| AELGH (disrupted metalloprotease motif) | SEQ ID NO: 45 |
| AALGH (disrupted metalloprotease motif) | SEQ ID NO: 46 |
| GKPRPYSPRPTSHPRPIRV (glycodrosoctn peptide with O-gly site on the T) | SEQ ID NO: 47 |
| YIYGSFK (Non-O-glycosylated peptide) | SEQ ID NO: 48 |
| KKLVFFA (Non-O-glycosylated peptide) | SEQ ID NO: 49 |
| FLPLILGKLVKGLL (Non-O-glycosylated peptide) | SEQ ID NO: 50 |

The invention claimed is:

1. A method of hydrolysing an O-glycoprotein, wherein the method comprises contacting a sample comprising the O-glycoprotein with a polypeptide having endoprotease activity specific for O-glycosylated proteins which comprises:
   (a) the amino acid sequence of SEQ ID NO: 1; or
   (b) an amino acid sequence which is at least 95% identical to the amino acid sequence of SEQ ID NO: 1 and comprises a motif comprising the sequence HEIGH (SEQ ID NO: 42) or HELGH (SEQ ID NO: 41).

2. A method for assessing the glycosylation status of a protein, comprising:
   contacting a sample comprising the protein with a polypeptide having endoprotease activity specific for O-glycosylated proteins which comprises:
   (a) the amino acid sequence of SEQ ID NO: 1; or
   (b) an amino acid sequence which is at least 95% identical to the amino acid sequence of SEQ ID NO: 1 and comprises a motif comprising the sequence HEIGH (SEQ ID NO: 42) or HELGH (SEQ ID NO: 41); and
   detecting and/or analysing the products produced.

3. The method according to claim 2, wherein the detection and/or analysis is carried out by affinity chromatography, SDS-PAGE, HPLC or mass spectrometry.

4. The method according to claim 1, wherein the sample is incubated with a sialidase prior to or at the same time as contacting the O-glycoprotein or the sample with the polypeptide.

5. The method according to claim 1, wherein the polypeptide comprises a motif comprising the sequence HELGH (SEQ ID NO: 41).

6. The method according to claim 1, further comprising detecting or analysing the hydrolysis products.

7. The method according to claim 4, wherein said sialidase is Am1757 or a mixture of Am1757 and Am0707.

8. The method according to claim 7, wherein Am1757 is a polypeptide consisting of SEQ ID NO: 11 and/or wherein Am0707 is a polypeptide consisting of SEQ ID NO: 14.

9. The method according to claim 1, wherein the polypeptide includes an additional methionine at the N terminus and/or a His tag at the C terminus.

10. The method according to claim 9, wherein said polypeptide comprises or consists of the amino acid sequence of SEQ ID NO: 2.

11. The method according to claim 2, wherein the polypeptide comprises a motif comprising the sequence HELGH (SEQ ID NO: 41).

12. The method according to claim 2, further comprising determining the presence or absence of an O-glycoprotein in the sample based on the presence or absence of cleavage products.

13. The method according to claim 2, wherein said analysis is conducted to identify the type of a O-glycan chain and/or its position of attachment to an O-glycoprotein.

14. The method according to claim 2, wherein the analysis or detection is carried out by affinity chromatography, SDS-PAGE, HPLC or mass spectrometry.

15. The method according to claim 2, wherein the sample is incubated with a sialidase prior to or at the same time as contacting the protein or the sample with the polypeptide.

16. The method according to claim 15, wherein said sialidase is Am1757 or a mixture of Am1757 and Am0707.

17. The method according to claim 16, wherein Am1757 is a polypeptide consisting of SEQ ID NO: 11 and/or wherein Am0707 is a polypeptide consisting of SEQ ID NO: 14.

18. The method according to claim 2, wherein the polypeptide includes an additional methionine at the N terminus and/or a His tag at the C terminus.

19. The method according to claim 18, wherein said polypeptide comprises or consists of the amino acid sequence of SEQ ID NO: 2.

20. The method according to claim 9, wherein the His tag is joined to the C terminus by a linker.

21. The method according to claim 18, wherein the His tag is joined to the C terminus by a linker.

* * * * *

SEQUENCE LISTING

<160> NUMBER OF SEQ ID NOS: 78

<210> SEQ ID NO 1
<211> LENGTH: 361
<212> TYPE: PRT
<213> ORGANISM: Akkermansia muciniphila

<400> SEQUENCE: 1

Glu Val Thr Val Pro Asp Ala Leu Lys Asp Arg Ile Ala Leu Lys Lys
1               5                   10                  15

Thr Ala Arg Gln Leu Asn Ile Val Tyr Phe Leu Gly Ser Asp Thr Glu
            20                  25                  30

Pro Val Pro Asp Tyr Glu Arg Arg Leu Ser Glu Leu Leu Leu Tyr Leu
        35                  40                  45

Gln Gln Phe Tyr Gly Lys Glu Met Gln Arg His Gly Tyr Gly Ala Arg
    50                  55                  60

Ser Phe Gly Leu Asp Ile Lys Ser Pro Gly Arg Val Asn Ile Ile Glu
65                  70                  75                  80

Tyr Lys Ala Lys Asn Pro Ala Ala His Tyr Pro Tyr Glu Asn Gly Gly
                85                  90                  95

Gly Trp Lys Ala Ala Gln Glu Leu Asp Glu Phe Phe Lys Ala His Pro
            100                 105                 110

Asp Arg Lys Lys Ser Gln His Thr Leu Ile Ile Met Pro Thr Trp Asn
        115                 120                 125

```
Asp Glu Lys Asn Gly Pro Asp Asn Pro Gly Val Pro Phe Tyr Gly
    130                 135                 140

Met Gly Arg Asn Cys Phe Ala Leu Asp Tyr Pro Ala Phe Asp Ile Lys
145                 150                 155                 160

His Leu Gly Gln Lys Thr Arg Glu Gly Arg Leu Leu Thr Lys Trp Tyr
                165                 170                 175

Gly Gly Met Ala His Glu Leu Gly His Gly Leu Asn Leu Pro His Asn
            180                 185                 190

His Gln Thr Ala Ser Asp Gly Lys Lys Tyr Gly Thr Ala Leu Met Gly
        195                 200                 205

Ser Gly Asn Tyr Thr Phe Gly Thr Ser Pro Thr Phe Leu Thr Pro Ala
210                 215                 220

Ser Cys Ala Leu Leu Asp Ala Cys Glu Val Phe Ser Val Thr Pro Ser
225                 230                 235                 240

Gln Gln Phe Tyr Glu Gly Lys Pro Glu Val Glu Val Gly Asp Val Ala
                245                 250                 255

Ile Ser Phe Lys Gly Asp Gln Ile Leu Val Ser Gly Asn Tyr Lys Ser
            260                 265                 270

Pro Gln Thr Val Lys Ala Leu Asn Val Tyr Ile Gln Asp Pro Pro Tyr
        275                 280                 285

Ala Val Asn Gln Asp Tyr Asp Ala Val Ser Phe Ser Arg Arg Leu Gly
290                 295                 300

Lys Lys Ser Gly Lys Phe Ser Met Lys Ile Asp Lys Lys Glu Leu Glu
305                 310                 315                 320

Gly Leu Asn Asn Asn Glu Phe Arg Ile Ser Leu Met Phe Ile Leu Ala
                325                 330                 335

Asn Gly Leu His Met Gln Lys His Phe Thr Phe His Trp Asp Ala Leu
            340                 345                 350

Gln Asp Tyr Arg Asp Gly Ser Lys Ser
        355                 360

<210> SEQ ID NO 2
<211> LENGTH: 371
<212> TYPE: PRT
<213> ORGANISM: Artificial Sequence
<220> FEATURE:
<223> OTHER INFORMATION: LS (N terminal methionine and a C-terminal
      linker + His6 tag)

<400> SEQUENCE: 2

Met Glu Val Thr Val Pro Asp Ala Leu Lys Asp Arg Ile Ala Leu Lys
1               5                   10                  15

Lys Thr Ala Arg Gln Leu Asn Ile Val Tyr Phe Leu Gly Ser Asp Thr
            20                  25                  30

Glu Pro Val Pro Asp Tyr Glu Arg Arg Leu Ser Glu Leu Leu Leu Tyr
        35                  40                  45

Leu Gln Gln Phe Tyr Gly Lys Glu Met Gln Arg His Gly Tyr Gly Ala
    50                  55                  60

Arg Ser Phe Gly Leu Asp Ile Lys Ser Pro Gly Arg Val Asn Ile Ile
65                  70                  75                  80

Glu Tyr Lys Ala Lys Asn Pro Ala Ala His Tyr Pro Tyr Glu Asn Gly
                85                  90                  95

Gly Gly Trp Lys Ala Ala Gln Glu Leu Asp Glu Phe Phe Lys Ala His
            100                 105                 110

Pro Asp Arg Lys Lys Ser Gln His Thr Leu Ile Ile Met Pro Thr Trp
        115                 120                 125
```

Asn Asp Glu Lys Asn Gly Pro Asp Asn Pro Gly Gly Val Pro Phe Tyr
    130                 135                 140

Gly Met Gly Arg Asn Cys Phe Ala Leu Asp Tyr Pro Ala Phe Asp Ile
145                 150                 155                 160

Lys His Leu Gly Gln Lys Thr Arg Glu Gly Arg Leu Leu Thr Lys Trp
                165                 170                 175

Tyr Gly Gly Met Ala His Glu Leu Gly His Gly Leu Asn Leu Pro His
            180                 185                 190

Asn His Gln Thr Ala Ser Asp Gly Lys Lys Tyr Gly Thr Ala Leu Met
        195                 200                 205

Gly Ser Gly Asn Tyr Thr Phe Gly Thr Ser Pro Thr Phe Leu Thr Pro
210                 215                 220

Ala Ser Cys Ala Leu Leu Asp Ala Cys Glu Val Phe Ser Val Thr Pro
225                 230                 235                 240

Ser Gln Gln Phe Tyr Glu Gly Lys Pro Glu Val Glu Val Gly Asp Val
                245                 250                 255

Ala Ile Ser Phe Lys Gly Asp Gln Ile Leu Val Ser Gly Asn Tyr Lys
            260                 265                 270

Ser Pro Gln Thr Val Lys Ala Leu Asn Val Tyr Ile Gln Asp Pro Pro
        275                 280                 285

Tyr Ala Val Asn Gln Asp Tyr Asp Ala Val Ser Phe Ser Arg Arg Leu
290                 295                 300

Gly Lys Lys Ser Gly Lys Phe Ser Met Lys Ile Asp Lys Lys Glu Leu
305                 310                 315                 320

Glu Gly Leu Asn Asn Asn Glu Phe Arg Ile Ser Leu Met Phe Ile Leu
                325                 330                 335

Ala Asn Gly Leu His Met Gln Lys His Phe Thr Phe His Trp Asp Ala
            340                 345                 350

Leu Gln Asp Tyr Arg Asp Gly Ser Lys Ser Gly Ser Gly His His His
        355                 360                 365

His His His
    370

<210> SEQ ID NO 3
<211> LENGTH: 1116
<212> TYPE: DNA
<213> ORGANISM: Artificial Sequence
<220> FEATURE:
<223> OTHER INFORMATION: Nucleotide sequence of LS

<400> SEQUENCE: 3
atggaagtca ctgtgccgga cgccctgaaa gatcgcatcg cgctgaagaa aaccgctcgt      60
cagctgaata tcgtctactt cctgggttct gataccgaac cggttccgga ctacgagcgc     120
cgtctgagcg agctgctgtt gtatctgcag caattctatg gtaaagaaat gcagcgccat     180
ggctatggcg cacgcagctt tggtctggac attaagtcac cgggtcgtgt gaacattatc     240
gagtacaaag cgaagaaccc ggcagcgcat tacccgtatg agaatggtgg cggctggaaa     300
gctgcacaag aactggacga atttttcaag gcccatccag accgcaagaa agccagcac     360 accctgatca tcatgcctac ctggaatgat gagaaaaatg gtcctgacaa tccgggtggc     420
gttccgttct atggtatggg tcgtaattgt tttgcgttgg actacccggc gtttgatatc     480
aagcacctgg gtcagaaaac gcgtgagggt cgtctgctga cgaaatggta cggtggcatg     540
gcgcacgaac tgggccacgg cctgaatctg ccgcacaatc accagaccgc gagcgatggc     600
aagaaatatg gcaccgccct gatgggtagc ggcaactaca cgttcggtac cagcccgacg     660

-continued

```
ttcctgaccc cggcgagctg tgcgctgctg gatgcctgcg aagtgttcag cgttaccccg     720
agccaacagt tttatgaggg taagccagaa gtcgaggttg gtgatgttgc aatttccttc     780
aagggtgatc aaatcttggt cagcggtaac tacaagagcc cgcaaaccgt gaaagctctg     840
aacgtttaca ttcaggatcc gccgtacgcc gtgaaccaag actacgatgc agtgagcttt     900
agccgtcgtc tgggcaaaaa gtccggtaag tttagcatga agattgacaa aaaagaactg     960
gaaggcctga taacaacga attccgtatt tccttgatgt tcattctggc aaacggctta    1020
cacatgcaga agcactttac gtttcactgg gatgcgctgc aagactaccg tgacggtagc    1080
aaatctggtt cgggtcatca tcaccaccat cactga                              1116
```

<210> SEQ ID NO 4
<211> LENGTH: 385
<212> TYPE: PRT
<213> ORGANISM: Akkermansia muciniphila

<400> SEQUENCE: 4

```
Met Leu Lys Arg Leu Leu Ser Ala Phe Phe Ser Leu Phe Phe Leu Gly
1               5                   10                  15

Ala Ala Ser Gly Thr Ser Phe Ala Glu Val Thr Val Pro Asp Ala Leu
            20                  25                  30

Lys Asp Arg Ile Ala Leu Lys Lys Thr Ala Arg Gln Leu Asn Ile Val
        35                  40                  45

Tyr Phe Leu Gly Ser Asp Thr Glu Pro Val Pro Asp Tyr Glu Arg Arg
    50                  55                  60

Leu Ser Glu Leu Leu Leu Tyr Leu Gln Gln Phe Tyr Gly Lys Glu Met
65                  70                  75                  80

Gln Arg His Gly Tyr Gly Ala Arg Ser Phe Gly Leu Asp Ile Lys Ser
                85                  90                  95

Pro Gly Arg Val Asn Ile Ile Glu Tyr Lys Ala Lys Asn Pro Ala Ala
            100                 105                 110

His Tyr Pro Tyr Glu Asn Gly Gly Trp Lys Ala Ala Gln Glu Leu
        115                 120                 125

Asp Glu Phe Phe Lys Ala His Pro Asp Arg Lys Lys Ser Gln His Thr
    130                 135                 140

Leu Ile Ile Met Pro Thr Trp Asn Asp Glu Lys Asn Gly Pro Asp Asn
145                 150                 155                 160

Pro Gly Gly Val Pro Phe Tyr Gly Met Gly Arg Asn Cys Phe Ala Leu
                165                 170                 175

Asp Tyr Pro Ala Phe Asp Ile Lys His Leu Gly Gln Lys Thr Arg Glu
            180                 185                 190

Gly Arg Leu Leu Thr Lys Trp Tyr Gly Gly Met Ala His Glu Leu Gly
        195                 200                 205

His Gly Leu Asn Leu Pro His Asn His Gln Thr Ala Ser Asp Gly Lys
    210                 215                 220

Lys Tyr Gly Thr Ala Leu Met Gly Ser Gly Asn Tyr Thr Phe Gly Thr
225                 230                 235                 240

Ser Pro Thr Phe Leu Thr Pro Ser Cys Ala Leu Leu Asp Ala Cys
                245                 250                 255

Glu Val Phe Ser Val Thr Pro Ser Gln Gln Phe Tyr Glu Gly Lys Pro
            260                 265                 270

Glu Val Glu Val Gly Asp Val Ala Ile Ser Phe Lys Gly Asp Gln Ile
        275                 280                 285
```

```
Leu Val Ser Gly Asn Tyr Lys Ser Pro Gln Thr Val Lys Ala Leu Asn
    290                 295                 300

Val Tyr Ile Gln Asp Pro Pro Tyr Ala Val Asn Gln Asp Tyr Asp Ala
305                 310                 315                 320

Val Ser Phe Ser Arg Arg Leu Gly Lys Lys Ser Gly Lys Phe Ser Met
                325                 330                 335

Lys Ile Asp Lys Lys Glu Leu Glu Gly Leu Asn Asn Asn Glu Phe Arg
            340                 345                 350

Ile Ser Leu Met Phe Ile Leu Ala Asn Gly Leu His Met Gln Lys His
                355                 360                 365

Phe Thr Phe His Trp Asp Ala Leu Gln Asp Tyr Arg Asp Gly Ser Lys
370                 375                 380

Ser
385

<210> SEQ ID NO 5
<211> LENGTH: 361
<212> TYPE: PRT
<213> ORGANISM: Artificial Sequence
<220> FEATURE:
<223> OTHER INFORMATION: Polypeptide capable of binding to O-glycans but
      lacks or has reduced O-glycoprotein-specific endoprotease activity

<400> SEQUENCE: 5

Glu Val Thr Val Pro Asp Ala Leu Lys Asp Arg Ile Ala Leu Lys Lys
1               5                   10                  15

Thr Ala Arg Gln Leu Asn Ile Val Tyr Phe Leu Gly Ser Asp Thr Glu
            20                  25                  30

Pro Val Pro Asp Tyr Glu Arg Arg Leu Ser Glu Leu Leu Leu Tyr Leu
        35                  40                  45

Gln Gln Phe Tyr Gly Lys Glu Met Gln Arg His Gly Tyr Gly Ala Arg
    50                  55                  60

Ser Phe Gly Leu Asp Ile Lys Ser Pro Gly Arg Val Asn Ile Ile Glu
65                  70                  75                  80

Tyr Lys Ala Lys Asn Pro Ala Ala His Tyr Pro Tyr Glu Asn Gly Gly
                85                  90                  95

Gly Trp Lys Ala Ala Gln Glu Leu Asp Glu Phe Phe Lys Ala His Pro
            100                 105                 110

Asp Arg Lys Lys Ser Gln His Thr Leu Ile Ile Met Pro Thr Trp Asn
        115                 120                 125

Asp Glu Lys Asn Gly Pro Asp Asn Pro Gly Gly Val Pro Phe Tyr Gly
    130                 135                 140

Met Gly Arg Asn Cys Phe Ala Leu Asp Tyr Pro Ala Phe Asp Ile Lys
145                 150                 155                 160

His Leu Gly Gln Lys Thr Arg Glu Gly Arg Leu Leu Thr Lys Trp Tyr
                165                 170                 175

Gly Gly Met Ala His Ala Leu Gly His Gly Leu Asn Leu Pro His Asn
            180                 185                 190

His Gln Thr Ala Ser Asp Gly Lys Lys Tyr Gly Thr Ala Leu Met Gly
        195                 200                 205

Ser Gly Asn Tyr Thr Phe Gly Thr Ser Pro Thr Phe Leu Thr Pro Ala
    210                 215                 220

Ser Cys Ala Leu Leu Asp Ala Cys Glu Val Phe Ser Val Thr Pro Ser
225                 230                 235                 240

Gln Gln Phe Tyr Glu Gly Lys Pro Glu Val Glu Val Gly Asp Val Ala
                245                 250                 255
```

-continued

```
Ile Ser Phe Lys Gly Asp Gln Ile Leu Val Ser Gly Asn Tyr Lys Ser
            260                 265                 270

Pro Gln Thr Val Lys Ala Leu Asn Val Tyr Ile Gln Asp Pro Pro Tyr
        275                 280                 285

Ala Val Asn Gln Asp Tyr Asp Ala Val Ser Phe Ser Arg Arg Leu Gly
    290                 295                 300

Lys Lys Ser Gly Lys Phe Ser Met Lys Ile Asp Lys Lys Glu Leu Glu
305                 310                 315                 320

Gly Leu Asn Asn Asn Glu Phe Arg Ile Ser Leu Met Phe Ile Leu Ala
                325                 330                 335

Asn Gly Leu His Met Gln Lys His Phe Thr Phe His Trp Asp Ala Leu
            340                 345                 350

Gln Asp Tyr Arg Asp Gly Ser Lys Ser
        355                 360

<210> SEQ ID NO 6
<211> LENGTH: 371
<212> TYPE: PRT
<213> ORGANISM: Artificial Sequence
<220> FEATURE:
<223> OTHER INFORMATION: LS E206A (N-terminal methionine and a
      C-terminal linker + His6 tag)

<400> SEQUENCE: 6

Met Glu Val Thr Val Pro Asp Ala Leu Lys Asp Arg Ile Ala Leu Lys
1               5                   10                  15

Lys Thr Ala Arg Gln Leu Asn Ile Val Tyr Phe Leu Gly Ser Asp Thr
            20                  25                  30

Glu Pro Val Pro Asp Tyr Glu Arg Arg Leu Ser Glu Leu Leu Leu Tyr
        35                  40                  45

Leu Gln Gln Phe Tyr Gly Lys Glu Met Gln Arg His Gly Tyr Gly Ala
    50                  55                  60

Arg Ser Phe Gly Leu Asp Ile Lys Ser Pro Gly Arg Val Asn Ile Ile
65                  70                  75                  80

Glu Tyr Lys Ala Lys Asn Pro Ala Ala His Tyr Pro Tyr Glu Asn Gly
                85                  90                  95

Gly Gly Trp Lys Ala Ala Gln Glu Leu Asp Glu Phe Phe Lys Ala His
            100                 105                 110

Pro Asp Arg Lys Lys Ser Gln His Thr Leu Ile Ile Met Pro Thr Trp
        115                 120                 125

Asn Asp Glu Lys Asn Gly Pro Asp Asn Pro Gly Gly Val Pro Phe Tyr
    130                 135                 140

Gly Met Gly Arg Asn Cys Phe Ala Leu Asp Tyr Pro Ala Phe Asp Ile
145                 150                 155                 160

Lys His Leu Gly Gln Lys Thr Arg Glu Gly Arg Leu Leu Thr Lys Trp
                165                 170                 175

Tyr Gly Gly Met Ala His Ala Leu Gly His Gly Leu Asn Leu Pro His
            180                 185                 190

Asn His Gln Thr Ala Ser Asp Gly Lys Lys Tyr Gly Thr Ala Leu Met
        195                 200                 205

Gly Ser Gly Asn Tyr Thr Phe Gly Thr Ser Pro Thr Phe Leu Thr Pro
    210                 215                 220

Ala Ser Cys Ala Leu Leu Asp Ala Cys Glu Val Phe Ser Val Thr Pro
225                 230                 235                 240

Ser Gln Gln Phe Tyr Glu Gly Lys Pro Glu Val Glu Val Gly Asp Val
                245                 250                 255
```

```
Ala Ile Ser Phe Lys Gly Asp Gln Ile Leu Val Ser Gly Asn Tyr Lys
            260                 265                 270

Ser Pro Gln Thr Val Lys Ala Leu Asn Val Tyr Ile Gln Asp Pro Pro
        275                 280                 285

Tyr Ala Val Asn Gln Asp Tyr Asp Ala Val Ser Phe Ser Arg Arg Leu
    290                 295                 300

Gly Lys Lys Ser Gly Lys Phe Ser Met Lys Ile Asp Lys Lys Glu Leu
305                 310                 315                 320

Glu Gly Leu Asn Asn Asn Glu Phe Arg Ile Ser Leu Met Phe Ile Leu
                325                 330                 335

Ala Asn Gly Leu His Met Gln Lys His Phe Thr Phe His Trp Asp Ala
            340                 345                 350

Leu Gln Asp Tyr Arg Asp Gly Ser Lys Ser Gly Ser Gly His His His
        355                 360                 365

His His His
    370

<210> SEQ ID NO 7
<211> LENGTH: 1116
<212> TYPE: DNA
<213> ORGANISM: Artificial Sequence
<220> FEATURE:
<223> OTHER INFORMATION: Nucleotide sequence encoding LS E206A

<400> SEQUENCE: 7
atggaagtca ctgtgccgga cgccctgaaa gatcgcatcg cgctgaagaa aaccgctcgt      60
cagctgaata tcgtctactt cctgggttct gataccgaac cggttccgga ctacgagcgc     120
cgtctgagcg agctgctgtt gtatctgcag caattctatg gtaaagaaat gcagcgccat     180
ggctatggcg cacgcagctt tggtctggac attaagtcac cgggtcgtgt gaacattatc     240
gagtacaaag cgaagaaccc ggcagcgcat tacccgtatg agaatggtgg cggctggaaa     300
gctgcacaag aactggacga ttttttcaag gcccatccag accgcaagaa agccagcac      360 accctgatca tcatgcctac ctggaatgat gagaaaaatg gtcctgacaa tccgggtggc     420
gttccgttct atggtatggg tcgtaattgt tttgcgttgg actacccggc gtttgatatc     480
aagcacctgg gtcagaaaac gcgtgagggt cgtctgctga cgaaatggta cggtggcatg     540
gcgcacgcgc tggccacgg cctgaatctg ccgcacaatc accagaccgc gagcgatggc     600
aagaaatatg gcaccgccct gatgggtagc ggcaactaca cgttcggtac cagcccgacg     660
ttcctgaccc cggcgagctg tgcgctgctg gatgcctgcg aagtgttcag cgttaccccg     720
agccaacagt tttatgaggg taagccagaa gtcgaggttg gtgatgttgc aatttccttc     780
aagggtgatc aaatcttggt cagcggtaac tacaagagcc cgcaaaccgt gaaagctctg     840
aacgtttaca ttcaggatcc gccgtacgcc gtgaaccaag actacgatgc agtgagcttt     900
agccgtcgtc tgggcaaaaa gtccggtaag tttagcatga agattgacaa aaagaactg     960 gaaggcctga taacaacga attccgtatt tccttgatgt tcattctggc aaacggctta    1020
cacatgcaga agcactttac gtttcactgg gatgcgctgc aagactaccg tgacggtagc    1080
aaatctggtt cgggtcatca tcaccaccat cactga                               1116

<210> SEQ ID NO 8
<211> LENGTH: 10
<212> TYPE: PRT
<213> ORGANISM: Artificial Sequence
<220> FEATURE:
<223> OTHER INFORMATION: Metalloprotease domain motif
```

<400> SEQUENCE: 8

```
Gly Met Ala His Glu Leu Gly His Gly Leu
1               5                   10
```

<210> SEQ ID NO 9
<211> LENGTH: 595
<212> TYPE: PRT
<213> ORGANISM: Akkermansia muciniphila

<400> SEQUENCE: 9

```
Met Lys Asn Leu Leu Phe Ala Leu Leu Thr Gly Ser Phe Cys Cys Cys
1               5                   10                  15

Tyr Ala Gln Gln Lys Ala Ala Pro Val Pro Glu Pro Glu Val Val Ala
                20                  25                  30

Thr Pro Pro Ala Asp Ala Gly Arg Gly Leu Ile Arg Val Asp Ser Arg
            35                  40                  45

Glu Ile Arg His Tyr Ser Gly Thr Arg Lys Glu Pro Asp Tyr Leu Val
        50                  55                  60

Ser Arg Asp Asn Gly Lys Thr Trp Glu Met Lys Ala Ala Pro Ala Gly
65                  70                  75                  80

Tyr Pro Pro Asn Tyr Gly Gly Ile Pro Lys Glu Ser Pro Ala Ile Val
                85                  90                  95

Arg Asn Pro Leu Thr Arg Glu Phe Ile Arg Val Gln Pro Ile Gly Gly
            100                 105                 110

Phe Val Phe Leu Ser Arg Gly Gly Leu Asp Gly Lys Trp Leu Ala Val
        115                 120                 125

Thr Asn Asp Gly Lys Leu Glu Glu Asp Trp Lys Asp Pro Glu Lys Arg
130                 135                 140

Lys Asn Leu Lys Lys Leu Gly Gly Ile Met Arg Thr Pro Val Phe Val
145                 150                 155                 160

Asn Lys Gly Arg Arg Val Ile Val Pro Phe His Asn Met Gly Gly Gly
                165                 170                 175

Thr Lys Phe His Ile Ser Asp Asp Gly Gly Leu Thr Trp His Val Ser
            180                 185                 190

Arg Asn Gly Val Thr Ser Pro Arg His Glu Ala Arg Pro Pro His Gln
        195                 200                 205

Gly Val Arg Trp Phe Asn Asn Ala Val Glu Ala Thr Val Leu Glu Met
    210                 215                 220

Lys Asp Gly Thr Leu Trp Ala Leu Ala Arg Thr Ser Gln Asp Gln Ala
225                 230                 235                 240

Trp Gln Ala Phe Ser Lys Asp Tyr Gly Glu Thr Trp Ser Lys Pro Glu
                245                 250                 255

Pro Ser Arg Phe Phe Gly Thr Leu Thr Met Asn Thr Leu Gly Arg Leu
            260                 265                 270

Asp Asp Gly Thr Ile Val Ser Leu Trp Thr Asn Thr Met Ala Leu Pro
        275                 280                 285

Glu Asn Ala Thr Ala Gly Asn Gly Thr Trp Glu Asp Val Phe Thr Asn
    290                 295                 300

Arg Asp Ser His His Ile Ala Met Ser Gly Asp Glu Gly Lys Thr Trp
305                 310                 315                 320

Tyr Gly Phe Arg Glu Ile Ile Leu Asp Glu His Arg Asn His Pro Gly
                325                 330                 335

Tyr Ala Thr Leu Asp Gly Pro Glu Asp Arg Gly Lys His Gln Ser Glu
            340                 345                 350
```

```
Met Val Gln Leu Asp Lys Asn Arg Ile Leu Ile Ser Leu Gly Gln His
            355                 360                 365

Lys Asn His Arg Arg Leu Val Ile Val Asp Arg Arg Trp Val Gly Ala
        370                 375                 380

Lys Thr Arg Ala Thr Gln Thr Gly Lys Asp Leu Asp Ser Gln Trp Thr
385                 390                 395                 400

Ile His Thr Tyr Ile Pro Gln Lys Lys Gly His Cys Ser Tyr Asn Arg
                405                 410                 415

Lys Pro Ser Ala Glu Leu Val Gln Asp Pro Ser Gly Gly Thr Lys Lys
                420                 425                 430

Val Leu Gln Ile Lys Arg Leu Asp Asp Pro Glu Leu Val Asn Glu Lys
            435                 440                 445

Ser Asn Val Asp Tyr Arg Asn Gly Gly Ala Thr Trp Asn Phe Pro Asn
    450                 455                 460

Gly Thr Thr Gly Leu Val Lys Phe Arg Phe Arg Val Val Asp Gly Glu
465                 470                 475                 480

Gln Ala Asp Asp Ser Gly Leu Gln Val Ser Leu Thr Asp Arg Leu Phe
                485                 490                 495

Asn Ala Cys Asp Ser Thr Thr Lys Asp Tyr Ala Leu Phe Thr Phe Pro
                500                 505                 510

Ile Arg Leu Lys Pro Ala Pro His Leu Leu Leu Gly Met Lys Lys Val
        515                 520                 525

Pro Phe Thr Pro Gly Ala Trp His Glu Ile Ser Leu Leu Trp Gln Gly
    530                 535                 540

Gly Gln Ala Val Val Ser Leu Asp Gly Lys Lys Ala Gly Thr Leu Lys
545                 550                 555                 560

Met Ala Asn Lys Ser Pro Asn Gly Ala Ser Tyr Ile His Phe Ile Ser
                565                 570                 575

Thr Gly Ser Gln Pro Asp Ala Gly Ile Leu Leu Asp Thr Val Asn Ala
            580                 585                 590

Arg Val Lys
        595

<210> SEQ ID NO 10
<211> LENGTH: 577
<212> TYPE: PRT
<213> ORGANISM: Akkermansia muciniphila

<400> SEQUENCE: 10

Gln Gln Lys Ala Ala Pro Val Pro Glu Pro Glu Val Val Ala Thr Pro
1               5                   10                  15

Pro Ala Asp Ala Gly Arg Gly Leu Ile Arg Val Asp Ser Arg Glu Ile
            20                  25                  30

Arg His Tyr Ser Gly Thr Arg Lys Glu Pro Asp Tyr Leu Val Ser Arg
        35                  40                  45

Asp Asn Gly Lys Thr Trp Glu Met Lys Ala Ala Pro Ala Gly Tyr Pro
    50                  55                  60

Pro Asn Tyr Gly Gly Ile Pro Lys Glu Ser Pro Ala Ile Val Arg Asn
65                  70                  75                  80

Pro Leu Thr Arg Glu Phe Ile Arg Val Gln Pro Ile Gly Gly Phe Val
                85                  90                  95

Phe Leu Ser Arg Gly Gly Leu Asp Gly Lys Trp Leu Ala Val Thr Asn
            100                 105                 110

Asp Gly Lys Leu Glu Glu Asp Trp Lys Asp Pro Glu Lys Arg Lys Asn
        115                 120                 125
```

```
Leu Lys Lys Leu Gly Gly Ile Met Arg Thr Pro Val Phe Val Asn Lys
130                 135                 140

Gly Arg Arg Val Ile Val Pro Phe His Asn Met Gly Gly Gly Thr Lys
145                 150                 155                 160

Phe His Ile Ser Asp Asp Gly Gly Leu Thr Trp His Val Ser Arg Asn
            165                 170                 175

Gly Val Thr Ser Pro Arg His Glu Ala Arg Pro Pro His Gln Gly Val
        180                 185                 190

Arg Trp Phe Asn Asn Ala Val Glu Ala Thr Val Leu Glu Met Lys Asp
                195                 200                 205

Gly Thr Leu Trp Ala Leu Ala Arg Thr Ser Gln Asp Gln Ala Trp Gln
210                 215                 220

Ala Phe Ser Lys Asp Tyr Gly Glu Thr Trp Ser Lys Pro Glu Pro Ser
225                 230                 235                 240

Arg Phe Phe Gly Thr Leu Thr Met Asn Thr Leu Gly Arg Leu Asp Asp
            245                 250                 255

Gly Thr Ile Val Ser Leu Trp Thr Asn Thr Met Ala Leu Pro Glu Asn
        260                 265                 270

Ala Thr Ala Gly Asn Gly Thr Trp Glu Asp Val Phe Thr Asn Arg Asp
    275                 280                 285

Ser His His Ile Ala Met Ser Gly Asp Glu Gly Lys Thr Trp Tyr Gly
290                 295                 300

Phe Arg Glu Ile Ile Leu Asp Glu His Arg Asn His Pro Gly Tyr Ala
305                 310                 315                 320

Thr Leu Asp Gly Pro Glu Asp Arg Gly Lys His Gln Ser Glu Met Val
            325                 330                 335

Gln Leu Asp Lys Asn Arg Ile Leu Ile Ser Leu Gly Gln His Lys Asn
        340                 345                 350

His Arg Arg Leu Val Ile Val Asp Arg Arg Trp Val Gly Ala Lys Thr
    355                 360                 365

Arg Ala Thr Gln Thr Gly Lys Asp Leu Asp Ser Gln Trp Thr Ile His
370                 375                 380

Thr Tyr Ile Pro Gln Lys Lys Gly His Cys Ser Tyr Asn Arg Lys Pro
385                 390                 395                 400

Ser Ala Glu Leu Val Gln Asp Pro Ser Gly Gly Thr Lys Lys Val Leu
            405                 410                 415

Gln Ile Lys Arg Leu Asp Asp Pro Glu Leu Val Asn Glu Lys Ser Asn
        420                 425                 430

Val Asp Tyr Arg Asn Gly Gly Ala Thr Trp Asn Phe Pro Asn Gly Thr
    435                 440                 445

Thr Gly Leu Val Lys Phe Arg Phe Arg Val Val Asp Gly Glu Gln Ala
450                 455                 460

Asp Asp Ser Gly Leu Gln Val Ser Leu Thr Asp Arg Leu Phe Asn Ala
465                 470                 475                 480

Cys Asp Ser Thr Thr Lys Asp Tyr Ala Leu Phe Thr Phe Pro Ile Arg
            485                 490                 495

Leu Lys Pro Ala Pro His Leu Leu Gly Met Lys Lys Val Pro Phe
        500                 505                 510

Thr Pro Gly Ala Trp His Glu Ile Ser Leu Leu Trp Gln Gly Gly Gln
    515                 520                 525

Ala Val Val Ser Leu Asp Gly Lys Lys Ala Gly Thr Leu Lys Met Ala
530                 535                 540
```

-continued

```
Asn Lys Ser Pro Asn Gly Ala Ser Tyr Ile His Phe Ile Ser Thr Gly
545                 550                 555                 560

Ser Gln Pro Asp Ala Gly Ile Leu Leu Asp Thr Val Asn Ala Arg Val
                565                 570                 575

Lys
```

<210> SEQ ID NO 11
<211> LENGTH: 589
<212> TYPE: PRT
<213> ORGANISM: Artificial Sequence
<220> FEATURE:
<223> OTHER INFORMATION: Am1757 (N-terminal methionine and a C-terminal linker + His6 tag)

<400> SEQUENCE: 11

```
Met Gln Gln Lys Ala Ala Pro Val Pro Glu Pro Glu Val Val Ala Thr
1               5                   10                  15

Pro Pro Ala Asp Ala Gly Arg Gly Leu Ile Arg Val Asp Ser Arg Glu
                20                  25                  30

Ile Arg His Tyr Ser Gly Thr Arg Lys Glu Pro Asp Tyr Leu Val Ser
                35                  40                  45

Arg Asp Asn Gly Lys Thr Trp Glu Met Lys Ala Ala Pro Ala Gly Tyr
50                  55                  60

Pro Pro Asn Tyr Gly Gly Ile Pro Lys Glu Ser Pro Ala Ile Val Arg
65                  70                  75                  80

Asn Pro Leu Thr Arg Glu Phe Ile Arg Val Gln Pro Ile Gly Gly Phe
                85                  90                  95

Val Phe Leu Ser Arg Gly Gly Leu Asp Gly Lys Trp Leu Ala Val Thr
                100                 105                 110

Asn Asp Gly Lys Leu Glu Glu Asp Trp Lys Asp Pro Glu Lys Arg Lys
                115                 120                 125

Asn Leu Lys Lys Leu Gly Gly Ile Met Arg Thr Pro Val Phe Val Asn
                130                 135                 140

Lys Gly Arg Arg Val Ile Val Pro Phe His Asn Met Gly Gly Gly Thr
145                 150                 155                 160

Lys Phe His Ile Ser Asp Asp Gly Gly Leu Thr Trp His Val Ser Arg
                165                 170                 175

Asn Gly Val Thr Ser Pro Arg His Glu Ala Arg Pro His Gln Gly
                180                 185                 190

Val Arg Trp Phe Asn Asn Ala Val Glu Ala Thr Val Leu Glu Met Lys
                195                 200                 205

Asp Gly Thr Leu Trp Ala Leu Ala Arg Thr Ser Gln Asp Gln Ala Trp
210                 215                 220

Gln Ala Phe Ser Lys Asp Tyr Gly Glu Thr Trp Ser Lys Pro Glu Pro
225                 230                 235                 240

Ser Arg Phe Phe Gly Thr Leu Thr Met Asn Thr Leu Gly Arg Leu Asp
                245                 250                 255

Asp Gly Thr Ile Val Ser Leu Trp Thr Asn Thr Met Ala Leu Pro Glu
                260                 265                 270

Asn Ala Thr Ala Gly Asn Gly Thr Trp Glu Asp Val Phe Thr Asn Arg
                275                 280                 285

Asp Ser His His Ile Ala Met Ser Gly Asp Glu Gly Lys Thr Trp Tyr
                290                 295                 300

Gly Phe Arg Glu Ile Ile Leu Asp Glu His Arg Asn His Pro Gly Tyr
305                 310                 315                 320
```

```
Ala Thr Leu Asp Gly Pro Glu Asp Arg Gly Lys His Gln Ser Glu Met
            325                 330                 335

Val Gln Leu Asp Lys Asn Arg Ile Leu Ile Ser Leu Gly Gln His Lys
        340                 345                 350

Asn His Arg Arg Leu Val Ile Val Asp Arg Arg Trp Val Gly Ala Lys
            355                 360                 365

Thr Arg Ala Thr Gln Thr Gly Lys Asp Leu Asp Ser Gln Trp Thr Ile
370                 375                 380

His Thr Tyr Ile Pro Gln Lys Lys Gly His Cys Ser Tyr Asn Arg Lys
385                 390                 395                 400

Pro Ser Ala Glu Leu Val Gln Asp Pro Ser Gly Gly Thr Lys Lys Val
            405                 410                 415

Leu Gln Ile Lys Arg Leu Asp Asp Pro Glu Leu Val Asn Glu Lys Ser
            420                 425                 430

Asn Val Asp Tyr Arg Asn Gly Gly Ala Thr Trp Asn Phe Pro Asn Gly
            435                 440                 445

Thr Thr Gly Leu Val Lys Phe Arg Phe Arg Val Val Asp Gly Glu Gln
        450                 455                 460

Ala Asp Asp Ser Gly Leu Gln Val Ser Leu Thr Asp Arg Leu Phe Asn
465                 470                 475                 480

Ala Cys Asp Ser Thr Thr Lys Asp Tyr Ala Leu Phe Thr Phe Pro Ile
                485                 490                 495

Arg Leu Lys Pro Ala Pro His Leu Leu Leu Gly Met Lys Lys Val Pro
            500                 505                 510

Phe Thr Pro Gly Ala Trp His Glu Ile Ser Leu Leu Trp Gln Gly Gly
        515                 520                 525

Gln Ala Val Val Ser Leu Asp Gly Lys Lys Ala Gly Thr Leu Lys Met
    530                 535                 540

Ala Asn Lys Ser Pro Asn Gly Ala Ser Tyr Ile His Phe Ile Ser Thr
545                 550                 555                 560

Gly Ser Gln Pro Asp Ala Gly Ile Leu Leu Asp Thr Val Asn Ala Arg
                565                 570                 575

Val Lys Gly Ser Gly Leu Glu His His His His His His
            580                 585

<210> SEQ ID NO 12
<211> LENGTH: 419
<212> TYPE: PRT
<213> ORGANISM: Akkermansia muciniphila

<400> SEQUENCE: 12

Met Thr Trp Leu Leu Cys Gly Arg Gly Lys Trp Asn Lys Val Lys Arg
1               5                   10                  15

Met Met Asn Ser Val Phe Lys Cys Leu Met Ser Ala Val Cys Ala Val
            20                  25                  30

Ala Leu Pro Ala Phe Gly Gln Glu Lys Thr Gly Phe Pro Thr Asp
        35                  40                  45

Arg Ala Val Thr Val Phe Ser Ala Gly Glu Gly Asn Pro Tyr Ala Ser
    50                  55                  60

Ile Arg Ile Pro Ala Leu Leu Ser Ile Gly Lys Gly Gln Leu Leu Ala
65                  70                  75                  80

Phe Ala Glu Gly Arg Tyr Lys Asn Thr Asp Gln Gly Glu Asn Asp Ile
                85                  90                  95

Ile Met Ser Val Ser Lys Asn Gly Gly Lys Thr Trp Ser Arg Pro Arg
            100                 105                 110
```

```
Ala Ile Ala Lys Ala His Gly Ala Thr Phe Asn Asn Pro Cys Pro Val
            115                 120                 125

Tyr Asp Ala Lys Thr Arg Thr Val Thr Val Val Phe Gln Arg Tyr Pro
130                 135                 140

Ala Gly Val Lys Glu Arg Gln Pro Asn Ile Pro Asp Gly Trp Asp Asp
145                 150                 155                 160

Glu Lys Cys Ile Arg Asn Phe Met Ile Gln Ser Arg Asn Gly Gly Ser
                165                 170                 175

Ser Trp Thr Lys Pro Gln Glu Ile Lys Thr Lys Arg Pro Ser
            180                 185                 190

Gly Val Asp Ile Met Ala Ser Gly Pro Asn Ala Gly Thr Gln Leu Lys
            195                 200                 205

Ser Gly Ala His Lys Gly Arg Leu Val Ile Pro Met Asn Glu Gly Pro
210                 215                 220

Phe Gly Lys Trp Val Ile Ser Cys Ile Tyr Ser Asp Asp Gly Gly Lys
225                 230                 235                 240

Ser Trp Lys Leu Gly Gln Pro Thr Ala Asn Met Lys Gly Met Val Asn
                245                 250                 255

Glu Thr Ser Ile Ala Glu Thr Asp Asn Gly Val Val Met Val Ala
                260                 265                 270

Arg His Trp Gly Ala Gly Asn Cys Arg Arg Ile Ala Trp Ser Gln Asp
            275                 280                 285

Gly Gly Glu Thr Trp Gly Gln Val Glu Asp Ala Pro Glu Leu Phe Cys
290                 295                 300

Asp Ser Thr Gln Asn Ser Leu Met Thr Tyr Ser Leu Ser Asp Gln Pro
305                 310                 315                 320

Ala Tyr Gly Gly Lys Ser Arg Ile Leu Phe Ser Gly Pro Ser Ala Gly
                325                 330                 335

Arg Arg Ile Lys Gly Gln Val Ala Met Ser Tyr Asp Asn Gly Lys Thr
            340                 345                 350

Trp Pro Val Lys Lys Leu Leu Gly Glu Gly Phe Ala Tyr Ser Ser
            355                 360                 365

Leu Ala Met Val Glu Pro Gly Ile Val Gly Val Leu Tyr Glu Glu Asn
370                 375                 380

Gln Glu His Ile Lys Lys Leu Lys Phe Val Pro Ile Thr Met Glu Trp
385                 390                 395                 400

Leu Thr Asp Gly Glu Asp Thr Gly Leu Ala Pro Gly Lys Lys Ala Pro
                405                 410                 415

Val Leu Lys

<210> SEQ ID NO 13
<211> LENGTH: 381
<212> TYPE: PRT
<213> ORGANISM: Akkermansia muciniphila

<400> SEQUENCE: 13

Gln Glu Glu Lys Thr Gly Phe Pro Thr Asp Arg Ala Val Thr Val Phe
1               5                   10                  15

Ser Ala Gly Glu Gly Asn Pro Tyr Ala Ser Ile Arg Ile Pro Ala Leu
            20                  25                  30

Leu Ser Ile Gly Lys Gly Gln Leu Leu Ala Phe Ala Glu Gly Arg Tyr
        35                  40                  45

Lys Asn Thr Asp Gln Gly Glu Asn Asp Ile Ile Met Ser Val Ser Lys
    50                  55                  60
```

Asn Gly Gly Lys Thr Trp Ser Arg Pro Arg Ala Ile Ala Lys Ala His
 65                  70                  75                  80

Gly Ala Thr Phe Asn Asn Pro Cys Pro Val Tyr Asp Ala Lys Thr Arg
                 85                  90                  95

Thr Val Thr Val Val Phe Gln Arg Tyr Pro Ala Gly Val Lys Glu Arg
            100                 105                 110

Gln Pro Asn Ile Pro Asp Gly Trp Asp Glu Lys Cys Ile Arg Asn
        115                 120                 125

Phe Met Ile Gln Ser Arg Asn Gly Gly Ser Ser Trp Thr Lys Pro Gln
130                 135                 140

Glu Ile Thr Lys Thr Thr Lys Arg Pro Ser Gly Val Asp Ile Met Ala
145                 150                 155                 160

Ser Gly Pro Asn Ala Gly Thr Gln Leu Lys Ser Gly Ala His Lys Gly
                165                 170                 175

Arg Leu Val Ile Pro Met Asn Glu Gly Pro Phe Gly Lys Trp Val Ile
                180                 185                 190

Ser Cys Ile Tyr Ser Asp Asp Gly Gly Lys Ser Trp Lys Leu Gly Gln
                195                 200                 205

Pro Thr Ala Asn Met Lys Gly Met Val Asn Glu Thr Ser Ile Ala Glu
210                 215                 220

Thr Asp Asn Gly Gly Val Val Met Val Ala Arg His Trp Gly Ala Gly
225                 230                 235                 240

Asn Cys Arg Arg Ile Ala Trp Ser Gln Asp Gly Gly Glu Thr Trp Gly
                245                 250                 255

Gln Val Glu Asp Ala Pro Glu Leu Phe Cys Asp Ser Thr Gln Asn Ser
            260                 265                 270

Leu Met Thr Tyr Ser Leu Ser Asp Gln Pro Ala Tyr Gly Gly Lys Ser
                275                 280                 285

Arg Ile Leu Phe Ser Gly Pro Ser Ala Gly Arg Arg Ile Lys Gly Gln
290                 295                 300

Val Ala Met Ser Tyr Asp Asn Gly Lys Thr Trp Pro Val Lys Lys Leu
305                 310                 315                 320

Leu Gly Glu Gly Gly Phe Ala Tyr Ser Ser Leu Ala Met Val Glu Pro
                325                 330                 335

Gly Ile Val Gly Val Leu Tyr Glu Glu Asn Gln Glu His Ile Lys Lys
            340                 345                 350

Leu Lys Phe Val Pro Ile Thr Met Glu Trp Leu Thr Asp Gly Glu Asp
                355                 360                 365

Thr Gly Leu Ala Pro Gly Lys Lys Ala Pro Val Leu Lys
            370                 375                 380

<210> SEQ ID NO 14
<211> LENGTH: 393
<212> TYPE: PRT
<213> ORGANISM: Artificial Sequence
<220> FEATURE:
<223> OTHER INFORMATION: Am0707 (including N-terminal methionine and a
      C-terminal linker + His6 tag)

<400> SEQUENCE: 14

Met Gln Glu Glu Lys Thr Gly Phe Pro Thr Asp Arg Ala Val Thr Val
1               5                   10                  15

Phe Ser Ala Gly Glu Gly Asn Pro Tyr Ala Ser Ile Arg Ile Pro Ala
            20                  25                  30

Leu Leu Ser Ile Gly Lys Gly Gln Leu Leu Ala Phe Ala Glu Gly Arg
        35                  40                  45

```
Tyr Lys Asn Thr Asp Gln Gly Glu Asn Asp Ile Ile Met Ser Val Ser
    50                  55                  60

Lys Asn Gly Gly Lys Thr Trp Ser Arg Pro Arg Ala Ile Ala Lys Ala
65                  70                  75                  80

His Gly Ala Thr Phe Asn Asn Pro Cys Pro Val Tyr Asp Ala Lys Thr
                85                  90                  95

Arg Thr Val Thr Val Val Phe Gln Arg Tyr Pro Ala Gly Val Lys Glu
            100                 105                 110

Arg Gln Pro Asn Ile Pro Asp Gly Trp Asp Asp Glu Lys Cys Ile Arg
        115                 120                 125

Asn Phe Met Ile Gln Ser Arg Asn Gly Gly Ser Ser Trp Thr Lys Pro
130                 135                 140

Gln Glu Ile Thr Lys Thr Thr Lys Arg Pro Ser Gly Val Asp Ile Met
145                 150                 155                 160

Ala Ser Gly Pro Asn Ala Gly Thr Gln Leu Lys Ser Gly Ala His Lys
                165                 170                 175

Gly Arg Leu Val Ile Pro Met Asn Glu Gly Pro Phe Gly Lys Trp Val
            180                 185                 190

Ile Ser Cys Ile Tyr Ser Asp Asp Gly Gly Lys Ser Trp Lys Leu Gly
        195                 200                 205

Gln Pro Thr Ala Asn Met Lys Gly Met Val Asn Glu Thr Ser Ile Ala
210                 215                 220

Glu Thr Asp Asn Gly Gly Val Val Met Val Ala Arg His Trp Gly Ala
225                 230                 235                 240

Gly Asn Cys Arg Arg Ile Ala Trp Ser Gln Asp Gly Gly Glu Thr Trp
                245                 250                 255

Gly Gln Val Glu Asp Ala Pro Glu Leu Phe Cys Asp Ser Thr Gln Asn
            260                 265                 270

Ser Leu Met Thr Tyr Ser Leu Ser Asp Gln Pro Ala Tyr Gly Gly Lys
        275                 280                 285

Ser Arg Ile Leu Phe Ser Gly Pro Ser Ala Gly Arg Arg Ile Lys Gly
290                 295                 300

Gln Val Ala Met Ser Tyr Asp Asn Gly Lys Thr Trp Pro Val Lys Lys
305                 310                 315                 320

Leu Leu Gly Glu Gly Gly Phe Ala Tyr Ser Ser Leu Ala Met Val Glu
                325                 330                 335

Pro Gly Ile Val Gly Val Leu Tyr Glu Glu Asn Gln Glu His Ile Lys
            340                 345                 350

Lys Leu Lys Phe Val Pro Ile Thr Met Glu Trp Leu Thr Asp Gly Glu
        355                 360                 365

Asp Thr Gly Leu Ala Pro Gly Lys Lys Ala Pro Val Leu Lys Gly Ser
370                 375                 380

Gly Leu Glu His His His His His His
385                 390

<210> SEQ ID NO 15
<211> LENGTH: 2133
<212> TYPE: PRT
<213> ORGANISM: Streptococcus oralis

<400> SEQUENCE: 15

Met Asp Lys Arg Phe Phe Glu Lys Arg Cys Lys Phe Ser Ile Arg Lys
1               5                   10                  15

Phe Thr Leu Gly Val Ala Ser Val Met Ile Gly Ala Thr Phe Phe Ala
            20                  25                  30
```

-continued

Ala Ser Pro Val Leu Ala Asp Gln Ala Arg Val Gly Ser Thr Asp Asn
         35                  40                  45

Leu Pro Ser Glu Leu Ala Asp Leu Asp Lys Lys Ala Ser Asp Glu Gly
 50                  55                  60

His Asp Phe Asp Lys Glu Ala Ala Gln Asn Pro Gly Ser Ala Glu
 65              70                  75                  80

Thr Thr Glu Gly Pro Gln Thr Glu Glu Leu Leu Ala Gln Glu Lys
                 85                  90                  95

Glu Lys Ser Glu Lys Pro Ser Asn Leu Pro Lys Glu Leu Glu Asp Lys
             100                 105                 110

Leu Glu Lys Ala Glu Asp Asn Gly Arg Glu Val Asp Lys Asp Gln Leu
         115                 120                 125

Ala Gln Asp Thr Gly Lys Leu Val Pro Glu Asp Val Ala Lys Thr Thr
 130                 135                 140

Asn Gly Glu Leu Asn Tyr Gly Ala Thr Val Lys Ile Lys Thr Pro Ser
145                 150                 155                 160

Gly Glu Gly Ser Gly Ile Val Val Ala Lys Asp Leu Val Leu Thr Val
                 165                 170                 175

Ser His Asn Phe Ile Lys Asp Ser Gln Glu Gly Asn Ile Arg Lys Val
             180                 185                 190

Val Asp Asn Asp Gln Gly Asp Gly Asp Ile Tyr Ser Ile Ser Tyr Pro
         195                 200                 205

Gly Leu Pro Asp Val Lys Phe Ser Lys Lys Asp Ile Ile His Trp Asp
         210                 215                 220

Arg Glu Gly Tyr Leu Lys Gly Phe Lys Asn Asp Leu Ala Leu Val Arg
225                 230                 235                 240

Leu Arg Thr Val Leu Glu Asn Thr Pro Val Glu Val Thr Lys Lys Pro
                 245                 250                 255

Val Val Lys Lys Ile Gly Asp Lys Leu His Val Phe Gly Tyr Pro Glu
             260                 265                 270

Gly Lys Leu Asn Pro Ile Val Asn Thr Thr Val Asp Phe Ala Glu Pro
         275                 280                 285

Tyr Gly Glu Gly Val Gln Gly Ile Gly Tyr Gln Gly Gly Lys Pro Gly
         290                 295                 300

Ala Ser Gly Gly Gly Ile Phe Asp Thr Glu Gly Lys Leu Val Gly Val
305                 310                 315                 320

His Gln Asn Gly Val Val Gly Lys Arg Ser Gly Gly Ile Leu Phe Ser
                 325                 330                 335

Pro Ala Gln Leu Lys Trp Ile Gln Asp His Met Gln Gly Ile Ser Ser
             340                 345                 350

Val Lys Pro Ala Asp Leu Glu Glu Lys Glu Lys Pro Ala Glu Glu Lys
         355                 360                 365

Pro Lys Glu Asp Lys Pro Ala Ala Ala Lys Pro Glu Thr Pro Lys Ala
         370                 375                 380

Val Thr Pro Glu Trp Gln Thr Val Ala Asn Lys Glu Gln Gln Gly Thr
385                 390                 395                 400

Val Thr Ile Arg Glu Glu Lys Gly Val Arg Tyr Asn Gln Leu Ser Ser
                 405                 410                 415

Thr Ala Gln Asn Asp Asn Asp Gly Lys Pro Ala Leu Phe Glu Lys Gln
             420                 425                 430

Gly Leu Thr Val Asp Ala Asn Gly Asn Ala Thr Val Asp Leu Thr Phe
         435                 440                 445

-continued

```
Lys Asp Asp Ser Glu Lys Gly Lys Ser Arg Phe Gly Val Phe Leu Lys
        450                 455                 460
Phe Lys Asp Thr Lys Asn Asn Val Phe Val Gly Tyr Asp Gln Gly Gly
465                 470                 475                 480
Trp Phe Trp Glu Tyr Lys Thr Pro Gly Asn Ser Thr Trp Tyr Lys Gly
                485                 490                 495
Asn Arg Val Ala Ala Pro Glu Pro Gly Ser Val Asn Arg Leu Ser Ile
            500                 505                 510
Thr Leu Lys Ser Asp Gly Gln Leu Asn Ala Ser Asn Asn Asp Val Asn
        515                 520                 525
Leu Phe Asp Thr Val Thr Leu Pro Gly Ala Val Asn Glu Asn Leu Lys
530                 535                 540
Asn Glu Lys Lys Ile Leu Leu Lys Ala Gly Thr Tyr Ser Asn Asp Arg
545                 550                 555                 560
Thr Val Val Ser Val Lys Thr Asp Asn Gln Glu Gly Val Lys Ala Asp
                565                 570                 575
Asp Thr Pro Ala Gln Lys Glu Thr Gly Pro Ala Val Asp Ser Lys
            580                 585                 590
Val Thr Tyr Asp Thr Ile Gln Ser Lys Val Leu Lys Ala Val Ile Asp
        595                 600                 605
Gln Ala Phe Pro Arg Val Lys Glu Tyr Thr Leu Asn Gly His Thr Leu
610                 615                 620
Pro Gly Gln Val Gln Gln Phe Asn Gln Val Phe Ile Asn Asn His Arg
625                 630                 635                 640
Ile Thr Pro Glu Val Thr Tyr Lys Lys Ile Asn Glu Thr Thr Ala Glu
                645                 650                 655
Tyr Leu Met Lys Leu Arg Asp Asp Ala His Leu Ile Asn Ala Glu Met
            660                 665                 670
Thr Val Arg Leu Gln Val Val Asp Asn Gln Leu His Phe Asp Val Thr
        675                 680                 685
Lys Ile Val Asn His Asn Gln Val Thr Pro Gly Gln Lys Ile Asp Asp
690                 695                 700
Glu Arg Lys Leu Leu Ser Thr Ile Ser Phe Leu Gly Asn Ala Leu Val
705                 710                 715                 720
Ser Val Ser Ser Asp Gln Ala Gly Ala Lys Phe Asp Gly Ala Thr Met
                725                 730                 735
Ser Asn Asn Thr His Val Ser Gly Asp Asp His Ile Asp Val Thr Asn
            740                 745                 750
Pro Met Lys Asp Leu Ala Lys Gly Tyr Met Tyr Gly Phe Val Ser Thr
        755                 760                 765
Asp Lys Leu Ala Ala Gly Val Trp Ser Asn Ser Gln Asn Ser Tyr Gly
770                 775                 780
Gly Gly Ser Asn Asp Trp Thr Arg Leu Thr Ala Tyr Lys Glu Thr Val
785                 790                 795                 800
Gly Asn Ala Asn Tyr Val Gly Ile His Ser Ser Glu Trp Gln Trp Glu
                805                 810                 815
Lys Ala Tyr Lys Gly Ile Val Phe Pro Glu Tyr Thr Lys Glu Leu Pro
            820                 825                 830
Ser Ala Lys Val Val Ile Thr Glu Asp Ala Asn Ala Asp Asn Lys Val
        835                 840                 845
Asp Trp Gln Asp Gly Ala Ile Ala Tyr Arg Ser Ile Met Asn Asn Pro
850                 855                 860
```

```
Gln Gly Trp Glu Lys Val Lys Asp Ile Thr Ala Tyr Arg Ile Ala Met
865                 870                 875                 880

Asn Phe Gly Ser Gln Ala Gln Asn Pro Phe Leu Met Thr Leu Asp Gly
            885                 890                 895

Ile Lys Lys Ile Asn Leu His Thr Asp Gly Leu Gly Gln Gly Val Leu
        900                 905                 910

Leu Lys Gly Tyr Gly Ser Glu Gly His Asp Ser Gly His Leu Asn Tyr
        915                 920                 925

Ala Asp Ile Gly Lys Arg Ile Gly Gly Val Glu Asp Phe Lys Thr Leu
        930                 935                 940

Ile Glu Lys Ala Lys Lys Tyr Gly Ala His Leu Gly Ile His Val Asn
945                 950                 955                 960

Ala Ser Glu Thr Tyr Pro Glu Ser Lys Tyr Phe Asn Glu Asn Ile Leu
            965                 970                 975

Arg Lys Asn Pro Asp Gly Ser Tyr Ser Tyr Gly Trp Asn Trp Leu Asp
            980                 985                 990

Gln Gly Ile Asn Ile Asp Ala Ala Tyr Asp Leu Ala His Gly Arg Leu
            995                 1000                1005

Ala Arg Trp Glu Asp Leu Lys Lys Lys Leu Gly Glu Gly Leu Asp
    1010                1015                1020

Phe Ile Tyr Val Asp Val Trp Gly Asn Gly Gln Ser Gly Asp Asn
    1025                1030                1035

Gly Ala Trp Ala Thr His Val Leu Ala Lys Glu Ile Asn Lys Gln
    1040                1045                1050

Gly Trp Arg Phe Ala Ile Glu Trp Gly His Gly Gly Glu Tyr Asp
    1055                1060                1065

Ser Thr Phe Gln His Trp Ala Ala Asp Leu Thr Tyr Gly Gly Tyr
    1070                1075                1080

Thr Asn Lys Gly Ile Asn Ser Ala Ile Thr Arg Phe Ile Arg Asn
    1085                1090                1095

His Gln Lys Asp Ser Trp Val Gly Asp Tyr Arg Ser Tyr Gly Gly
    1100                1105                1110

Ala Ala Asn Tyr Pro Leu Leu Gly Gly Tyr Ser Met Lys Asp Phe
    1115                1120                1125

Glu Gly Trp Gln Gly Arg Ser Asp Tyr Asn Gly Tyr Val Thr Asn
    1130                1135                1140

Leu Phe Ala His Asp Val Met Thr Lys Tyr Phe Gln His Phe Thr
    1145                1150                1155

Val Ser Lys Trp Glu Asn Gly Thr Pro Val Thr Met Thr Asp Asn
    1160                1165                1170

Gly Ser Thr Tyr Lys Trp Thr Pro Glu Met Lys Val Glu Leu Val
    1175                1180                1185

Asp Ala Ala Gly Asn Lys Val Val Thr Arg Lys Ser Asn Asp
    1190                1195                1200

Val Asn Ser Pro Gln Tyr Arg Glu Arg Thr Val Thr Leu Asn Gly
    1205                1210                1215

Arg Val Ile Gln Asp Gly Ser Ala Tyr Leu Thr Pro Trp Asn Trp
    1220                1225                1230

Asp Ala Asn Gly Lys Lys Leu Pro Thr Glu Lys Glu Lys Met Tyr
    1235                1240                1245

Tyr Phe Asn Thr Gln Ala Gly Ala Thr Thr Trp Thr Leu Pro Ser
    1250                1255                1260
```

-continued

```
Asp Trp Ala Asn Ser Lys Val Tyr Leu Tyr Lys Leu Thr Asp Gln
    1265                1270                1275

Gly Lys Thr Glu Glu Gln Glu Leu Thr Val Thr Asp Gly Lys Ile
    1280                1285                1290

Thr Leu Asp Leu Leu Ala Asn Gln Pro Tyr Val Leu Tyr Arg Ser
    1295                1300                1305

Lys Gln Thr Asn Pro Glu Met Ser Trp Ser Glu Gly Met His Ile
    1310                1315                1320

Tyr Asp Gln Gly Phe Asn Ser Gly Thr Leu Lys His Trp Thr Ile
    1325                1330                1335

Ser Gly Asp Ala Ser Lys Ala Glu Ile Val Lys Ser Gln Gly Ala
    1340                1345                1350

Asn Glu Met Leu Arg Ile Gln Gly Asn Lys Ser Lys Val Ser Leu
    1355                1360                1365

Thr Gln Lys Leu Thr Gly Leu Lys Pro Asn Thr Lys Tyr Ala Val
    1370                1375                1380

Tyr Val Gly Val Asp Asn Arg Ser Asn Ala Lys Ala Ser Ile Thr
    1385                1390                1395

Val Asn Thr Gly Glu Lys Glu Val Thr Thr Tyr Thr Asn Lys Ser
    1400                1405                1410

Leu Ala Leu Asn Tyr Ile Lys Ala Tyr Ala His Asn Asn Arg Arg
    1415                1420                1425

Glu Asn Ala Thr Val Asp Asp Thr Ser Tyr Phe Gln Asn Met Tyr
    1430                1435                1440

Ala Phe Phe Thr Thr Gly Ser Asp Val Ser Asn Val Thr Leu Thr
    1445                1450                1455

Leu Ser Arg Glu Ala Gly Asp Glu Ala Thr Tyr Phe Asp Glu Ile
    1460                1465                1470

Arg Thr Phe Glu Asn Asn Ser Ser Met Tyr Gly Asp Lys His Asp
    1475                1480                1485

Thr Gly Gln Gly Thr Phe Lys Gln Asp Phe Glu Asn Val Ala Gln
    1490                1495                1500

Gly Ile Phe Pro Phe Val Val Gly Gly Val Glu Gly Val Glu Asp
    1505                1510                1515

Asn Arg Thr His Leu Ser Glu Lys His Asp Pro Tyr Thr Gln Arg
    1520                1525                1530

Gly Trp Asn Gly Lys Lys Val Asp Asp Val Ile Glu Gly Asn Trp
    1535                1540                1545

Ser Leu Lys Thr Asn Gly Leu Val Ser Arg Arg Asn Leu Val Tyr
    1550                1555                1560

Gln Thr Ile Pro Gln Asn Phe Arg Phe Glu Ala Gly Lys Thr Tyr
    1565                1570                1575

Arg Val Thr Phe Glu Tyr Glu Ala Gly Ser Asp Asn Thr Tyr Ala
    1580                1585                1590

Phe Val Val Gly Lys Gly Glu Phe Gln Ser Gly Arg Arg Gly Thr
    1595                1600                1605

Gln Ala Ser Asn Leu Glu Met His Glu Leu Pro Asn Thr Trp Thr
    1610                1615                1620

Asp Ser Lys Lys Ala Lys Lys Val Thr Phe Leu Val Thr Gly Ala
    1625                1630                1635

Glu Thr Gly Asp Thr Trp Val Gly Ile Tyr Ser Thr Gly Asn Ala
    1640                1645                1650
```

```
Ser Asn Thr Arg Gly Asp Ala Gly Gly Asn Ala Asn Phe Arg Gly
    1655                1660                1665

Tyr Asn Asp Phe Met Met Asp Asn Leu Gln Ile Glu Glu Ile Thr
    1670                1675                1680

Leu Thr Gly Lys Met Leu Thr Glu Asn Ala Leu Lys Asn Tyr Leu
    1685                1690                1695

Pro Thr Val Ala Met Thr Asn Tyr Thr Lys Glu Ser Met Asp Ala
    1700                1705                1710

Leu Lys Glu Ala Val Phe Asn Leu Ser Gln Ala Asp Asp Ile
    1715                1720                1725

Ser Val Glu Glu Ala Arg Ala Glu Ile Ala Lys Ile Glu Ala Leu
    1730                1735                1740

Lys Asn Ala Leu Val Gln Lys Lys Thr Ala Leu Val Ala Glu Asp
    1745                1750                1755

Phe Glu Ser Leu Asp Ala Pro Ala Gln Pro Gly Glu Gly Leu Glu
    1760                1765                1770

Asn Ala Phe Asp Gly Asn Val Ser Ser Leu Trp His Thr Ser Trp
    1775                1780                1785

Asn Gly Gly Asp Val Gly Lys Pro Ala Thr Met Val Leu Lys Glu
    1790                1795                1800

Pro Thr Glu Ile Thr Gly Leu Arg Tyr Val Pro Arg Ala Ser Asp
    1805                1810                1815

Ser Asn Gly Asn Leu Arg Asp Val Lys Leu Val Val Thr Asp Glu
    1820                1825                1830

Ser Gly Lys Glu His Thr Phe Asn Val Thr Asp Trp Pro Asn Asn
    1835                1840                1845

Asn Lys Pro Lys Asp Ile Asp Phe Gly Lys Thr Ile Lys Ala Lys
    1850                1855                1860

Lys Ile Val Leu Thr Gly Thr Lys Thr Tyr Gly Asp Gly Gly Asp
    1865                1870                1875

Lys Tyr Gln Ser Ala Ala Glu Leu Ile Phe Thr Arg Pro Gln Val
    1880                1885                1890

Ala Glu Thr Pro Leu Asp Leu Ser Gly Tyr Glu Ala Ala Leu Ala
    1895                1900                1905

Lys Ala Gln Lys Leu Thr Asp Lys Asp Asn Gln Glu Glu Val Ala
    1910                1915                1920

Ser Val Gln Ala Ser Met Lys Tyr Ala Thr Asp Asn His Leu Leu
    1925                1930                1935

Thr Glu Arg Met Val Ala Tyr Phe Ala Asp Tyr Leu Asn Gln Leu
    1940                1945                1950

Lys Asp Ser Ala Thr Lys Pro Asp Ala Pro Thr Ser Ser Lys Gly
    1955                1960                1965

Glu Glu Gln Pro Pro Val Leu Asp Val Pro Glu Phe Lys Gly Gly
    1970                1975                1980

Val Asn Ala Thr Glu Ala Ala Val His Glu Val Pro Glu Phe Lys
    1985                1990                1995

Gly Gly Val Asn Ala Val Gln Ala Leu Val His Glu Leu Pro Glu
    2000                2005                2010

Tyr Lys Gly Gly Ala Asn Ala Val Leu Ala Ala Ala Asn Glu Val
    2015                2020                2025

Pro Glu Tyr Lys Gly Gly Ala Asn Ala Val Glu Ala Leu Val Asn
    2030                2035                2040
```

-continued

```
Glu Lys Pro Ala Tyr Thr Gly Val Leu Ala Thr Ala Gly Asp Gln
    2045                2050                2055

Ala Ala Pro Thr Val Glu Lys Pro Glu Tyr Pro Leu Thr Pro Ser
    2060                2065                2070

Pro Val Ala Asp Thr Lys Thr Pro Gly Ala Lys Asp Glu Glu Lys
    2075                2080                2085

Leu Pro Ala Thr Gly Glu His Ser Ser Glu Val Ala Leu Phe Leu
    2090                2095                2100

Ala Ser Val Ser Ile Ala Leu Ser Ala Ala Val Leu Ala Thr Lys
    2105                2110                2115

Arg Lys Glu Glu Gly Ser Gly Leu Glu His His His His His His
    2120                2125                2130
```

<210> SEQ ID NO 16
<211> LENGTH: 22
<212> TYPE: DNA
<213> ORGANISM: Artificial Sequence
<220> FEATURE:
<223> OTHER INFORMATION: E206A forward primer

<400> SEQUENCE: 16
atggcgcacg cgctgggcca cg                                              22

<210> SEQ ID NO 17
<211> LENGTH: 19
<212> TYPE: DNA
<213> ORGANISM: Artificial Sequence
<220> FEATURE:
<223> OTHER INFORMATION: E206A reverse primer

<400> SEQUENCE: 17
gccaccgtac catttcgtc                                                  19

<210> SEQ ID NO 18
<211> LENGTH: 166
<212> TYPE: PRT
<213> ORGANISM: Artificial Sequence
<220> FEATURE:
<223> OTHER INFORMATION: EPO

<400> SEQUENCE: 18

```
Ala Pro Pro Arg Leu Ile Cys Asp Ser Arg Val Leu Glu Arg Tyr Leu
1               5                   10                  15

Leu Glu Ala Lys Glu Ala Glu Asp Ile Thr Thr Gly Cys Ala Glu His
                20                  25                  30

Cys Ser Leu Asp Glu Asn Ile Thr Val Pro Asp Thr Lys Val Asp Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

```
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 19

<400> SEQUENCE: 19

000

<210> SEQ ID NO 20
<211> LENGTH: 361
<212> TYPE: PRT
<213> ORGANISM: Artificial Sequence
<220> FEATURE:
<223> OTHER INFORMATION: Polypeptide capable of binding to O-glycans but
      lacks or has reduced O-glycoprotein-specific endoprotease activity

<400> SEQUENCE: 20

Glu Val Thr Val Pro Asp Ala Leu Lys Asp Arg Ile Ala Leu Lys Lys
1               5                   10                  15

Thr Ala Arg Gln Leu Asn Ile Val Tyr Phe Leu Gly Ser Asp Thr Glu
                20                  25                  30

Pro Val Pro Asp Tyr Glu Arg Arg Leu Ser Glu Leu Leu Leu Tyr Leu
            35                  40                  45

Gln Gln Phe Tyr Gly Lys Glu Met Gln Arg His Gly Tyr Gly Ala Arg
    50                  55                  60

Ser Phe Gly Leu Asp Ile Lys Ser Pro Gly Arg Val Asn Ile Ile Glu
65                  70                  75                  80

Tyr Lys Ala Lys Asn Pro Ala Ala His Tyr Pro Tyr Glu Asn Gly Gly
                85                  90                  95

Gly Trp Lys Ala Ala Gln Glu Leu Asp Glu Phe Phe Lys Ala His Pro
            100                 105                 110

Asp Arg Lys Lys Ser Gln His Thr Leu Ile Ile Met Pro Thr Trp Asn
        115                 120                 125

Asp Glu Lys Asn Gly Pro Asp Asn Pro Gly Gly Val Pro Phe Tyr Gly
    130                 135                 140

Met Gly Arg Asn Cys Phe Ala Leu Asp Tyr Pro Ala Phe Asp Ile Lys
145                 150                 155                 160

His Leu Gly Gln Lys Thr Arg Glu Gly Arg Leu Leu Thr Lys Trp Tyr
                165                 170                 175

Gly Gly Met Ala Ala Ala Leu Gly His Gly Leu Asn Leu Pro His Asn
            180                 185                 190

His Gln Thr Ala Ser Asp Gly Lys Lys Tyr Gly Thr Ala Leu Met Gly
        195                 200                 205

Ser Gly Asn Tyr Thr Phe Gly Thr Ser Pro Thr Phe Leu Thr Pro Ala
    210                 215                 220

Ser Cys Ala Leu Leu Asp Ala Cys Glu Val Phe Ser Val Thr Pro Ser
225                 230                 235                 240

Gln Gln Phe Tyr Glu Gly Lys Pro Glu Val Glu Val Gly Asp Val Ala
                245                 250                 255

Ile Ser Phe Lys Gly Asp Gln Ile Leu Val Ser Gly Asn Tyr Lys Ser
            260                 265                 270

Pro Gln Thr Val Lys Ala Leu Asn Val Tyr Ile Gln Asp Pro Pro Tyr
        275                 280                 285
```

```
Ala Val Asn Gln Asp Tyr Asp Ala Val Ser Phe Ser Arg Arg Leu Gly
    290                 295                 300

Lys Lys Ser Gly Lys Phe Ser Met Lys Ile Asp Lys Lys Glu Leu Glu
305                 310                 315                 320

Gly Leu Asn Asn Asn Glu Phe Arg Ile Ser Leu Met Phe Ile Leu Ala
                325                 330                 335

Asn Gly Leu His Met Gln Lys His Phe Thr Phe His Trp Asp Ala Leu
                340                 345                 350

Gln Asp Tyr Arg Asp Gly Ser Lys Ser
    355                 360
```

<210> SEQ ID NO 21
<211> LENGTH: 371
<212> TYPE: PRT
<213> ORGANISM: Artificial Sequence
<220> FEATURE:
<223> OTHER INFORMATION: LS HE206AA or LS H205A/E206A (including N-terminal methionine and C-terminal linker)

<400> SEQUENCE: 21

```
Met Glu Val Thr Val Pro Asp Ala Leu Lys Asp Arg Ile Ala Leu Lys
1               5                   10                  15

Lys Thr Ala Arg Gln Leu Asn Ile Val Tyr Phe Leu Gly Ser Asp Thr
                20                  25                  30

Glu Pro Val Pro Asp Tyr Glu Arg Arg Leu Ser Glu Leu Leu Leu Tyr
            35                  40                  45

Leu Gln Gln Phe Tyr Gly Lys Glu Met Gln Arg His Gly Tyr Gly Ala
    50                  55                  60

Arg Ser Phe Gly Leu Asp Ile Lys Ser Pro Gly Arg Val Asn Ile Ile
65                  70                  75                  80

Glu Tyr Lys Ala Lys Asn Pro Ala His Tyr Pro Tyr Glu Asn Gly
                85                  90                  95

Gly Gly Trp Lys Ala Ala Gln Glu Leu Asp Glu Phe Phe Lys Ala His
            100                 105                 110

Pro Asp Arg Lys Lys Ser Gln His Thr Leu Ile Ile Met Pro Thr Trp
        115                 120                 125

Asn Asp Glu Lys Asn Gly Pro Asp Asn Pro Gly Gly Val Pro Phe Tyr
    130                 135                 140

Gly Met Gly Arg Asn Cys Phe Ala Leu Asp Tyr Pro Ala Phe Asp Ile
145                 150                 155                 160

Lys His Leu Gly Gln Lys Thr Arg Glu Gly Arg Leu Leu Thr Lys Trp
                165                 170                 175

Tyr Gly Gly Met Ala Ala Ala Leu Gly His Gly Leu Asn Leu Pro His
            180                 185                 190

Asn His Gln Thr Ala Ser Asp Gly Lys Lys Tyr Gly Thr Ala Leu Met
        195                 200                 205

Gly Ser Gly Asn Tyr Thr Phe Gly Thr Ser Pro Thr Phe Leu Thr Pro
    210                 215                 220

Ala Ser Cys Ala Leu Leu Asp Ala Cys Glu Val Phe Ser Val Thr Pro
225                 230                 235                 240

Ser Gln Gln Phe Tyr Glu Gly Lys Pro Glu Val Glu Val Gly Asp Val
                245                 250                 255

Ala Ile Ser Phe Lys Gly Asp Gln Ile Leu Val Ser Gly Asn Tyr Lys
            260                 265                 270

Ser Pro Gln Thr Val Lys Ala Leu Asn Val Tyr Ile Gln Asp Pro Pro
        275                 280                 285
```

Tyr Ala Val Asn Gln Asp Tyr Asp Ala Val Ser Phe Ser Arg Arg Leu
        290                 295                 300

Gly Lys Lys Ser Gly Lys Phe Ser Met Lys Ile Asp Lys Lys Glu Leu
305                 310                 315                 320

Glu Gly Leu Asn Asn Glu Phe Arg Ile Ser Leu Met Phe Ile Leu
                325                 330                 335

Ala Asn Gly Leu His Met Gln Lys His Phe Thr Phe His Trp Asp Ala
            340                 345                 350

Leu Gln Asp Tyr Arg Asp Gly Ser Lys Ser Gly Ser Gly His His His
        355                 360                 365

His His His
    370

<210> SEQ ID NO 22
<211> LENGTH: 1116
<212> TYPE: DNA
<213> ORGANISM: Artificial Sequence
<220> FEATURE:
<223> OTHER INFORMATION: Nucleotide sequence encoding LS HE206AA or LS
      H205A/E206A

<400> SEQUENCE: 22

```
atggaagtca ctgtgccgga cgccctgaaa gatcgcatcg cgctgaagaa aaccgctcgt       60
cagctgaata tcgtctactt cctgggttct gataccgaac cggttccgga ctacgagcgc      120
cgtctgagcg agctgctgtt gtatctgcag caattctatg gtaaagaaat gcagcgccat      180
ggctatggcg cacgcagctt tggtctggac attaagtcac cgggtcgtgt gaacattatc      240
gagtacaaag cgaagaaccc ggcagcgcat acccgtatg agaatggtgg cggctggaaa       300
gctgcacaag aactggacga atttttcaag gcccatccag accgcaagaa aagccagcac      360
accctgatca tcatgcctac ctggaatgat gagaaaaatg gtcctgacaa tccgggtggc      420
gttccgttct atggtatggg tcgtaattgt tttgcgttgg actacccggc gtttgatatc      480
aagcacctgg gtcagaaaac gcgtgagggt cgtctgctga cgaaatggta cggtggcatg      540
gcggccgcgc tgggccacgg cctgaatctg ccgcacaatc accagaccgc gagcgatggc      600
aagaaatatg gcaccgccct gatgggtagc ggcaactaca cgttcggtac cagcccgacg      660
ttcctgaccc cggcgagctg tgcgctgctg gatgcctgcg aagtgttcag cgttaccccg      720
agccaacagt tttatgaggg taagccagaa gtcgaggttg gtgatgttgc aatttccttc      780
aagggtgatc aaatcttggt cagcggtaac tacaagagcc gcaaaccgt gaaagctctg       840
aacgtttaca ttcaggatcc gccgtacgcc gtgaaccaag actacgatgc agtgagcttt      900
agccgtcgtc tgggcaaaaa gtccggtaag tttagcatga agattgacaa aaaagaactg      960
gaaggcctga ataacaacga attccgtatt tccttgatgt tcattctggc aaacggctta     1020
cacatgcaga agcactttac gtttcactgg gatgcgctgc aagactaccg tgacggtagc     1080
aaatctggtt cgggtcatca tcaccaccat cactga                               1116
```

<210> SEQ ID NO 23
<211> LENGTH: 10
<212> TYPE: PRT
<213> ORGANISM: Artificial Sequence
<220> FEATURE:
<223> OTHER INFORMATION: disrupted metalloprotease motif

<400> SEQUENCE: 23

Gly Met Ala His Ala Leu Gly His Gly Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: disrupted metalloprotease motif

<400> SEQUENCE: 24

```
Gly Met Ala Ala Glu Leu Gly His Gly Leu
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: disrupted metalloprotease motif

<400> SEQUENCE: 25

```
Gly Met Ala Ala Ala Leu Gly His Gly Leu
1               5                   10
```

<210> SEQ ID NO 26
<211> LENGTH: 882
<212> TYPE: PRT
<213> ORGANISM: Pseudomonas aeruginosa

<400> SEQUENCE: 26

```
Ala Thr Gln Glu Glu Ile Leu Asp Ala Leu Val Ser Gly Asp Ser
1               5                   10                  15

Ser Gln Leu Thr Asp Ser His Leu Val Ala Leu Arg Leu Gln Gln Gln
                20                  25                  30

Val Glu Arg Ile Arg Gln Thr Arg Thr Gln Leu Leu Asp Gly Leu Tyr
            35                  40                  45

Gln Asn Leu Ser Gln Ala Tyr Asp Pro Gly Ala Ala Ser Met Trp Val
        50                  55                  60

Leu Pro Ala Asn Pro Asp Asn Thr Leu Pro Phe Leu Ile Gly Asp Lys
65                  70                  75                  80

Gly Arg Val Leu Ala Ser Leu Ser Leu Glu Ala Gly Gly Arg Gly Leu
                85                  90                  95

Ala Tyr Gly Thr Asn Val Leu Thr Gln Leu Ser Gly Thr Asn Ala Ala
            100                 105                 110

His Ala Pro Leu Leu Lys Arg Ala Val Gln Trp Leu Val Asn Gly Asp
        115                 120                 125

Pro Gly Ala Ala Thr Ala Lys Asp Phe Lys Val Ser Val Val Gly Val
    130                 135                 140

Asp Lys Thr Ala Ala Leu Asn Gly Leu Lys Ser Ala Gly Leu Gln Pro
145                 150                 155                 160

Ala Asp Ala Ala Cys Asn Ala Leu Thr Asp Ala Ser Cys Ala Ser Thr
                165                 170                 175

Ser Lys Leu Leu Val Leu Gly Asn Gly Ala Ser Ala Ala Ser Leu Ser
            180                 185                 190

Ala Thr Val Arg Ala Arg Leu Gln Ala Gly Leu Pro Ile Leu Phe Val
        195                 200                 205

His Thr Asn Gly Trp Asn Gln Ser Ser Thr Gly Gln Gln Ile Leu Ala
    210                 215                 220
```

```
Gly Leu Gly Leu Gln Glu Gly Pro Tyr Gly Gly Asn Tyr Trp Asp Lys
225                 230                 235                 240

Asp Arg Val Pro Ser Ser Arg Thr Arg Thr Arg Ser Val Glu Leu Gly
            245                 250                 255

Gly Ala Tyr Gly Gln Asp Pro Ala Leu Val Gln Gln Ile Val Asp Gly
        260                 265                 270

Ser Trp Arg Thr Asp Tyr Asp Trp Ser Lys Cys Thr Ser Tyr Val Gly
        275                 280                 285

Arg Thr Thr Cys Asp Asp Val Pro Gly Leu Ser Asp Phe Ser Lys Arg
290                 295                 300

Val Asp Val Leu Lys Gly Ala Leu Asp Ala Tyr Asn Gln Lys Ala Gln
305                 310                 315                 320

Asn Leu Phe Ala Leu Pro Gly Thr Thr Ser Leu Arg Leu Trp Leu Leu
            325                 330                 335

Trp Ala Asp Ala Val Arg Gln Asn Ile Arg Tyr Pro Met Asp Lys Ala
            340                 345                 350

Ala Asp Thr Ala Arg Phe Gln Glu Thr Phe Val Ala Asp Ala Ile Val
        355                 360                 365

Gly Tyr Val Arg Glu Ala Gly Ala Gln Lys Glu Leu Gly Ser Tyr
370                 375                 380

Ala Gly Gln Arg Gln Gln Ser Met Pro Val Ser Gly Ser Glu Glu Thr
385                 390                 395                 400

Leu Thr Leu Thr Leu Pro Ser Ala Gln Gly Phe Thr Ala Ile Gly Arg
                405                 410                 415

Met Ala Ala Pro Gly Lys Arg Leu Ser Ile Arg Ile Glu Asp Ala Gly
            420                 425                 430

Gln Ala Ser Leu Ala Val Gly Leu Asn Thr Gln Arg Ile Gly Ser Thr
        435                 440                 445

Arg Leu Trp Asn Thr Arg Gln Tyr Asp Arg Pro Arg Phe Leu Lys Ser
450                 455                 460

Pro Asp Ile Lys Leu Gln Ala Asn Gln Ser Val Ala Leu Val Ser Pro
465                 470                 475                 480

Tyr Gly Gly Leu Leu Gln Leu Val Tyr Ser Gly Ala Thr Pro Gly Gln
            485                 490                 495

Thr Val Thr Val Lys Val Thr Gly Ala Ala Ser Gln Pro Phe Leu Asp
        500                 505                 510

Ile Gln Pro Gly Glu Asp Ser Ser Gln Ala Ile Ala Asp Phe Ile Gln
            515                 520                 525

Ala Leu Asp Ala Asp Lys Ala Asp Trp Leu Glu Ile Arg Ser Gly Ser
530                 535                 540

Val Glu Val His Ala Lys Val Glu Lys Val Arg Gly Ser Ile Asp Lys
545                 550                 555                 560

Asp Tyr Gly Gly Asp Val Gln Arg Phe Ile Arg Glu Leu Asn Glu Val
            565                 570                 575

Phe Ile Asp Asp Ala Tyr Thr Leu Ala Gly Phe Ala Ile Pro Asn Gln
        580                 585                 590

Ala Lys Thr Pro Ala Ile Gln Gln Glu Cys Ala Ala Arg Gly Trp Asp
            595                 600                 605

Cys Asp Ser Glu Thr Leu His Lys Leu Pro Gly Thr Gln His Ile Asn
610                 615                 620

Val Asp Gln Tyr Ala Gln Cys Gly Gly Gly Cys Ser Gly Asn Pro Tyr
625                 630                 635                 640
```

```
Asp Gln Thr Trp Gly Leu Asn Pro Arg Gly Trp Glu Ser His Glu
                645                 650                 655

Leu Gly His Asn Leu Gln Val Asn Arg Leu Lys Val Tyr Gly Gly Arg
            660                 665                 670

Ser Gly Glu Ile Ser Asn Gln Ile Phe Pro Leu His Lys Asp Trp Arg
            675                 680                 685

Val Leu Arg Glu Phe Gly Gln Asn Leu Asp Asp Thr Arg Val Asn Tyr
        690                 695                 700

Arg Asn Ala Tyr Asn Leu Ile Val Ala Gly Ala Glu Ala Asp Pro
705                 710                 715                 720

Leu Ala Gly Val Tyr Lys Arg Leu Trp Glu Asp Pro Gly Thr Tyr Ala
                725                 730                 735

Leu Asn Gly Glu Arg Met Ala Phe Tyr Thr Gln Trp Val His Tyr Trp
            740                 745                 750

Ala Asp Leu Lys Asn Asp Pro Leu Gln Gly Trp Asp Ile Trp Thr Leu
            755                 760                 765

Leu Tyr Leu His Gln Arg Gln Val Asp Lys Ser Asp Trp Asp Ala Asn
        770                 775                 780

Lys Ala Ala Leu Gly Tyr Gly Thr Tyr Ala Gln Arg Pro Gly Asn Ser
785                 790                 795                 800

Gly Asp Ala Ser Ser Thr Asp Gly Asn Asp Asn Leu Leu Gly Leu
                805                 810                 815

Ser Trp Leu Thr Gln Arg Asp Gln Arg Pro Thr Phe Ala Leu Trp Gly
            820                 825                 830

Ile Arg Thr Ser Ala Ala Gln Ala Gln Val Ala Ala Tyr Gly Phe
            835                 840                 845

Ala Glu Gln Pro Ala Phe Phe Tyr Ala Asn Asn Arg Thr Asn Glu Tyr
        850                 855                 860

Ser Thr Val Lys Leu Leu Asp Met Ser Gln Gly Ser Pro Ala Trp Pro
865                 870                 875                 880

Phe Pro

<210> SEQ ID NO 27
<211> LENGTH: 536
<212> TYPE: PRT
<213> ORGANISM: Bacteroides thetaiotaomicron

<400> SEQUENCE: 27

Asp Lys Trp Glu Lys Glu Phe Arg Ile Arg Ser Tyr Glu Pro Tyr Ser
1                   5                   10                  15

Asn Ile Ala Glu Trp Ala Asp Lys Leu Met Thr Lys Lys Tyr Ser Asp
                20                  25                  30

Leu Asp Asn Pro Thr Gly Ile Ser Val Lys Ala Gly Asp Ile Ile
            35                  40                  45

Val Leu Val Gly Asp Thr Tyr Gly Gln Asn Ile Ser Met Gln Cys Ile
        50                  55                  60

Trp Glu Thr Gly Thr Glu Tyr Lys Gln Thr Ala Ser Ser Gly Asp Val
65                  70                  75                  80

Tyr Met Leu Asn Pro Gly Val Asn Lys Leu Thr Met Lys Gly Glu Gly
                85                  90                  95

Gln Leu Phe Val Met Tyr Asn Thr Glu Leu Thr Ser Asn Thr Ala Lys
            100                 105                 110

Pro Ile Lys Ile His Ile Pro Leu Gly Ser Gly Thr Val Asn Gly Phe
        115                 120                 125
```

```
Phe Asp Leu Lys Glu His Lys Thr Asp Glu Lys Tyr Ala Glu Leu Leu
130                 135                 140

Lys Lys Ser Thr His Lys Tyr Phe Cys Ile Arg Gly Glu Lys Ile Met
145                 150                 155                 160

Phe Tyr Phe His Arg Asn Lys Leu Leu Glu Tyr Val Pro Asn Asn Ile
                165                 170                 175

Leu Ser Ala Ile His Leu Trp Asp Asn Ile Val Gly Trp Gln Gln Glu
                180                 185                 190

Leu Met Gly Ile Asp Asp Val Arg Pro Ser Gln Val Asn Asn His Leu
            195                 200                 205

Phe Ala Ile Ser Pro Glu Gly Ser Tyr Met Trp Ala Ser Asp Tyr Gln
210                 215                 220

Ile Gly Phe Val Tyr Thr Tyr Leu Gly Asn Ile Leu Leu Glu Asp Asn
225                 230                 235                 240

Val Met Ala Ala Glu Asp Asn Ala Trp Gly Pro Ala His Glu Ile Gly
                245                 250                 255

His Val His Gln Ala Ala Ile Asn Trp Ala Ser Ser Thr Glu Ser Ser
            260                 265                 270

Asn Asn Leu Phe Ser Asn Phe Ile Ile Tyr Lys Leu Gly Lys Tyr Lys
            275                 280                 285

Ser Arg Gly Asn Gly Leu Gly Ser Val Ala Thr Ala Arg Tyr Ala Asn
290                 295                 300

Gly Gln Ala Trp Tyr Asn Met Gly Asp Ala Thr His Gln Asn Glu Asp
305                 310                 315                 320

Thr Glu Thr His Met Arg Met Asn Trp Gln Leu Trp Ile Tyr Tyr His
                325                 330                 335

Arg Cys Glu Tyr Lys Thr Asp Phe Trp Gln Thr Leu Phe Lys Leu Met
                340                 345                 350

Arg Glu Val Asn Met Thr Glu Gly Asp Pro Gly Lys Lys Gln Leu
                355                 360                 365

Glu Phe Ala Lys Met Ala Ser Lys Ala Ala Asn Gln Asn Leu Thr Asp
370                 375                 380

Phe Phe Glu Met Trp Gly Phe Phe Glu Pro Val Asn Thr Thr Ile Glu
385                 390                 395                 400

Gln Tyr Gly Thr Tyr Lys Tyr Tyr Val Ser Asp Ala Met Ile Arg Glu
                405                 410                 415

Ala Lys Glu Tyr Met Ala Gln Phe Pro Ala Pro Lys His Ala Phe Gln
                420                 425                 430

Tyr Ile Glu Asp Arg Lys Lys Ser Glu Phe Pro Ser Asn Asp Tyr Arg
                435                 440                 445

Tyr Ser Ala Val Gly Asp Val Gly Tyr Tyr Thr Gln Phe Lys Glu Asn
450                 455                 460

Gln Lys Ile Thr Lys Ala Ile Thr Ala Glu Leu Ala Gly Arg Lys Val
465                 470                 475                 480

Ser Ile Gln Asn Gly Asp Glu Ala Val Ala Phe Glu Leu Arg Glu Asn
                485                 490                 495

Asp Glu Asn Gly Lys Leu Leu Tyr Phe Ser Thr Phe Thr Phe Glu
            500                 505                 510

Ile Pro Ser Ser Ile Leu Met Val Asn Ala Lys Leu Tyr Ala Val Gln
                515                 520                 525

Ala Asp Gly Lys Arg Ile Leu Leu
530                 535
```

```
<210> SEQ ID NO 28
<211> LENGTH: 507
<212> TYPE: PRT
<213> ORGANISM: Clostridium perfringens

<400> SEQUENCE: 28
```

| | | | | | | | | | | | | | | |
|---|---|---|---|---|---|---|---|---|---|---|---|---|---|---|
|Val|Leu|Glu|Leu|Glu|Met|Arg|Gly|Asp|Ser|Ile|Ser|Glu|Ala|Lys|Lys|
|1| | | |5| | | | |10| | | | |15|

| | | | | | | | | | | | | | | |
|---|---|---|---|---|---|---|---|---|---|---|---|---|---|---|
|Arg|Lys|Val|Trp|Asn|Phe|Gln|Asp|Trp|Gln|Ile|Thr|Gly|Leu|Ser|Ala|
| | | |20| | | | |25| | | | |30| | |

| | | | | | | | | | | | | | | |
|---|---|---|---|---|---|---|---|---|---|---|---|---|---|---|
|Arg|Ala|Gly|Asp|Lys|Ile|Thr|Val|Tyr|Val|Asp|Val|Ala|Glu|Gly|Asp|
| | | |35| | | | |40| | | | |45| | |

| | | | | | | | | | | | | | | |
|---|---|---|---|---|---|---|---|---|---|---|---|---|---|---|
|Pro|Thr|Pro|Thr|Leu|Leu|Tyr|Lys|Gln|Ser|Leu|Thr|Gln|His|Gly|Gly|
| |50| | | | |55| | | | |60| | | | |

| | | | | | | | | | | | | | | |
|---|---|---|---|---|---|---|---|---|---|---|---|---|---|---|
|Ala|Thr|Ser|Phe|Gln|Leu|Lys|Pro|Gly|Lys|Asn|Glu|Ile|Thr|Ile|Pro|
|65| | | | |70| | | | |75| | | | |80|

| | | | | | | | | | | | | | | |
|---|---|---|---|---|---|---|---|---|---|---|---|---|---|---|
|Glu|Ile|Asn|Tyr|Glu|Ser|Asn|Gly|Ile|Pro|Lys|Asp|Val|Ile|Gln|Gly|
| | | | |85| | | | |90| | | | |95| |

| | | | | | | | | | | | | | | |
|---|---|---|---|---|---|---|---|---|---|---|---|---|---|---|
|Gly|Asp|Leu|Phe|Phe|Thr|Asn|Tyr|Lys|Ser|Asp|Ser|Gln|Lys|Arg|Ala|
| | | |100| | | | |105| | | | |110| | |

| | | | | | | | | | | | | | | |
|---|---|---|---|---|---|---|---|---|---|---|---|---|---|---|
|Pro|Lys|Val|Arg|Ile|Glu|Gly|Ala|Ser|Lys|Tyr|Pro|Val|Phe|Ile|Leu|
| | | |115| | | | |120| | | | |125| | |

| | | | | | | | | | | | | | | |
|---|---|---|---|---|---|---|---|---|---|---|---|---|---|---|
|Gly|Lys|Ser|Asp|Glu|Asn|Glu|Val|Met|Lys|Glu|Leu|Glu|Ala|Tyr|Val|
| |130| | | | |135| | | | |140| | | | |

| | | | | | | | | | | | | | | |
|---|---|---|---|---|---|---|---|---|---|---|---|---|---|---|
|Glu|Lys|Ile|Lys|Ala|Glu|Pro|Lys|Thr|Thr|Pro|Asn|Ile|Phe|Ala|Val|
|145| | | | |150| | | | |155| | | | |160|

| | | | | | | | | | | | | | | |
|---|---|---|---|---|---|---|---|---|---|---|---|---|---|---|
|Ser|Ser|Asn|Lys|Ser|Leu|Glu|Phe|Val|Gln|Ala|Thr|Tyr|Ala|Leu|Asp|
| | | | |165| | | | |170| | | | |175| |

| | | | | | | | | | | | | | | |
|---|---|---|---|---|---|---|---|---|---|---|---|---|---|---|
|Trp|Tyr|Lys|Lys|Asn|Asn|Lys|Thr|Pro|Lys|Tyr|Thr|Ala|Glu|Gln|Trp|
| | | |180| | | | |185| | | | |190| | |

| | | | | | | | | | | | | | | |
|---|---|---|---|---|---|---|---|---|---|---|---|---|---|---|
|Asp|Gln|Tyr|Ile|Ala|Asp|Ala|Met|Gly|Phe|Trp|Gly|Phe|Asp|Asn|Ser|
| | | |195| | | | |200| | | | |205| | |

| | | | | | | | | | | | | | | |
|---|---|---|---|---|---|---|---|---|---|---|---|---|---|---|
|Lys|Asp|Val|Asn|Ser|Asp|Phe|Asn|Phe|Arg|Ile|Met|Pro|Met|Val|Lys|
| |210| | | | |215| | | | |220| | | | |

| | | | | | | | | | | | | | | |
|---|---|---|---|---|---|---|---|---|---|---|---|---|---|---|
|Asn|Leu|Ser|Gly|Gly|Ala|Phe|Met|Asn|Ala|Gly|Asn|Gly|Val|Ile|Gly|
|225| | | | |230| | | | |235| | | | |240|

| | | | | | | | | | | | | | | |
|---|---|---|---|---|---|---|---|---|---|---|---|---|---|---|
|Ile|Arg|Pro|Gly|Asn|Gln|Asp|Ala|Ile|Leu|Ala|Ala|Asn|Lys|Gly|Trp|
| | | | |245| | | | |250| | | | |255| |

| | | | | | | | | | | | | | | |
|---|---|---|---|---|---|---|---|---|---|---|---|---|---|---|
|Gly|Val|Ala|His|Glu|Leu|Gly|His|Asn|Phe|Asp|Thr|Gly|Gly|Arg|Thr|
| | | |260| | | | |265| | | | |270| | |

| | | | | | | | | | | | | | | |
|---|---|---|---|---|---|---|---|---|---|---|---|---|---|---|
|Ile|Val|Glu|Val|Thr|Asn|Asn|Met|Met|Pro|Leu|Phe|Phe|Glu|Ser|Lys|
| |275| | | | |280| | | | |285| | | | |

| | | | | | | | | | | | | | | |
|---|---|---|---|---|---|---|---|---|---|---|---|---|---|---|
|Tyr|Lys|Thr|Lys|Thr|Arg|Ile|Thr|Asp|Gln|Asn|Ile|Trp|Glu|Asn|Asn|
| |290| | | | |295| | | | |300| | | | |

| | | | | | | | | | | | | | | |
|---|---|---|---|---|---|---|---|---|---|---|---|---|---|---|
|Thr|Tyr|Pro|Lys|Val|Gly|Leu|Asp|Asp|Tyr|Ser|Asn|Asn|Glu|Leu|Tyr|
|305| | | | |310| | | | |315| | | | |320|

| | | | | | | | | | | | | | | |
|---|---|---|---|---|---|---|---|---|---|---|---|---|---|---|
|Asn|Lys|Ala|Asp|Ser|Thr|His|Leu|Ala|Gln|Leu|Ala|Pro|Leu|Trp|Gln|
| | | | |325| | | | |330| | | | |335| |

| | | | | | | | | | | | | | | |
|---|---|---|---|---|---|---|---|---|---|---|---|---|---|---|
|Leu|Tyr|Leu|Tyr|Asp|Asn|Thr|Phe|Tyr|Gly|Lys|Phe|Glu|Arg|Gln|Phe|
| | | |340| | | | |345| | | | |350| | |

| | | | | | | | | | | | | | | |
|---|---|---|---|---|---|---|---|---|---|---|---|---|---|---|
|Arg|Glu|Arg|Asp|Phe|Gly|Asn|Lys|Asn|Arg|Glu|Asp|Ile|Tyr|Lys|Ser|
| | | |355| | | | |360| | | | |365| | |

| | | | | | | | | | | |
|---|---|---|---|---|---|---|---|---|---|---|---|
|Trp|Val|Val|Ala|Ala|Ser|Asp|Ala|Met|Glu|Leu|Asp|Leu|Thr|Glu|Phe|
| |370| | | | |375| | | | |380| | | | |

```
Phe Ala Arg His Gly Ile Arg Val Asp Asp Lys Val Lys Glu Asp Leu
385                 390                 395                 400

Ala Lys Tyr Pro Lys Pro Asp Lys Lys Ile Tyr Tyr Leu Asn Asp Leu
            405                 410                 415

Ala Met Asn Tyr Lys Gly Asp Gly Phe Thr Glu Asn Ala Lys Val Ser
            420                 425                 430

Val Ser Thr Ser Gly Ser Asn Gly Asn Ile Lys Leu Ser Phe Ser Val
        435                 440                 445

Asp Asp Glu Asn Lys Asp Asn Ile Leu Gly Tyr Glu Ile Arg Arg Asp
        450                 455                 460

Gly Lys Tyr Val Gly Phe Thr Ser Asn Asp Ser Phe Val Asp Thr Lys
465                 470                 475                 480

Ser Asn Leu Asp Glu Asp Gly Val Tyr Val Val Thr Pro Tyr Asp Arg
            485                 490                 495

Lys Leu Asn Thr Leu Asn Pro Ile Glu Val Asn
            500                 505
```

<210> SEQ ID NO 29
<211> LENGTH: 892
<212> TYPE: PRT
<213> ORGANISM: Artificial Sequence
<220> FEATURE:
<223> OTHER INFORMATION: polypeptide having O-glycoprotein-specific
    endoprotease activity (including N-terminal methionine and a
    C-terminal linker + His6 tag)

<400> SEQUENCE: 29

```
Met Ala Thr Gln Glu Glu Ile Leu Asp Ala Ala Leu Val Ser Gly Asp
1               5                   10                  15

Ser Ser Gln Leu Thr Asp Ser His Leu Val Ala Leu Arg Leu Gln Gln
            20                  25                  30

Gln Val Glu Arg Ile Arg Gln Thr Arg Thr Gln Leu Leu Asp Gly Leu
        35                  40                  45

Tyr Gln Asn Leu Ser Gln Ala Tyr Asp Pro Gly Ala Ala Ser Met Trp
    50                  55                  60

Val Leu Pro Ala Asn Pro Asp Asn Thr Leu Pro Phe Leu Ile Gly Asp
65                  70                  75                  80

Lys Gly Arg Val Leu Ala Ser Leu Ser Leu Glu Ala Gly Arg Gly
            85                  90                  95

Leu Ala Tyr Gly Thr Asn Val Leu Thr Gln Leu Ser Gly Thr Asn Ala
            100                 105                 110

Ala His Ala Pro Leu Leu Lys Arg Ala Val Gln Trp Leu Val Asn Gly
        115                 120                 125

Asp Pro Gly Ala Ala Thr Ala Lys Asp Phe Lys Val Ser Val Val Gly
    130                 135                 140

Val Asp Lys Thr Ala Ala Leu Asn Gly Leu Lys Ser Ala Gly Leu Gln
145                 150                 155                 160

Pro Ala Asp Ala Ala Cys Asn Ala Leu Thr Asp Ala Ser Cys Ala Ser
            165                 170                 175

Thr Ser Lys Leu Leu Val Leu Gly Asn Gly Ala Ser Ala Ala Ser Leu
            180                 185                 190

Ser Ala Thr Val Arg Ala Arg Leu Gln Ala Gly Leu Pro Ile Leu Phe
        195                 200                 205

Val His Thr Asn Gly Trp Asn Gln Ser Ser Thr Gly Gln Gln Ile Leu
    210                 215                 220
```

-continued

Ala Gly Leu Gly Leu Gln Glu Gly Pro Tyr Gly Gly Asn Tyr Trp Asp
225                 230                 235                 240

Lys Asp Arg Val Pro Ser Ser Arg Thr Arg Thr Arg Ser Val Glu Leu
            245                 250                 255

Gly Gly Ala Tyr Gly Gln Asp Pro Ala Leu Val Gln Gln Ile Val Asp
            260                 265                 270

Gly Ser Trp Arg Thr Asp Tyr Asp Trp Ser Lys Cys Thr Ser Tyr Val
        275                 280                 285

Gly Arg Thr Thr Cys Asp Asp Val Pro Gly Leu Ser Asp Phe Ser Lys
        290                 295                 300

Arg Val Asp Val Leu Lys Gly Ala Leu Asp Ala Tyr Asn Gln Lys Ala
305                 310                 315                 320

Gln Asn Leu Phe Ala Leu Pro Gly Thr Thr Ser Leu Arg Leu Trp Leu
            325                 330                 335

Leu Trp Ala Asp Ala Val Arg Gln Asn Ile Arg Tyr Pro Met Asp Lys
            340                 345                 350

Ala Ala Asp Thr Ala Arg Phe Gln Glu Thr Phe Val Asp Ala Ile
            355                 360                 365

Val Gly Tyr Val Arg Glu Ala Gly Ala Ala Gln Lys Glu Leu Gly Ser
    370                 375                 380

Tyr Ala Gly Gln Arg Gln Gln Ser Met Pro Val Ser Gly Ser Glu Glu
385                 390                 395                 400

Thr Leu Thr Leu Thr Leu Pro Ser Ala Gln Gly Phe Thr Ala Ile Gly
                405                 410                 415

Arg Met Ala Ala Pro Gly Lys Arg Leu Ser Ile Arg Ile Glu Asp Ala
            420                 425                 430

Gly Gln Ala Ser Leu Ala Val Gly Leu Asn Thr Gln Arg Ile Gly Ser
            435                 440                 445

Thr Arg Leu Trp Asn Thr Arg Gln Tyr Asp Arg Pro Arg Phe Leu Lys
    450                 455                 460

Ser Pro Asp Ile Lys Leu Gln Ala Asn Gln Ser Val Ala Leu Val Ser
465                 470                 475                 480

Pro Tyr Gly Gly Leu Leu Gln Leu Val Tyr Ser Gly Ala Thr Pro Gly
                485                 490                 495

Gln Thr Val Thr Val Lys Val Thr Gly Ala Ala Ser Gln Pro Phe Leu
            500                 505                 510

Asp Ile Gln Pro Gly Glu Asp Ser Ser Gln Ala Ile Ala Asp Phe Ile
            515                 520                 525

Gln Ala Leu Asp Ala Asp Lys Ala Asp Trp Leu Glu Ile Arg Ser Gly
    530                 535                 540

Ser Val Glu Val His Ala Lys Val Glu Lys Val Arg Gly Ser Ile Asp
545                 550                 555                 560

Lys Asp Tyr Gly Gly Asp Val Gln Arg Phe Ile Arg Glu Leu Asn Glu
                565                 570                 575

Val Phe Ile Asp Asp Ala Tyr Thr Leu Ala Gly Phe Ala Ile Pro Asn
            580                 585                 590

Gln Ala Lys Thr Pro Ala Ile Gln Gln Glu Cys Ala Ala Arg Gly Trp
    595                 600                 605

Asp Cys Asp Ser Glu Thr Leu His Lys Leu Pro Gly Thr Gln His Ile
            610                 615                 620

Asn Val Asp Gln Tyr Ala Gln Cys Gly Gly Gly Cys Ser Gly Asn Pro
625                 630                 635                 640

```
Tyr Asp Gln Thr Trp Gly Leu Asn Pro Arg Gly Trp Gly Glu Ser His
            645                 650                 655

Glu Leu Gly His Asn Leu Gln Val Asn Arg Leu Lys Val Tyr Gly Gly
        660                 665                 670

Arg Ser Gly Glu Ile Ser Asn Gln Ile Phe Pro Leu His Lys Asp Trp
    675                 680                 685

Arg Val Leu Arg Glu Phe Gly Gln Asn Leu Asp Asp Thr Arg Val Asn
690                 695                 700

Tyr Arg Asn Ala Tyr Asn Leu Ile Val Ala Gly Arg Ala Glu Ala Asp
705                 710                 715                 720

Pro Leu Ala Gly Val Tyr Lys Arg Leu Trp Glu Asp Pro Gly Thr Tyr
                725                 730                 735

Ala Leu Asn Gly Glu Arg Met Ala Phe Tyr Thr Gln Trp Val His Tyr
            740                 745                 750

Trp Ala Asp Leu Lys Asn Asp Pro Leu Gln Gly Trp Asp Ile Trp Thr
        755                 760                 765

Leu Leu Tyr Leu His Gln Arg Gln Val Asp Lys Ser Asp Trp Asp Ala
    770                 775                 780

Asn Lys Ala Ala Leu Gly Tyr Gly Thr Tyr Ala Gln Arg Pro Gly Asn
785                 790                 795                 800

Ser Gly Asp Ala Ser Ser Thr Asp Gly Asn Asp Asn Leu Leu Leu Gly
                805                 810                 815

Leu Ser Trp Leu Thr Gln Arg Asp Gln Arg Pro Thr Phe Ala Leu Trp
            820                 825                 830

Gly Ile Arg Thr Ser Ala Ala Gln Ala Gln Val Ala Ala Tyr Gly
        835                 840                 845

Phe Ala Glu Gln Pro Ala Phe Phe Tyr Ala Asn Asn Arg Thr Asn Glu
    850                 855                 860

Tyr Ser Thr Val Lys Leu Leu Asp Met Ser Gln Gly Ser Pro Ala Trp
865                 870                 875                 880

Pro Phe Pro Gly Ser Gly His His His His His His
                885                 890

<210> SEQ ID NO 30
<211> LENGTH: 546
<212> TYPE: PRT
<213> ORGANISM: Artificial Sequence
<220> FEATURE:
<223> OTHER INFORMATION: polypeptide having O-glycoprotein-specific
      endoprotease activity (including N-terminal methionine and a
      C-terminal linker + His6 tag)

<400> SEQUENCE: 30

Met Asp Lys Trp Glu Lys Glu Phe Arg Ile Arg Ser Tyr Glu Pro Tyr
1               5                   10                  15

Ser Asn Ile Ala Glu Trp Ala Asp Lys Leu Met Thr Lys Lys Tyr Ser
            20                  25                  30

Asp Leu Asp Asn Pro Thr Gly Ile Ser Val Lys Ala Gly Asp Asp Ile
        35                  40                  45

Ile Val Leu Val Gly Asp Thr Tyr Gly Gln Asn Ile Ser Met Gln Cys
    50                  55                  60

Ile Trp Glu Thr Gly Thr Glu Tyr Lys Gln Thr Ala Ser Ser Gly Asp
65                  70                  75                  80

Val Tyr Met Leu Asn Pro Gly Val Asn Lys Leu Thr Met Lys Gly Glu
                85                  90                  95
```

```
Gly Gln Leu Phe Val Met Tyr Asn Thr Glu Leu Thr Ser Asn Thr Ala
                100                 105                 110

Lys Pro Ile Lys Ile His Ile Pro Leu Gly Ser Gly Thr Val Asn Gly
            115                 120                 125

Phe Phe Asp Leu Lys Glu His Lys Thr Asp Glu Lys Tyr Ala Glu Leu
130                 135                 140

Leu Lys Lys Ser Thr His Lys Tyr Phe Cys Ile Arg Gly Glu Lys Ile
145                 150                 155                 160

Met Phe Tyr Phe His Arg Asn Lys Leu Leu Glu Tyr Val Pro Asn Asn
                165                 170                 175

Ile Leu Ser Ala Ile His Leu Trp Asp Asn Ile Val Gly Trp Gln Gln
            180                 185                 190

Glu Leu Met Gly Ile Asp Asp Val Arg Pro Ser Gln Val Asn Asn His
        195                 200                 205

Leu Phe Ala Ile Ser Pro Glu Gly Ser Tyr Met Trp Ala Ser Asp Tyr
210                 215                 220

Gln Ile Gly Phe Val Tyr Thr Tyr Leu Gly Asn Ile Leu Leu Glu Asp
225                 230                 235                 240

Asn Val Met Ala Ala Glu Asp Asn Ala Trp Gly Pro Ala His Glu Ile
                245                 250                 255

Gly His Val His Gln Ala Ala Ile Asn Trp Ala Ser Ser Thr Glu Ser
            260                 265                 270

Ser Asn Asn Leu Phe Ser Asn Phe Ile Ile Tyr Lys Leu Gly Lys Tyr
        275                 280                 285

Lys Ser Arg Gly Asn Gly Leu Gly Ser Val Ala Thr Ala Arg Tyr Ala
290                 295                 300

Asn Gly Gln Ala Trp Tyr Asn Met Gly Asp Ala Thr His Gln Asn Glu
305                 310                 315                 320

Asp Thr Glu Thr His Met Arg Met Asn Trp Gln Leu Trp Ile Tyr Tyr
                325                 330                 335

His Arg Cys Glu Tyr Lys Thr Asp Phe Trp Gln Thr Leu Phe Lys Leu
            340                 345                 350

Met Arg Glu Val Asn Met Thr Glu Gly Glu Asp Pro Gly Lys Lys Gln
        355                 360                 365

Leu Glu Phe Ala Lys Met Ala Ser Lys Ala Ala Asn Gln Asn Leu Thr
370                 375                 380

Asp Phe Phe Glu Met Trp Gly Phe Phe Glu Pro Val Asn Thr Thr Ile
385                 390                 395                 400

Glu Gln Tyr Gly Thr Tyr Lys Tyr Tyr Val Ser Asp Ala Met Ile Arg
                405                 410                 415

Glu Ala Lys Glu Tyr Met Ala Gln Phe Pro Ala Pro Lys His Ala Phe
            420                 425                 430

Gln Tyr Ile Glu Asp Arg Lys Lys Ser Glu Phe Pro Ser Asn Asp Tyr
        435                 440                 445

Arg Tyr Ser Ala Val Gly Asp Val Gly Tyr Tyr Thr Gln Phe Lys Glu
450                 455                 460

Asn Gln Lys Ile Thr Lys Ala Ile Thr Ala Glu Leu Ala Gly Arg Lys
465                 470                 475                 480

Val Ser Ile Gln Asn Gly Asp Glu Ala Val Ala Phe Glu Leu Arg Glu
                485                 490                 495

Asn Asp Glu Asn Gly Lys Leu Leu Tyr Phe Ser Thr Phe Thr Thr Phe
            500                 505                 510
```

```
Glu Ile Pro Ser Ser Ile Leu Met Val Asn Ala Lys Leu Tyr Ala Val
            515                 520                 525

Gln Ala Asp Gly Lys Arg Ile Leu Leu Gly Ser Gly His His His
530                 535                 540

His His
545

<210> SEQ ID NO 31
<211> LENGTH: 517
<212> TYPE: PRT
<213> ORGANISM: Artificial Sequence
<220> FEATURE:
<223> OTHER INFORMATION: polypeptide having O-glycoprotein-specific
      endoprotease activity (including N-terminal methionine and a
      C-terminal linker + His6 tag)

<400> SEQUENCE: 31

Met Val Leu Glu Leu Glu Met Arg Gly Asp Ser Ile Ser Glu Ala Lys
1               5                   10                  15

Lys Arg Lys Val Trp Asn Phe Gln Asp Trp Gln Ile Thr Gly Leu Ser
            20                  25                  30

Ala Arg Ala Gly Asp Lys Ile Thr Val Tyr Val Asp Val Ala Glu Gly
        35                  40                  45

Asp Pro Thr Pro Thr Leu Leu Tyr Lys Gln Ser Leu Thr Gln His Gly
50                  55                  60

Gly Ala Thr Ser Phe Gln Leu Lys Pro Gly Lys Asn Glu Ile Thr Ile
65                  70                  75                  80

Pro Glu Ile Asn Tyr Glu Ser Asn Gly Ile Pro Lys Asp Val Ile Gln
                85                  90                  95

Gly Gly Asp Leu Phe Phe Thr Asn Tyr Lys Ser Asp Ser Gln Lys Arg
            100                 105                 110

Ala Pro Lys Val Arg Ile Glu Gly Ala Ser Lys Tyr Pro Val Phe Ile
        115                 120                 125

Leu Gly Lys Ser Asp Glu Asn Glu Val Met Lys Glu Leu Glu Ala Tyr
130                 135                 140

Val Glu Lys Ile Lys Ala Glu Pro Lys Thr Thr Pro Asn Ile Phe Ala
145                 150                 155                 160

Val Ser Ser Asn Lys Ser Leu Glu Phe Val Gln Ala Thr Tyr Ala Leu
                165                 170                 175

Asp Trp Tyr Lys Lys Asn Asn Lys Thr Pro Lys Tyr Thr Ala Glu Gln
            180                 185                 190

Trp Asp Gln Tyr Ile Ala Asp Ala Met Gly Phe Trp Gly Phe Asp Asn
        195                 200                 205

Ser Lys Asp Val Asn Ser Asp Phe Asn Phe Arg Ile Met Pro Met Val
210                 215                 220

Lys Asn Leu Ser Gly Gly Ala Phe Met Asn Ala Gly Asn Gly Val Ile
225                 230                 235                 240

Gly Ile Arg Pro Gly Asn Gln Asp Ala Ile Leu Ala Ala Asn Lys Gly
                245                 250                 255

Trp Gly Val Ala His Glu Leu Gly His Asn Phe Asp Thr Gly Gly Arg
            260                 265                 270

Thr Ile Val Glu Val Thr Asn Asn Met Met Pro Leu Phe Phe Glu Ser
        275                 280                 285

Lys Tyr Lys Thr Lys Thr Arg Ile Thr Asp Gln Asn Ile Trp Glu Asn
290                 295                 300
```

Asn Thr Tyr Pro Lys Val Gly Leu Asp Asp Tyr Ser Asn Asn Glu Leu
305                 310                 315                 320

Tyr Asn Lys Ala Asp Ser Thr His Leu Ala Gln Leu Ala Pro Leu Trp
            325                 330                 335

Gln Leu Tyr Leu Tyr Asp Asn Thr Phe Tyr Gly Lys Phe Glu Arg Gln
            340                 345                 350

Phe Arg Glu Arg Asp Phe Gly Asn Lys Asn Arg Glu Asp Ile Tyr Lys
355                 360                 365

Ser Trp Val Val Ala Ala Ser Asp Ala Met Glu Leu Asp Leu Thr Glu
370                 375                 380

Phe Phe Ala Arg His Gly Ile Arg Val Asp Asp Lys Val Lys Glu Asp
385                 390                 395                 400

Leu Ala Lys Tyr Pro Lys Pro Asp Lys Lys Ile Tyr Tyr Leu Asn Asp
            405                 410                 415

Leu Ala Met Asn Tyr Lys Gly Asp Gly Phe Thr Glu Asn Ala Lys Val
            420                 425                 430

Ser Val Ser Thr Ser Gly Ser Asn Gly Asn Ile Lys Leu Ser Phe Ser
            435                 440                 445

Val Asp Asp Glu Asn Lys Asp Asn Ile Leu Gly Tyr Glu Ile Arg Arg
450                 455                 460

Asp Gly Lys Tyr Val Gly Phe Thr Ser Asn Asp Ser Phe Val Asp Thr
465                 470                 475                 480

Lys Ser Asn Leu Asp Glu Asp Gly Val Tyr Val Val Thr Pro Tyr Asp
            485                 490                 495

Arg Lys Leu Asn Thr Leu Asn Pro Ile Glu Val Asn Gly Ser Gly His
            500                 505                 510

His His His His His
            515

<210> SEQ ID NO 32
<211> LENGTH: 923
<212> TYPE: PRT
<213> ORGANISM: Pseudomonas aeruginosa

<400> SEQUENCE: 32

Met Ser Leu Ser Thr Thr Ala Phe Pro Ser Leu Gln Gly Glu Asn Met
1               5                   10                  15

Ser Arg Ser Pro Ile Pro Arg His Arg Ala Leu Leu Ala Gly Phe Cys
            20                  25                  30

Leu Ala Gly Ala Leu Ser Ala Gln Ala Ala Thr Gln Glu Glu Ile Leu
            35                  40                  45

Asp Ala Ala Leu Val Ser Gly Asp Ser Ser Gln Leu Thr Asp Ser His
50                  55                  60

Leu Val Ala Leu Arg Leu Gln Gln Gln Val Glu Arg Ile Arg Gln Thr
65                  70                  75                  80

Arg Thr Gln Leu Leu Asp Gly Leu Tyr Gln Asn Leu Ser Gln Ala Tyr
            85                  90                  95

Asp Pro Gly Ala Ala Ser Met Trp Val Leu Pro Ala Asn Pro Asp Asn
            100                 105                 110

Thr Leu Pro Phe Leu Ile Gly Asp Lys Gly Arg Val Leu Ala Ser Leu
            115                 120                 125

Ser Leu Glu Ala Gly Gly Arg Gly Leu Ala Tyr Gly Thr Asn Val Leu
            130                 135                 140

Thr Gln Leu Ser Gly Thr Asn Ala Ala His Ala Pro Leu Leu Lys Arg
145                 150                 155                 160

-continued

```
Ala Val Gln Trp Leu Val Asn Gly Asp Pro Gly Ala Thr Ala Lys
            165                 170                 175
Asp Phe Lys Val Ser Val Gly Val Asp Lys Thr Ala Ala Leu Asn
            180                 185                 190
Gly Leu Lys Ser Ala Gly Leu Gln Pro Ala Asp Ala Ala Cys Asn Ala
            195                 200                 205
Leu Thr Asp Ala Ser Cys Ala Ser Thr Ser Lys Leu Leu Val Leu Gly
            210                 215                 220
Asn Gly Ala Ser Ala Ala Ser Leu Ser Ala Thr Val Arg Ala Arg Leu
225                 230                 235                 240
Gln Ala Gly Leu Pro Ile Leu Phe Val His Thr Asn Gly Trp Asn Gln
            245                 250                 255
Ser Ser Thr Gly Gln Gln Ile Leu Ala Gly Leu Gly Leu Gln Glu Gly
            260                 265                 270
Pro Tyr Gly Gly Asn Tyr Trp Asp Lys Asp Arg Val Pro Ser Ser Arg
            275                 280                 285
Thr Arg Thr Arg Ser Val Glu Leu Gly Gly Ala Tyr Gly Gln Asp Pro
            290                 295                 300
Ala Leu Val Gln Gln Ile Val Asp Gly Ser Trp Arg Thr Asp Tyr Asp
305                 310                 315                 320
Trp Ser Lys Cys Thr Ser Tyr Val Gly Arg Thr Thr Cys Asp Asp Val
                        325                 330                 335
Pro Gly Leu Ser Asp Phe Ser Lys Arg Val Asp Val Leu Lys Gly Ala
            340                 345                 350
Leu Asp Ala Tyr Asn Gln Lys Ala Gln Asn Leu Phe Ala Leu Pro Gly
            355                 360                 365
Thr Thr Ser Leu Arg Leu Trp Leu Leu Trp Ala Asp Ala Val Arg Gln
            370                 375                 380
Asn Ile Arg Tyr Pro Met Asp Lys Ala Ala Asp Thr Ala Arg Phe Gln
385                 390                 395                 400
Glu Thr Phe Val Ala Asp Ala Ile Val Gly Tyr Val Arg Glu Ala Gly
                        405                 410                 415
Ala Ala Gln Lys Glu Leu Gly Ser Tyr Ala Gly Gln Arg Gln Gln Ser
            420                 425                 430
Met Pro Val Ser Gly Ser Glu Glu Thr Leu Thr Leu Thr Leu Pro Ser
            435                 440                 445
Ala Gln Gly Phe Thr Ala Ile Gly Arg Met Ala Ala Pro Gly Lys Arg
            450                 455                 460
Leu Ser Ile Arg Ile Glu Asp Ala Gly Gln Ala Ser Leu Ala Val Gly
465                 470                 475                 480
Leu Asn Thr Gln Arg Ile Gly Ser Thr Arg Leu Trp Asn Thr Arg Gln
                        485                 490                 495
Tyr Asp Arg Pro Arg Phe Leu Lys Ser Pro Asp Ile Lys Leu Gln Ala
            500                 505                 510
Asn Gln Ser Val Ala Leu Val Ser Pro Tyr Gly Gly Leu Leu Gln Leu
            515                 520                 525
Val Tyr Ser Gly Ala Thr Pro Gly Gln Thr Val Thr Val Lys Val Thr
            530                 535                 540
Gly Ala Ala Ser Gln Pro Phe Leu Asp Ile Gln Pro Gly Glu Asp Ser
545                 550                 555                 560
Ser Gln Ala Ile Ala Asp Phe Ile Gln Ala Leu Asp Ala Asp Lys Ala
                        565                 570                 575
```

```
Asp Trp Leu Glu Ile Arg Ser Gly Ser Val Glu Val His Ala Lys Val
            580                 585                 590

Glu Lys Val Arg Gly Ser Ile Asp Lys Asp Tyr Gly Gly Asp Val Gln
        595                 600                 605

Arg Phe Ile Arg Glu Leu Asn Glu Val Phe Ile Asp Asp Ala Tyr Thr
    610                 615                 620

Leu Ala Gly Phe Ala Ile Pro Asn Gln Ala Lys Thr Pro Ala Ile Gln
625                 630                 635                 640

Gln Glu Cys Ala Ala Arg Gly Trp Asp Cys Asp Ser Glu Thr Leu His
                645                 650                 655

Lys Leu Pro Gly Thr Gln His Ile Asn Val Asp Gln Tyr Ala Gln Cys
            660                 665                 670

Gly Gly Gly Cys Ser Gly Asn Pro Tyr Asp Gln Thr Trp Gly Leu Asn
        675                 680                 685

Pro Arg Gly Trp Gly Glu Ser His Glu Leu Gly His Asn Leu Gln Val
    690                 695                 700

Asn Arg Leu Lys Val Tyr Gly Arg Ser Gly Glu Ile Ser Asn Gln
705                 710                 715                 720

Ile Phe Pro Leu His Lys Asp Trp Arg Val Leu Arg Glu Phe Gly Gln
                725                 730                 735

Asn Leu Asp Asp Thr Arg Val Asn Tyr Arg Asn Ala Tyr Asn Leu Ile
            740                 745                 750

Val Ala Gly Arg Ala Glu Ala Asp Pro Leu Ala Gly Val Tyr Lys Arg
        755                 760                 765

Leu Trp Glu Asp Pro Gly Thr Tyr Ala Leu Asn Gly Glu Arg Met Ala
    770                 775                 780

Phe Tyr Thr Gln Trp Val His Tyr Trp Ala Asp Leu Lys Asn Asp Pro
785                 790                 795                 800

Leu Gln Gly Trp Asp Ile Trp Thr Leu Leu Tyr Leu His Gln Arg Gln
                805                 810                 815

Val Asp Lys Ser Asp Trp Asp Ala Asn Lys Ala Ala Leu Gly Tyr Gly
            820                 825                 830

Thr Tyr Ala Gln Arg Pro Gly Asn Ser Gly Asp Ala Ser Ser Thr Asp
        835                 840                 845

Gly Asn Asp Asn Leu Leu Leu Gly Leu Ser Trp Leu Thr Gln Arg Asp
850                 855                 860

Gln Arg Pro Thr Phe Ala Leu Trp Gly Ile Arg Thr Ser Ala Ala Ala
865                 870                 875                 880

Gln Ala Gln Val Ala Ala Tyr Gly Phe Ala Glu Gln Pro Ala Phe Phe
                885                 890                 895

Tyr Ala Asn Asn Arg Thr Asn Glu Tyr Ser Thr Val Lys Leu Leu Asp
            900                 905                 910

Met Ser Gln Gly Ser Pro Ala Trp Pro Phe Pro
        915                 920

<210> SEQ ID NO 33
<211> LENGTH: 857
<212> TYPE: PRT
<213> ORGANISM: Bacteroides thetaiotaomicron

<400> SEQUENCE: 33

Met Thr Ile Lys Arg Phe Ile Thr Asn Leu Leu Ala Leu Phe Thr Leu
1               5                   10                  15

Phe Thr Val Ser Leu Ala Cys Lys Asp Thr Glu Lys Ser Ile Ile Asn
                20                  25                  30
```

-continued

```
Ser Ser Phe Ser Ile Ser Glu Glu Tyr Leu Ile Gln Asn Leu Asp Lys
            35                  40                  45

Ser Ser Thr Ser Val Gln Ile Pro Ile Asn Thr Ser Met Glu Leu Ala
 50                  55                  60

Gln Trp Ser Val Ser Tyr Glu Ala Asn Trp Leu Gln Cys Ser Lys Gln
 65                  70                  75                  80

Lys Thr Ala Ala Glu Gly Thr Phe Leu Arg Ile Thr Val Asn Glu Asn
                85                  90                  95

Thr Gly Glu Thr Lys Arg Thr Ala Asn Ile Lys Val Thr Ser Thr Thr
            100                 105                 110

Ala Thr Tyr Thr Ile Thr Val Asn Gln Tyr Ala Lys Gly Glu Val Ile
            115                 120                 125

Val Glu Gly Asp Ile Lys Val Thr Pro Thr Gly Gly Lys Ala Ser Glu
130                 135                 140

His Gln Glu Gly Gln Asp Ile Glu Asn Thr Tyr Asp Gly Lys Phe Ser
145                 150                 155                 160

Thr Asp Gly Ala Ala Pro Phe His Thr Pro Trp Gly Gln Ser Ala Lys
                165                 170                 175

Phe Pro Val Thr Leu Glu Tyr Tyr Phe Lys Gly Asp Thr Glu Ile Asp
            180                 185                 190

Tyr Leu Ile Tyr Tyr Thr Arg Ser Gly Asn Gly Asn Phe Gly Lys Val
            195                 200                 205

Lys Val Tyr Thr Thr Asn Pro Asp Arg Ser Asp Tyr Thr Leu Gln
210                 215                 220

Gly Glu Tyr Asp Phe Lys Glu Gln Asn Ala Pro Ser Lys Val Ser Phe
225                 230                 235                 240

Ser Glu Gly Ile Lys Ala Thr Gly Ile Lys Phe Glu Val Leu Ser Gly
                245                 250                 255

Leu Gly Asp Phe Val Ser Cys Asp Glu Met Glu Phe Tyr Lys Thr Asn
            260                 265                 270

Thr Asp Lys Thr Leu Asp Lys Gln Leu Leu Thr Val Phe Thr Asp Ile
            275                 280                 285

Thr Cys Thr Glu Ile Lys Asn Asn Val Thr Asn Glu Gln Ile Gln Ala
290                 295                 300

Leu Pro Asp Tyr Phe Val Arg Ile Ala Glu Ala Val Arg Asp Asn Thr
305                 310                 315                 320

Tyr Asp Lys Trp Glu Lys Glu Phe Arg Ile Arg Ser Tyr Glu Pro Tyr
                325                 330                 335

Ser Asn Ile Ala Glu Trp Ala Asp Lys Leu Met Thr Lys Lys Tyr Ser
            340                 345                 350

Asp Leu Asp Asn Pro Thr Gly Ile Ser Val Lys Ala Gly Asp Asp Ile
            355                 360                 365

Ile Val Leu Val Gly Asp Thr Tyr Gly Gln Asn Ile Ser Met Gln Cys
370                 375                 380

Ile Trp Glu Thr Gly Thr Glu Tyr Lys Gln Thr Ala Ser Ser Gly Asp
385                 390                 395                 400

Val Tyr Met Leu Asn Pro Gly Val Asn Lys Leu Thr Met Lys Gly Glu
                405                 410                 415

Gly Gln Leu Phe Val Met Tyr Asn Thr Glu Leu Thr Ser Asn Thr Ala
            420                 425                 430

Lys Pro Ile Lys Ile His Ile Pro Leu Gly Ser Gly Thr Val Asn Gly
            435                 440                 445
```

```
Phe Phe Asp Leu Lys Glu His Lys Thr Asp Glu Lys Tyr Ala Glu Leu
450                 455                 460

Leu Lys Lys Ser Thr His Lys Tyr Phe Cys Ile Arg Gly Glu Lys Ile
465                 470                 475                 480

Met Phe Tyr Phe His Arg Asn Lys Leu Leu Glu Tyr Val Pro Asn Asn
                485                 490                 495

Ile Leu Ser Ala Ile His Leu Trp Asp Asn Ile Val Gly Trp Gln Gln
                500                 505                 510

Glu Leu Met Gly Ile Asp Asp Val Arg Pro Ser Gln Val Asn Asn His
                515                 520                 525

Leu Phe Ala Ile Ser Pro Glu Gly Ser Tyr Met Trp Ala Ser Asp Tyr
530                 535                 540

Gln Ile Gly Phe Val Tyr Thr Tyr Leu Gly Asn Ile Leu Leu Glu Asp
545                 550                 555                 560

Asn Val Met Ala Ala Glu Asp Asn Ala Trp Gly Pro Ala His Glu Ile
                565                 570                 575

Gly His Val His Gln Ala Ala Ile Asn Trp Ala Ser Ser Thr Glu Ser
                580                 585                 590

Ser Asn Asn Leu Phe Ser Asn Phe Ile Ile Tyr Lys Leu Gly Lys Tyr
        595                 600                 605

Lys Ser Arg Gly Asn Gly Leu Gly Ser Val Ala Thr Ala Arg Tyr Ala
610                 615                 620

Asn Gly Gln Ala Trp Tyr Asn Met Gly Asp Ala Thr His Gln Asn Glu
625                 630                 635                 640

Asp Thr Glu Thr His Met Arg Met Asn Trp Gln Leu Trp Ile Tyr Tyr
                645                 650                 655

His Arg Cys Glu Tyr Lys Thr Asp Phe Trp Gln Thr Leu Phe Lys Leu
                660                 665                 670

Met Arg Glu Val Asn Met Thr Glu Gly Glu Asp Pro Gly Lys Lys Gln
                675                 680                 685

Leu Glu Phe Ala Lys Met Ala Ser Lys Ala Ala Asn Gln Asn Leu Thr
        690                 695                 700

Asp Phe Phe Glu Met Trp Gly Phe Phe Glu Pro Val Asn Thr Thr Ile
705                 710                 715                 720

Glu Gln Tyr Gly Thr Tyr Lys Tyr Tyr Val Ser Asp Ala Met Ile Arg
                725                 730                 735

Glu Ala Lys Glu Tyr Met Ala Gln Phe Pro Ala Pro Lys His Ala Phe
                740                 745                 750

Gln Tyr Ile Glu Asp Arg Lys Lys Ser Glu Phe Pro Ser Asn Asp Tyr
        755                 760                 765

Arg Tyr Ser Ala Val Gly Asp Val Gly Tyr Tyr Thr Gln Phe Lys Glu
770                 775                 780

Asn Gln Lys Ile Thr Lys Ala Ile Thr Ala Glu Leu Ala Gly Arg Lys
785                 790                 795                 800

Val Ser Ile Gln Asn Gly Asp Glu Ala Val Ala Phe Glu Leu Arg Glu
                805                 810                 815

Asn Asp Glu Asn Gly Lys Leu Leu Tyr Phe Ser Thr Phe Thr Thr Phe
                820                 825                 830

Glu Ile Pro Ser Ser Ile Leu Met Val Asn Ala Lys Leu Tyr Ala Val
        835                 840                 845

Gln Ala Asp Gly Lys Arg Ile Leu Leu
850                 855
```

```
<210> SEQ ID NO 34
<211> LENGTH: 1687
<212> TYPE: PRT
<213> ORGANISM: Clostridium perfringens

<400> SEQUENCE: 34
```

| | | | | | | | | | | | | | | |
|---|---|---|---|---|---|---|---|---|---|---|---|---|---|---|
| Met | Asn | Lys | Arg | Lys | Ile | Ala | Ala | Ile | Ile | Leu | Ala | Thr | Met | Ile | Thr |
| 1 | | | | 5 | | | | | 10 | | | | | 15 | |
| Asn | Leu | Ser | Ala | Thr | Thr | Ile | Asp | Val | Leu | Ala | Gln | Glu | Leu | Asn | Thr |
| | | | 20 | | | | | 25 | | | | | 30 | | |
| Lys | Asn | Asn | Ser | Lys | Val | Glu | Val | Ser | His | Asp | Asp | Glu | Ser | His | Gln |
| | | | | 35 | | | | | 40 | | | | | 45 | |
| Ala | Arg | Val | Ser | Lys | Phe | Asp | Leu | Tyr | Asn | Ser | Asp | Lys | Leu | Asp | Ala |
| | 50 | | | | | 55 | | | | | 60 | | | | |
| Tyr | Asn | Gln | Glu | Phe | Gln | Val | Ser | Arg | Ser | Asn | Ile | Lys | Ser | Ile | Asn |
| 65 | | | | | 70 | | | | | 75 | | | | | 80 |
| Asn | Asn | Gly | Gly | Lys | Tyr | Asn | Ser | Ser | Thr | Ile | Asp | Lys | Ala | Ile | Asp |
| | | | | 85 | | | | | 90 | | | | | 95 | |
| Gly | Asn | Leu | Glu | Thr | His | Trp | Glu | Thr | Gly | Lys | Pro | Asn | Asp | Ala | Asn |
| | | | 100 | | | | | 105 | | | | | 110 | | |
| Phe | Thr | Asn | Glu | Val | Val | Thr | Phe | Asn | Glu | Ile | Thr | Asn | Ile | Asp |
| | | | | 115 | | | | | 120 | | | | | 125 | |
| Arg | Ile | Val | Tyr | Ser | Ala | Arg | Arg | Asp | Ser | Ala | Arg | Gly | Lys | Gly | Phe |
| | 130 | | | | | 135 | | | | | 140 | | | | |
| Ala | Lys | Glu | Phe | Glu | Ile | Tyr | Ala | Ser | Leu | Lys | Asp | Glu | Gly | Asp | Asp |
| 145 | | | | | 150 | | | | | 155 | | | | | 160 |
| Phe | Asn | Leu | Val | Ser | Ser | Gly | Glu | Tyr | Thr | Glu | Ser | Thr | Arg | Asp | Leu |
| | | | | 165 | | | | | 170 | | | | | 175 | |
| Val | Glu | Ile | Lys | Phe | Asn | Pro | Thr | Asp | Phe | Lys | Arg | Leu | Lys | Phe | Lys |
| | | | 180 | | | | | 185 | | | | | 190 | | |
| Phe | Lys | Lys | Ala | Asp | Gln | Asn | Trp | Ala | Ser | Ala | Ala | Glu | Phe | Met | Phe |
| | | 195 | | | | | 200 | | | | | 205 | | | |
| Tyr | Lys | Glu | Asp | Lys | Leu | Asn | Glu | Lys | Phe | Asn | Gly | Leu | Phe | Thr | Asp |
| | 210 | | | | | 215 | | | | | 220 | | | | |
| Ser | Ser | Met | Asn | Lys | Val | Ser | Glu | Glu | Phe | Asn | Thr | Leu | Glu | Lys | Leu |
| 225 | | | | | 230 | | | | | 235 | | | | | 240 |
| Asn | Ala | Phe | Glu | Asn | Glu | Leu | Lys | Asp | His | Pro | Ile | Tyr | Asp | Leu | Tyr |
| | | | | 245 | | | | | 250 | | | | | 255 | |
| Lys | Glu | Gly | Leu | Asn | Asn | Ala | Arg | Ala | Ile | Leu | Thr | Glu | Thr | Ser | Glu |
| | | | 260 | | | | | 265 | | | | | 270 | | |
| Asn | Pro | Thr | Lys | Ala | Thr | Leu | Gly | Gln | Ile | Thr | Tyr | Asn | Leu | Asn | Asp |
| | | 275 | | | | | 280 | | | | | 285 | | | |
| Asp | Tyr | Asn | Asn | Gln | Tyr | Arg | Met | Pro | Tyr | Lys | Asn | Ile | Lys | Ala | Ile |
| | 290 | | | | | 295 | | | | | 300 | | | | |
| Lys | Asn | Asn | Gly | Arg | His | Tyr | Ala | Ala | Gln | Asn | Ile | Glu | Lys | Ala | Ile |
| 305 | | | | | 310 | | | | | 315 | | | | | 320 |
| Asp | Asn | Asp | Val | Asn | Thr | Tyr | Trp | Glu | Thr | Gly | Thr | Leu | Asn | Ser | Ser |
| | | | | 325 | | | | | 330 | | | | | 335 | |
| Ser | Phe | Asn | Glu | Val | Glu | Val | Glu | Phe | Asn | Asp | Leu | Val | Thr | Leu |
| | | | 340 | | | | | 345 | | | | | 350 | | |
| Asp | Arg | Ile | Val | Tyr | Gly | Ser | Arg | Gln | Ser | Asp | Leu | Lys | Gly | Phe | Ala |
| | | 355 | | | | | 360 | | | | | 365 | | | |
| Glu | Glu | Val | Tyr | Ile | Tyr | Ala | Ser | Arg | Thr | Ser | Lys | Gly | Asp | Thr | Tyr |
| | 370 | | | | | 375 | | | | | 380 | | | | |

-continued

```
Lys Leu Val Ala Thr Gly Ala His Glu Ala Thr Lys Gly Leu Val Glu
385                 390                 395                 400

Ala Lys Phe Glu Pro Thr Glu Phe Lys Arg Val Lys Phe Lys Phe Lys
            405                 410                 415

Lys Ser Lys Gln Asn Ser Ala Thr Leu Asn Glu Leu Met Phe Tyr Lys
        420                 425                 430

Pro Asp Glu Val Tyr Ser Ser Ile Pro Lys Leu Phe Thr Asp Gly Thr
    435                 440                 445

Met Ser Glu Leu Ser Glu Glu Phe Asn Ser Leu Glu Lys Ile Asn Ala
    450                 455                 460

Phe Lys Glu Lys Ala Lys Asn His Pro Leu Tyr Asn Asp Phe Asn Glu
465                 470                 475                 480

Thr Ile Glu Leu Ala Glu Ser Leu Ile Ser Asn Pro Arg Lys Glu Asp
            485                 490                 495

Val Leu Glu Leu Glu Met Arg Gly Asp Ser Ile Ser Glu Ala Lys Lys
        500                 505                 510

Arg Lys Val Trp Asn Phe Gln Asp Trp Gln Ile Thr Gly Leu Ser Ala
            515                 520                 525

Arg Ala Gly Asp Lys Ile Thr Val Tyr Val Asp Val Ala Glu Gly Asp
530                 535                 540

Pro Thr Pro Thr Leu Leu Tyr Lys Gln Ser Leu Thr Gln His Gly Gly
545                 550                 555                 560

Ala Thr Ser Phe Gln Leu Lys Pro Gly Lys Asn Glu Ile Thr Ile Pro
            565                 570                 575

Glu Ile Asn Tyr Glu Ser Asn Gly Ile Pro Lys Asp Val Ile Gln Gly
        580                 585                 590

Gly Asp Leu Phe Phe Thr Asn Tyr Lys Ser Asp Ser Gln Lys Arg Ala
            595                 600                 605

Pro Lys Val Arg Ile Glu Gly Ala Ser Lys Tyr Pro Val Phe Ile Leu
    610                 615                 620

Gly Lys Ser Asp Glu Asn Glu Val Met Lys Glu Leu Glu Ala Tyr Val
625                 630                 635                 640

Glu Lys Ile Lys Ala Glu Pro Lys Thr Thr Pro Asn Ile Phe Ala Val
            645                 650                 655

Ser Ser Asn Lys Ser Leu Glu Phe Val Gln Ala Thr Tyr Ala Leu Asp
        660                 665                 670

Trp Tyr Lys Lys Asn Asn Lys Thr Pro Lys Tyr Thr Ala Glu Gln Trp
            675                 680                 685

Asp Gln Tyr Ile Ala Asp Ala Met Gly Phe Trp Gly Phe Asp Asn Ser
    690                 695                 700

Lys Asp Val Asn Ser Asp Phe Asn Phe Arg Ile Met Pro Met Val Lys
705                 710                 715                 720

Asn Leu Ser Gly Gly Ala Phe Met Asn Ala Gly Asn Gly Val Ile Gly
            725                 730                 735

Ile Arg Pro Gly Asn Gln Asp Ala Ile Leu Ala Ala Asn Lys Gly Trp
        740                 745                 750

Gly Val Ala His Glu Leu Gly His Asn Phe Asp Thr Gly Gly Arg Thr
            755                 760                 765

Ile Val Glu Val Thr Asn Asn Met Met Pro Leu Phe Phe Glu Ser Lys
    770                 775                 780

Tyr Lys Thr Lys Thr Arg Ile Thr Asp Gln Asn Ile Trp Glu Asn Asn
785                 790                 795                 800
```

-continued

```
Thr Tyr Pro Lys Val Gly Leu Asp Asp Tyr Ser Asn Asn Glu Leu Tyr
            805                 810                 815

Asn Lys Ala Asp Ser Thr His Leu Ala Gln Leu Ala Pro Leu Trp Gln
            820                 825                 830

Leu Tyr Leu Tyr Asp Asn Thr Phe Tyr Gly Lys Phe Glu Arg Gln Phe
            835                 840                 845

Arg Glu Arg Asp Phe Gly Asn Lys Asn Arg Glu Asp Ile Tyr Lys Ser
850                 855                 860

Trp Val Ala Ala Ser Asp Ala Met Glu Leu Asp Leu Thr Glu Phe
865                 870                 875                 880

Phe Ala Arg His Gly Ile Arg Val Asp Asp Lys Val Lys Glu Asp Leu
                885                 890                 895

Ala Lys Tyr Pro Lys Pro Asp Lys Lys Ile Tyr Tyr Leu Asn Asp Leu
            900                 905                 910

Ala Met Asn Tyr Lys Gly Asp Gly Phe Thr Glu Asn Ala Lys Val Ser
            915                 920                 925

Val Ser Thr Ser Gly Ser Asn Gly Asn Ile Lys Leu Ser Phe Ser Val
            930                 935                 940

Asp Asp Glu Asn Lys Asp Asn Ile Leu Gly Tyr Glu Ile Arg Arg Asp
945                 950                 955                 960

Gly Lys Tyr Val Gly Phe Thr Ser Asn Asp Ser Phe Val Asp Thr Lys
                965                 970                 975

Ser Asn Leu Asp Glu Asp Gly Val Tyr Val Val Thr Pro Tyr Asp Arg
            980                 985                 990

Lys Leu Asn Thr Leu Asn Pro Ile Glu Val Asn Ala Leu Gln Pro Thr
            995                 1000                1005

Leu Ser Val Asn Pro Val Ile Thr Leu Ala Leu Gly Glu Glu Phe
            1010                1015                1020

Asn Glu Glu Glu Tyr Ile Val Ala Lys Asp Ile Lys Gly Asn Ser
            1025                1030                1035

Leu Ser Glu Ser Val Lys Val Lys Ser Ser Asn Val Asn Thr Ser
            1040                1045                1050

Lys Val Gly Glu Tyr Glu Val Leu Tyr Ser Leu Glu Asp Ser Lys
            1055                1060                1065

Gly Asn Glu Tyr Thr Lys Thr Ser Lys Val Asn Val Val Ser Arg
            1070                1075                1080

Lys Glu Tyr Met Ser Asp Leu Thr Pro Lys Gln Ser Ser Asn Gly
            1085                1090                1095

Trp Gly Thr Val Arg Lys Asp Lys Ser Ile Ser Gly Gly Val Ile
            1100                1105                1110

Gly Leu Thr Arg Asp Gly Asp Phe Val Asp Tyr Asn Lys Gly Leu
            1115                1120                1125

Gly Leu His Ser Asn Ala Glu Tyr Val Tyr Asp Leu Glu Gly Lys
            1130                1135                1140

Asp Tyr Asp Tyr Phe Glu Ser Tyr Val Gly Val Asp Lys Ala Met
            1145                1150                1155

Ser Ser Arg Pro Ala Ser Ser Val Ile Phe Lys Val Leu Val Asp
            1160                1165                1170

Gly Glu Glu Lys Phe Asn Ser Gly Val Met Arg Ser Thr Thr Pro
            1175                1180                1185

Gln Lys Tyr Val Lys Val Asp Val Lys Asn Ala Lys Glu Leu Lys
            1190                1195                1200
```

-continued

Leu Ile Val Asn Asp Ala Gly Asp Gly Asp Ser Ser Asp His Ala
1205                1210                1215

Ser Phe Gly Asp Ala Lys Leu Ala Thr Leu Ser Ser Lys Pro Ile
1220                1225                1230

Ile Lys Gly Glu Asn Leu Ala Tyr Ser Met Asp Glu Lys Val Asp
1235                1240                1245

Leu Met Lys Gly Ile Thr Ala Thr Asp Ile Glu Asp Gly Asn Ile
1250                1255                1260

Thr Ser Lys Val Gln Ile Lys Ser Ser Asp Phe Val Glu Gly Lys
1265                1270                1275

Ser Gly Ile Phe Thr Val Val Tyr Ser Val Thr Asp Ser Asp Gly
1280                1285                1290

Leu Thr Ser Glu Cys Ser Arg Thr Ile Ala Val Thr Asp Lys Glu
1295                1300                1305

Thr Gln Leu Ser Asp Leu Asn Trp Lys Ser Ala Thr Ile Gly Ser
1310                1315                1320

Gly Ser Val Arg Lys Asp Arg Ala Val Ser Gly Asn Gln Ile Arg
1325                1330                1335

Leu Leu Asn Glu Asp Asn Ser Val Glu Thr Phe Ala Lys Gly Ile
1340                1345                1350

Gly Thr His Ser Tyr Ser Glu Ile Val Tyr Asn Ser Glu Gly Tyr
1355                1360                1365

Asp Ile Phe Asp Thr Trp Val Gly Ile Asp Arg His Val Ala Asp
1370                1375                1380

Lys Lys Val Ser Ser Val Lys Phe Lys Val Tyr Val Asp Gly Glu
1385                1390                1395

Leu Lys Ala Glu Thr Asp Val Met Arg Ile Asp Thr Pro Lys Lys
1400                1405                1410

Arg Leu Val Val Asp Val Arg Asn Ser Lys Glu Ile Lys Leu Val
1415                1420                1425

Val Asp Val Ala Asp Asn Gly Asn Asn Trp Asp His Ala Asp Trp
1430                1435                1440

Ala Asp Ala Lys Phe Arg Asn Leu Ala Glu Tyr Asp Ala Ser Glu
1445                1450                1455

Leu Asn Lys Ala Ile Glu Glu Ala Lys Lys Leu Asp Leu Asn Asn
1460                1465                1470

Tyr Thr Glu Glu Ser Ser Glu Ala Leu Lys Asn Ala Ile Ser Lys
1475                1480                1485

Gly Glu Glu Ala Leu Leu Ser Lys Asp Lys Glu Thr Ile Asn Ser
1490                1495                1500

Ala Leu Glu Glu Leu Asn Lys Glu Met Asn Ser Leu Val Lys Val
1505                1510                1515

Asp Leu Asn Ala Val Ile Asn Ile Pro Asp Lys Tyr Leu Leu Lys
1520                1525                1530

Ser Ile Gln Asn Gln Leu Asn Lys Thr Gly Asp Ile Thr Leu Gly
1535                1540                1545

Asp Met Tyr Ser Leu Thr Thr Leu Thr Leu Ser Gly Val Glu Asp
1550                1555                1560

Leu Thr Gly Leu Glu Asn Ala Lys Asn Leu Glu Thr Leu Asn Met
1565                1570                1575

Asp Tyr Asn Glu Val Lys Asp Leu Arg Pro Leu Ser Lys Leu Lys
1580                1585                1590

```
Lys Leu Asn Thr Leu Asn Ala Gln Glu Gln Phe Ile Ala Ala Gly
    1595                1600                1605

Glu Leu Lys Pro Ser Asn Gly Lys Val Ile Gly Asp Ser Lys Val
    1610                1615                1620

Tyr Asn Arg Glu Gly Lys Asn Val Ala Lys Thr Ile Arg Val Val
    1625                1630                1635

Asp Lys Asn Gly Asn Thr Ile Leu Glu Gln Asp Ala Lys Asp Glu
    1640                1645                1650

Phe Thr Ile Asn Thr Lys Asp Leu Ser Ser Gly Leu Tyr Gly Val
    1655                1660                1665

His Val Leu Phe Glu Asp Glu Gly Phe Ser Gly Val Met Phe Tyr
    1670                1675                1680

Leu Phe Asn Val
    1685

<210> SEQ ID NO 35
<211> LENGTH: 882
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Pseudomonas aeruginosa PAO1 (double mutant with removed
      signal sequence)

<400> SEQUENCE: 35

Ala Thr Gln Glu Glu Ile Leu Asp Ala Ala Leu Val Ser Gly Asp Ser
1               5                   10                  15

Ser Gln Leu Thr Asp Ser His Leu Val Ala Leu Arg Leu Gln Gln Gln
                20                  25                  30

Val Glu Arg Ile Arg Gln Thr Arg Thr Gln Leu Leu Asp Gly Leu Tyr
            35                  40                  45

Gln Asn Leu Ser Gln Ala Tyr Asp Pro Gly Ala Ala Ser Met Trp Val
        50                  55                  60

Leu Pro Ala Asn Pro Asp Asn Thr Leu Pro Phe Leu Ile Gly Asp Lys
65                  70                  75                  80

Gly Arg Val Leu Ala Ser Leu Ser Leu Glu Ala Gly Arg Gly Leu
                85                  90                  95

Ala Tyr Gly Thr Asn Val Leu Thr Gln Leu Ser Gly Thr Asn Ala Ala
            100                 105                 110

His Ala Pro Leu Leu Lys Arg Ala Val Gln Trp Leu Val Asn Gly Asp
        115                 120                 125

Pro Gly Ala Ala Thr Ala Lys Asp Phe Lys Val Ser Val Val Gly Val
    130                 135                 140

Asp Lys Thr Ala Ala Leu Asn Gly Leu Lys Ser Ala Gly Leu Gln Pro
145                 150                 155                 160

Ala Asp Ala Ala Cys Asn Ala Leu Thr Asp Ala Ser Cys Ala Ser Thr
                165                 170                 175

Ser Lys Leu Leu Val Leu Gly Asn Gly Ala Ser Ala Ala Ser Leu Ser
            180                 185                 190

Ala Thr Val Arg Ala Arg Leu Gln Ala Gly Leu Pro Ile Leu Phe Val
        195                 200                 205

His Thr Asn Gly Trp Asn Gln Ser Ser Thr Gly Gln Gln Ile Leu Ala
    210                 215                 220

Gly Leu Gly Leu Gln Glu Gly Pro Tyr Gly Gly Asn Tyr Trp Asp Lys
225                 230                 235                 240
```

-continued

```
Asp Arg Val Pro Ser Ser Arg Thr Arg Thr Arg Ser Val Glu Leu Gly
            245                 250                 255
Gly Ala Tyr Gly Gln Asp Pro Ala Leu Val Gln Gln Ile Val Asp Gly
        260                 265                 270
Ser Trp Arg Thr Asp Tyr Asp Trp Ser Lys Cys Thr Ser Tyr Val Gly
        275                 280                 285
Arg Thr Thr Cys Asp Asp Val Pro Gly Leu Ser Asp Phe Ser Lys Arg
        290                 295                 300
Val Asp Val Leu Lys Gly Ala Leu Asp Ala Tyr Asn Gln Lys Ala Gln
305                 310                 315                 320
Asn Leu Phe Ala Leu Pro Gly Thr Thr Ser Leu Arg Leu Trp Leu Leu
            325                 330                 335
Trp Ala Asp Ala Val Arg Gln Asn Ile Arg Tyr Pro Met Asp Lys Ala
            340                 345                 350
Ala Asp Thr Ala Arg Phe Gln Glu Thr Phe Val Ala Asp Ala Ile Val
        355                 360                 365
Gly Tyr Val Arg Glu Ala Gly Ala Gln Lys Glu Leu Gly Ser Tyr
        370                 375                 380
Ala Gly Gln Arg Gln Ser Met Pro Val Ser Gly Ser Glu Glu Thr
385                 390                 395                 400
Leu Thr Leu Thr Leu Pro Ser Ala Gln Gly Phe Thr Ala Ile Gly Arg
            405                 410                 415
Met Ala Ala Pro Gly Lys Arg Leu Ser Ile Arg Ile Glu Asp Ala Gly
            420                 425                 430
Gln Ala Ser Leu Ala Val Gly Leu Asn Thr Gln Arg Ile Gly Ser Thr
        435                 440                 445
Arg Leu Trp Asn Thr Arg Gln Tyr Asp Arg Pro Arg Phe Leu Lys Ser
        450                 455                 460
Pro Asp Ile Lys Leu Gln Ala Asn Gln Ser Val Ala Leu Val Ser Pro
465                 470                 475                 480
Tyr Gly Gly Leu Leu Gln Leu Val Tyr Ser Gly Ala Thr Pro Gly Gln
            485                 490                 495
Thr Val Thr Val Lys Val Thr Gly Ala Ala Ser Gln Pro Phe Leu Asp
        500                 505                 510
Ile Gln Pro Gly Glu Asp Ser Ser Gln Ala Ile Ala Asp Phe Ile Gln
        515                 520                 525
Ala Leu Asp Ala Asp Lys Ala Asp Trp Leu Glu Ile Arg Ser Gly Ser
        530                 535                 540
Val Glu Val His Ala Lys Val Glu Lys Val Arg Gly Ser Ile Asp Lys
545                 550                 555                 560
Asp Tyr Gly Gly Asp Val Gln Arg Phe Ile Arg Glu Leu Asn Glu Val
            565                 570                 575
Phe Ile Asp Asp Ala Tyr Thr Leu Ala Gly Phe Ala Ile Pro Asn Gln
        580                 585                 590
Ala Lys Thr Pro Ala Ile Gln Gln Glu Cys Ala Ala Arg Gly Trp Asp
        595                 600                 605
Cys Asp Ser Glu Thr Leu His Lys Leu Pro Gly Thr Gln His Ile Asn
        610                 615                 620
Val Asp Gln Tyr Ala Gln Cys Gly Gly Cys Ser Gly Asn Pro Tyr
625                 630                 635                 640
Asp Gln Thr Trp Gly Leu Asn Pro Arg Gly Trp Gly Glu Ser Ala Ala
            645                 650                 655
```

```
Leu Gly His Asn Leu Gln Val Asn Arg Leu Lys Val Tyr Gly Arg
            660                 665                 670

Ser Gly Glu Ile Ser Asn Gln Ile Phe Pro Leu His Lys Asp Trp Arg
            675                 680                 685

Val Leu Arg Glu Phe Gly Gln Asn Leu Asp Asp Thr Arg Val Asn Tyr
        690                 695                 700

Arg Asn Ala Tyr Asn Leu Ile Val Ala Gly Arg Ala Glu Ala Asp Pro
705                 710                 715                 720

Leu Ala Gly Val Tyr Lys Arg Leu Trp Glu Asp Pro Gly Thr Tyr Ala
            725                 730                 735

Leu Asn Gly Glu Arg Met Ala Phe Tyr Thr Gln Trp Val His Tyr Trp
            740                 745                 750

Ala Asp Leu Lys Asn Asp Pro Leu Gln Gly Trp Asp Ile Trp Thr Leu
            755                 760                 765

Leu Tyr Leu His Gln Arg Gln Val Asp Lys Ser Asp Trp Asp Ala Asn
            770                 775                 780

Lys Ala Ala Leu Gly Tyr Gly Thr Tyr Ala Gln Arg Pro Gly Asn Ser
785                 790                 795                 800

Gly Asp Ala Ser Ser Thr Asp Gly Asn Asp Asn Leu Leu Gly Leu
            805                 810                 815

Ser Trp Leu Thr Gln Arg Asp Gln Arg Pro Thr Phe Ala Leu Trp Gly
            820                 825                 830

Ile Arg Thr Ser Ala Ala Ala Gln Ala Gln Val Ala Ala Tyr Gly Phe
            835                 840                 845

Ala Glu Gln Pro Ala Phe Phe Tyr Ala Asn Asn Arg Thr Asn Glu Tyr
850                 855                 860

Ser Thr Val Lys Leu Leu Asp Met Ser Gln Gly Ser Pro Ala Trp Pro
865                 870                 875                 880

Phe Pro

<210> SEQ ID NO 36
<211> LENGTH: 536
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Bacteroides thetaiotaomicron VPI-5482 (double mutant
      with removed signal and other immature sequences)

<400> SEQUENCE: 36

Asp Lys Trp Glu Lys Glu Phe Arg Ile Arg Ser Tyr Glu Pro Tyr Ser
1               5                   10                  15

Asn Ile Ala Glu Trp Ala Asp Lys Leu Met Thr Lys Lys Tyr Ser Asp
            20                  25                  30

Leu Asp Asn Pro Thr Gly Ile Ser Val Lys Ala Gly Asp Asp Ile Ile
            35                  40                  45

Val Leu Val Gly Asp Thr Tyr Gly Gln Asn Ile Ser Met Gln Cys Ile
        50                  55                  60

Trp Glu Thr Gly Thr Glu Tyr Lys Gln Thr Ala Ser Ser Gly Asp Val
65                  70                  75                  80

Tyr Met Leu Asn Pro Gly Val Asn Lys Leu Thr Met Lys Gly Glu Gly
                85                  90                  95

Gln Leu Phe Val Met Tyr Asn Thr Glu Leu Thr Ser Asn Thr Ala Lys
            100                 105                 110
```

```
Pro Ile Lys Ile His Ile Pro Leu Gly Ser Gly Thr Val Asn Gly Phe
            115                 120                 125

Phe Asp Leu Lys Glu His Lys Thr Asp Glu Lys Tyr Ala Glu Leu Leu
    130                 135                 140

Lys Lys Ser Thr His Lys Tyr Phe Cys Ile Arg Gly Glu Lys Ile Met
145                 150                 155                 160

Phe Tyr Phe His Arg Asn Lys Leu Leu Glu Tyr Val Pro Asn Asn Ile
                165                 170                 175

Leu Ser Ala Ile His Leu Trp Asp Asn Ile Val Gly Trp Gln Gln Glu
            180                 185                 190

Leu Met Gly Ile Asp Asp Val Arg Pro Ser Gln Val Asn Asn His Leu
            195                 200                 205

Phe Ala Ile Ser Pro Glu Gly Ser Tyr Met Trp Ala Ser Asp Tyr Gln
        210                 215                 220

Ile Gly Phe Val Tyr Thr Tyr Leu Gly Asn Ile Leu Leu Glu Asp Asn
225                 230                 235                 240

Val Met Ala Ala Glu Asp Asn Ala Trp Gly Pro Ala Ala Ala Ile Gly
                245                 250                 255

His Val His Gln Ala Ala Ile Asn Trp Ala Ser Ser Thr Glu Ser Ser
            260                 265                 270

Asn Asn Leu Phe Ser Asn Phe Ile Ile Tyr Lys Leu Gly Lys Tyr Lys
            275                 280                 285

Ser Arg Gly Asn Gly Leu Gly Ser Val Ala Thr Ala Arg Tyr Ala Asn
    290                 295                 300

Gly Gln Ala Trp Tyr Asn Met Gly Asp Ala Thr His Gln Asn Glu Asp
305                 310                 315                 320

Thr Glu Thr His Met Arg Met Asn Trp Gln Leu Trp Ile Tyr Tyr His
                325                 330                 335

Arg Cys Glu Tyr Lys Thr Asp Phe Trp Gln Thr Leu Phe Lys Leu Met
            340                 345                 350

Arg Glu Val Asn Met Thr Glu Gly Glu Asp Pro Gly Lys Lys Gln Leu
            355                 360                 365

Glu Phe Ala Lys Met Ala Ser Lys Ala Ala Asn Gln Asn Leu Thr Asp
        370                 375                 380

Phe Phe Glu Met Trp Gly Phe Glu Pro Val Asn Thr Thr Ile Glu
385                 390                 395                 400

Gln Tyr Gly Thr Tyr Lys Tyr Tyr Val Ser Asp Ala Met Ile Arg Glu
                405                 410                 415

Ala Lys Glu Tyr Met Ala Gln Phe Pro Ala Pro Lys His Ala Phe Gln
            420                 425                 430

Tyr Ile Glu Asp Arg Lys Lys Ser Glu Phe Pro Ser Asn Asp Tyr Arg
        435                 440                 445

Tyr Ser Ala Val Gly Asp Val Gly Tyr Tyr Thr Gln Phe Lys Glu Asn
    450                 455                 460

Gln Lys Ile Thr Lys Ala Ile Thr Ala Glu Leu Ala Gly Arg Lys Val
465                 470                 475                 480

Ser Ile Gln Asn Gly Asp Glu Ala Val Ala Phe Glu Leu Arg Glu Asn
                485                 490                 495

Asp Glu Asn Gly Lys Leu Leu Tyr Phe Ser Thr Phe Thr Thr Phe Glu
            500                 505                 510
```

```
Ile Pro Ser Ser Ile Leu Met Val Asn Ala Lys Leu Tyr Ala Val Gln
            515                 520                 525

Ala Asp Gly Lys Arg Ile Leu Leu
        530                 535

<210> SEQ ID NO 37
<211> LENGTH: 507
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Clostridium perfringens (double mutant with removed
      signal and other immature sequences)

<400> SEQUENCE: 37

Val Leu Glu Leu Glu Met Arg Gly Asp Ser Ile Ser Glu Ala Lys Lys
1               5                   10                  15

Arg Lys Val Trp Asn Phe Gln Asp Trp Gln Ile Thr Gly Leu Ser Ala
            20                  25                  30

Arg Ala Gly Asp Lys Ile Thr Val Tyr Val Asp Val Ala Glu Gly Asp
        35                  40                  45

Pro Thr Pro Thr Leu Leu Tyr Lys Gln Ser Leu Thr Gln His Gly Gly
    50                  55                  60

Ala Thr Ser Phe Gln Leu Lys Pro Gly Lys Asn Glu Ile Thr Ile Pro
65                  70                  75                  80

Glu Ile Asn Tyr Glu Ser Asn Gly Ile Pro Lys Asp Val Ile Gln Gly
                85                  90                  95

Gly Asp Leu Phe Phe Thr Asn Tyr Lys Ser Asp Ser Gln Lys Arg Ala
            100                 105                 110

Pro Lys Val Arg Ile Glu Gly Ala Ser Lys Tyr Pro Val Phe Ile Leu
        115                 120                 125

Gly Lys Ser Asp Glu Asn Glu Val Met Lys Glu Leu Glu Ala Tyr Val
    130                 135                 140

Glu Lys Ile Lys Ala Glu Pro Lys Thr Thr Pro Asn Ile Phe Ala Val
145                 150                 155                 160

Ser Ser Asn Lys Ser Leu Glu Phe Val Gln Ala Thr Tyr Ala Leu Asp
                165                 170                 175

Trp Tyr Lys Lys Asn Asn Lys Thr Pro Lys Tyr Thr Ala Glu Gln Trp
            180                 185                 190

Asp Gln Tyr Ile Ala Asp Ala Met Gly Phe Trp Gly Phe Asp Asn Ser
        195                 200                 205

Lys Asp Val Asn Ser Asp Phe Asn Phe Arg Ile Met Pro Met Val Lys
    210                 215                 220

Asn Leu Ser Gly Gly Ala Phe Met Asn Ala Gly Asn Gly Val Ile Gly
225                 230                 235                 240

Ile Arg Pro Gly Asn Gln Asp Ala Ile Leu Ala Ala Asn Lys Gly Trp
                245                 250                 255

Gly Val Ala Ala Ala Leu Gly His Asn Phe Asp Thr Gly Gly Arg Thr
            260                 265                 270

Ile Val Glu Val Thr Asn Asn Met Met Pro Leu Phe Phe Glu Ser Lys
        275                 280                 285

Tyr Lys Thr Lys Thr Arg Ile Thr Asp Gln Asn Ile Trp Glu Asn Asn
    290                 295                 300

Thr Tyr Pro Lys Val Gly Leu Asp Asp Tyr Ser Asn Asn Glu Leu Tyr
305                 310                 315                 320
```

```
Asn Lys Ala Asp Ser Thr His Leu Ala Gln Leu Ala Pro Leu Trp Gln
                325                 330                 335

Leu Tyr Leu Tyr Asp Asn Thr Phe Tyr Gly Lys Phe Glu Arg Gln Phe
            340                 345                 350

Arg Glu Arg Asp Phe Gly Asn Lys Asn Arg Glu Asp Ile Tyr Lys Ser
        355                 360                 365

Trp Val Val Ala Ala Ser Asp Ala Met Glu Leu Asp Leu Thr Glu Phe
370                 375                 380

Phe Ala Arg His Gly Ile Arg Val Asp Asp Lys Val Lys Glu Asp Leu
385                 390                 395                 400

Ala Lys Tyr Pro Lys Pro Asp Lys Lys Ile Tyr Tyr Leu Asn Asp Leu
                405                 410                 415

Ala Met Asn Tyr Lys Gly Asp Gly Phe Thr Glu Asn Ala Lys Val Ser
            420                 425                 430

Val Ser Thr Ser Gly Ser Asn Gly Asn Ile Lys Leu Ser Phe Ser Val
        435                 440                 445

Asp Asp Glu Asn Lys Asp Asn Ile Leu Gly Tyr Glu Ile Arg Arg Asp
450                 455                 460

Gly Lys Tyr Val Gly Phe Thr Ser Asn Asp Ser Phe Val Asp Thr Lys
465                 470                 475                 480

Ser Asn Leu Asp Glu Asp Gly Val Tyr Val Val Thr Pro Tyr Asp Arg
                485                 490                 495

Lys Leu Asn Thr Leu Asn Pro Ile Glu Val Asn
            500                 505

<210> SEQ ID NO 38
<211> LENGTH: 892
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Pseudomonas aeruginosa PAO1 (double mutant with removed
      signal sequence, with N-term Met, C-term linker/tag)

<400> SEQUENCE: 38

Met Ala Thr Gln Glu Glu Ile Leu Asp Ala Ala Leu Val Ser Gly Asp
1               5                   10                  15

Ser Ser Gln Leu Thr Asp Ser His Leu Val Ala Leu Arg Leu Gln Gln
            20                  25                  30

Gln Val Glu Arg Ile Arg Gln Thr Arg Thr Gln Leu Leu Asp Gly Leu
        35                  40                  45

Tyr Gln Asn Leu Ser Gln Ala Tyr Asp Pro Gly Ala Ala Ser Met Trp
    50                  55                  60

Val Leu Pro Ala Asn Pro Asp Asn Thr Leu Pro Phe Leu Ile Gly Asp
65                  70                  75                  80

Lys Gly Arg Val Leu Ala Ser Leu Ser Leu Glu Ala Gly Gly Arg Gly
                85                  90                  95

Leu Ala Tyr Gly Thr Asn Val Leu Thr Gln Leu Ser Gly Thr Asn Ala
            100                 105                 110

Ala His Ala Pro Leu Leu Lys Arg Ala Val Gln Trp Leu Val Asn Gly
        115                 120                 125

Asp Pro Gly Ala Ala Thr Ala Lys Asp Phe Lys Val Ser Val Val Gly
    130                 135                 140

Val Asp Lys Thr Ala Ala Leu Asn Gly Leu Lys Ser Ala Gly Leu Gln
145                 150                 155                 160
```

```
Pro Ala Asp Ala Ala Cys Asn Ala Leu Thr Asp Ala Ser Cys Ala Ser
                165                 170                 175

Thr Ser Lys Leu Leu Val Leu Gly Asn Gly Ala Ser Ala Ser Leu
    180                 185                 190

Ser Ala Thr Val Arg Ala Arg Leu Gln Ala Gly Leu Pro Ile Leu Phe
        195                 200                 205

Val His Thr Asn Gly Trp Asn Gln Ser Ser Thr Gly Gln Gln Ile Leu
    210                 215                 220

Ala Gly Leu Gly Leu Gln Glu Gly Pro Tyr Gly Gly Asn Tyr Trp Asp
225                 230                 235                 240

Lys Asp Arg Val Pro Ser Ser Arg Thr Arg Thr Arg Ser Val Glu Leu
                245                 250                 255

Gly Gly Ala Tyr Gly Gln Asp Pro Ala Leu Val Gln Gln Ile Val Asp
            260                 265                 270

Gly Ser Trp Arg Thr Asp Tyr Asp Trp Ser Lys Cys Thr Ser Tyr Val
        275                 280                 285

Gly Arg Thr Thr Cys Asp Val Pro Gly Leu Ser Asp Phe Ser Lys
    290                 295                 300

Arg Val Asp Val Leu Lys Gly Ala Leu Asp Ala Tyr Asn Gln Lys Ala
305                 310                 315                 320

Gln Asn Leu Phe Ala Leu Pro Gly Thr Thr Ser Leu Arg Leu Trp Leu
                325                 330                 335

Leu Trp Ala Asp Ala Val Arg Gln Asn Ile Arg Tyr Pro Met Asp Lys
            340                 345                 350

Ala Ala Asp Thr Ala Arg Phe Gln Glu Thr Phe Val Ala Asp Ala Ile
        355                 360                 365

Val Gly Tyr Val Arg Glu Ala Gly Ala Gln Lys Glu Leu Gly Ser
    370                 375                 380

Tyr Ala Gly Gln Arg Gln Gln Ser Met Pro Val Ser Gly Ser Glu Glu
385                 390                 395                 400

Thr Leu Thr Leu Thr Leu Pro Ser Ala Gln Gly Phe Thr Ala Ile Gly
                405                 410                 415

Arg Met Ala Ala Pro Gly Lys Arg Leu Ser Ile Arg Ile Glu Asp Ala
            420                 425                 430

Gly Gln Ala Ser Leu Ala Val Gly Leu Asn Thr Gln Arg Ile Gly Ser
        435                 440                 445

Thr Arg Leu Trp Asn Thr Arg Gln Tyr Asp Arg Pro Arg Phe Leu Lys
    450                 455                 460

Ser Pro Asp Ile Lys Leu Gln Ala Asn Gln Ser Val Ala Leu Val Ser
465                 470                 475                 480

Pro Tyr Gly Gly Leu Leu Gln Leu Val Tyr Ser Gly Ala Thr Pro Gly
                485                 490                 495

Gln Thr Val Thr Val Lys Val Thr Gly Ala Ala Ser Gln Pro Phe Leu
            500                 505                 510

Asp Ile Gln Pro Gly Glu Asp Ser Ser Gln Ala Ile Ala Asp Phe Ile
        515                 520                 525

Gln Ala Leu Asp Ala Asp Lys Ala Asp Trp Leu Glu Ile Arg Ser Gly
    530                 535                 540

Ser Val Glu Val His Ala Lys Val Glu Lys Val Arg Gly Ser Ile Asp
545                 550                 555                 560

Lys Asp Tyr Gly Gly Asp Val Gln Arg Phe Ile Arg Glu Leu Asn Glu
                565                 570                 575
```

Val Phe Ile Asp Asp Ala Tyr Thr Leu Ala Gly Phe Ala Ile Pro Asn
            580                 585                 590

Gln Ala Lys Thr Pro Ala Ile Gln Gln Glu Cys Ala Ala Arg Gly Trp
        595                 600                 605

Asp Cys Asp Ser Glu Thr Leu His Lys Leu Pro Gly Thr Gln His Ile
    610                 615                 620

Asn Val Asp Gln Tyr Ala Gln Cys Gly Gly Cys Ser Gly Asn Pro
625                 630                 635                 640

Tyr Asp Gln Thr Trp Gly Leu Asn Pro Arg Gly Trp Gly Glu Ser Ala
                645                 650                 655

Ala Leu Gly His Asn Leu Gln Val Asn Arg Leu Lys Val Tyr Gly Gly
                660                 665                 670

Arg Ser Gly Glu Ile Ser Asn Gln Ile Phe Pro Leu His Lys Asp Trp
            675                 680                 685

Arg Val Leu Arg Glu Phe Gly Gln Asn Leu Asp Asp Thr Arg Val Asn
    690                 695                 700

Tyr Arg Asn Ala Tyr Asn Leu Ile Val Ala Gly Arg Ala Glu Ala Asp
705                 710                 715                 720

Pro Leu Ala Gly Val Tyr Lys Arg Leu Trp Glu Asp Pro Gly Thr Tyr
                725                 730                 735

Ala Leu Asn Gly Glu Arg Met Ala Phe Tyr Thr Gln Trp Val His Tyr
                740                 745                 750

Trp Ala Asp Leu Lys Asn Asp Pro Leu Gln Gly Trp Asp Ile Trp Thr
            755                 760                 765

Leu Leu Tyr Leu His Gln Arg Gln Val Asp Lys Ser Asp Trp Asp Ala
    770                 775                 780

Asn Lys Ala Ala Leu Gly Tyr Gly Thr Tyr Ala Gln Arg Pro Gly Asn
785                 790                 795                 800

Ser Gly Asp Ala Ser Ser Thr Asp Gly Asn Asp Leu Leu Leu Gly
                805                 810                 815

Leu Ser Trp Leu Thr Gln Arg Asp Gln Arg Pro Thr Phe Ala Leu Trp
            820                 825                 830

Gly Ile Arg Thr Ser Ala Ala Gln Ala Gln Val Ala Ala Tyr Gly
    835                 840                 845

Phe Ala Glu Gln Pro Ala Phe Phe Tyr Ala Asn Asn Arg Thr Asn Glu
850                 855                 860

Tyr Ser Thr Val Lys Leu Leu Asp Met Ser Gln Gly Ser Pro Ala Trp
865                 870                 875                 880

Pro Phe Pro Gly Ser Gly His His His His His
                885                 890

<210> SEQ ID NO 39
<211> LENGTH: 546
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Bacteroides thetaiotaomicron VPI-5482 (double mutant
      with removed signal and other sequences from immature protein,
      with N-term

<400> SEQUENCE: 39

Met Asp Lys Trp Glu Lys Glu Phe Arg Ile Arg Ser Tyr Glu Pro Tyr
1               5                   10                  15

Ser Asn Ile Ala Glu Trp Ala Asp Lys Leu Met Thr Lys Lys Tyr Ser
            20                  25                  30

Asp Leu Asp Asn Pro Thr Gly Ile Ser Val Lys Ala Gly Asp Ile
             35                  40                  45

Ile Val Leu Val Gly Asp Thr Tyr Gly Gln Asn Ile Ser Met Gln Cys
 50                  55                  60

Ile Trp Glu Thr Gly Thr Glu Tyr Lys Gln Thr Ala Ser Ser Gly Asp
 65                  70                  75                  80

Val Tyr Met Leu Asn Pro Gly Val Asn Lys Leu Thr Met Lys Gly Glu
                 85                  90                  95

Gly Gln Leu Phe Val Met Tyr Asn Thr Glu Leu Thr Ser Asn Thr Ala
            100                 105                 110

Lys Pro Ile Lys Ile His Ile Pro Leu Gly Ser Gly Thr Val Asn Gly
        115                 120                 125

Phe Phe Asp Leu Lys Glu His Lys Thr Asp Glu Lys Tyr Ala Glu Leu
130                 135                 140

Leu Lys Lys Ser Thr His Lys Tyr Phe Cys Ile Arg Gly Glu Lys Ile
145                 150                 155                 160

Met Phe Tyr Phe His Arg Asn Lys Leu Leu Glu Tyr Val Pro Asn Asn
                165                 170                 175

Ile Leu Ser Ala Ile His Leu Trp Asp Asn Ile Val Gly Trp Gln Gln
            180                 185                 190

Glu Leu Met Gly Ile Asp Asp Val Arg Pro Ser Gln Val Asn Asn His
        195                 200                 205

Leu Phe Ala Ile Ser Pro Glu Gly Ser Tyr Met Trp Ala Ser Asp Tyr
210                 215                 220

Gln Ile Gly Phe Val Tyr Thr Tyr Leu Gly Asn Ile Leu Leu Glu Asp
225                 230                 235                 240

Asn Val Met Ala Ala Glu Asp Asn Ala Trp Gly Pro Ala Ala Ala Ile
                245                 250                 255

Gly His Val His Gln Ala Ala Ile Asn Trp Ala Ser Ser Thr Glu Ser
            260                 265                 270

Ser Asn Asn Leu Phe Ser Asn Phe Ile Ile Tyr Lys Leu Gly Lys Tyr
        275                 280                 285

Lys Ser Arg Gly Asn Gly Leu Gly Ser Val Ala Thr Ala Arg Tyr Ala
290                 295                 300

Asn Gly Gln Ala Trp Tyr Asn Met Gly Asp Ala Thr His Gln Asn Glu
305                 310                 315                 320

Asp Thr Glu Thr His Met Arg Met Asn Trp Gln Leu Trp Ile Tyr Tyr
                325                 330                 335

His Arg Cys Glu Tyr Lys Thr Asp Phe Trp Gln Thr Leu Phe Lys Leu
            340                 345                 350

Met Arg Glu Val Asn Met Thr Glu Gly Glu Asp Pro Gly Lys Lys Gln
        355                 360                 365

Leu Glu Phe Ala Lys Met Ala Ser Lys Ala Ala Asn Gln Asn Leu Thr
370                 375                 380

Asp Phe Phe Glu Met Trp Gly Phe Phe Glu Pro Val Asn Thr Thr Ile
385                 390                 395                 400

Glu Gln Tyr Gly Thr Tyr Lys Tyr Tyr Val Ser Asp Ala Met Ile Arg
                405                 410                 415

Glu Ala Lys Glu Tyr Met Ala Gln Phe Pro Ala Pro Lys His Ala Phe
            420                 425                 430

Gln Tyr Ile Glu Asp Arg Lys Lys Ser Glu Phe Pro Ser Asn Asp Tyr
        435                 440                 445

```
Arg Tyr Ser Ala Val Gly Asp Val Gly Tyr Tyr Thr Gln Phe Lys Glu
    450                 455                 460

Asn Gln Lys Ile Thr Lys Ala Ile Thr Ala Glu Leu Ala Gly Arg Lys
465                 470                 475                 480

Val Ser Ile Gln Asn Gly Asp Glu Ala Val Ala Phe Glu Leu Arg Glu
                485                 490                 495

Asn Asp Glu Asn Gly Lys Leu Leu Tyr Phe Ser Thr Phe Thr Thr Phe
                500                 505                 510

Glu Ile Pro Ser Ser Ile Leu Met Val Asn Ala Lys Leu Tyr Ala Val
                515                 520                 525

Gln Ala Asp Gly Lys Arg Ile Leu Leu Gly Ser Gly His His His His
530                 535                 540

His His
545

<210> SEQ ID NO 40
<211> LENGTH: 517
<212> TYPE: PRT
<213> ORGANISM: Artificial Sequence
<220> FEATURE:
<223> OTHER INFORMATION: Polypeptide capable of binding to O-glycans but
      lack or has reduced O-glycoprotein-specific endoprotease
      activity - Clostridium perfringens (double mutant with removed
      signal and other sequences from immature protein, with N-term Met,
      C-term

<400> SEQUENCE: 40

Met Val Leu Glu Leu Glu Met Arg Gly Asp Ser Ile Ser Glu Ala Lys
1               5                   10                  15

Lys Arg Lys Val Trp Asn Phe Gln Asp Trp Gln Ile Thr Gly Leu Ser
                20                  25                  30

Ala Arg Ala Gly Asp Lys Ile Thr Val Tyr Val Asp Val Ala Glu Gly
            35                  40                  45

Asp Pro Thr Pro Thr Leu Leu Tyr Lys Gln Ser Leu Thr Gln His Gly
    50                  55                  60

Gly Ala Thr Ser Phe Gln Leu Lys Pro Gly Lys Asn Glu Ile Thr Ile
65                  70                  75                  80

Pro Glu Ile Asn Tyr Glu Ser Asn Gly Ile Pro Lys Asp Val Ile Gln
                85                  90                  95

Gly Gly Asp Leu Phe Phe Thr Asn Tyr Lys Ser Asp Ser Gln Lys Arg
            100                 105                 110

Ala Pro Lys Val Arg Ile Glu Gly Ala Ser Lys Tyr Pro Val Phe Ile
        115                 120                 125

Leu Gly Lys Ser Asp Glu Asn Glu Val Met Lys Glu Leu Glu Ala Tyr
    130                 135                 140

Val Glu Lys Ile Lys Ala Glu Pro Lys Thr Thr Pro Asn Ile Phe Ala
145                 150                 155                 160

Val Ser Ser Asn Lys Ser Leu Glu Phe Val Gln Ala Thr Tyr Ala Leu
                165                 170                 175

Asp Trp Tyr Lys Lys Asn Asn Lys Thr Pro Lys Tyr Thr Ala Glu Gln
            180                 185                 190

Trp Asp Gln Tyr Ile Ala Asp Ala Met Gly Phe Trp Gly Phe Asp Asn
        195                 200                 205

Ser Lys Asp Val Asn Ser Asp Phe Asn Phe Arg Ile Met Pro Met Val
    210                 215                 220

Lys Asn Leu Ser Gly Gly Ala Phe Met Asn Ala Gly Asn Gly Val Ile
225                 230                 235                 240
```

```
Gly Ile Arg Pro Gly Asn Gln Asp Ala Ile Leu Ala Ala Asn Lys Gly
                245                 250                 255

Trp Gly Val Ala Ala Ala Leu Gly His Asn Phe Asp Thr Gly Gly Arg
            260                 265                 270

Thr Ile Val Glu Val Thr Asn Asn Met Met Pro Leu Phe Phe Glu Ser
        275                 280                 285

Lys Tyr Lys Thr Lys Thr Arg Ile Thr Asp Gln Asn Ile Trp Glu Asn
    290                 295                 300

Asn Thr Tyr Pro Lys Val Gly Leu Asp Asp Tyr Ser Asn Asn Glu Leu
305                 310                 315                 320

Tyr Asn Lys Ala Asp Ser Thr His Leu Ala Gln Leu Ala Pro Leu Trp
                325                 330                 335

Gln Leu Tyr Leu Tyr Asp Asn Thr Phe Tyr Gly Lys Phe Glu Arg Gln
            340                 345                 350

Phe Arg Glu Arg Asp Phe Gly Asn Lys Asn Arg Glu Asp Ile Tyr Lys
        355                 360                 365

Ser Trp Val Val Ala Ala Ser Asp Ala Met Glu Leu Asp Leu Thr Glu
    370                 375                 380

Phe Phe Ala Arg His Gly Ile Arg Val Asp Asp Lys Val Lys Glu Asp
385                 390                 395                 400

Leu Ala Lys Tyr Pro Lys Pro Asp Lys Lys Ile Tyr Tyr Leu Asn Asp
                405                 410                 415

Leu Ala Met Asn Tyr Lys Gly Asp Gly Phe Thr Glu Asn Ala Lys Val
            420                 425                 430

Ser Val Ser Thr Ser Gly Ser Asn Gly Asn Ile Lys Leu Ser Phe Ser
        435                 440                 445

Val Asp Asp Glu Asn Lys Asp Asn Ile Leu Gly Tyr Glu Ile Arg Arg
    450                 455                 460

Asp Gly Lys Tyr Val Gly Phe Thr Ser Asn Asp Ser Phe Val Asp Thr
465                 470                 475                 480

Lys Ser Asn Leu Asp Glu Asp Gly Val Tyr Val Val Thr Pro Tyr Asp
                485                 490                 495

Arg Lys Leu Asn Thr Leu Asn Pro Ile Glu Val Asn Gly Ser Gly His
            500                 505                 510

His His His His His
        515

<210> SEQ ID NO 41
<211> LENGTH: 5
<212> TYPE: PRT
<213> ORGANISM: Artificial Sequence
<220> FEATURE:
<223> OTHER INFORMATION: Metalloprotease motif

<400> SEQUENCE: 41

His Glu Leu Gly His
1               5

<210> SEQ ID NO 42
<211> LENGTH: 5
<212> TYPE: PRT
<213> ORGANISM: Artificial Sequence
<220> FEATURE:
<223> OTHER INFORMATION: Metalloprotease motif

<400> SEQUENCE: 42

His Glu Ile Gly His
1               5
```

<210> SEQ ID NO 43
<211> LENGTH: 10
<212> TYPE: PRT
<213> ORGANISM: Artificial Sequence
<220> FEATURE:
<223> OTHER INFORMATION: Metalloprotease motif

<400> SEQUENCE: 43

Gly Val Ala His Glu Leu Gly His Asn Phe
1               5                   10

<210> SEQ ID NO 44
<211> LENGTH: 5
<212> TYPE: PRT
<213> ORGANISM: Artificial Sequence
<220> FEATURE:
<223> OTHER INFORMATION: disrupted metalloprotease motif

<400> SEQUENCE: 44

His Ala Leu Gly His
1               5

<210> SEQ ID NO 45
<211> LENGTH: 5
<212> TYPE: PRT
<213> ORGANISM: Artificial Sequence
<220> FEATURE:
<223> OTHER INFORMATION: disrupted metalloprotease motif

<400> SEQUENCE: 45

Ala Glu Leu Gly His
1               5

<210> SEQ ID NO 46
<211> LENGTH: 5
<212> TYPE: PRT
<213> ORGANISM: Artificial Sequence
<220> FEATURE:
<223> OTHER INFORMATION: disrupted metalloprotease motif

<400> SEQUENCE: 46

Ala Ala Leu Gly His
1               5

<210> SEQ ID NO 47
<211> LENGTH: 19
<212> TYPE: PRT
<213> ORGANISM: Artificial Sequence
<220> FEATURE:
<223> OTHER INFORMATION: glycodrosocin peptide with O-gly site on the T

<400> SEQUENCE: 47

Gly Lys Pro Arg Pro Tyr Ser Pro Arg Pro Thr Ser His Pro Arg Pro
1               5                   10                  15

Ile Arg Val

<210> SEQ ID NO 48
<211> LENGTH: 7
<212> TYPE: PRT
<213> ORGANISM: Artificial Sequence
<220> FEATURE:
<223> OTHER INFORMATION: Non-O-glycosylated peptide

<400> SEQUENCE: 48

Tyr Ile Tyr Gly Ser Phe Lys
1               5

-continued

```
<210> SEQ ID NO 49
<211> LENGTH: 7
<212> TYPE: PRT
<213> ORGANISM: Artificial Sequence
<220> FEATURE:
<223> OTHER INFORMATION: Non-O-glycosylated peptide

<400> SEQUENCE: 49

Lys Lys Leu Val Phe Phe Ala
1               5

<210> SEQ ID NO 50
<211> LENGTH: 14
<212> TYPE: PRT
<213> ORGANISM: Artificial Sequence
<220> FEATURE:
<223> OTHER INFORMATION: Non-O-glycosylated peptide

<400> SEQUENCE: 50

Phe Leu Pro Leu Ile Leu Gly Lys Leu Val Lys Gly Leu Leu
1               5                   10

<210> SEQ ID NO 51
<211> LENGTH: 467
<212> TYPE: PRT
<213> ORGANISM: Artificial sequence
<220> FEATURE:
<223> OTHER INFORMATION: synthetic sequence

<400> SEQUENCE: 51

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240
```

```
Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 52
<211> LENGTH: 40
<212> TYPE: PRT
<213> ORGANISM: Artificial sequence
<220> FEATURE:
<223> OTHER INFORMATION: synthetic sequence
<220> FEATURE:
<221> NAME/KEY: CARBOHYD
<222> LOCATION: (1)..(1)
<223> OTHER INFORMATION: The amino acid at postion 1 is attached to
      N-Acetylglucosamine and galactose

<400> SEQUENCE: 52

Ser Ala Ala Pro Leu Arg Thr Ile Thr Ala Asp Thr Phe Arg Lys Leu
1               5                   10                  15

Phe Arg Val Tyr Ser Asn Phe Leu Arg Gly Lys Leu Lys Leu Tyr Thr
            20                  25                  30

Gly Glu Ala Cys Arg Thr Gly Asp
        35                  40

<210> SEQ ID NO 53
<211> LENGTH: 40
<212> TYPE: PRT
<213> ORGANISM: Artificial sequence
<220> FEATURE:
<223> OTHER INFORMATION: synthetic sequence
```

```
<220> FEATURE:
<221> NAME/KEY: CARBOHYD
<222> LOCATION: (1)..(1)
<223> OTHER INFORMATION: The amino acid at postition 1 is attached to
      N-Acetylglucosamine

<400> SEQUENCE: 53

Ser Ala Ala Pro Leu Arg Thr Ile Thr Ala Asp Thr Phe Arg Lys Leu
1               5                   10                  15

Phe Arg Val Tyr Ser Asn Phe Leu Arg Gly Lys Leu Lys Leu Tyr Thr
            20                  25                  30

Gly Glu Ala Cys Arg Thr Gly Asp
        35                  40

<210> SEQ ID NO 54
<211> LENGTH: 125
<212> TYPE: PRT
<213> ORGANISM: Artificial sequence
<220> FEATURE:
<223> OTHER INFORMATION: synthetic sequence

<400> SEQUENCE: 54

Ala Pro Pro Arg Leu Ile Cys Asp Ser Arg Val Leu Glu Arg Tyr Leu
1               5                   10                  15

Leu Glu Ala Lys Glu Ala Glu Asp Ile Thr Thr Gly Cys Ala Glu His
            20                  25                  30

Cys Ser Leu Asp Glu Asn Ile Thr Val Pro Asp Thr Lys Val Asp Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala
        115                 120                 125

<210> SEQ ID NO 55
<211> LENGTH: 165
<212> TYPE: PRT
<213> ORGANISM: Artificial sequence
<220> FEATURE:
<223> OTHER INFORMATION: synthetic sequence
<220> FEATURE:
<221> NAME/KEY: CARBOHYD
<222> LOCATION: (126)..(126)
<223> OTHER INFORMATION: The amino acid at position 126 is attached to
      N-Acetylglucosamine and galactose

<400> SEQUENCE: 55

Ala Pro Pro Arg Leu Ile Cys Asp Ser Arg Val Leu Glu Arg Tyr Leu
1               5                   10                  15

Leu Glu Ala Lys Glu Ala Glu Asp Ile Thr Thr Gly Cys Ala Glu His
            20                  25                  30

Cys Ser Leu Asp Glu Asn Ile Thr Val Pro Asp Thr Lys Val Asp Phe
        35                  40                  45

Tyr Ala Trp Lys Arg Met Glu Val Gly Gln Gln Ala Val Glu Val Trp
    50                  55                  60
```

```
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 56

<400> SEQUENCE: 56

000

<210> SEQ ID NO 57

<400> SEQUENCE: 57

000

<210> SEQ ID NO 58
<211> LENGTH: 353
<212> TYPE: PRT
<213> ORGANISM: Artificial sequence
<220> FEATURE:
<223> OTHER INFORMATION: synthetic sequence

<400> SEQUENCE: 58

Ala Ser Pro Thr Ser Pro Lys Val Phe Pro Leu Ser Leu Cys Ser Thr
  1               5                  10                  15

Gln Pro Asp Gly Asn Val Val Ile Ala Cys Leu Val Gln Gly Phe Phe
                 20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175
```

```
Arg Asp Leu Cys Gly Cys Tyr Ser Val Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 59
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (3)..(4)
<223> OTHER INFORMATION: The amino acids at positions 3 and 4 can be any
      uncharged amino acid

<400> SEQUENCE: 59

```
His Glu Xaa Xaa His
1               5
```

<210> SEQ ID NO 60
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: The amino acid at position 1 is Val, Thr or Gly
<220> FEATURE:
<221> NAME/KEY: VARIANT
<222> LOCATION: (2)..(2)
<223> OTHER INFORMATION: The amino acid at position 2 is any uncharged
      amino acid
<220> FEATURE:
<221> NAME/KEY: VARIANT
<222> LOCATION: (3)..(3)
<223> OTHER INFORMATION: The amino acid at position 3 is any amino acid
<220> FEATURE:
<221> NAME/KEY: VARIANT
<222> LOCATION: (6)..(7)
<223> OTHER INFORMATION: Each amino acid at positions 6 and 7 is any
      uncharged amino acid

```
<220> FEATURE:
<221> NAME/KEY: VARIANT
<222> LOCATION: (9)..(9)
<223> OTHER INFORMATION: The amino acid at position 9 is any uncharged
      amino acid
<220> FEATURE:
<221> NAME/KEY: VARIANT
<222> LOCATION: (10)..(10)
<223> OTHER INFORMATION: The amino acid at position 10 is any
      hydrophobic amino acid

<400> SEQUENCE: 60

Xaa Xaa Xaa His Glu Xaa Xaa His Xaa Xaa
1               5                   10

<210> SEQ ID NO 61
<211> LENGTH: 5
<212> TYPE: PRT
<213> ORGANISM: Artificial sequence
<220> FEATURE:
<223> OTHER INFORMATION: synthetic sequence

<400> SEQUENCE: 61

Gly Ser Gly Leu Glu
1               5

<210> SEQ ID NO 62
<211> LENGTH: 6
<212> TYPE: PRT
<213> ORGANISM: Artificial sequence
<220> FEATURE:
<223> OTHER INFORMATION: synthetic sequence

<400> SEQUENCE: 62

His His His His His His
1               5

<210> SEQ ID NO 63
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: The amino acid at position 1 is any amino acid
      except His
<220> FEATURE:
<221> NAME/KEY: VARIANT
<222> LOCATION: (2)..(4)
<223> OTHER INFORMATION: Each amino acid at positions 2 to 4 is any
      uncharged amino acid
<220> FEATURE:
<221> NAME/KEY: VARIANT
<222> LOCATION: (5)..(5)
<223> OTHER INFORMATION: The amino acid at position 5 is any amino acid
      except His

<400> SEQUENCE: 63

Xaa Xaa Xaa Xaa Xaa
1               5

<210> SEQ ID NO 64
<211> LENGTH: 10
<212> TYPE: PRT
<213> ORGANISM: Artificial sequence
<220> FEATURE:
<223> OTHER INFORMATION: synthetic sequence
```

```
<220> FEATURE:
<221> NAME/KEY: VARIANT
<222> LOCATION: (1)..(1)
<223> OTHER INFORMATION: The amino acid at position 1 is Val, Thr or Gly
<220> FEATURE:
<221> NAME/KEY: VARIANT
<222> LOCATION: (2)..(2)
<223> OTHER INFORMATION: The amino acid at position 2 is any uncharged
      amino acid
<220> FEATURE:
<221> NAME/KEY: VARIANT
<222> LOCATION: (3)..(4)
<223> OTHER INFORMATION: Each amino acid at positions 3 and 4 is any
      amino acid
<220> FEATURE:
<221> NAME/KEY: VARIANT
<222> LOCATION: (5)..(7)
<223> OTHER INFORMATION: Each amino acid at positions 5 to 7 is any
      uncharged amino acid
<220> FEATURE:
<221> NAME/KEY: VARIANT
<222> LOCATION: (8)..(8)
<223> OTHER INFORMATION: The amino acid at position 8 is any amino acid
<220> FEATURE:
<221> NAME/KEY: VARIANT
<222> LOCATION: (9)..(9)
<223> OTHER INFORMATION: The amino acid at position 9 is any uncharged
      amino acid
<220> FEATURE:
<221> NAME/KEY: VARIANT
<222> LOCATION: (10)..(10)
<223> OTHER INFORMATION: The amino acid at position 10 is any
      hydrophobic amino acid

<400> SEQUENCE: 64

Xaa Xaa Xaa Xaa Xaa Xaa Xaa Xaa Xaa Xaa
1               5                   10

<210> SEQ ID NO 65
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: The amino acid at position 1 is Val, Thr or Gly
<220> FEATURE:
<221> NAME/KEY: VARIANT
<222> LOCATION: (2)..(2)
<223> OTHER INFORMATION: The amino acid at position 2 is any uncharged
      amino acid
<220> FEATURE:
<221> NAME/KEY: VARIANT
<222> LOCATION: (3)..(3)
<223> OTHER INFORMATION: The amino acid at position 3 is any amino acid
<220> FEATURE:
<221> NAME/KEY: VARIANT
<222> LOCATION: (6)..(7)
<223> OTHER INFORMATION: Each amino acid at positions 6 and 7 is any
      uncharged amino acid
<220> FEATURE:
<221> NAME/KEY: VARIANT
<222> LOCATION: (9)..(9)
<223> OTHER INFORMATION: The amino acid at position 9 is any uncharged
      amino acid
<220> FEATURE:
<221> NAME/KEY: VARIANT
<222> LOCATION: (10)..(10)
<223> OTHER INFORMATION: The amino acid at position 10 is any
      hydrophobic amino acid

<400> SEQUENCE: 65

Xaa Xaa Xaa His Ala Xaa Xaa His Xaa Xaa
1               5                   10
```

```
<210> SEQ ID NO 66
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: The amino acid at position 1 is Val, Thr or Gly
<220> FEATURE:
<221> NAME/KEY: VARIANT
<222> LOCATION: (2)..(2)
<223> OTHER INFORMATION: The amino acid at position 2 is any uncharged
      amino acid
<220> FEATURE:
<221> NAME/KEY: VARIANT
<222> LOCATION: (3)..(3)
<223> OTHER INFORMATION: The amino acid at position 3 is any amino acid
<220> FEATURE:
<221> NAME/KEY: VARIANT
<222> LOCATION: (6)..(7)
<223> OTHER INFORMATION: Each amino acid at positions 6 to 7 is any
      uncharged amino acid
<220> FEATURE:
<221> NAME/KEY: VARIANT
<222> LOCATION: (9)..(9)
<223> OTHER INFORMATION: The amino acid at position 9 is any uncharged
      amino acid
<220> FEATURE:
<221> NAME/KEY: VARIANT
<222> LOCATION: (10)..(10)
<223> OTHER INFORMATION: The amino acid at postion 10 is any hydrophobic
      amino acid

<400> SEQUENCE: 66

Xaa Xaa Xaa Ala Ala Xaa Xaa His Xaa Xaa
1               5                   10

<210> SEQ ID NO 67
<211> LENGTH: 5
<212> TYPE: PRT
<213> ORGANISM: Artificial sequence
<220> FEATURE:
<223> OTHER INFORMATION: synthetic sequence

<400> SEQUENCE: 67

Tyr Thr Gln Lys Ser
1               5

<210> SEQ ID NO 68
<211> LENGTH: 6
<212> TYPE: PRT
<213> ORGANISM: Artificial sequence
<220> FEATURE:
<223> OTHER INFORMATION: synthetic sequence

<400> SEQUENCE: 68

Thr Ser Pro Thr Arg Ser
1               5

<210> SEQ ID NO 69
<211> LENGTH: 12
<212> TYPE: PRT
<213> ORGANISM: Artificial sequence
<220> FEATURE:
<223> OTHER INFORMATION: synthetic sequence

<400> SEQUENCE: 69

Pro Ser Thr Ser Phe Leu Leu Pro Met Gly Pro Ser
1               5                   10
```

```
<210> SEQ ID NO 70
<211> LENGTH: 23
<212> TYPE: PRT
<213> ORGANISM: Artificial sequence
<220> FEATURE:
<223> OTHER INFORMATION: synthetic sequence

<400> SEQUENCE: 70

Pro Thr Arg Ser Met Ala Pro Gly Ala Val His Leu Pro Gln Pro Val
1               5                   10                  15

Ser Thr Arg Ser Gln His Thr
            20

<210> SEQ ID NO 71
<211> LENGTH: 17
<212> TYPE: PRT
<213> ORGANISM: Artificial sequence
<220> FEATURE:
<223> OTHER INFORMATION: synthetic sequence

<400> SEQUENCE: 71

Pro Thr Arg Ser Met Ala Pro Gly Ala Val His Leu Pro Gln Pro Val
1               5                   10                  15

Ser

<210> SEQ ID NO 72
<211> LENGTH: 11
<212> TYPE: PRT
<213> ORGANISM: Artificial sequence
<220> FEATURE:
<223> OTHER INFORMATION: synthetic sequence

<400> SEQUENCE: 72

Ser Thr Ser Phe Leu Leu Pro Met Gly Pro Ser
1               5                   10

<210> SEQ ID NO 73
<211> LENGTH: 16
<212> TYPE: PRT
<213> ORGANISM: Artificial sequence
<220> FEATURE:
<223> OTHER INFORMATION: synthetic sequence

<400> SEQUENCE: 73

Arg Ser Met Ala Pro Gly Ala Val His Leu Pro Gln Pro Val Ser Thr
1               5                   10                  15

<210> SEQ ID NO 74
<211> LENGTH: 8
<212> TYPE: PRT
<213> ORGANISM: Artificial sequence
<220> FEATURE:
<223> OTHER INFORMATION: synthetic sequence

<400> SEQUENCE: 74

Leu Pro Ala Gln Val Ala Phe Thr
1               5

<210> SEQ ID NO 75
<211> LENGTH: 18
<212> TYPE: PRT
<213> ORGANISM: Artificial sequence
<220> FEATURE:
<223> OTHER INFORMATION: synthetic sequence
```

```
<400> SEQUENCE: 75

Pro Ser Thr Ser Phe Leu Leu Pro Met Gly Pro Ser Pro Pro Ala Glu
1               5                   10                  15

Gly Ser

<210> SEQ ID NO 76
<211> LENGTH: 19
<212> TYPE: PRT
<213> ORGANISM: Artificial sequence
<220> FEATURE:
<223> OTHER INFORMATION: synthetic sequence

<400> SEQUENCE: 76

Pro Ser Thr Ser Phe Leu Leu Pro Met Gly Pro Ser Pro Pro Ala Glu
1               5                   10                  15

Gly Ser Thr

<210> SEQ ID NO 77
<211> LENGTH: 18
<212> TYPE: PRT
<213> ORGANISM: Artificial sequence
<220> FEATURE:
<223> OTHER INFORMATION: synthetic sequence

<400> SEQUENCE: 77

Pro Thr Arg Ser Met Ala Pro Gly Ala Val His Leu Pro Gln Pro Val
1               5                   10                  15

Ser Thr

<210> SEQ ID NO 78
<211> LENGTH: 20
<212> TYPE: PRT
<213> ORGANISM: Artificial sequence
<220> FEATURE:
<223> OTHER INFORMATION: synthetic sequence

<400> SEQUENCE: 78

Pro Thr Pro Glu Pro Ser Thr Ala Pro Ser Thr Ser Phe Leu Leu Pro
1               5                   10                  15

Met Gly Pro Ser
            20
```